(12) United States Patent
Ip et al.

(10) Patent No.: US 9,029,414 B2
(45) Date of Patent: *May 12, 2015

(54) TRITERPENOID COMPOUNDS AND METHODS OF USE THEREOF

(75) Inventors: Nancy Yuk-Yu Ip, Hong Kong (CN); Fanny Chui-Fun Ip, Kowloon (CN); Yueqing Hu, Kowloon (CN)

(73) Assignee: Biotechnology Research Corporation, Kowloon (HK)

( * ) Notice: Subject to any disclaimer, the term of this patent is extended or adjusted under 35 U.S.C. 154(b) by 375 days.

This patent is subject to a terminal disclaimer.

(21) Appl. No.: 13/119,692

(22) PCT Filed: Sep. 19, 2009

(86) PCT No.: PCT/IB2009/006894
§ 371 (c)(1),
(2), (4) Date: Aug. 1, 2011

(87) PCT Pub. No.: WO2010/032123
PCT Pub. Date: Mar. 25, 2010

(65) Prior Publication Data
US 2011/0288169 A1 Nov. 24, 2011

Related U.S. Application Data

(60) Provisional application No. 61/098,666, filed on Sep. 19, 2008.

(51) Int. Cl.
*C07J 63/00* (2006.01)
*A61K 31/56* (2006.01)

(52) U.S. Cl.
CPC . *C07J 63/00* (2013.01); *A61K 31/56* (2013.01)

(58) Field of Classification Search
CPC ................................. C07J 63/00; A61K 31/56

USPC ............... 514/26, 178, 182, 510, 557, 715; 560/116; 562/498; 568/665, 817
See application file for complete search history.

(56) References Cited

FOREIGN PATENT DOCUMENTS

CN 1861627 A * 11/2006 ............... C07J 63/00
WO WO 2008/138200 A1 11/2008

OTHER PUBLICATIONS

Bi et al, Bioorganic & Medicinal Chemistry, 2007, 17, 1475-78.*
Lee et al, Bipolar Disorders, 2002, 4, 117-28.*
The Merck Manual, 16th Edn. 1992, pp. 1403-1404, 1472-1473, 1488-1489, 1493-1494.*
Constantinescu et al, Brit. J. Pharm. 2011, 164, 1079-1106.*
Zhou et al, Chinese Chemical Letters, 2007, 18, 1195-98.*
Smith et al, Journal of Inflammation, 2004, 1(3), pp. 1-12.*
Vergnolle, N., Mem. Inst. Oswaldo Cruz, Rio de Janeiro, 2005, 100 (suppl. 1), pp. 173-176.*
Zhou et al., "Synthesis and Antitumor Activity of Derivatives of 23-Hydroybetulinic Acid," Chinese Chemical Letters, 2007, vol. 18, No. 10, pp. 1195-1198.
Bi et al., "Synthesis and cytotoxic activity of 17-carboxylic acid modified 23-hydroxy betulinic acid ester derivatives," Bioorganic & Medicinal Chemistry Letters, 2007, vol. 17, pp. 1475-1478.

* cited by examiner

*Primary Examiner* — Ganapathy Krishnan
(74) *Attorney, Agent, or Firm* — Kilpatrick Townsend & Stockton LLP

(57) ABSTRACT

The present invention provides therapeutically active compounds and compositions as receptor antagonists and methods of use thereof. In one aspect, the compounds are useful in modulating pain, inflammation and acute phase reactions by inhibiting the PGE2 receptors including PGE2 EP1, EP2 and EP4 receptors.

40 Claims, 31 Drawing Sheets

A

B

A

B

A

B

TRITERPENOID COMPOUNDS AND METHODS OF USE THEREOF

CROSS-REFERENCES TO RELATED APPLICATIONS

This application is a U.S. National Stage filing under 35 U.S.C. §371 of PCT/IB2009/006894, filed Sep. 19, 2009 which is an application claiming benefit under 35 USC §119 (e) of U.S. Provisional Patent Application No. 61/098,666 filed Sep. 19, 2008, each of which is herein incorporated by reference in its entirety.

BACKGROUND OF THE INVENTION

PGE2 belongs to the family of prostaglandins (PGs), which are a group of biologically active compounds found in virtually all tissues and organs. They are synthesized from the metabolism of a membrane lipid, arachidonic acid, by cyclooxygenases to the intermediate PGH2, which then serves as the substrate for generation of five prostanoids: PGE2, PGF2, PGD2, PGI2 (prostacyclin), and TxA2 (thromboxane A2) (Romanovsky et al. (2005) Fever and hypothermia in systemic inflammation: recent discoveries and revisions. *Front Biosci.* 10:2193-2216). PGs have a variety of functions in the human body including regulation of blood pressure, blood clotting, and sleep. However, they also play a major role in the mediation and modulation of pain and inflammation, and are therefore targets of NSAIDs (non-steroid anti-inflammatory drugs).

PGE2 is synthesized by various enzymes including numerous phospholipases (PL) A2, cyclooxygenases (COX)-1 and 2, and several newly discovered terminal PGE synthases. It is involved in important biological events such as female reproduction, neuronal function, inflammation, vascular hypertension, tumorigenesis, kidney function, and also plays key roles in inflammatory and neurologic disorders (Kobayashi et al., (2002) In vivo progestin treatments inhibit nitric oxide and endothelin-1-induced bovine endometrial prostaglandin (PG)E(PGE) secretion in vitro. *Prostaglandin and Other Lipid Mediat;* 68-69:557-574). PGE2 exerts its effects through four G-protein-coupled receptor subtypes known as EP1, EP2, EP3, and EP4, which it binds with similar affinity (Narumiya et al, (1999) Prostanoid receptors: structures, properties, and functions. *Physiol Rev.* 79:1193-1226).

The four different receptor subtypes results in diverse functional responses (Breyer et al., (2001) Prostanoid receptors: subtypes and signaling. *Annu Rev Pharmacol Toxicol.* 41: 661-690). The EP1 receptor has been shown to mediate pro-algesic responses, since knockout mice studies result in reduced pain sensitivity (Stock et al., 2001) and EP1 antagonism reduces hyperalgesia and allodynia in the chronic constriction injury (CCI) model of neuropathic pain (Kawahara et al., 2001). Similarly, studies show that EP3 receptor antagonism is also analgesic (Hosoi et al., Prostaglandin E receptor EP3 subtype is involved in thermal hyperalgesia through its actions in the preoptic hypothalamus and the diagonal band of Broca in rats, *Pain* 71:303-311).

PGE2 signaling via the EP2 receptor has been linked to a proinflammatory and proamyloidogenic pathway towards the development of Alzheimer's disease (AD) pathology in a model of familial AD (Liang et al, (2005) Deletion of the prostaglandin E2 EP2 receptor reduces oxidative damage and amyloid burden in a model of Alzheimer's disease. *J. Neurosci.* 25(44):10180-7), while activation of EP2 and EP4 receptors has been shown to be involved in the in vivo production of Abeta in the pathogenesis of AD (Hoshino et al., (2007) Involvement of prostaglandin E2 in production of amyloid-beta peptides both in vitro and in vivo. *J Biol. Chem.* 282: 32676-32688).

Recent studies have also implicated the EP4 receptor in proinflammatory responses. EP4 receptor signaling has been shown to be involved in increased inflammation and disease progression in rheumathoid arthritis (McCoy et al., (2002) The role of prostaglandin E2 receptors in the pathogenesis of rheumatoid arthritis, *J. Clin. Invest.* 110, pp. 651-658), while studies with EP4 receptor antagonists have demonstrated reduction of inflammatory pain in vitro and in animal models. Investigations with an EP4 antagonist as well as EP4 knockdown studies resulted in reduction of inflammation-induced thermal and mechanical behavioral hypersensitivity as well as sensitization of capsaicin-evoked currents in DRG neurons in vitro (Lin et al., (2006) Prostaglandin E2 receptor EP4 contributes to inflammatory pain hypersensitivity. *J Pharmacol Exp Ther.* 319:1096-103). In another study, EP4 receptor antagonists administered to adjuvant-induced arthritis rats reversed paw swelling to normal levels (Murase et al., (2008) Effect of prostanoid EP4 receptor antagonist, CJ-042,794, in rat models of pain and inflammation. *Eur J. Pharmacol.* 580: 116-121). Thus, the EP4 receptor is a potential target for the pharmacological treatment of inflammation and pain.

A recent study has demonstrated that EP2-EP4 signaling promotes T helper (Th) 1 cell differentiation, and EP4 signaling is essential for IL-23 production in the expansion of Th17 cells (Yao et al., (2009) Prostaglandin E2-EP4 signaling promotes immune inflammation through Th1 cell differentiation and Th17 cell expansion. *Nat. Med.* 15:633-640). They showed that daily oral administration (twice per day) of an EP4 antagonist (ONO-AE3-208) was able to suppress the symptoms of an experimental mouse model exhibiting multiple sclerosis-like symptoms, namely, the experimental autoimmune encephalomyelitis (EAE) model.

Experimental autoimmune encephalomyelitis (EAE) is the most frequently used animal model for immune mediated effects of multiple sclerosis (MS), studying the progression of the demyelination of axons and test the efficacy of potential therapeutic effects by candidate compounds (Gold et al., (2006) Understanding pathogenesis and therapy of multiple sclerosis via animal models: 70 years of merits and culprits in experimental autoimmune encephalomyelitis research. *Brain.* 129:1953-1971).

In the active EAE model where myelin oligodendrocyte glycoprotein (MOG) is directly injected into an animal, a chronic progressive form of EAE is exhibited in response to the immunization. MOG is a transmembrane protein that is expressed on the surface of oligodendrocytes in the central nervous system. It is used as a target antigen in facilitating demyelination which leads to multiple sclerosis (MS) like symptoms that are observed in mice (Silber and Sharief, (1999) Axonal degeneration in the pathogenesis of multiple sclerosis. *J. Neurol. Sci.* 170:11-18). Upon introduction of MOG, symptomatic manifestation takes anywhere between 7 to 10 days. The clinical scores were given on a 9 point score scale based on the previously published literature (Stromnes and Goverman, (2008) Active induction of experimental allergic encephalomyelitis. *Nat. Protoc.* 1:1810-1818).

There are several molecular targets in the EAE model that must be studied in order to demonstrate the efficacy of candidate compounds in becoming a potential therapeutic agent for treating autoimmune diseases (Sloane et al., (2009) Anti-inflammatory cytokine gene therapy decreases sensory and motor dysfunction in experimental multiple sclerosis: MOG-EAE behavioral and anatomical symptom treatment with cytokine gene therapy. *Brain, Behav. Immunity.* 22:600-605).

Cytokines are one such target where numerous studies showing an increase in myelinotoxic inflammatory cytokines such as interferon-γ (IFN-γ) coinciding with the active phase of EAE (Zaheer et al., (2007) Diminished cytokine and chemokine expression in the central nervous system of GMF-deficient mice with experimental autoimmune encephalomyelitis. *Brain Res.* 1144:239-247).

Cytokines are small secreted proteins which mediate and regulate immunity, inflammation, and hematopoiesis and are believed to be one of the key signaling molecules in the disease progression of EAE. They must be produced de novo in response to an immune stimulus. Autoimmune responses observed in EAE are believed to be mediated via helper T (Th) 1 pathway and interferon-gamma (IFN-γ) is the hallmark cytokine of the Th1 immune response (Muthian et al., (2006) 1,25 Dihydroxivitamin-D3 modulates JAK-STAT pathway in IL-12/INF-γ axis leading to Th1 response in experimental allergic encephalomyelitis. *J. Neurosci. Res.* 83:1299-1309). Therefore, being able to reduce the amount of cytokines such as IFN-γ is imperative in determining the effectiveness of compounds as potential therapeutic agents for the EAE model and ultimately in treating autoimmune diseases such as multiple sclerosis.

Recently, another distinct helper T subset termed Th17 pathway has been suggested as a long term mediator of autoimmune pathology (Narumiya et al., (2009) Prostaglandin $E_2$-EP4 signaling promotes immune inflammation through $T_h1$ cell differentiation and $T_H17$ cell expansion. *Nat. Med.* 15:633-640). Previously, the T-cell mediated autoimmune responses seen in diseases such as EAE and MS were thought to be caused by Th1 pathway alone. However, recent evidence points toward much more intricate balances between Th1/Th2 and the newly discovered and designated Th17 pathways. It has been suggested that although the initial pathological responses are still initiated by the Th1 pathway, the sustained tissue damage typically observed in autoimmune diseases is mediated by the Th17 pathway (Steinman, (2007) A brief history of $T_H17$, the first major revision in the $T_H1/T_h2$ hypothesis of T cell-mediated tissue damage. *Nat. Med.* 13:139-145). The initiation of Th17 differentiation is believed to involve TGF-β and IL-6 which in turn activate orphan nuclear receptor RORγt (Korn et al., 2009 IL-17 and Th17 cells. *Annu. Rev. Immunol.* 27:485-517). RORγt is a transcriptional factor for IL-17 whose role in tissue inflammation and autoimmune response has been extensively documented previously.

Interleukin-6 (IL-6) is another key cytokine in the acute phase of the proinflammatory reaction in the immune response. IL-6 signals through a cell-surface type I cytokine receptor complex which in turn activates the JAK-STAT pathway (Khoury et al., (2005) Cytokines in multiple sclerosis: form bench to bedside. *Pharm. Ther.* 106:163-177). In addition, IL-6 is believed to be one of the co-affectors in T helper (Th) 17 differentiation along with transforming growth factor-β (TGF-β) and interleukin-23 (IL-23).

Another major molecular target is signal transducers and activators of transcription (STAT) protein pathway. STAT proteins are nuclear proteins involved in cell survival, differentiation, proinflammatory reactions, and cytokine signaling. It is a family of seven member proteins with each STAT protein activated by different cytokines. In addition, STAT proteins are a part of Janus (JAK)-STAT pathway, one of the main signaling pathways for cytokine and growth factors.

STAT3, upon activation by IL-6, translocates into the nucleus where it induces gene expression (Ihle. (2001) The Stat family in cytokine signaling. *Curr. Opin. Cell Biol.* 13:211-217). STAT4 is believed to be activated by IL-12 and the study of STAT4 knockout mice has been shown to have impaired Th1 response which is responsible for adaptive immunity (Bright et al., (2008) Stat 4 isoforms differentially regulate inflammation and demyelination in experimental allergic encephalomyelitis. *J. Immun.* 181:5681-5690). STAT6 is activated by IL-4 and IL-13 and the mice lacking STAT6 genes have been shown to have impaired Th2 response which is responsible for humoral immunity (Takeda and Akira, (2000) STAT family of transcription factors in cytokine-mediated biological responses. *Cytokine & Growth Factor Rev.* 11:199-207). STAT3, in particular, has been linked to autoimmune diseases such as multiple sclerosis and EAE where high levels of STAT 3 have been detected during the acute phase of EAE (Yang et al., STAT3 regulates cytokine-mediated generation of inflammatory helper T cells. *J. Biol. Chem.* 282:9358-9363).

Aside from chronic forms of inflammation such as autoimmune diseases, acute inflammation is one of the most basic defense mechanisms an organism uses. Acute inflammation is mainly initiated by macrophages and dendritic cells. Upon introduction of allergens, these immune cells mount proinflammatory response initiating cytokines such as tumor necrosis factor-α (TNF-α) and INF-β. There is also an increase in blood flow from vasodilation. This increase in blood flow results in the formation of edema and swelling around the site of the inflammation. Many potential immune-mediating substances are tested on in vivo models of endotoxin-induction of proinflammatory cytokines (Tang et al., (2007) LPS-induced TNF-alpha factor (LITAF)-deficient mice express reduced LPS-induced cytokine. Evidence for LITAF-dependent LPS signaling pathway. *PNAS.* 103: 13777-13782) and allergen-induced edema formation (Tamura et al., (2004) Effects of olopatadine hydrochloride, an antihistamine drug, on skin inflammation induced by repeated topical application of oxazolone in mice. *Br. J. Dermatol.* 151(6):1133-1142).

N-methyl-D-aspartate (NMDA) receptors are ligand-gated ion channels located primarily within the central nervous system (CNS). They belong to the family of ionotropic glutamate receptors and exist as multiple subtypes due to the different combinations of subunits—NR1, NR2 (NR2A, NR2B, NR2C, NR2D) and NR3—that can be expressed. In addition to the agonist binding site, NMDA receptors have multiple distinct binding sites for various compounds that enhance, modulate and inhibit the activation of the receptors.

It is known that NMDA receptors are involved in neuronal communication and play important roles in synaptic plasticity and mechanisms that underlie learning and memory. Under normal conditions, NMDA receptors engage in synaptic transmission via the neurotransmitter glutamate, which regulates and refines synaptic growth and plasticity. However, when there are abnormally high levels of glutamate (i.e. under pathological conditions), NMDA receptors become over-activated, resulting in an excess of $Ca^{2+}$ influx into neuronal cells, which in turn causes excitotoxicity and the activation of several signaling pathways that trigger neuronal apoptosis. Glutamate-induced apoptosis in brain tissue also accompanies oxidative stress resulting in loss of ATP, loss of mitochondrial membrane potential, and the release of reactive oxygen species and reactive nitrogen species (e.g. $H_2O_2$, NO, $OONO^-$, $O_2^-$) causing associated cell damage and death. Decreased nerve cell function and neuronal cell death eventually occur. Excitotoxicity also occurs if the cell's energy metabolism is compromised.

Over-activation of the NMDA receptors is implicated in neurodegenerative diseases and other neuro-related conditions as it causes neuronal loss and cognitive impairment, and also plays a part in the final common pathway leading to neuronal injury in a variety of neurodegenerative disorders such as amyotrophic lateral sclerosis, Parkinson's disease, Alzheimer's disease and Huntington's disease, as well as conditions such as stroke. Recent findings have implicated NMDA receptors in many other neurological disorders, such as multiple sclerosis, cerebral palsy (periventricular leukomalacia), and spinal cord injury, as well as in chronic and severe mood disorders (Mathew S J et al., *Rev Bras Psiquiatr,* 27:243-248 (2005)).

For instance, glutamate excitotoxicity has been linked to inflammatory autoimmune demyelination in MS. The disease pathology involves loss of myelin, oligodendrocytes and axons due to an inflammatory attack on the central nervous system. Several studies indicate the role of excessive glutamate in the pathology of MS (Flanagan et al. (1995) Neurotoxin quinolinic acid is selectively elevated in spinal cords of rats with experimental allergic encephalomyelitis. *Journal of Neurochemistry;* 64 (3): 1192-1196); Sarchielli et al., (2003) Excitatory amino acids and multiple sclerosis: evidence from cerebrospinal fluid. *Archives of Neurology.* 2003; 60(8):1082-1088).

Excessive glutamate levels have also been observed in the cerebrospinal fluid obtained from patients with MS (Stover et al. (1997) Neurotransmitters in cerebrospinal fluid reflect pathological activity. *European Journal of Clinical Investigation.* 27(12):1038-1043). Furthermore, investigations with NMDA receptor antagonists such as Memantine results in suppression of MS pathogenesis as well as improvement of neurovascular functions (Paul and Bolton (2002) Modulation of blood-brain barrier dysfunction and neurological deficits during acute experimental allergic encephalomyelitis by the N-methyl-D-aspartate receptor antagonist memantine. *The Journal of Pharmacology and Experimental Therapeutics.* 2002; 302(1):50-57). Thus, compounds designed to antagonise the actions of NMDA receptors could potentially offer therapeutic benefits to MS patients and are currently in development (Farrell et al. (2005) Emerging therapies in multiple sclerosis. *Expert Opin Emerg Drugs.* 2005; 10(4):797-816).

Melanocortins (MC) receptors belong to the class of G protein-coupled receptors. More specifically, they are a group of pituitary peptide hormones, which include the adrenocorticotropic hormone (ACTH) and the alpha, beta and gamma melanocyte-stimulating hormones (MSH). They are derived from the pro-hormone proopiomelanocortin (Adan et al., (2000) Melanocortins and the brain: from effects via receptors to drug targets. *Eur J Pharmacol* 405: 13-24). MCs act through a multitude of melanocortin receptors designated MC1 through MC5. MC1 receptors are expressed in macrophages and monocytes, keratinocytes and melanocytes, endothelial cells, glioma cells and astrocytes, and pituitary and periaqueductal grey matter, where they are involved in melanogenesis and anti-inflammatory processes (Kang et al., (2006) A selective small molecule agonist of the melanocortin-1 receptor inhibits lipopolysaccharide-induced cytokine accumulation and leukocyte infiltration in mice. *J Leukoc Biol* 80: 897-904; and Slominski et al., (2004) Melanin pigmentation in mammalian skin and its hormonal regulation. *Physiol Rev* 84: 1155-228).

ACTH binds to the MC2 receptor (ACTH receptor) and is mainly expressed in the adrenal glands and the adrenal cortex. While MC3 is expressed in both periphery and neural tissues, MC4 is mainly found in the CNS and is the second neural MC receptor as they are expressed in multiple regions of the brain including the cortex, thalamus, hypothalamus, brainstem, and spinal cord. The receptor is also highly expressed in the paraventricular nucleus and is involved in the modulation of pituitary function. MC5, highly homologous to MC4, is the only MC receptor found in skeletal muscle. It is broadly expressed in peripheral tissue, while also present in specific brain regions.

MC4 receptor activity has been linked to neurite outgrowth and peripheral nerve regeneration (Tanabe et al., (2007) Melanocortin receptor 4 is induced in nerve-injured motor and sensory neurons of mouse. *J Neurochem* 101:1145-52; and Adan et al., (1996) Melanocortin receptors mediate and neuroprotection in brain ischemia stroke (Giuliani et al., 2006), and inflammatory responses in astrocytes (Caruso et al., (2007) Activation of melanocortin 4 receptors reduces the inflammatory response and prevents apoptosis induced by lipopolysaccharide and interferon-gamma in astrocytes. *Endocrinology* 148: 4918-26).

DA001 also induces CCAAT/enhancer binding protein beta (C/EBP-b) mRNA expression in cortical neuron cultures. C/EBP-b is an important transcriptional activator in the regulation of genes involved in immune and inflammatory responses. It specifically binds to an IL-1 response element in the IL-6 gene, and thought to play a role in the regulation of acute-phase reactions, inflammation and hemopoiesis. It is also involved in the differentiation process of various cell types including liver cells, adipoctyes and skin cells (reviewed in Sebastian and Johnson, (2006) Stop and go: antiproliferative and mitogenic functions of the transcription factor C/EBPbeta. *Cell Cycle* 5(9):953-7; and Kalvakolanu and Roy, (2005) CCAAT/enhancer binding proteins and interferon signaling pathways. *J Interferon Cytokine Res.* 25(12): 757-69). Homozygotes for targeted null mutations exhibit post-natal lethality and immature death. In neurons, it is involved in neurotrophin signaling and neuronal differentiation (Sterneck and Johnson, (1998) CCAAT/enhancer binding protein beta is a neuronal transcriptional regulator activated by nerve growth factor receptor signaling. *J Neurochem.* 70(6):2424-33; Menard et al., (2002) An Essential Role for a MEK-C/EBP Pathway during Growth Factor-Regulated Cortical Neurogenesis. *Neuron* 36, 597-610; and Cortés-Canteli et al., (2002) CCAAT/enhancer-binding protein beta plays a regulatory role in differentiation and apoptosis of neuroblastoma cells. *J Biol. Chem.* 277(7):5460-7).

Recently, a novel cell survival function for C/EBP-b has been reported. The activity of C/EBP-b is lost before the onset of cell death and the pathologic response in cortical neurons induced by hypoxia involves C/EBP-b-mediated survival signals (Halteman et al., (2008) Loss of c/EBP-beta activity promotes the adaptive to apoptotic switch in hypoxic cortical neurons. *Mol Cell Neurosci.* 38(2):125-37). On the other hand, C/EBP-b is also essential in response to neuronal injury by transcriptionally activated regeneration-associated gene expression (Nadeau et al., (2005) A transcriptional role for C/EBP beta in the neuronal response to axonal injury. *Mol Cell Neurosci.* 29(4):525-35). C/EPB-b may therefore play a role in DA001-mediated activities.

Therefore, there is a need to develop other effective receptor antagonists, such as NMDA, MC and PGE2 receptor antagonists that have high potency and are capable of preventing, treating and/or ameliorating inflammation and/or pain, central nervous system disorder and other diseases and conditions. The present invention satisfies this and other needs.

BRIEF SUMMARY OF THE INVENTION

The present invention provides a group of triterpenoid compounds exhibiting therapeutic effects. They have the potential to modulate pain and mediate anti-inflammatory responses via the PG receptors, NMDA receptors and melanocortin receptors.

The compounds of the present invention and the designated DA compounds, inhibit the ligand binding of E type prostaglandins (PGE2) to its receptor family but not for the receptors of the other prostaglandins. Furthermore, 3-O-[α-L-rhamnopyranosyl-(1→2)-α-L-arabinopyranosyl]-3,23-dihydroxy-20(29)-lupen-28-oic acid (DA001) specifically inhibits the EP1 and EP4 receptor of PGE2, and more weakly, the EP2 receptor, which are implicated in inflammatory and proamyloidogenic responses.

These compounds also exhibit marked improvement in experimental autoimmune encephalomyelitis (EAE), a widely-used model that exhibits multiple sclerosis (MS)-like inflammation in the CNS and spinal cord. Due to the nature of the axonal damage that occur during this particular type of EAE model, very few therapeutic agents are known to be effective in improving the symptoms of EAE. However, oral administration of the DA compounds attenuates the neurological deficits in EAE mice. The compounds also inhibit the level of interferon-gamma (IFN-γ) in splenocytes isolated from EAE mice.

Furthermore, re-stimulating the isolated EAE splenocytes with CNS antigens increases the expression of pro-inflammatory STAT proteins and cytokines, and this can be suppressed efficiently by exogenous addition of the compounds of the invention and the DA compounds. In addition, these compounds also suppress bacterial and allergen-induced inflammation as well. Taken together, the compounds encompassing the invention exhibit therapeutic effect in the treatment of multiple sclerosis and other inflammatory diseases.

In one aspect, the present invention provides a compound of formula (I):

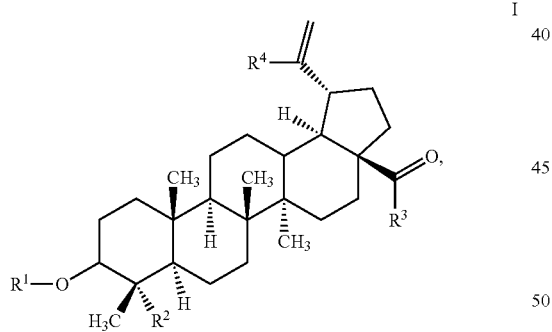

I or a pharmaceutically acceptable salt, hydrate, solvate isomer thereof; wherein:
  $R^1$ is —H, alkyl-C(O)— or arylalkyl-C(O)—;
  $R^2$ is selected from the group consisting of hydroxy-$C_{1-4}$ alkyl, alkoxy-$C_{1-4}$alkyl, aryloxy-$C_{1-4}$alkyl, alkyl-C(O)O—$C_{1-4}$alkyl and arylalkyl-C(O)O—$C_{1-4}$alkyl;
  $R^3$ is selected from the group consisting of —$NH_2$, —$NHR^a$, —$N(R^a)_2$, —OH and —$OR^b$, wherein $R^a$ and $R^b$ are each independently alkyl, aryl, arylalkyl, hydroxyalkyl or aminoalkyl; wherein the aliphatic portion of the $R^3$ substituent is optionally substituted with from 1-2 $R^c$ substituents independently selected from —OH, —$NH_2$, alkoxy, arylalkoxy, halogen, alkyl-C(O)O—, arylalkyl-C(O)O, aryl-C(O)O, alkyl-C(O)NH—, arylalkyl-C(O)NH—, aryl-C(O)NH—, alkylamino or dialkylamino; or optionally any two adjacent $R^c$ substituents together with the atoms to which they are attached form a 5- or 6-membered heterocyclic ring having from 1-3 heteroatoms selected from N, O or S, wherein the heterocyclic ring is optionally substituted with 1-2 $C_{1-8}$alkyl;
  $R^4$ is $C_{1-4}$alkyl, haloalkyl, hydroxyalkyl, alkyl-C(O)O—$C_{1-4}$alkyl, arylalkyl-NH—$C_{1-4}$alkyl or alkoxyalkyl;
  wherein the aromatic portion of the $R^3$ or $R^4$ group is optionally substituted with from 1-2 $R^d$ substituents independently selected from the group consisting of halo, —CN, —$NO_2$, —OH, —$R^e$, —$OR^e$, —OC(O)NHR$^e$, —OC(O)N($R^e$)$_2$, —OC(O)$R^e$, —OC(O)H, —$NH_2$, —NHR$^e$, —N($R^e$)$_2$, —S(O)$_2R^e$, —$SO_2NH_2$, —$SO_2NHR^e$, —$SO_2N(R^e)_2$, —NHS(O)$_2R^e$, —NR$^e$S(O)$_2R^e$, —C(O)$NH_2$, —C(O)NHR$^e$, —C(O)N($R^e$)$_2$, —C(O)H, —C(O)$R^e$, —NHC(O)$R^e$, —NR$^e$C(O)$R^e$, —$CO_2R^e$, —$NHCO_2R^e$ and —$NR^eCO_2R^e$, wherein each $R^e$ is independently a $C_{1-8}$alkyl; and with the proviso when $R^1$ is —H or $CH_3C(O)$—, $R^2$ is —$CH_2OH$ or —$CH_2OC(O)CH_3$ and $R^4$ is —$CH_3$ or $HOCH_2$—, then $R^3$ is other than —OH, —OMe, —OEt, —$NHCH_2Ph$, —O($CH_2)_2OH$, —$CH_2CH(OH)CH_2(OH)$ or 2,2-dimethyl-1,3-dioxolan-4-yl-methyl.

In another aspect, the present invention provides a compound of formula (IA):

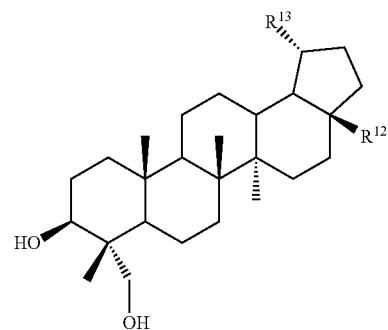

or a pharmaceutically acceptable salt, hydrate, solvate or isomer thereof; wherein $R^{12}$ is selected from the group consisting of hydroxyalkyl, alkyl-OC(O)—, aryl-$C_{1-4}$alkyl-OC(O)—, alkyl-C(O)O-alkyl, aryl-$C_{1-4}$alkyl-C(O)O-alkyl, aryl-$C_{1-4}$alkoxy or alkoxyalkyl, wherein the aryl moiety of which is optionally substituted with from 1-3 members selected from halogen, alkyl, aryl-$C_{1-4}$alkyl, hydroxyalkyl, alkoxy, aryl-$C_{1-4}$alkoxy, alkyl-OC(O)—, alkyl-C(O)O—, aryl-$C_{1-4}$alkyl-C(O)O—, aryl-$C_{1-4}$alkyl-OC(O)O—, alkoxyalkyl or aryl-$C_{1-4}$alkoxy-alkyl; and $R^{13}$ is selected from $C_{2-6}$alkenyl or $C_{2-6}$epoxyalkyl, each of which is optionally substituted with from 1-3 members selected from —OH, —$OC_{1-6}$alkyl, aryl-$C_{1-4}$alkyl, alkyl-C(O)O—, aryl-$C_{1-4}$alkyl-C(O)O—.

In yet another aspect, the present invention provides a method of inhibiting the activities of a PGE2 receptor. The method includes contacting the compounds of formula (I) or formula (II) or any of compounds DA001-090 with a cell or the PGE2 receptor. The compounds of formula (II) have the following structure:

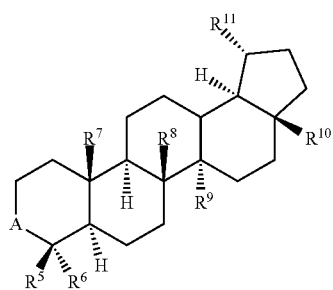

(II)

$R^5$, $R^7$, $R^8$ and $R^9$ are each independently $C_{1-4}$alkyl;

$R^6$ is selected from the group consisting of $C_{1-6}$haloalkyl, $C_{3-6}$cycloalkyl, $-X^1CN$, $-X^1NO_2$, $-X^1C(O)R^a$, $-CR^b$=$NOR^c$, $-X^1CO_2R^c$, $-X^1C(O)NR^cR^d$, $-X^1C(NR^cR^d)$=$NR^c$, $-X^1C(O)NR^cS(O)R^d$, $-X^1C(O)NR^cS(O)_2R^d$, $-X^1OR^e$, $-X^1SR^e$, $-X^1NHR^e$ and $-X^1N(R^e)_2$ and $-X^1R^e$, wherein each $X^1$ is independently a bond or $C_{1-4}$alkylene, wherein each $R^e$ is independently $C_{1-6}$alkyl, haloalkyl, arylC$_{0-6}$alkyl or cycloalkyl substituted with from 1-3 members of $R^f$, and wherein $R^a$, $R^b$, $R^c$ and $R^d$ are each independently H, $C_{1-6}$alkyl or aryl-$C_{1-6}$alkyl; wherein the aliphatic portion of each $R^6$ substituent is optionally substituted with from 1-3 $R^f$ groups, wherein $R^f$ is selected from the group consisting of halo, CN, NO$_2$, $-$OH, $-R^g$, $-OR^g$, $-OC(O)NHR^g$, $-OC(O)N(R^g)_2$, $-OC(O)R^g$, $-OC(O)H$, $-NH_2$, $-NHR^g$, $-N(R^g)_2$, $-SH$, $-SR^g$, $-S(O)_2R^g$, $-SO_2NH_2$, $-SO_2NHR^g$, $-SO_2N(R^g)_2$, $-NHS(O)_2R^g$, $-NR^gS(O)_2R^g$, $-C(O)NH_2$, $-C(O)NHR^g$, $-C(O)N(R^g)_2$, $-C(O)H$, $-C(O)R^g$, $-NHC(O)R^g$, $-NR^gC(O)R^g$, $-NHC(O)NH_2$, $-NR^gC(O)NH_2$, $-NR^gC(O)NHR^g$, $-NHC(O)NHR^g$, $-NR^gC(O)N(R^g)_2$, $-NHC(O)N(R^g)_2$, $-COOH$, $-CO_2R^g$, $-NHCO_2R^g$, $-NR^gCO_2R^g$ and $-OSi(R^g)_3$, wherein each $R^g$ is independently a $C_{1-6}$alkyl;

A is selected from the group consisting of C=$Y^1$, C=$NOR^c$, C=$NOC(O)H$, C=$NOC(O)R^g$, C=$NOCO_2R^g$, C=$NOC(O)NH_2$, C=$NOC(O)NHR^g$, C=$NOC(O)N(R^g)_2$ and $-CR^cR^h$, wherein $Y^1$ is =O or =S, and $R^h$ is selected from the group consisting of halo, CN, NO$_2$, $-$OH, $-OR^i$, $-OC(O)NHR^i$, $-OC(O)N(R^i)_2$, $-OC(O)R^i$, $-OC(O)H$, $-NH_2$, $-NHR^i$, $-N(R^i)_2$, $-SH$, $-SR^i$, $-S(O)_2R^i$, $-SO_2NH_2$, $-SO_2NHR^i$, $-SO_2N(R^i)_2$, $-NHS(O)_2R^i$, $-NR^iS(O)_2R^i$, $-C(O)NH_2$, $-C(O)NHR^i$, $-C(O)N(R^i)_2$, $-C(O)H$, $-C(O)R^i$, $-NHC(O)R^i$, $-NR^iC(O)R^i$, $-NHC(O)NH_2$, $-NR^iC(O)NH_2$, $-NR^iC(O)NHR^i$, $-NHC(O)NHR^i$, $-NR^iC(O)N(R^i)_2$, $-NHC(O)N(R^i)_2$, $-COOH$, $-CO_2R^i$, $-NHCO_2R^i$, $-NR^iCO_2R^i$, $-OSi(R^i)_3$, $-O-(Z)_{1-6}$, $-S-(Z)_{1-6}$, $-NH(Z)_{1-6}$ and $-NR^c(Z)_{1-6}$, wherein each $R^i$ is independently a $C_{1-6}$alkyl, $C_{1-6}$haloalkyl, arylC$_{0-6}$alkyl or $C_{3-6}$cycloalkyl, optionally substituted with from 1-3 $R^f$ groups; $-(Z)_{1-6}$ is a sequence of 1-6 independently selected $C_{4-7}$monosaccharide residues linked together through ether bonds, optionally each Z is independently substituted with from 1-3 $R^f$ groups;

$R^{10}$ is selected from the group consisting of $C_{1-6}$haloalkyl, $C_{3-6}$cycloalkyl, $-X^2CN$, $-X^2NO_2$, $-X^2C(O)R^a$, $-X^2OC(O)R^a$, $-CR^b$=$NOR^c$, $-X^2CO_2R^c$, $-X^2C(O)NR^cR^d$, $-X^2C(NR^cR^d)$=$NR^c$, $-X^2C(O)NR^cS(O)R^d$, $-X^2C(O)NR^cS(O)_2R^d$, $-X^2OR^a$, $-X^2SR^a$, $-X^2NHR^a$ and $-X^2N(R^a)_2$, wherein each $X^2$ is independently a bond or $C_{1-4}$alkylene; wherein the aliphatic portion of $R^6$ substituent is optionally substituted with from 1-3 $R^f$ groups, wherein the two adjacent $R^f$ substituents together with the atoms to which they are attached optionally form a 5-membered heterocyclic ring having from 1-3 heteroatoms selected from N, O or S, wherein the heterocyclic ring is optionally substituted with from 1-3 $R^g$ groups, and the aromatic ring of $R^{10}$ is optionally substituted with from 1-5 $R^f$ groups; and $R^{11}$ is selected from the group consisting of $C_{1-6}$alkyl, $C_{1-6}$haloalkyl, $C_{3-6}$cycloalkyl, $C_{2-6}$alkenyl, $C_{2-6}$haloalkenyl, $C_{5-6}$cycloalkenyl and $C_{2-6}$epoxyalkyl, each of which is optionally substituted with from 1-3 $R^f$ groups. In one embodiment, the present invention provides a pharmaceutical composition comprising compounds of formula I and a pharmaceutically acceptable carriers, excipients or diluents.

In still another aspect, the present invention provides methods of preventing and/or treating and/or ameliorating and/or regulating pain and/or inflammation and/or acute phase reactions and/or hemopoiesis in a subject, such as a mammal or human. The methods include administering to the mammal a therapeutically effective amount of compounds of formulas I, IA, II or any of compounds DA001-090 or a compound as described herein or a pharmaceutically acceptable salt, hydrate, solvate or isomer thereof.

In another aspect, the present invention provides a method of inhibiting the activities of an NMDA and/or MC receptor. The method includes contacting any of compounds DA048-DA090 with the NMDA and or MC receptor.

In yet another aspect, the present invention provides methods of preventing and/or treating central nervous system disorders in a subject, such as a mammal or human. In one embodiment, the present invention provides methods for preventing and/or treating a neurodegenerative disease and neuropathological conditions in a mammal. In another embodiment, the present invention provides a method for enhancing the brain's cognitive function in a mammal. In yet another embodiment, the present invention provides a method of preventing neuronal damage under a stress condition, such as a stroke in a mammal. In still another embodiment, the present invention provides a method of treating depression, anxiety and cachexia induced by a chronic disease. The methods for treating and/or preventing CNS disorders in the above embodiments include administering to the mammal a therapeutically effective amount of any of compounds DA048-DA090 or a pharmaceutical composition comprising the compounds DA048-DA090.

Cortical neurons were incubated with DA001 or the DMSO control for 24 hrs, followed by treatment with NMDA (20 μM) or water for 20 min. Gene expression was normalized against the house-keeping gene, hypoxanthine phosphoribosyltransferase 1 (HPRT1) and glyceraldehyde 3-phosphate dehydrogenase (GAPDH) and compared to the control (DMSO) with NMDA treatment. Relative changes in gene expression induced by DA001+NMDA was compared with DMSO+NMDA.

Figure 4:
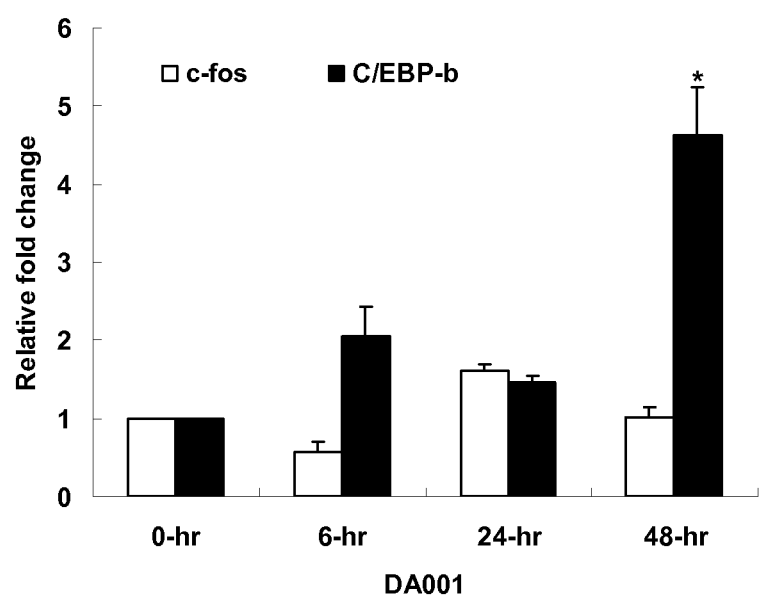

FIG. 4. DA001 induces CEBPb mRNA in cortical neurons. Cortical neurons were incubated with DA001 or the DMSO control for 3 different time intervals. Gene expression was normalized against the house-keeping gene, hypoxanthine phosphoribosyltransferase 1 (HPRT1) and glyceraldehyde 3-phosphate dehydrogenase (GAPDH) and compared to the control (DMSO) treatment. Relative change in gene expression induced by DA001 was compared with DMSO. Asterisk represents P<0.05.

Figure 5:
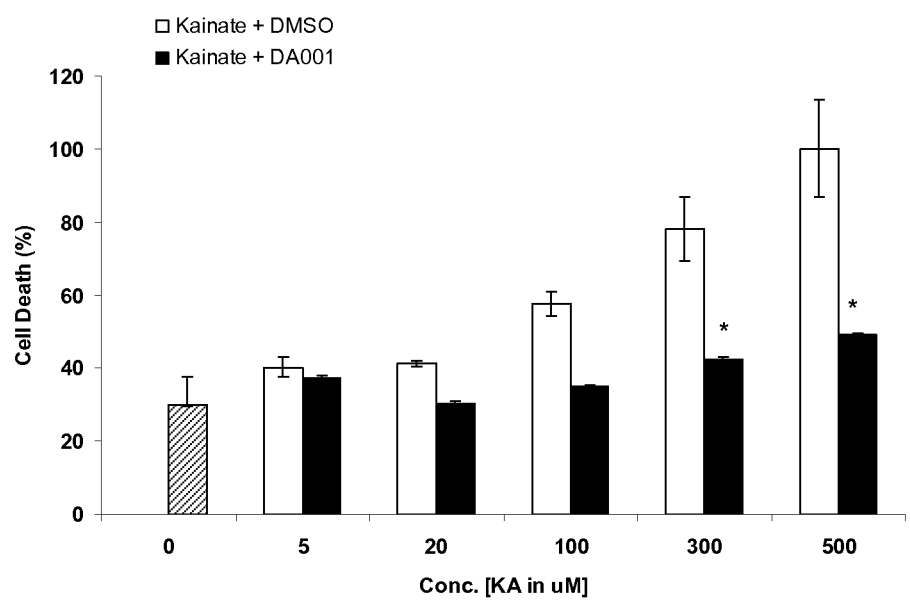

FIG. 5. DA001 protects neurons against differing concentrations of kainate. Cortical neurons were incubated with DA001 (40 μM) or control (DMSO) for 24 hrs, followed by co-treatment with different concentrations of kainate (KA, 5-500 μM) for 20 min. LDH release into the medium was then measured.

Figure 6:
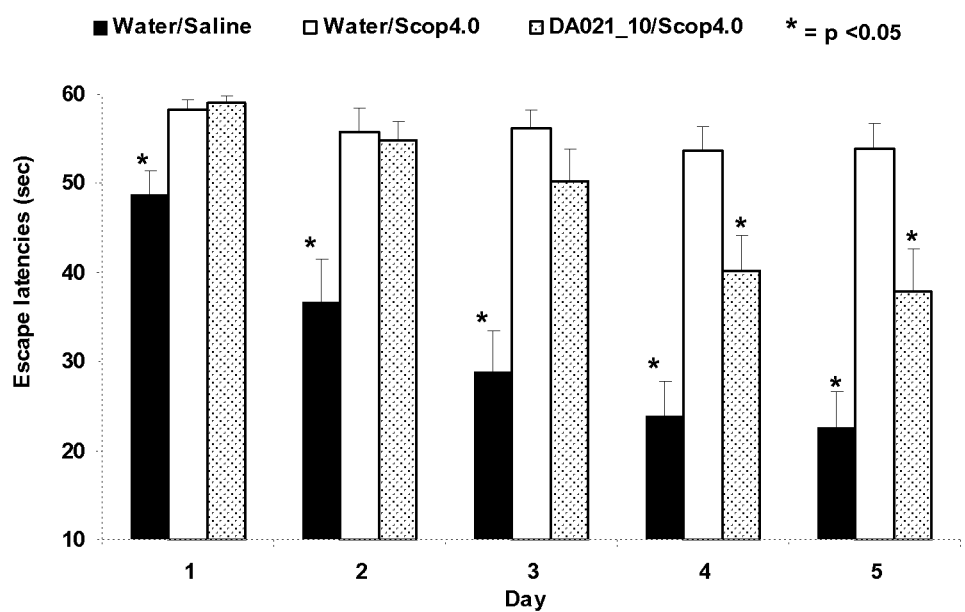

FIG. 6. DA021 reduces the escape latency in Morris Water Maze model

Figure 7:
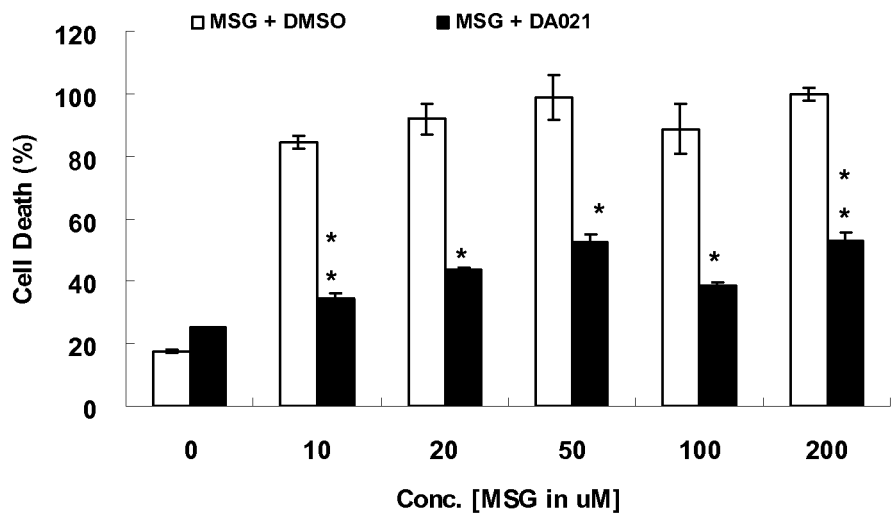
Figure 7:
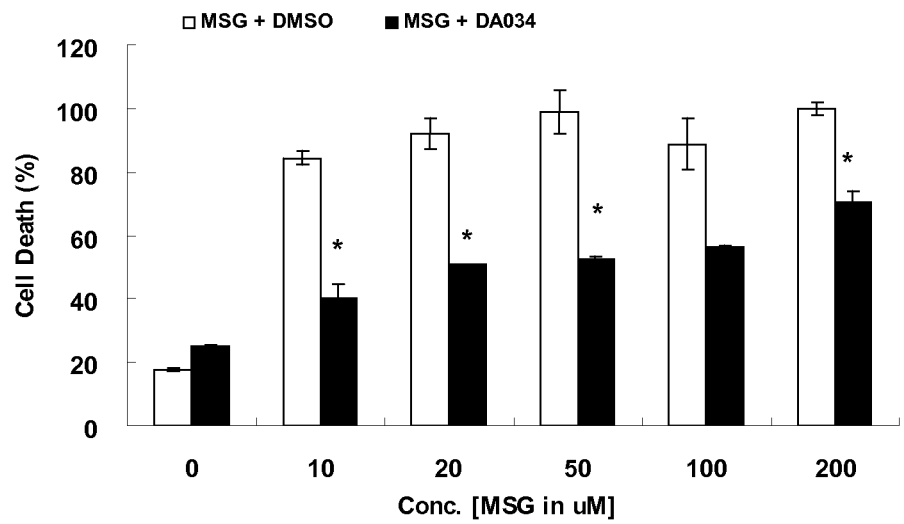

FIG. 7. DA021 and DA034 protect neurons against differing concentrations of glutamate. A: DA021; B: DA034.

Figure 8:
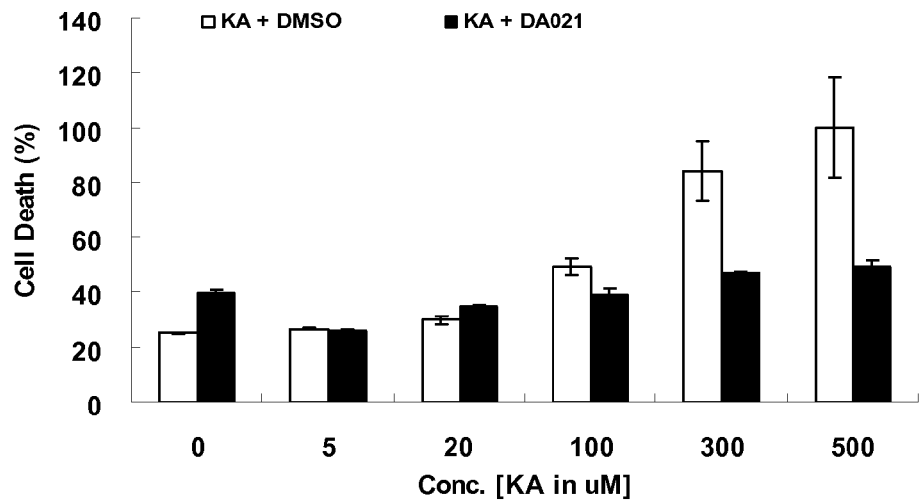
Figure 8:
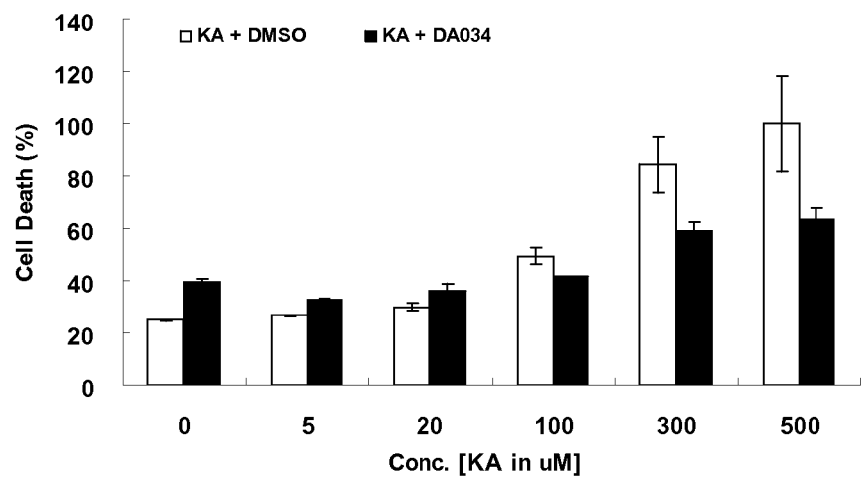

FIG. 8. DA021 and DA034 protect neurons against differing concentrations of Kainate. A: DA021; B: DA034.

Figure 9:
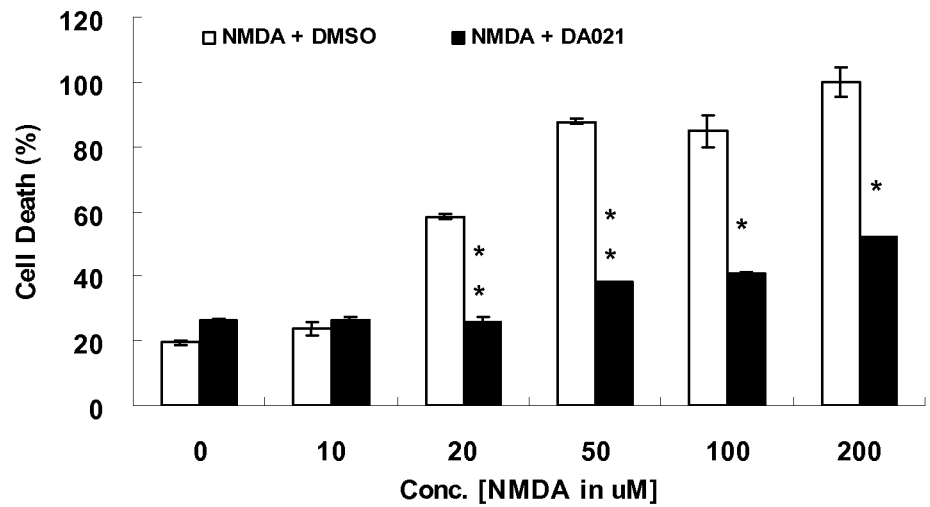
Figure 9:
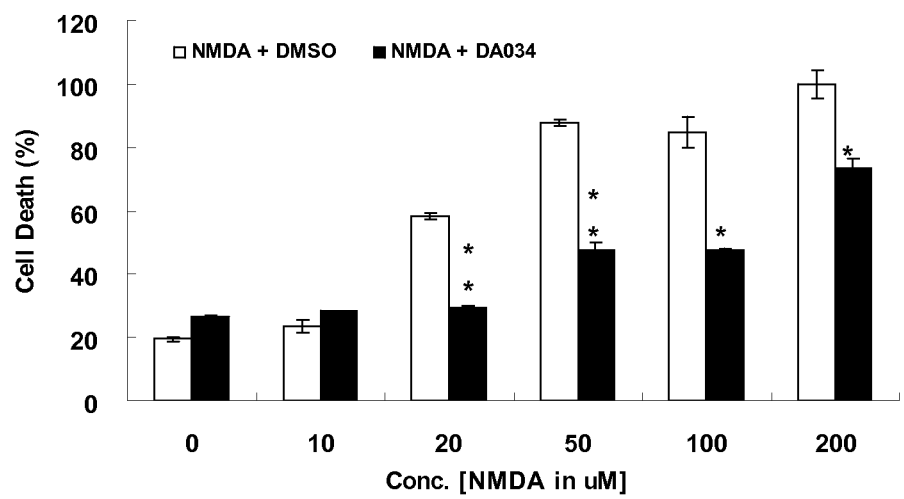

FIG. 9. DA021 and DA034 protect neurons against differing concentrations of NMDA. A: DA021; B: DA034.

Figure 10:
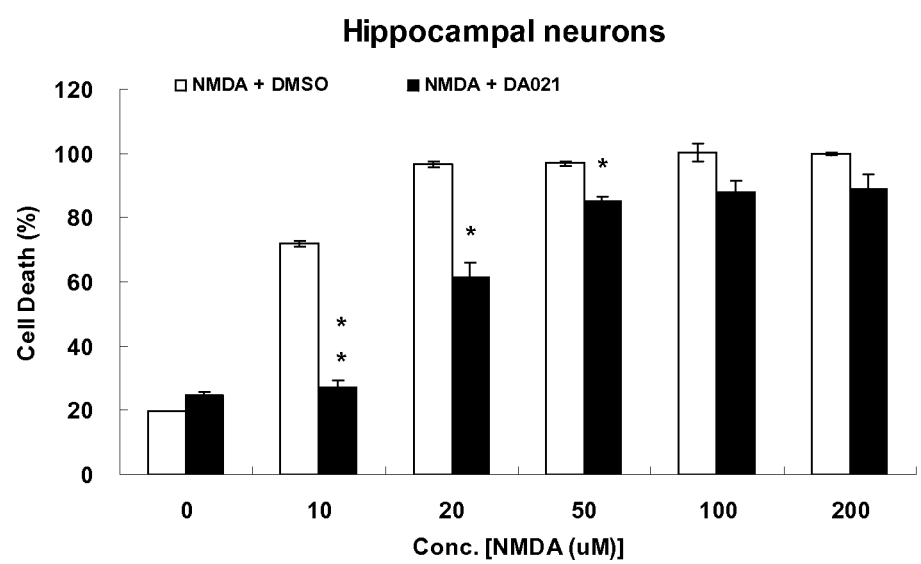

FIG. 10. DA021 protects neurons against differing concentrations of NMDA.

Figure 11:
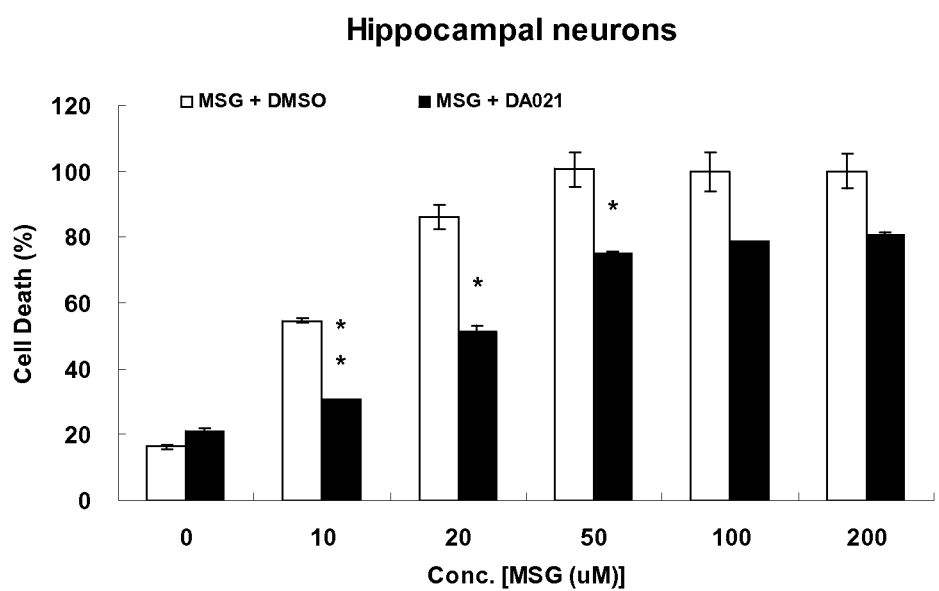

FIG. 11. DA021 protects neurons against differing concentrations of glutamate in hippocampal neurons.

Figure 12:
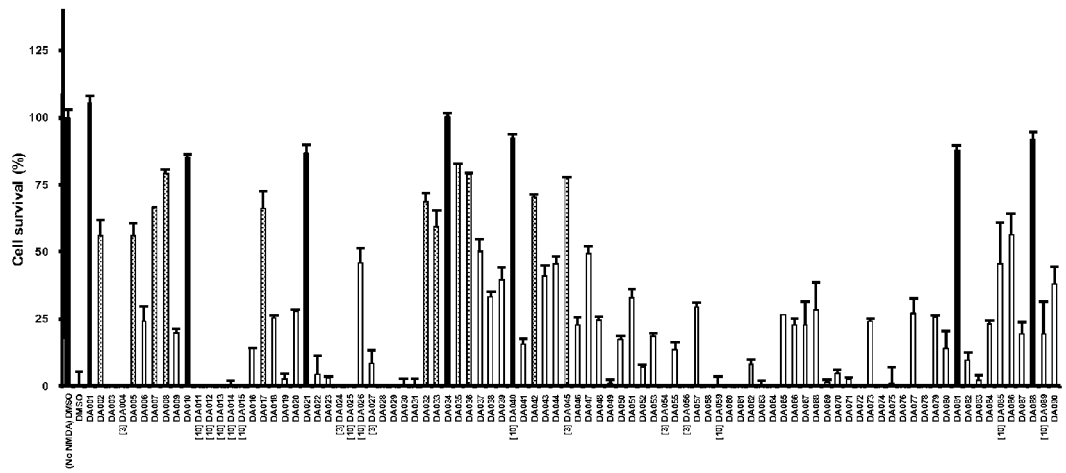

FIG. 12. Derivatives of DA001 rescue the cortical neurons from NMDA excitotoxicity. Cortical neurons were treated with compounds derived from of DA001 (30 μM) 24 hours prior to NMDA treatment. LDH released into the medium were measured 24 hours after NMDA treatment. Data are expressed as mean±s.e.m. and compared to solvent control (DMSO). *=P<0.05.

Figure 13:
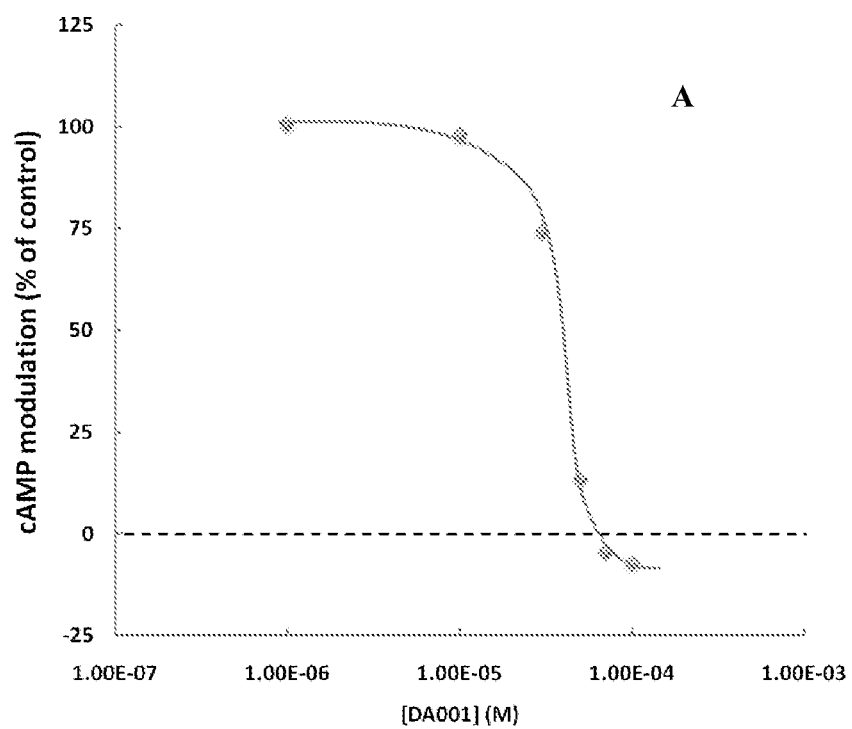
Figure 13:
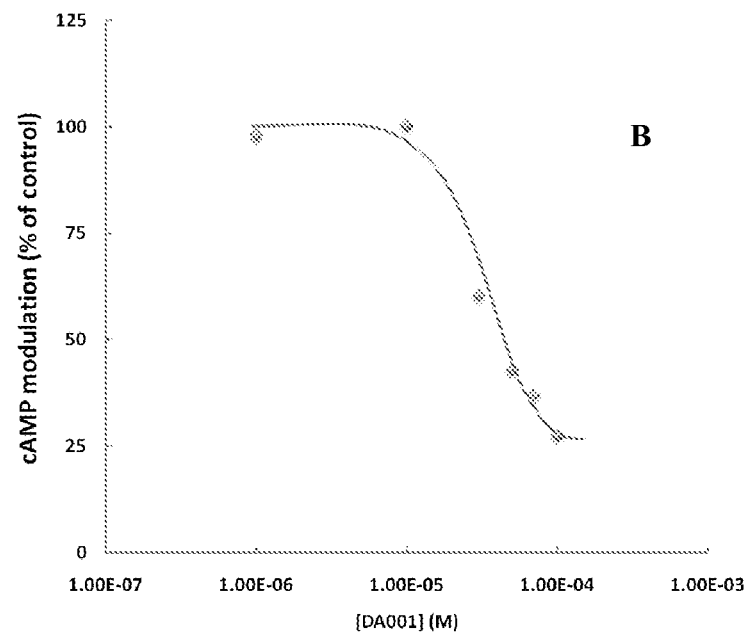

FIG. 13. DA001 shows a dose-dependent inhibitory effect on EP2 and EP4 receptor by reducing the cAMP increase upon the ligand (PGE2) binding. DA001 shows antagonist effect at the human EP2 and EP4 receptor with an $IC_{50}$ of 3.6E-05 M and 2.0E-05 M, respectively. A: Cellular functional assay for EP2; B: Cellular functional assay for EP2.

Figure 14:
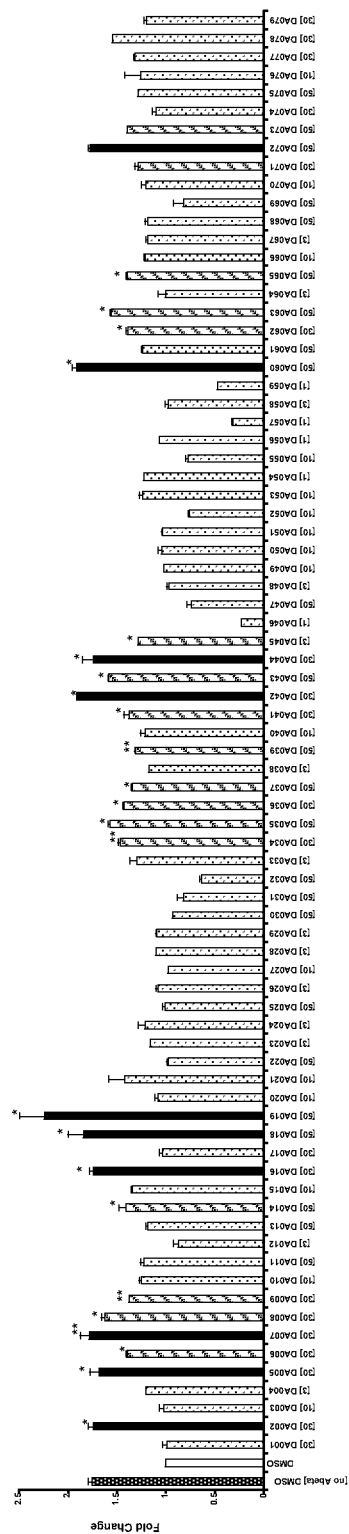

FIG. 14. Derivatives of DA001 protect the cortical neurons from $A\beta_{25-35}$ excitotoxicity. Cortical neurons were incubated with compounds (at various [μM]) derived from of DA001 2 hours prior to co-treatment with $A\beta_{25-35}$ (10 μM) for 24 hours. 3-(4,5-Dimethylthiazol-2-yl)-2,5-diphenyltetrazolium bromide (MTT) assay was performed 24 hours after $A\beta_{25-35}$ treatment. Data are expressed as mean fold change±s.e.m. compared to solvent control (DMSO). Dark-dotted bar represents data without addition of $A\beta_{25-35}$, open bar represents solvent control, black bars represent compounds with strong protective effect while striped bars represent compounds with moderate effect, light-dotted bars represent compounds without or with effect less than 25%. *=P<0.05, **=P<0.005.

Figure 15:
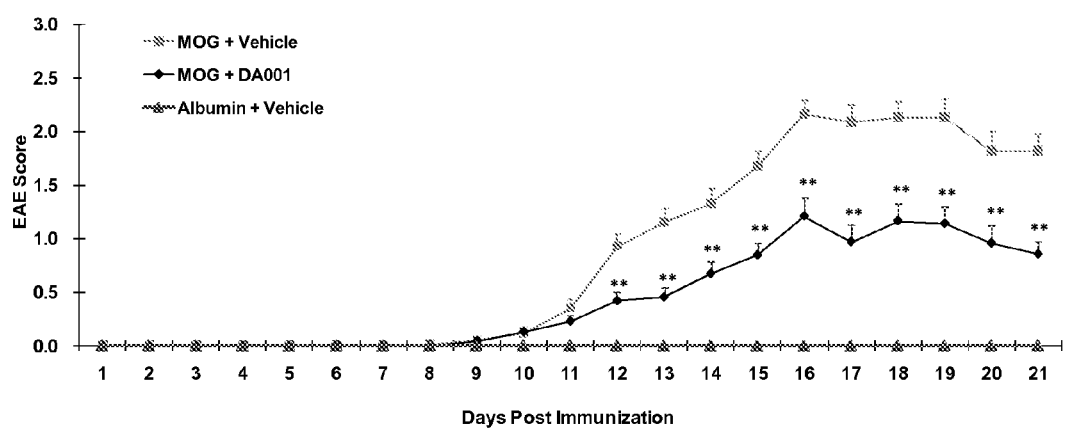

FIG. 15. DA001 improves the behavioral scores of mice with experimental autoimmune encephalomyelitis. C57BL/6 mice were immunized subcutaneously at both sides of their hind limbs with myelin oligodendrocyte glycoprotein (MOG)/Complete Freund's Adjuvant (CFA) kit (Hooke Laboratories) and performed as indicated in the manufacturer's instruction. Albumin/CFA kit (Hooke Laboratories) were used as an immunization control. Oral administration of DA001 at 100 mg/kg was given daily starting from the day of immunization. The vehicle (water) was given to mice injected with MOG or albumin daily via oral administration. Animals were weighed and monitored daily and behavioral impairment was quantified based on the clinical scale. The graph presented here is a composite of four separate EAE trials. **=p≤0.01.

Figure 16:
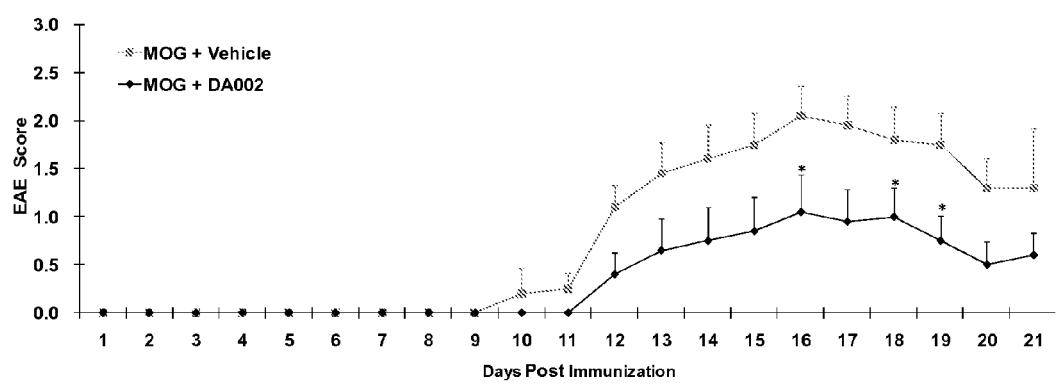

FIG. 16 illustrates that DA002 improves the behavioral scores of mice with experimental autoimmune encephalomyelitis. C57BL/6 mice were immunized subcutaneously at both sides of their hind limbs with myelin oligodendrocyte glycoprotein (MOG)/Complete Freund's Adjuvant (CFA) kit (Hooke Laboratories) and performed as indicated in the manufacturer's instruction. Oral administration of DA002 at 100 mg/kg was given daily starting from the day of immunization. The vehicle (water) was given to MOG-injected mice via oral administration. Animals were weighed and monitored daily and behavioral impairment was quantified based on the clinical scale. *=p≤0.05.

Figure 17:
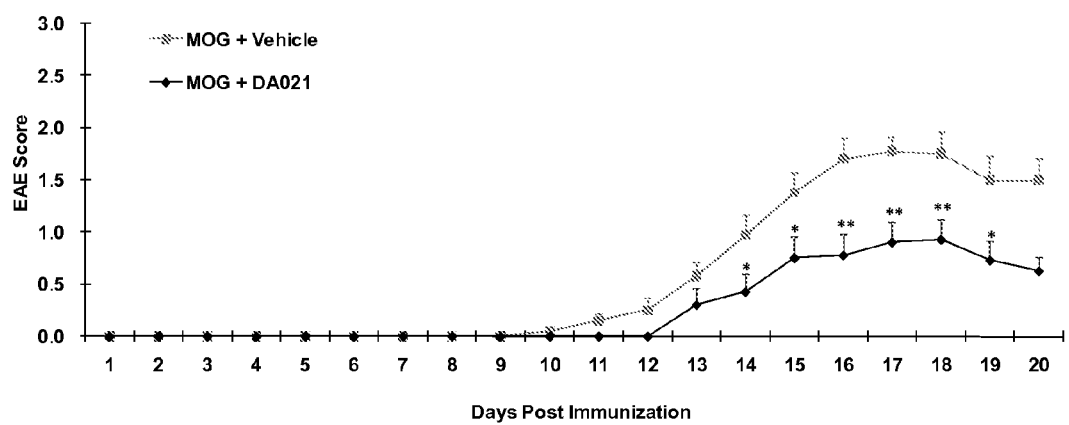

FIG. 17 shows that DA021 improves the behavioral scores of mice with experimental autoimmune encephalomyelitis. C57BL/6 mice were immunized subcutaneously at both sides of their hind limbs with myelin oligodendrocyte glycoprotein (MOG)/Complete Freund's Adjuvant (CFA) kit (Hooke Laboratories) and performed as in manufacturer's instruction. Oral administration of DA021 at 100 mg/kg was given daily starting from the day of immunization. The vehicle (water) was given to MOG-injected mice daily via oral administration. Animals were weighed and monitored daily and behavioral impairment was quantified based on the clinical scale. The graph presented here is a composite of three separate EAE trials. **=p≤0.01.

Figure 18:
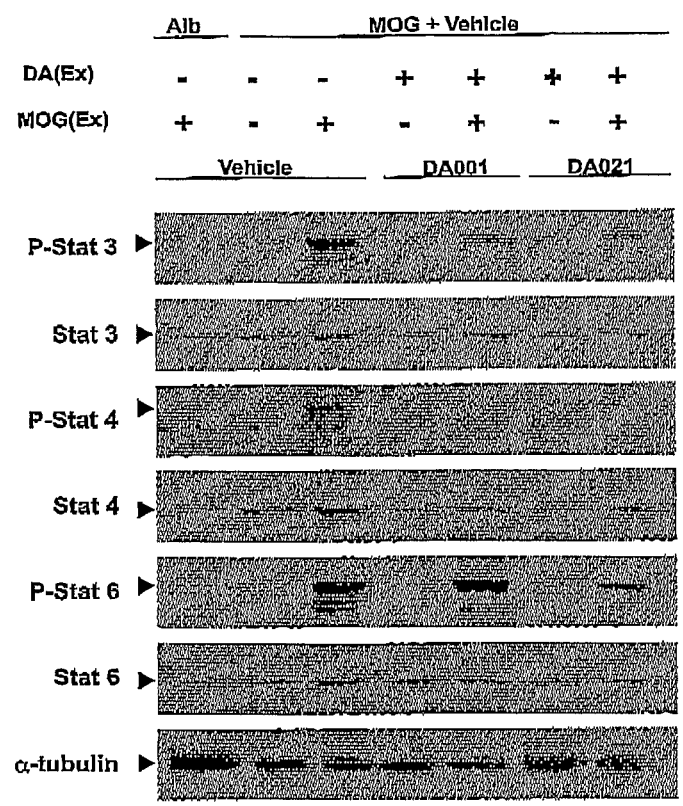

FIG. 18 shows that DA compounds decrease the expression of phosphorylated STAT3, STAT4, and STAT6 nuclear proteins in splenocytes isolated from the spleen of vehicle-treated EAE mice.

Figure 19:
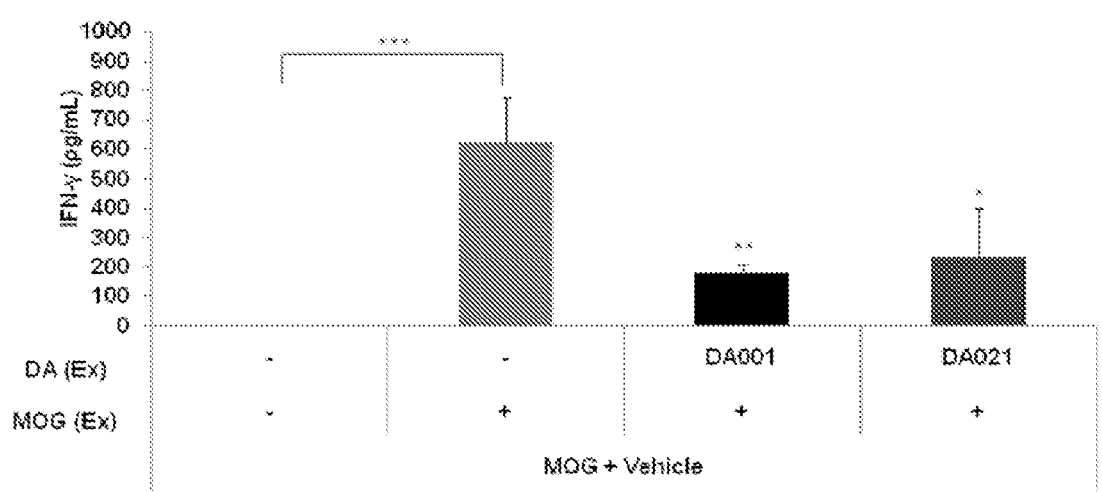

FIG. 19 shows that DA001 and DA021 decrease the level of exogenous MOG-induced IFN-γ in primary splenocytes isolated from the spleens of vehicle-treated EAE mice.

Figure 20:
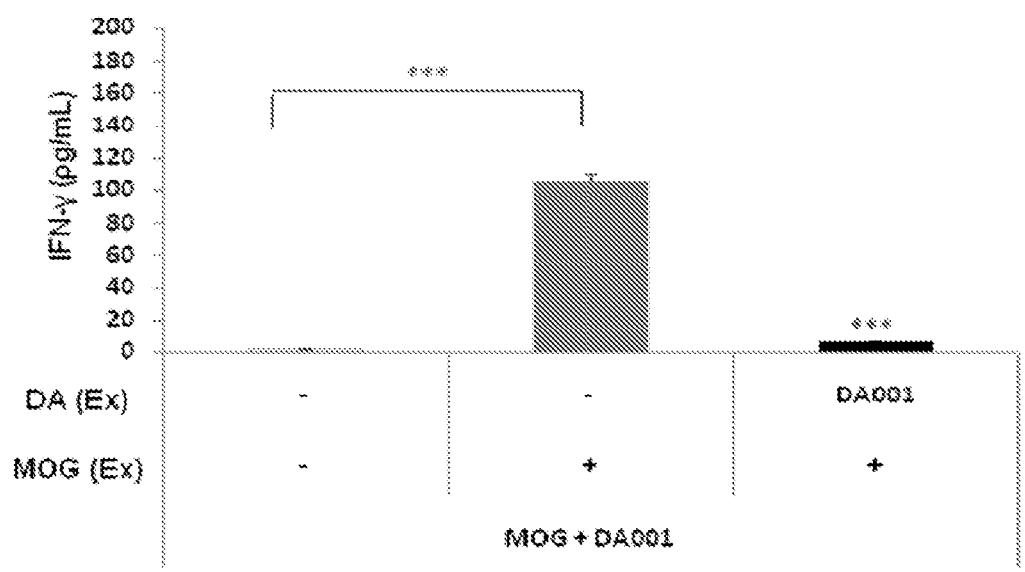

FIG. 20 illustrates that DA001 decreases the level of exogenous MOG-induced IFN-γ in primary splenocytes isolated from the spleens of DA001-treated EAE mice.

Figure 21:
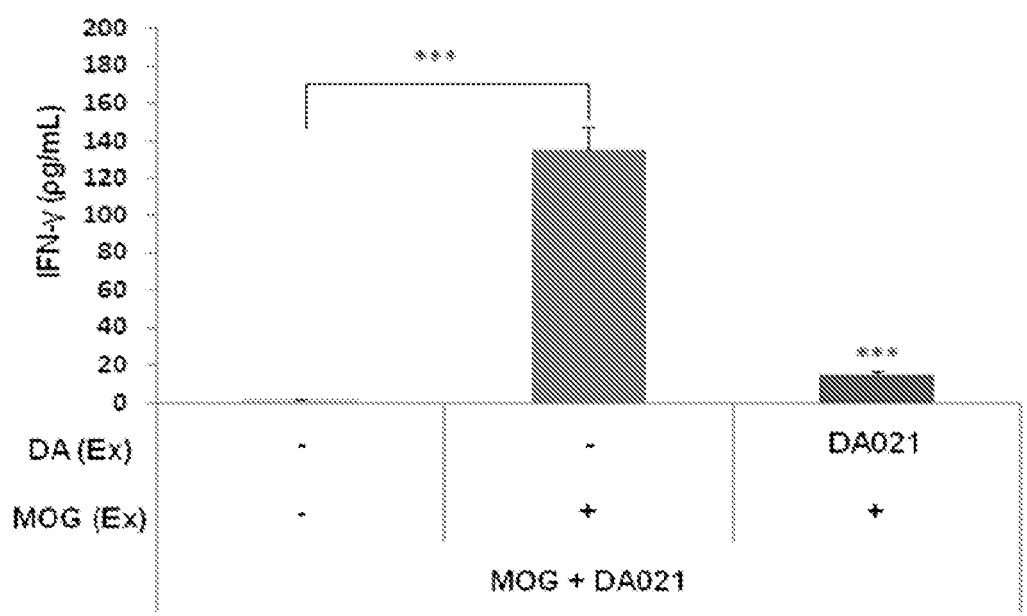

FIG. 21 illustrates that DA021 decreases the level of exogenous MOG-induced IFN-γ in primary splenocytes isolated from the spleens of DA021-treated EAE mice.

Figure 22:
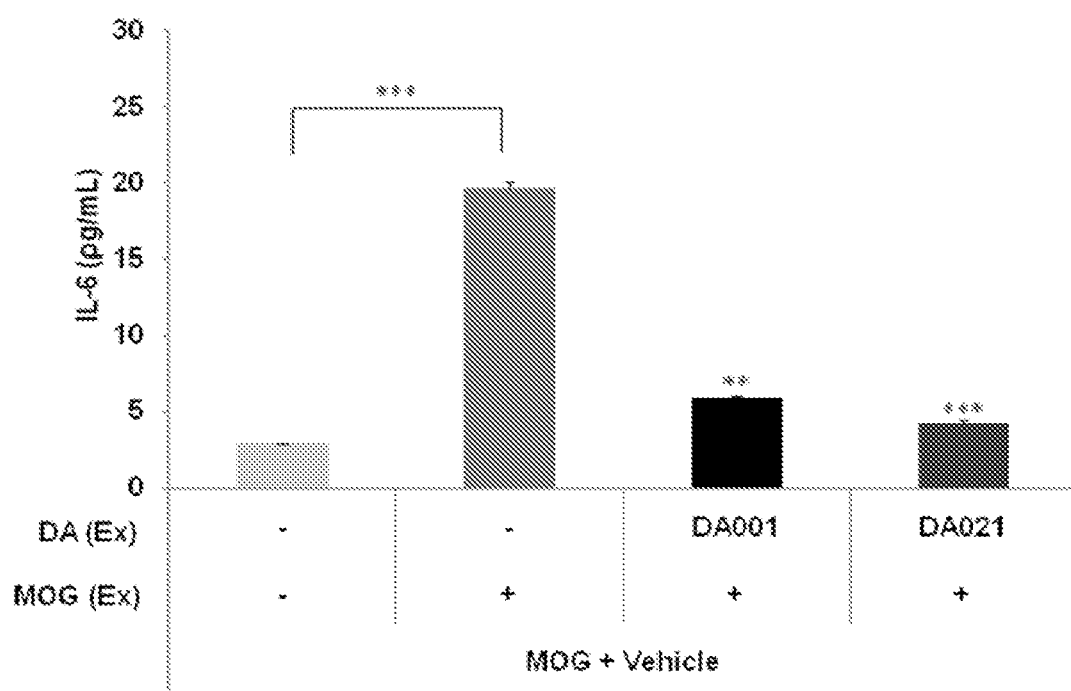

FIG. 22 illustrates that DA001 and DA021 decrease the level of exogenous MOG-induced IL-6 in primary splenocytes isolated from the spleens of vehicle-treated EAE mice.

Figure 23:
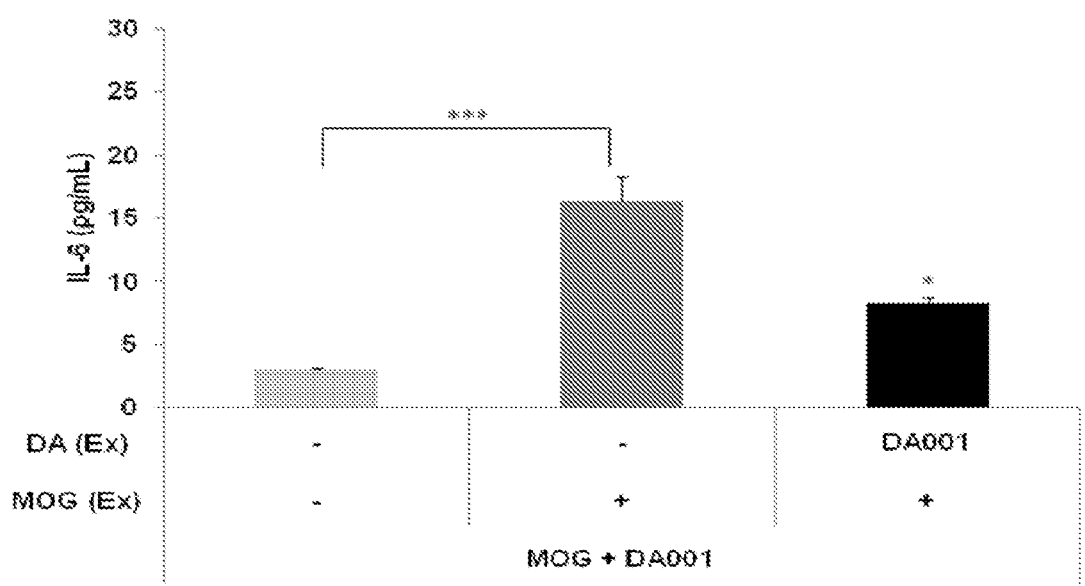

FIG. 23 illustrates that DA001 decreases the level of exogenous MOG-induced IL-6 in primary splenocytes isolated from the spleens of DA001-treated EAE mice.

Figure 24:
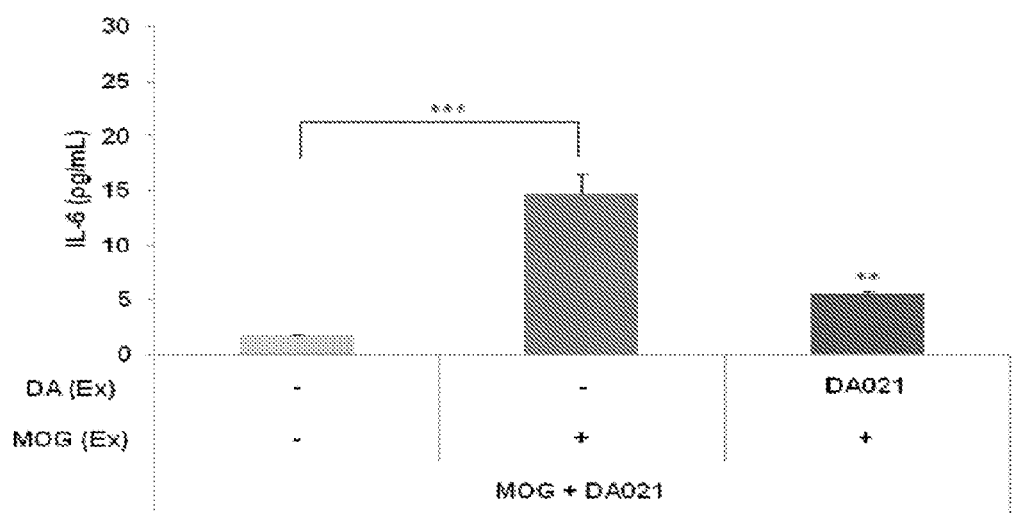

FIG. 24 illustrates that DA021 decreases the level of exogenous MOG-induced IL-6 in primary splenocytes isolated from the spleens of DA021-treated EAE mice.

Figure 25:
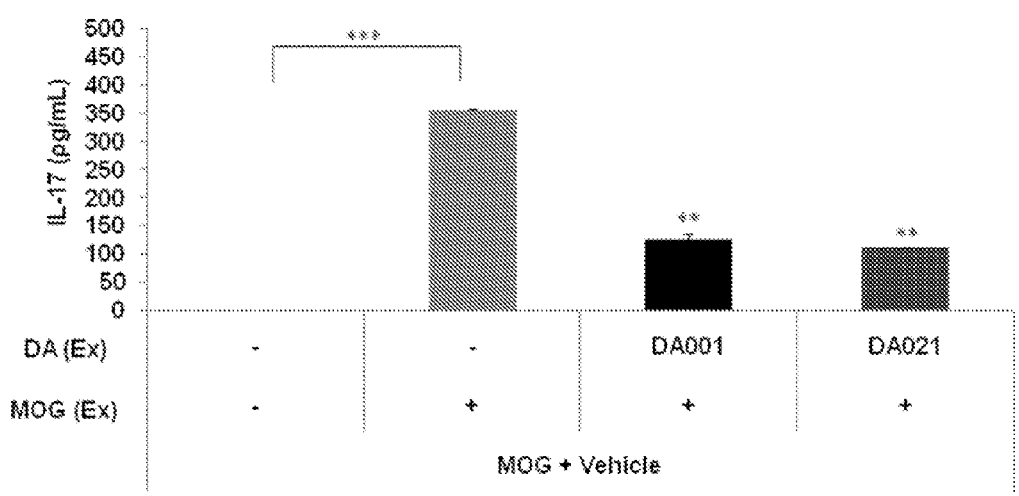

FIG. 25 shows that DA001 and DA021 decrease the level of exogenous MOG-induced IL-17 in splenocytes isolated from vehicle-treated EAE mice.

Figure 26:
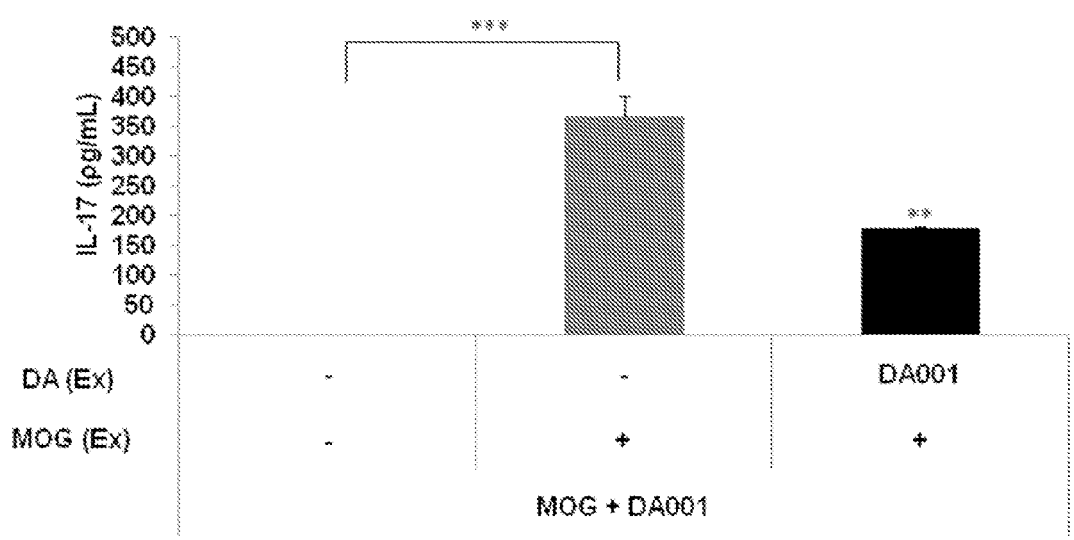

FIG. 26 illustrates that DA001 decreases the level of exogenous MOG-induced IL-17 in primary splenocytes isolated from the spleens of DA001-treated EAE mice.

Figure 27:
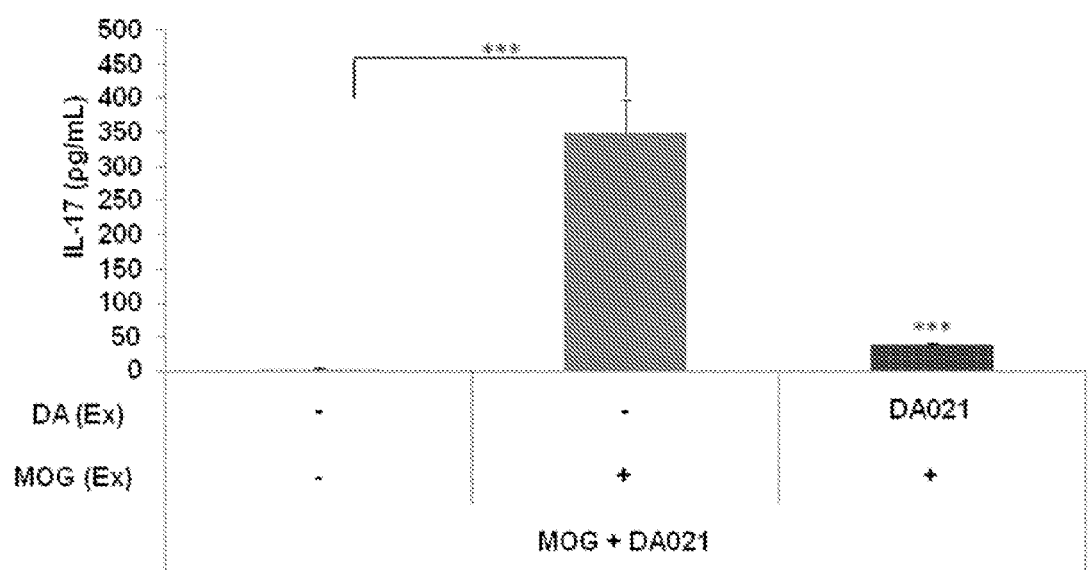

FIG. 27 shows that DA021 decreases the level of exogenous MOG-induced IL-17 in primary splenocytes isolated from the spleens of DA021-treated EAE mice.

Figure 28:
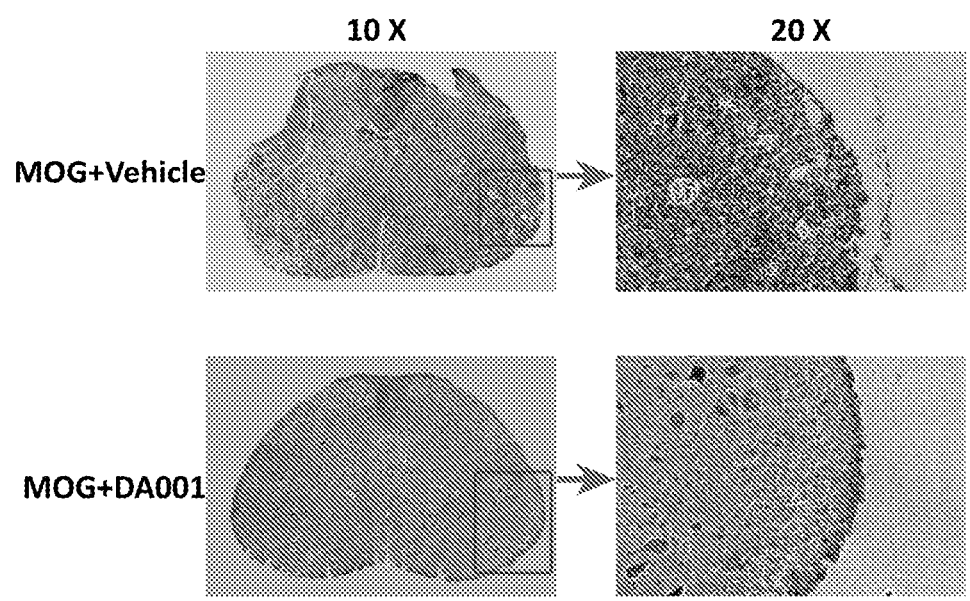

FIG. 28 illustrates that DA001 decreases the lymphocyte infiltrates in spinal cord of EAE mice.

Figure 29:
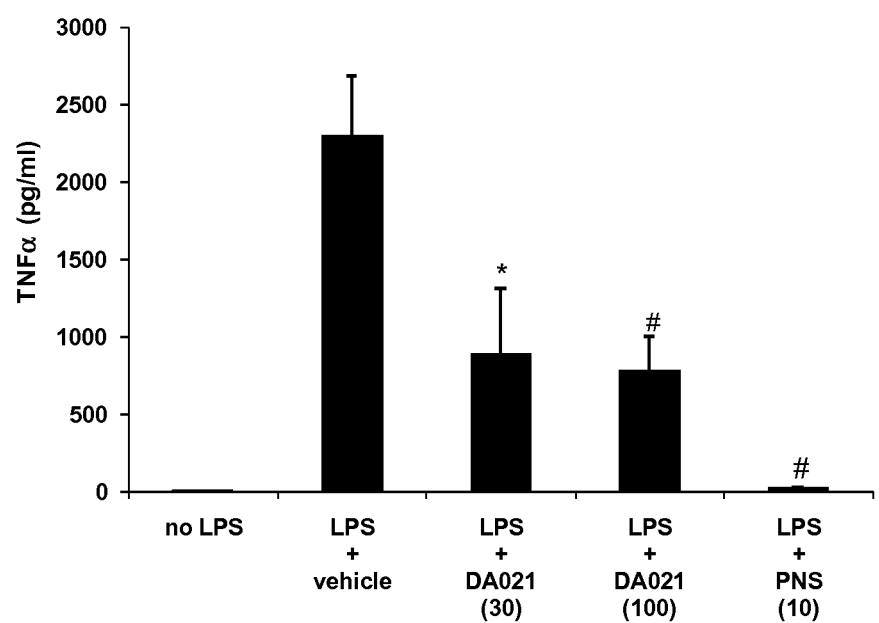

FIG. 29 shows that DA021 decreases *E-coli* lipopolysaccharide (LPS)-induced tumor necrosis factor-α (TNF-α) in serum of Swiss-Webster mice.

Figure 30:
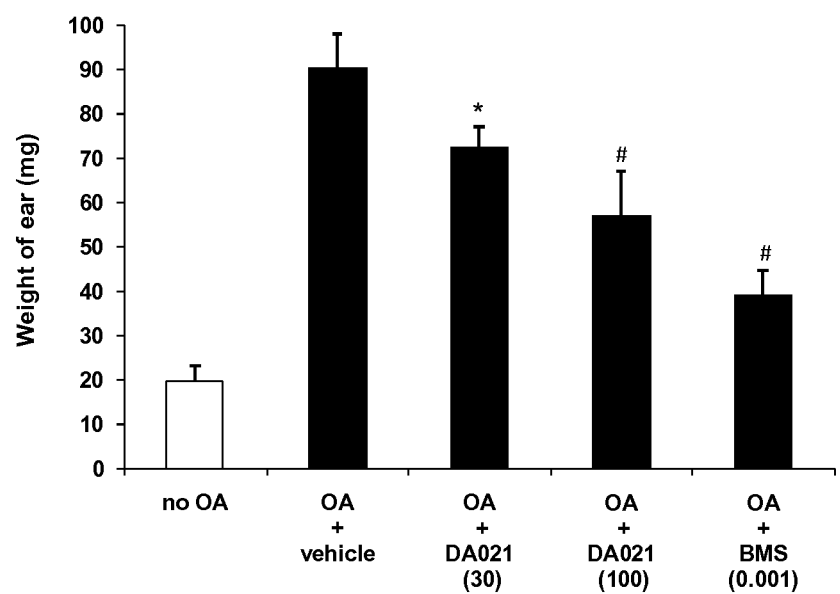

FIG. 30 illustrates that DA021 inhibits ear edema in mice treated with oxazolone.

Figure 31:
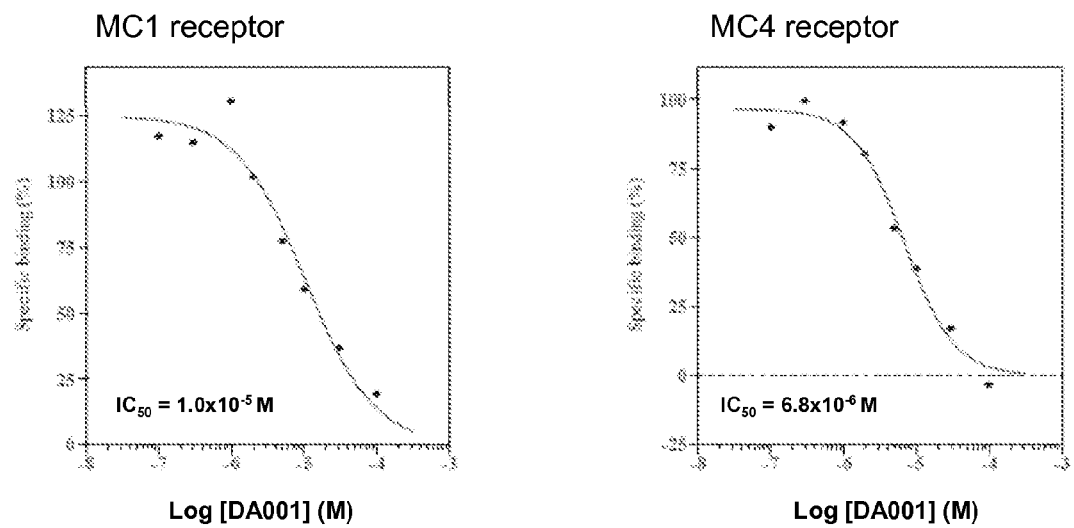

FIG. 31 shows that DA001 inhibits melanocortin binding to MC1 and MC4 receptors. Competition curve is obtained with DA001 at the human MC1 or MC4 receptor.

DETAILED DESCRIPTION OF THE INVENTION

I. Introduction

The present invention provides therapeutically active compounds and pharmaceutical compositions as NMDA receptors, melanocortin receptors and PG receptor antagonists, methods of inhibiting a receptor, such as an NMDA receptor, a melanocortin receptor and a receptor of PGE2, methods of treating, preventing or ameliorating pain or inflammation, methods of inducing CCAAT/enhancer binding protein beta (C/EBP-b) mRNA in cortical neuron cultures, and methods of regulating acute phase reactions, inflammation and hemopoiesis in mammals and humans. In particular, the compounds inhibit the EP1, EP2 and EP4 receptors of PGE2. Advantageously, the present invention provides PGE2 receptor antagonists that have therapeutic efficacy against pain and inflammation in a variety of diseases and conditions.

II. Definitions

Disease states that can be treated using the compounds of the invention to inhibit PGE2 receptors include, but are not limited to, autoimmune disorders, (e.g., rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Beheet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis), inflammatory bowel diseases (e.g., ulcerative colitis, Crohn's disease; chronic prostatitis), glomerulonephritis, transplant rejection, vasculitis, reperfusion injury, asthma, osteoarthritis, rhinitis, conjunctivitis and dermatitis, pain in terms of stimulus or nerve response (e.g., somatic pain and neuropathic pain), chronic pain and acute pain, pain that is a symptom or a result of a disease state or syndrome (e.g., inflammatory pain, cancer pain, AIDS pain, arthropathy, migraine, trigeminal neuralgia, cardiac ischaemia, and diabetic neuropathy), and visceral pain. Disease states that can be treated using the compounds of the invention to inhibit NMDA and/or MC receptor activity and protect against glutamate induced neurotoxicity include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, stroke, hydrocephalus, subarachnoid hemorrhage, vascular insufficiency, celebrovascular ischemia, brain tumor, epilepsy, Parkinson's disease, cerebral microangiopathy, pain medication, chemotherapy, oxygen deprivation, e.g, caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, fetal alcohol syndrome, depression, anxiety, anorexia, cachexia, and cognitive deterioration such as in schizophrenia, cerebral palsy and autism, for example.

The term "inflammation" refers to all categories of inflammation, including localized manifestations and systemic inflammation; inflammation that is categorized temporally, e.g., chronic inflammation and acute inflammation; inflammation that is categorized in terms of its severity, e.g., mild, moderate, or severe; and inflammation that is a symptom or a result of a disease state or syndrome. Inflammation, as used herein, can be characterized at the "whole body" level as several localized manifestations, including hemodynamic disorders (e.g., hyperemia and edema), pain, temperature increment, and functional lesion. All manifestations may be observed in certain instances, although any particular manifestation may not always be present in all instances. Concomitant cellular and molecular level changes that characterize inflammation may include leukocyte extravasation and platelet aggregation. Molecular level changes which characterize in flammation may include activation of at least three plasma defense systems and synthesis of cytokines and eicosanoids.

As used herein, the term "acute phase reactions" refers to the changes in synthesis of certain proteins within the serum during an inflammatory response, which provides rapid protection for the host against microorganisms via non-specific defense mechanisms. For example, the plasma concentrations of the protein can increase or decrease in response to inflammation. Exemplary acute phase reactions include fever, an increase in inflammatory humoral factors, and an increased synthesis by hepatocytes of a number of proteins or glycoproteins usually found in the plasma.

The term "autoimmune disorders or diseases" means disorders or diseases in which the body's immune system reacts against some of its own tissue and produces antibodies to attack itself. Exemplary autoimmune diseases include rheumatoid arthritis, multiple sclerosis, myasthenia gravis, lupus eryematosus and the like.

The term "rheumatoid arthritis" means an autoimmune disease which causes chronic inflammation of the joints, the tissue around the joints, as well as other organs in the body. Exemplary joints include the peripheral joints, e.g., finger joints, wrists, toes and knees and surrounding muscles, tendons, ligaments and blood vessels.

As used herein, the term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine*, pp. 93-98 (Wilson et al., eds., 12th ed. 1991); Williams et al., *J. of Medicinal Chem.* 42:1481-1485 (1999), herein each incorporated by reference in their entirety). Pain includes pain associated with CNS disorders comprising: multiple sclerosis, spinal cord injury, traumatic brain injury, Parkinson's disease and stroke.

As used herein, "Somatic pain" refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

As used herein, "Neuropathic pain" refers to pain resulting from injury to or chronic changes in peripheral and/or central sensory pathways, where the pain often occurs or persists without an obvious noxious input. Exemplary neuropathic pain include conditions including metabolic neuropathies (e.g., diabetic neuropathy), post-herpetic neuralgia, trigeminal neuralgia, cranial neuralgia, post-stroke neuropathic pain, multiple sclerosis-associated neuropathic pain, HIV/AIDS-associated neuropathic pain, cancer-associated neuropathic pain, carpal tunnel-associated neuropathic pain, spinal cord injury-associated neuropathic pain, complex regional pain syndrome, fibromyalgia-associated neuropathic pain, reflex sympathetic dystrophy, phantom limb syndrome or peripheral nerve or spinal cord trauma, nerve transection including surgery, limb amputation and stump pain, pain caused by the side effects of anti-cancer and anti-AIDS therapies, post-surgical neuropathic pain, neuropathy-associated pain such as in idiopathic or post-traumatic neuropathy and mononeuritis, and neuropathic pain caused by connective tissue disease such as rheumatoid arthritis, Wallenberg's syndrome, systemic lupus erythematosus, multiple sclerosis, or polyarteritis nodosa. The neuropathy can be classified as radiculopathy, mononeuropathy, mononeuropathy multiplex, polyneuropathy or plexopathy.

As used herein, "Acute pain" refers to pain which is marked by short duration or a sudden onset. Acute pain types include, but are not limited to, pain associated with tissue damage, postoperative pain, pain after trauma, pain caused by burns, pain caused by local or systemic infection, visceral pain associated with diseases comprising: pancreatits, intestinal cystitis, dysmenorrhea, Irritable Bowel syndrome, Crohn's disease, ureteral colic and myocardial infarction.

As used herein, "Chronic pain" refers to pain which is marked by long duration or frequent recurrence. In a preferred embodiment, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto.

As used herein, "Inflammatory pain" refers to pain which is produced as a symptom or a result of inflammation or an immune system disorder. For example, inflammatory pain associated with diseases including, but not limiting to, connective tissue diseases, rheumatoid arthritis, systemic lupus erythematosus, multiple sclerosis and arthritis.

As used herein, "Visceral pain" refers to pain which is located in an internal organ. Exemplar functional visceral pain includes chronic gastrointestinal inflammations like Crohn's disease, ulcerative colitis, gastritis, irritable bowel syndrome; orangic visceral pain including pain resulting from a traumatic, inflammatory or degenerative lesion of the gut or produced by a tumor impinging on sensory innervation; and treatment-induced visceral pain, for example, attendant to chemotherapy or radiation therapy.

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl, arylalkyl, arylalkoxy, hydroxylalkyl, alkoxyalkyl, aminoalkykl), when a prefix is not included to indicate the number of main chain carbon atoms in an alkyl portion, the radical or portion thereof will have 12 or fewer main chain carbon atoms or 8 or fewer main chain carbon atoms. For example, $C_{1-8}$alkyl refers to a hydrocarbon radical straight or branched having 1, 2, 3, 4, 5, 6, 7 or 8 carbon atoms and includes, but are not limited to, $C_{1-2}$alkyl, $C_{1-4}$alkyl, $C_{2-6}$alkyl, $C_{2-4}$alkyl, $C_{1-6}$alkyl, $C_{2-8}$alkyl, $C_{1-7}$alkyl, $C_{2-7}$alkyl and $C_{3-8}$alkyl.

As used herein, the term "alkenyl" refers to a straight or branched unsaturated alkyl group having one or more double bonds. Exemplary $C_{2-6}$alkenyl group include, but are not limited to, vinyl, 1-propenyl, 2-propenyl, 1-butenyl, 2-butenyl, 1-pentenyl, 2-pentenyl, 1-hexenyl, 2-hexenyl, 3-hexenyl, crotyl, 2-isopentenyl, 2-(butadienyl), 2,4-pentadienyl, 3-(1, 4-pentadienyl), and the higher homologs and isomers.

As used herein, the term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl.

As used herein, the term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred, and the groups having 8 or fewer carbon atoms being more preferred in the present invention.

As used herein, the term "aryl" refers to, unless otherwise stated, a polyunsaturated, aromatic, hydrocarbon radical of 6-14 ring carbon atoms, which can be a single ring or multiple rings (up to three rings) which are fused together or linked covalently. Non-limiting examples of aryl groups include phenyl, naphthyl and biphenyl.

As used herein, the term "heteroaryl" refers to aryl groups (or rings) that contains from one to five heteroatoms selected from N, O, or S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized, the remaining ring atoms being C. The heterocycloalkyl may be a monocyclic, a bicyclic or a polycylic ring system of 3 to 12, preferably 5 to 8, ring atoms in which one to five ring atoms are heteroatoms. Non limiting examples of heterocycloalkyl groups include pyrrolidinyl, piperidinyl, imidazolidinyl, pyrazolidinyl, butyrolactam radical, valerolactam radical, imidazolidinone radical, hydantoin, dioxolane radical, phthalimide radical, piperidine, 1,4-dioxane radical, morpholinyl, thiomorpholinyl, thiomorpholinyl-5-oxide, thiomorpholinyl-S,S-oxide, piperazinyl, pyranyl, pyridine radical, 3-pyrrolinyl, thiopyranyl, pyrone radical, tetrahydrofuranyl, tetrahydrothiophenyl, quinuclidinyl, and the like. A heterocycloalkyl group can be attached to the remainder of the molecule through a ring carbon or a heteroatom.

As used herein, the terms "heterocycle", "heterocyclyl" or "heterocyclic" refer to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like. The term heterocyclic ring includes both a heteroaryl ring, heterocycloalkyl and a heterocyclyl ring as defiend herein.

The term "composition" as used herein is intended to encompass a product comprising the specified ingredients in the specified amounts, as well as any product which results, directly or indirectly, from combination of the specified ingredients in the specified amounts.

As used herein, the term "epoxyalkyl" refers to an alkyl group defined hereinabove having an epoxide group. More particularly, $C_{2-6}$epoxyalkyl includes epoxyethyl, epoxypropyl, epoxybutyl, epoxypentyl, epoxyhexyl and the other isomeric forms thereof. For example, $C_{2-3}$epoxyalkyl includes epoxyethyl and epoxypropyl. As used herein, the term "epoxide" refers to chemical compounds or reagents comprising a bridging oxygen wherein the bridged atoms are also bonded to one another either directly for indirectly. Examples of epoxides include 1,2-epoxyethylene (oxirane), propylene oxide, and the like.

The terms "alkoxy" and "alkylamino" are used in their conventional sense, and refer to those alkyl groups attached to the remainder of the molecule via an oxygen atom or an amino group, respectively. Additionally, for dialkylamino groups, the alkyl portions can be the same or different and can also be combined to form a 3-7 membered ring with the nitrogen atom to which each is attached. Accordingly, a group represented as —NR'R" is meant to include piperidinyl, pyrrolidinyl, morpholinyl, azetidinyl and the like.

As used herein, the terms "halo" or "halogen," by themselves or as part of another substituent, mean, unless otherwise stated, a fluorine, chlorine, bromine, or iodine atom.

As used herein, the term "haloalkyl," includes monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, bromomethyl and the like.

As used herein, "arylalkyl" refers to a radical —R'R", where —R' is an alkylene group (having the indicated number of carbon atoms, or if unspecified having eight or fewer main chain carbon atoms) and R" is an aryl group as defined herein. Examples of arylalkyl include benzyl, phenethyl and the like.

As used herein, "arylalkoxy" refers to an arylalkyl-O— group, where arylalkyl is as defined herein. Examples of arylalkoxy include benzyloxy, phenethyloxy and the like.

As used herein, "hydroxyalkyl" refers to a hydroxy-alkylene-group, wherein alkylene is as defined herein. Examples of hydroxyalkyl include HOCH$_2$—, HOCH$_2$CH$_2$—, CH$_3$CH (OH)—CH$_2$— and the like.

As used herein, "alkoxyalkyl" refers to an alkoxy-alkylene-group, where alkoxy and alkylene are as defined herein. Examples of alkoxyalkyl include CH$_3$OCH$_2$—, CH$_3$CH$_2$OCH$_2$CH$_2$— and the like.

The term "aminoalkyl" means an amino-alkylene-group, wherein alkylene is as defined herein. Examples of aminoalkyl include NH$_2$CH$_2$—, NH$_2$CH$_2$CH$_2$—, NH$_2$CH$_2$CH (CH$_3$)CH$_2$— and the like.

The term "aryloxy" refers to a radical —OR' where R' is an aryl as defined herein. Examples of aryloxy include phenoxy and the like.

The term "aryloxyalkyl" refers to an aryloxy-alkylene-group, where aryloxy and alkylene are as defined herein. The prefix before the alkyl indicates the number of carbon atoms, or if unspecified having eight or fewer main chain carbon atoms. Examples of aryloxyalkyl include phenoxymethyl and the like.

The term "alkyl-C(O)O-alkyl" refers to an alkyl-C(O)O-alkylene-group, wherein alkyl and alkylene as defined herein. The prefix before the alkyl indicates the number of carbon atoms, or if unspecified having eight or fewer main chain carbon atoms. Examples of alkyl-C(O)O-alkyl include CH$_3$C (O)OCH$_2$— and the like.

The term "arylalky-C(O)O-alkyl" refers to an arylalky-C (O)O-alkylene, wherein arylalkyl and alkylene as defined herein. The prefix before the alkyl indicates the number of carbon atoms, or if unspecified having eight or fewer main chain carbon atoms. Examples of arylalkyl-C(O)O-alkyl include benzyl-C(O)O—CH$_2$— and the like.

The term "alky-NH-alkyl" refers to an alky-NH-alkylene-, wherein alkyl and alkylene as defined herein. The prefix before the alkyl indicates the number of carbon atoms, or if unspecified having eight or fewer main chain carbon atoms. Examples of alkyl-NH-alkyl include CH$_3$—NH—CH$_2$— and the like.

The term "arylalky-NH-alkyl" refers to an arylalky-NH-alkylene, wherein arylalkyl and alkylene as defined herein. The prefix before the alkyl indicates the number of carbon atoms, or if unspecified having eight or fewer main chain carbon atoms. Examples of arylalkyl-NH-alkyl include benzyl-NH—CH$_2$— and the like.

As used herein, the term "inhibiting" refers to a compound that partially or fully prohibits or a method of partially or fully prohibiting a specific action or function.

As used herein, the term "monosaccharide" or "sugar" refers to a carbohydrate molecule that are straight-chain aldehydes or ketones, which may be combined in acetal or ketal forms. The remaining carbons of the molecule usually have hydrogen and multiple hydroxyl groups. The monosaccharide has an empirical formula of (CH$_2$O)$_n$, wherein n is 3-7, and preferably 4-7, even more preferably 5-7. In some embodiments, the term refers to "simple sugars" that consist of a single polyhydroxy aldehyde or ketone unit. Representative examples of monosaccharides include, but are not limited to, glucose, fructose, mannose, and galactose. Representative examples of disaccharides include, but are not limited to, lactose, maltose, and sucrose.

As used herein, the term "patient in need", "mammal in need" or "subject in need" refers to a patient or a mammal suffering from inflammatory or pain conditions or acute phase reactions as described herein. Non-limiting examples include rheumatoid arthritis, multiple sclerosis, myesthenia gravis, lupus eryematosus, inflammatory bowel diseases (e.g., ulcerative colitis, Crohn's disease; chronic prostatitis), glomerulonephritis, transplant rejection, vasculitis, reperfusion injury, asthma, osteoarthritis, rhinitis, conjunctivitis and dermatitis, somatic pain and neuropathic pain, chronic pain and acute pain, inflammatory pain, cancer pain, AIDS pain, arthropathy, migraine, trigeminal neuralgia, cardiac ischaemia, diabetic neuropathy, and visceral pain. Patients suffering from other conditions treatable with the PGE2 antagonists are also treatable with the methods of the present invention. Patients treatable using the methods of the present invention are animals such as mammals, including, but not limited to, primates (e.g., humans), cows, sheep, goats, horses, dogs, cats, rabbits, rats, mice and the like. In certain embodiments, the patient is a human.

As used herein, the term "prodrug" refers to covalently bonded carriers which are capable of releasing the active agent of the methods of the present invention, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of the active agents of the present invention include active agents wherein a hydroxy, amidino, guanidino, amino, carboxylic or a similar group is modified.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, pharmaceutically acceptable salts of the basic compounds of the present invention are salts formed with acids, such as of mineral acids, organic carboxylic and organic sulfonic acids, e.g., hydrochloric acid, methanesulfonic acid, maleic acid, are also possible provided a basic group, such as pyridyl, constitutes part of the structure. The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S.

M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

As used herein, "pharmaceutically acceptable" is meant the carrier, diluent or excipient must be compatible with the other ingredients of the formulation and not deleterious to the recipient thereof.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

The term "tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N═C(H)—NH— ring atom arrangement, such as pyrazoles, imidazoles, benzimidazoles, triazoles, and tetrazoles. The compounds described herein may have one or more tautomers and therefore include various isomers. A person of ordinary skill in the art would recognize that other tautomeric ring atom arrangements are possible. All such isomeric forms of these compounds are expressly included in the present invention.

Certain compounds of the present invention can exist in unsolvated forms as well as solvated forms, including hydrated forms. "Hydrate" refers to a complex formed by combination of water molecules with molecules or ions of the solute. A hydrate refers to a compound that is complexed to at least one water molecule. The compounds of the present invention can be complexed with from 1 to 10 water molecules. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

III. Compounds

In one aspect, the present invention provides a compound of formula (I):

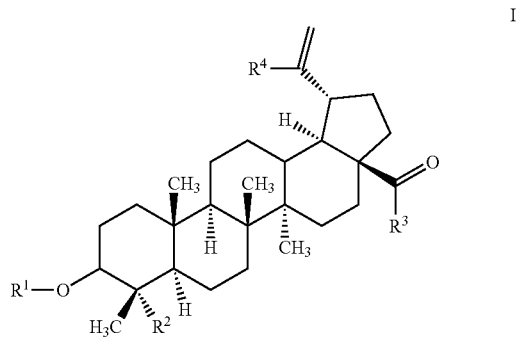

or a pharmaceutically acceptable salt, hydrate, solvate or isomer thereof.

In formula (I), $R^1$ is —H, alkyl-C(O)— or arylalkyl-C(O). In one embodiment, $R^1$ is —H, alkyl-C(O)— or Ph-$C_{1-4}$alkyl-C(O)—. In another embodiment, $R^1$ is —H, $CH_3C(O)$— or benzyl-C(O)—. In yet another embodiment, $R^1$ is —H, alkyl-C(O)— or Ph-$C_{1-4}$alkyl-C(O)—. In still another embodiment, $R^1$ is —H, $CH_3C(O)$— or benzyl-C(O)—. The other substituents $R^2$, $R^3$ and $R^4$ are as defined in above in the summary of invention.

In formula (I), $R^2$ is selected from the group consisting of hydroxy-$C_{1-4}$alkyl, alkoxy-$C_{1-4}$alkyl, aryloxy-$C_{1-4}$alkyl, alkyl-C(O)O—$C_{1-4}$alkyl and arylalky-C(O)O—$C_{1-4}$alkyl. In one group of embodiments, $R^2$ is hydroxy-$C_{1-4}$alkyl, alkoxy-$C_{1-4}$alkyl or alkyl-C(O)O—$C_{1-4}$alkyl. In certain instances, $R^2$ is hydroxymethyl, $CH_3OCH_2$— or $CH_3C(O)OCH_2$—. In some embodiments, $R^2$ other than alkoxy-$C_{1-4}$alkyl or aryloxy-$C_{1-4}$alkyl. In certain instances, $R^2$ is hydroxy-$C_{1-4}$alkyl, alkyl-C(O)O—$C_{1-4}$alkyl or arylalky-C(O)O—$C_{1-4}$alkyl. The other substituents $R^1$, $R^3$ and $R^4$ are as defined in any of the above embodiments and in the summary of the invention.

In formula (I), $R^3$ is selected from the group consisting of —$NH_2$, —$NHR^a$, —$N(R^a)_2$, —OH and —$OR^b$, wherein $R^a$ and $R^b$ are each independenly alkyl, aryl, arylalkyl, hydroxyalkyl or aminoalkyl; wherein the aliphatic portion of the $R^3$ substitutent is optionally substituted with from 1-2 $R^e$ substituents independently selected from —OH, —$NH_2$, alkoxy, arylalkoxy, halogen, alkyl-C(O)O—, arylalky-C(O)O, aryl-C(O)O, alkyl-C(O)NH—, arylalky-C(O)NH—, aryl-C(O)NH—, alkylamino or dialkylamino; or optionally any two adjacent $R^e$ substituents together with the atoms to which they are attached form a 5- or 6-membered heterocyclic ring having from 1-3 heteroatoms selected from N, O or S, wherein the heterocyclic ring is optionally substituted with 1-2 $C_{1-8}$alkyl. In some embodiments, $R^3$ is optionally substituted with from 1-2 $R^d$ substituents independently selected from the group consisting of halo, —CN, —$NO_2$, —OH, —$R^e$, —$OR^e$, —$OC(O)NHR^e$, —$OC(O)N(R^e)_2$, —$OC(O)R^e$, —OC(O)H, —$NH_2$, —$NHR^e$, —$N(R^e)_2$, —$S(O)_2R^e$, —$SO_2NH_2$, —$SO_2NHR^e$, —$SO_2N(R^e)_2$, —$NHS(O)_2R^e$, —$NR^eS(O)_2R^e$, —$C(O)NH_2$, —$C(O)NHR^e$, —$C(O)N(R^e)_2$, —C(O)H, —$C(O)R^e$, —$NHC(O)R^e$, —$NR^eC(O)R^e$, —$CO_2R^e$, —$NHCO_2R^e$ and —$NR^eCO_2R^e$, wherein each $R^e$ is independently a $C_{1-8}$alkyl. The other substituents $R^1$, $R^2$ and $R^4$ are as defined in any of the above embodiments and in the summary of the invention.

In one group of embodiments, $R^3$ is —$NH_2$, —$NHR^a$, —$N(R^a)_2$, —OH or —$OR^b$, wherein $R^a$ and $R^b$ are each independently alkyl, arylalkyl, hydroxyalkyl or aminoalkyl, wherein the aliphatic portion of the $R^3$ substitutent is optionally substituted with from 1-2 $R^e$ substituents independently selected from —OH, —$NH_2$, halogen, alkylamino or dialkylamino and the aromatic portion of the $R^3$ or $R^4$ group is optionally substituted with from 1-2 $R^d$ substituents. In certain instances, $R^3$ is —$NH_2$, —$NHR^a$, —$N(R^a)_2$, —OH or —$OR^b$, wherein $R^a$ and $R^b$ are each independently alkyl, aryl-$C_{1-4}$alkyl, hydroxy-$C_{1-4}$alkyl or amino-$C_{1-4}$alkyl, wherein the aliphatic portion of the $R^3$ substitutent is optionally substituted with a $R^e$ substituent independently selected from —OH, —$NH_2$, halogen, alkylamino or dialkylamino and the aromatic portion of the $R^3$ or $R^4$ group is optionally substituted with from 1-2 $R^d$ substituents. In other instances, $R^3$ is —OH, —$NH_2$, —NH—$C_{1-4}$alkyl, $CH_3NH$—, EtNH—, isopropyl-NH—, $C_{1-8}$alkyl-NH—, $PhCH_2NH$—, $PhCH_2O$—, PhO—, $HO(CH_2)$, —NH—, —$O(CH_2)_qOH$, —$O(CH_2)_2OH$, —$O(CH_2)_3OH$, $HO(CH_2)_2$—NH—, $HO(CH_2)_3$—NH—, $NH_2(CH_2)_mNH$—, $NH_2(CH_2)_2NH$—, $NH_2(CH_2)_3NH$—, $NH_2(CH_2)_p$—O—, $NH_2(CH_2)_2$—O— or $NH_2(CH_2)_3$—O—, wherein the script m, n, p and q are each independently an integer of from 1-4, such as 1, 2, 3, or 4. The other substituents $R^1$, $R^2$ and $R^4$ are as defined in any of the above embodiments and in the summary of the invention.

In formula (I), $R^4$ is $C_{1-8}$alkyl, haloalkyl, hydroxyalkyl, alkyl-C(O)—$C_{1-4}$alkyl, arylalkyl-NH—$C_{1-4}$alkyl or alkoxyalkyl. In some embodiments, $R^4$ is optionally substituted with from 1-2 $R^d$ substituents independently selected from the group consisting of halo, —CN, —$NO_2$, —OH, —$R^e$, —$OR^e$, —$OC(O)NHR^e$, —$OC(O)N(R^e)_2$, —$OC(O)R^e$, —OC(O)H, —$NH_2$, —$NHR^e$, —$N(R^e)_2$, —$S(O)_2R^e$, —$SO_2NH_2$, —$SO_2NHR^e$, —$SO_2N(R^e)_2$, —$NHS(O)_2R^e$, —$NR^eS(O)_2R^e$, —$C(O)NH_2$, —$C(O)NHR^e$, —$C(O)N(R^e)_2$, —C(O)H, —$C(O)R^e$, —$NHC(O)R^e$, —$NR^eC(O)R^e$, —$CO_2R^e$, —$NHCO_2R^e$ and —$NR^eCO_2R^e$, wherein each $R^e$ is independently a $C_{1-8}$alkyl. In one group of embodiments, $R^4$ is $C_{1-4}$alkyl, $haloCH_2$—, $C_{1-4}$alkyl, hydroxyalkyl, alkyl-C(O)—$C_{1-4}$alkyl, arylalkyl-NH—$C_{1-4}$alkyl or alkoxyalkyl. In certain instances, $R^4$ is —$CH_3$, $ClCH_2$—, $BrCH_2$—, methyl, ethyl, isopropyl, butyl, iso-butyl, $HOCH_2$—, hydroxyethyl, hydroxypropyl, hydroxylbutyl, $CH_3C(O)CH_2$—, $CH_3C(O)C_{1-4}$alkyl, benzyl-$NHCH_2$—, benzyl-NH—$C_{1-4}$alkyl, $C_{1-4}$alkyoxymethyl, $CH_3OCH_2$—, $CH_3CH_2OCH_2$— or $(CH_3)_2CHOCH_2$—. The other substituents $R^1$, $R^2$ and $R^3$ are as defined in any of the above embodiments and in the summary of the invention.

In formula (I), when $R^1$ is —H or $CH_3C(O)$—, $R^2$ is —$CH_2OH$ or —$CH_2OC(O)CH_3$ and $R^4$ is —$CH_3$ or $HOCH_2$—, then $R^3$ is other than —OH, —OMe, —OEt, —$NHCH_2Ph$, —$O(CH_2)_2OH$, —$CH_2CH(OH)CH_2(OH)$ or 2,2-dimethyl-1,3-dioxolan-4-yl-methyl. In some embodiments, when $R^1$ is —H or $CH_3C(O)$—, $R^2$ is —$CH_2OH$ or —$CH_2OC(O)CH_3$ and $R^4$ is —$CH_3$ or $HOCH_2$—, then $R^3$ is other than —OH, —$OC_{1-8}$alkyl, —$NHCH_2$aryl, —O—$C_{1-4}$alkylene-OH or —O—$(CH_2)_o$—OH, wherein the subscript o is an integer of from 1-4. In other embodiments, when $R^1$ is —H or $CH_3C(O)$—, $R^2$ is —$CH_2OH$ or —$CH_2OC(O)CH_3$ and $R^4$ is $C_{1-4}$alkyl or $HOCH_2$—, $R^3$ is other than —OH, —$OC_{1-8}$alkyl, —$NHCH_2$aryl, —O—$C_{1-4}$alkylene-OH. In yet other embodiments, when $R^4$ is —$CH_3$— or $C_{1-4}$alkyl, $R^3$ is other than —OH, —$OC_{1-8}$alkyl, —$NHCH_2$aryl, —O—$C_{1-4}$ alkylene-OH. In still other embodiments, when $R^1$ is —H or $C_{1-4}$alkylC(O)—, $R^2$ is HO—$C_{1-4}$alkyl or $C_{1-4}$alkyl-C(O)OCH_2$—, $R_4$ is $C_{1-4}$alkyl or HO—$C_{1-4}$alkyl, then $R^3$ is other than —OH, —$OC_{1-4}$alkyl, arylalkyl-NH— or HO—$C_{1-4}$ alkoxy. The other substituents are as defined in any of the above embodiments and in the summary of the invention.

In some embodiments, when $R^1$ is —H, alkyl-C(O)— or arylalkyl-C(O)—, then $R^2$ is hydroxy-$C_{1-4}$ alkyl, alkyl-C(O)O—$C_{1-4}$alkyl or arylalky-C(O)O—$C_{1-4}$alkyl. The other substituents $R^3$ and $R^4$ are as defined in any of the above embodiments and in the summary of the invention.

In one group of embodiments, the compounds of formula (I) have subformula (Ia):

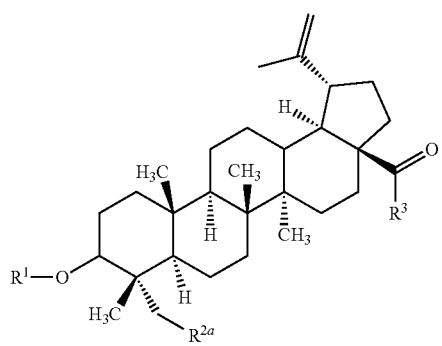

Ia wherein $R^{2a}$ is —OH, alkoxy or alkyl-C(O)O—. In certain instances, $R^{2a}$ is —OH or —OAc. In other instances, $R^1$ is —H or $CH_3C(O)$—. In yet other instances, $R^1$ is —H, alkyl-C(O)— or Ph-$C_{1-4}$alkyl-C(O)—. In still other instances, $R^1$ is —H, $CH_3C(O)$— or benzyl-C(O)—. In some instances, $R^3$ is —$NH_2$, —$NHR^a$ or —$N(R^a)_2$, wherein $R^a$ is alkyl, aryl, arylalkyl, hydroxyalkyl or aminoalkyl; wherein the aliphatic portion of the $R^3$ substitutent is optionally substituted with from 1-2 $R^c$ substituents independently selected from —OH, —$NH_2$, alkoxy, arylalkoxy, halogen, alkyl-C(O)O—, arylalky-C(O)O—, aryl-C(O)O—, alkyl-C(O)NH—, arylalky-C(O)NH, aryl-C(O)NH, alkylamino or dialkylamino. In some instances, wherein $R^3$ is —$NH_2$, —$NHR^a$ or —$N(R^a)_2$, wherein $R^a$ is alkyl, aryl, arylalkyl, hydroxyalkyl or aminoalkyl. In yet other instances, $R^3$ is —$NH_2$, —$NHR^a$ or —$N(R^a)_2$, wherein $R^a$ is selected from the group consisting of $HOCH_2CH_2$—, —$CH_3$, $C_{1-6}$alkyl, $NH_2CHCH_2CH_2$—, $HO(CH_2)_3$— and $NH_2(CH_2)_3$—. The other substituents are as defined in any of the above embodiments and in the summary of the invention.

In another group of embodiments, the compounds of formula (I) have subformula (Ib):

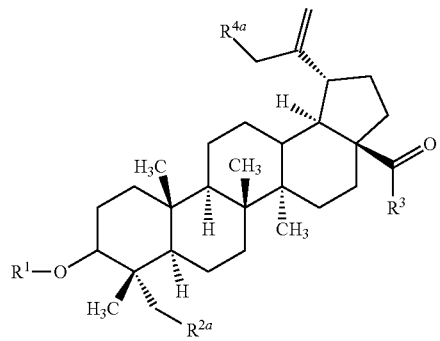

Ib wherein $R^{2a}$ is —OH, alkoxy or alkyl-C(O)O and $R^{4a}$ is —H, —OH, alkoxy, alkyl-C(O)— or arylalkyl-NH. In certain instances, $R^1$ is —H or $CH_3C(O)$—. In other instances, $R^1$ is —H, alkyl-C(O)— or Ph-$C_{1-4}$alkyl-C(O)—. In one occurrence, $R^1$ is benzyl-C(O)—. In some instances, $R^{4a}$ is —H, —OH or $CH_3C(O)O$—. In yet other instances, $R^{4a}$ is alkoxy or arylalkyl-NH. In still other instances, $R^{4a}$ is —H, —OH, —OAc or $PhCH_2NH$—. $R^3$ is as defined in any of above embodiments.

In yet another group of embodiments, the compounds of formula (I) have subformula (Ib-1):

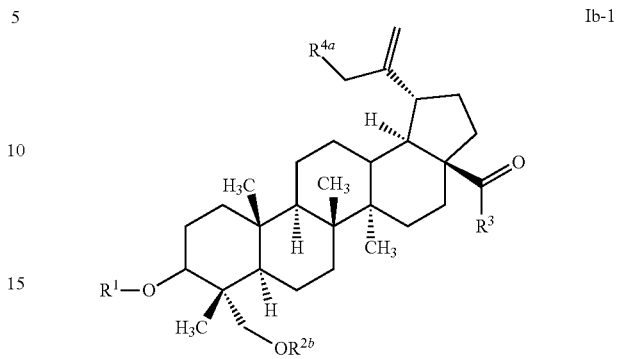

Ib-1 wherein $R^{2b}$ is —H or alkyl-C(O)— or arylalkyl-C(O)—. In certain instances, $R^{2b}$—H, $CH_3C(O)$— or $PhCH_2C(O)$— and $R^1$ is —H or $CH_3C(O)$—. In other instances, $R^3$ is —OH, —$NH_2$, —$OR^b$, —$NHR^a$ or —$N(R^a)_2$. The substituents, $R^a$, $R^b$ are as defined above in formula (I). $R^{4a}$ is as defined above in formula Ib.

In another aspect, the present invention provides a compound of formula (IA):

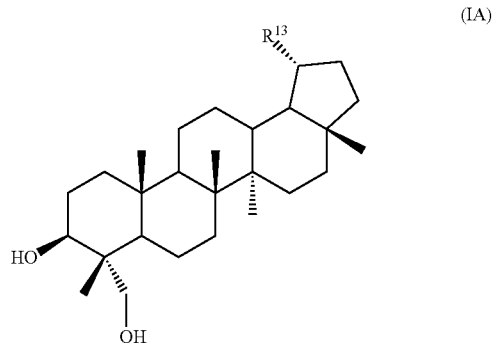

(IA)

or a pharmaceutically acceptable salt, hydrate, solvate or isomer thereof; wherein $R^{12}$ is selected from the group consisting of hydroxyalkyl, alkyl-OC(O)—, aryl-$C_{1-4}$alkyl-OC(O)—, alkyl-C(O)O-alkyl, aryl-$C_{1-4}$alkyl-C(O)O-alkyl, aryl-$C_{1-4}$alkoxy or alkoxyalkyl, wherein the aryl moiety of which is optionally substituted with from 1-3 members selected from halogen, alkyl, aryl-$C_{1-4}$alkyl, hydroxyalkyl, alkoxy, aryl-$C_{1-4}$alkoxy, alkyl-OC(O)—, alkyl-C(O)O—, aryl-$C_{1-4}$alkyl-C(O)O—, aryl-$C_{1-4}$alkyl-OC(O)O—, alkoxyalkyl or aryl-$C_{1-4}$alkoxy-alkyl; and $R^{13}$ is selected from $C_{2-6}$alkenyl or $C_{2-6}$epoxyalkyl, each of which is optionally substituted with from 1-3 members selected from —OH, —$OC_{1-6}$alkyl, aryl-$C_{1-4}$alkyl, alkyl-C(O)O— or aryl-$C_{1-4}$alkyl-C(O)O—.

In one group of embodiments, $R^{12}$ is hydroxyalkyl, alkyl-OC(O)—, aryl-$C_{1-4}$alkyl-OC(O)—, alkyl-C(O)O-alkyl, aryl-$C_{1-4}$alkyl-C(O)O-alkyl, aryl-$C_{1-4}$alkoxy or alkoxyalkyl, wherein the aryl moiety of which is optionally substituted with from 1-3 members selected from Cl, Br, F, $C_{1-6}$alkyl, benzyl, $OHCH_2$—, $CH_3O$—, $CH_3C(O)O$—, $C_{1-4}$alkyl-O—C(O)— or benzyloxy. In certain instances, $R^{12}$ is benzyloxycarbonyl, $C_{1-6}$alkyl-OC(O)—, EtOC(O)—, $CH_3C(O)OCH_2$—, $HOCH_2$—, benzyloxymethyl or $CH_3OCH_2$—. $R^{13}$ is as defined above.

In another group of embodiments, $R^{13}$ is $C_{2-6}$alkenyl or $C_{2-6}$epoxyalkyl, each of which is optionally substituted with from 1-3 members selected from —OH, —OC$_{1-6}$alkyl, benzyl-C$_{1-4}$alkyl, C$_{1-6}$alkyl-C(O)O— or benzyl-C(O)O—. In certain instances, $R^{13}$ is 2-propenyl, 3-hydroxy-2-propenyl, 3-acetoxy-2-propenyl or 2-methyl-2-oxiranyl optionally substituted with from 1-3 members selected from —OH, —OC$_{1-6}$alkyl, benzyl-C$_{1-4}$alkyl, C$_{1-6}$alkyl-C(O)O— or benzyl-C(O)O—. In other instances, $R^{13}$ is 2-propenyl, 2-butenyl, 2-pentenyl, 3-hydroxy-2-propenyl, 3-methyox-2-propenyl, 3-benzyloxy-propenyl, 3-phenyl-2-propenyl, 3-acetoxy-2-propenyl, 3-benzoyloxy-2-propenyl, 2-methyl-2-oxiranyl, 2-ethyl-2-oxiranyl, 2-methoxymethyl-2-oxiranyl, 2-acetoxymethyl-2-oxiranyl, 2-acetoxyethyl-2-oxiranyl, 2-benzyl-2-oxiranyl, 2-benzyloxymethyl-2-oxiranyl, or 2-benzoyloxymethyl-2-oxiranyl. In a preferred embodiment, $R^{13}$ is 2-propenyl, 3-hydroxy-2-propenyl, 3-acetoxy-2-propenyl or 2-methyl-2-oxiranyl.

Tables 1 and 2 list selected compounds according to some embodiments of the present invention. Exemplary compounds include selected 3-O-[α-L-rhamnopyranosyl-(1→2)-α-L-arabinopyranosyl]-3,23-dihydroxy-20(29)-lupen-28-oic acid (DA001) derivatives.

TABLE 1

(I)

| Compound | $R^1$ | $R^2$ | $R^3$ | $R^4$ |
|---|---|---|---|---|
| DA048 | CH$_3$C(O)— | CH$_3$C(O)OCH$_2$— | —NH$_2$ | —CH$_3$ |
| DA049 | CH$_3$C(O)— | CH$_3$C(O)OCH$_2$— | HOCH$_2$CH$_2$NH— | —CH$_3$ |
| DA050 | CH$_3$C(O)— | CH$_3$C(O)OCH$_2$— | CH$_3$NH— | —CH$_3$ |
| DA051 | H— | HOCH$_2$— | —NH$_2$ | —CH$_3$ |
| DA052 | H— | HOCH$_2$— | HOCH$_2$CH$_2$NH— | —CH$_3$ |
| DA053 | H— | HOCH$_2$— | CH$_3$NH— | —CH$_3$ |
| DA054 | CH$_3$C(O)— | CH$_3$C(O)OCH$_2$— | NH$_2$CH$_2$CH$_2$NH— | —CH$_3$ |
| DA055 | CH$_3$C(O)— | CH$_3$C(O)OCH$_2$— | HO(CH$_2$)$_3$NH— | —CH$_3$ |
| DA056 | CH$_3$C(O)— | CH$_3$C(O)OCH$_2$— | NH$_2$(CH$_2$)$_3$NH— | —CH$_3$ |
| DA057 | H— | HOCH$_2$— | NH$_2$CH$_2$CH$_2$NH— | —CH$_3$ |
| DA058 | H— | HOCH$_2$— | HO(CH$_2$)$_3$NH— | —CH$_3$ |
| DA059 | H— | HOCH$_2$— | NH$_2$(CH$_2$)$_3$NH— | —CH$_3$ |
| DA060 | CH$_3$C(O)— | CH$_3$C(O)OCH$_2$— | —OH | CH$_3$C(O)OCH$_2$— |
| DA061 | —H | —CH$_2$OH | —OH | —CH$_2$OH |
| DA062 | CH$_3$C(O)— | CH$_3$C(O)OCH$_2$— | PhCH$_2$NH— | CH$_3$C(O)OCH$_2$— |
| DA063 | —H | —CH$_2$OH | PhCH$_2$NH— | —CH$_2$OH |
| DA064 | CH$_3$C(O)— | CH$_3$C(O)OCH$_2$— | —NH$_2$ | CH$_3$C(O)OCH$_2$— |
| DA065 | CH$_3$C(O)— | CH$_3$C(O)OCH$_2$— | CH$_3$NH— | CH$_3$C(O)OCH$_2$— |
| DA066 | CH$_3$C(O)— | CH$_3$C(O)OCH$_2$— | HO(CH$_2$)$_2$NH— | CH$_3$C(O)OCH$_2$— |
| DA067 | CH$_3$C(O)— | CH$_3$C(O)OCH$_2$— | HO(CH$_2$)$_2$O— | CH$_3$C(O)OCH$_2$— |
| DA068 | —H | —CH$_2$OH | CH$_3$NH— | —CH$_2$OH |
| DA069 | —H | —CH$_2$OH | HO(CH$_2$)$_2$NH— | —CH$_2$OH |
| DA070 | —H | —CH$_2$OH | —NH$_2$ | —CH$_2$OH |
| DA071 | —H | —CH$_2$OH | HO(CH$_2$)$_2$O— | —CH$_2$OH |
| DA072 | CH$_3$C(O)— | CH$_3$C(O)OCH$_2$— | —OH | PhCH$_2$NHCH$_2$— |
| DA073 | —H | —CH$_2$OH | —OH | PhCH$_2$NHCH$_2$— |
| DA074 | CH$_3$C(O)— | CH$_3$C(O)OCH$_2$— | —OH | CH$_3$OCH$_2$— |
| DA075 | —H | —CH$_2$OH | —OH | CH$_3$OCH$_2$— |
| DA076 | CH$_3$C(O)— | CH$_3$C(O)OCH$_2$— | —OH | CH$_3$CH$_2$OCH$_2$— |
| DA077 | —H | —CH$_2$OH | —OH | CH$_3$CH$_2$OCH$_2$— |
| DA078 | CH$_3$C(O)— | CH$_3$C(O)OCH$_2$— | —OH | (CH$_3$)$_2$CHOCH$_2$— |
| DA079 | —H | —CH$_2$OH | —OH | (CH$_3$)$_2$CHOCH$_2$— |

TABLE 2

((IA))

[Structure of compound (IA) with R¹³ and R¹² substituents, HO and OH groups]

| Compound | R¹² | R¹³ |
|---|---|---|
| DA080 | —C(O)OCH₂Ph | 2-propenyl |
| DA081 | —C(O)OCH₂Ph | [epoxide/oxiranyl group] |
| DA083 | —C(O)OCH₂Ph | 3-hydroxy-2-propenyl |
| DA084 | —C(O)OEt | 3-hydroxy-2-propenyl |
| DA085 | CH₃C(O)OCH₂— | 3-acetoxy-2-propenyl |
| DA086 | CH₃C(O)OCH₂— | 3-hydroxy-2-propenyl |
| DA087 | HOCH₂— | 3-hydroxy-2-propenyl |
| DA088 | —CH₂OCH₂Ph | 3-hydroxy-2-propenyl |
| DA089 | —CH₂OCH₃ | 2-propenyl |
| DA090 | —CH₂OCH₃ | 3-hydroxy-2-propenyl |

Preparation of Compounds

As shown in the examples below, there are a variety of synthetic routes by which a skilled artisan can prepare compounds and intermediates of the present invention. Schemes 1-5 illustrate several methods for the preparation of certain 3-O-[α-L-rhamnopyranosyl-(1→2)-α-L-arabinopyranosyl]-3,23-dihydroxy-20(29)-lupen-28-oic acid (Pulchinenoside) derivatives. In each of these schemes R, R″ and R‴ are non-interferring substituents.

The schemes below provide certain synthetic routes that can be followed to access certain Pulchinenoside derivatives of the present invention. Other routes or modification of the routes presented below would be readily apparent to a skilled artisan and within the scope of the present invention.

Scheme 1 shows the general synthesis of certain compounds of the present invention by modification at the C28 position.

Scheme 1

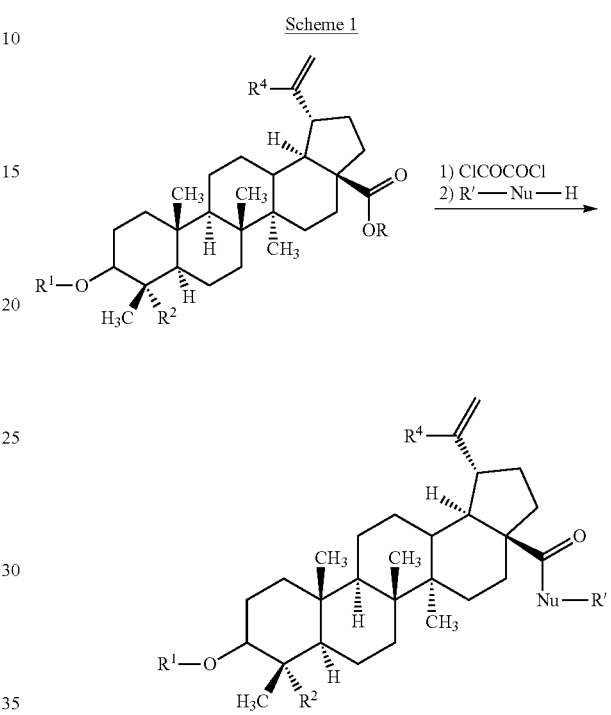

R: H or Ac
Nu: nucleophilic moiety
e.g. O, NR″, NH

Scheme 2 shows the synthesis of certain compounds of the present invention by modification at the C30 position.

Scheme 2

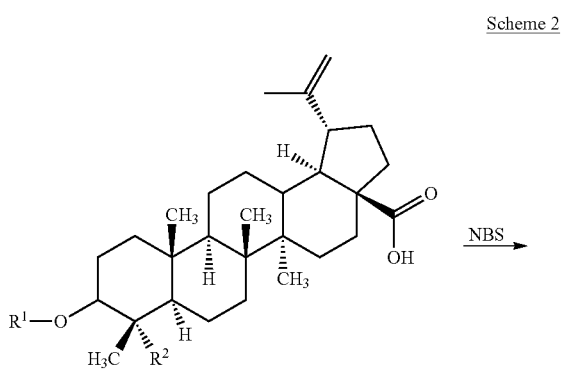

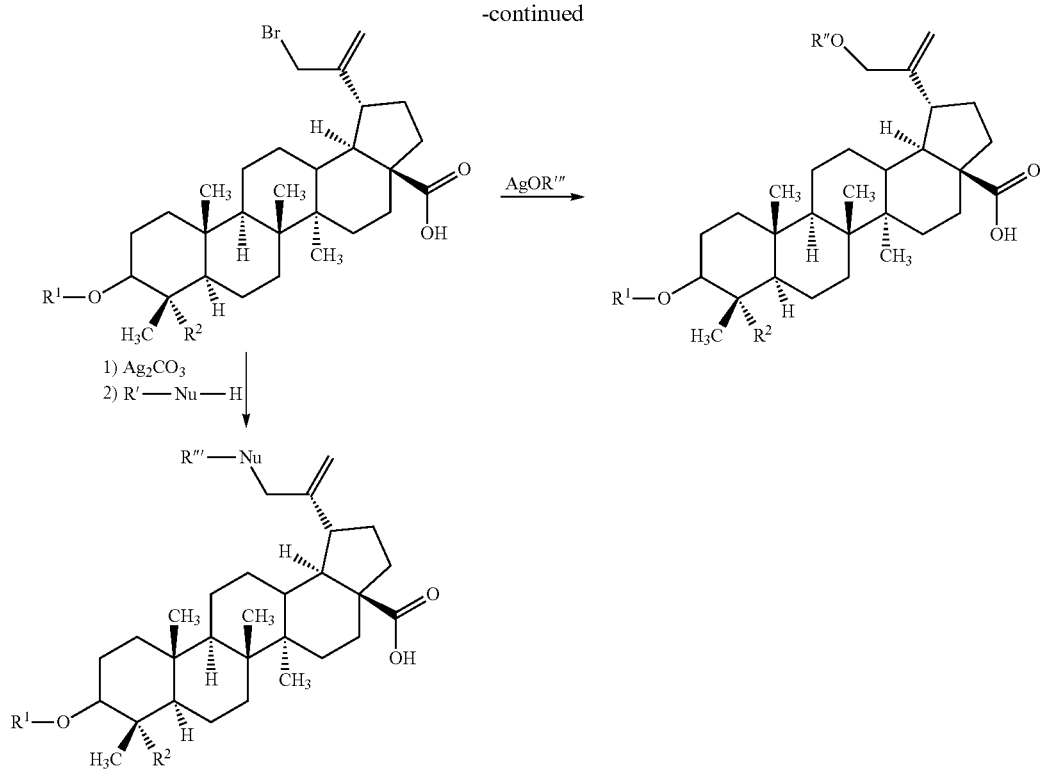

Nu: nucleophilic moiety, e.g. O, NR″, NH

The compounds having formulas I, Ia, Ib and Ib-1 as well as compounds DA048-079 set forth in Table 1 can be prepared by the methods described in Schemes 1-2 above and Schemes 3-5 described herein below.

IV. Pharmaceutical Compositions

In addition to the compounds provided above, the present invention provides a pharmaceutical composition comprising a compound of formulas I, IA, Ia, Ib, Ib-1 or any of compounds DA001-090 or a compound as described herein and pharmaceutical carrier, excipient or diluent. In one aspect, the compositions are useful for modulating PGE2 EP1, EP2 and EP4 receptors activity and inducing CCAAT/enhancer binding protein beta expression in humans and animals will typically contain a compound of formulas I, IA, Ia, Ib, Ib-1 or any of compounds DA001-090 or a compound as described herein and pharmaceutical carrier, excipient or diluent. In another aspect, the compositions are useful for modulating the activity of NMDA receptors and Melanocortin receptors.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled with a carrier that is a suitable polymer as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

V. Methods of Treating Diseases and Disorders Modulated by PGE2 EP1, EP2 and EP4 Receptors and Inducing of Ccaat/Enhancer Binding Protein Beta Expression In another aspect, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of any of formulas I, IA, Ia, Ib and Ib-1 or any of compounds DA001-090 or a compound as described herein or a pharmaceutically acceptable salt or solvate, or a pharmaceutical composition thereof with a cell. The method also includes administering to a mammal an effective amount of a compound of any of formulas I, Ia, Ib and Ib-1 or any of compounds DA001-090 or a pharmaceutically acceptable salt or solvate, or a pharmaceutical composition thereof. In one embodiment, the method includes contacting any of compounds DA001-DA090 with the PGE2 EP1, EP2 and EP4 receptors.

In yet another aspect, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (II):

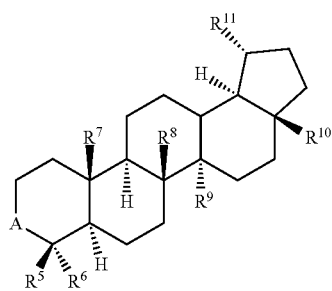

(II)

or a pharmaceutically acceptable salt, hydrate, solvate, isomer thereof, with a cell or a receptor of PGE2. Exemplary receptors include PGE2 EP1, EP2 and EP4 receptors.

In formula II, $R^5$, $R^7$, $R^8$ and $R^9$ are each independently $C_{1-4}$alkyl. In one embodiment, $R^5$, $R^7$, $R^8$ and $R^9$ are each independently selected from the group consisting of methyl, ethyl, propyl, isopropyl, butyl, iso-butyl and s-butyl. In another embodiment, $R^5$, $R^7$, $R^8$ and $R^9$ are each independently methyl.

In formula II, $R^6$ is selected from the group consisting of $C_{1-6}$haloalkyl, $C_{3-6}$cycloalkyl, —$X^1$CN, —$X^1$NO$_2$, —$X^1$C(O)$R^a$, —$CR^b$=$NOR^c$, —$X^1$CO$_2$$R^c$, —$X^1$C(O)NR$^c$R$^d$, —$X^1$C(NR$^c$R$^d$)=NR$^c$, —$X^1$C(O)NR$^c$S(O)R$^d$, —$X^1$C(O)NR$^c$S(O)R$^d$, —$X^1$OR$^e$, —$X^1$SR$^e$, —$X^1$NHR$^e$ and —$X^1$N(R$^e$)$_2$ and —$X^1$R$^e$, wherein each $X^1$ is independently a bond or $C_{1-4}$alkylene, wherein $R^e$ is $C_{1-6}$alkyl, $C_{1-6}$haloalkyl, arylC$_{0-6}$alkyl or $C_{3-6}$cycloalkyl substituted with from 1-3 members of R$^f$, and wherein R$^a$, R$^b$, R$^c$ and R$^d$ are each independently H, $C_{1-6}$alkyl or aryl-$C_{1-6}$alkyl; wherein the aliphatic portion of each $R^6$ substituent is optionally substituted with from 1-3 R$^f$, wherein R$^f$ is selected from the group consisting of halo, CN, NO$_2$, —OH, —R$^g$, —OR$^g$, —OC(O)NHR$^g$, —OC(O)N(R$^g$)$_2$, —OC(O)R$^g$, —OC(O)H, —NH$_2$, —NHR$^g$, —N(R$^g$)$_2$, —SH, —SR$^g$, —S(O)$_2$R$^g$, —SO$_2$NH$_2$, —SO$_2$NHR$^g$, —SO$_2$N(R$^g$)$_2$, —NHS(O)$_2$R$^g$, —NR$^g$S(O)$_2$R$^g$, —C(O)NH$_2$, —C(O)NHR$^g$, —C(O)N(R$^g$)$_2$, —C(O)H, —C(O)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —COOH, —CO$_2$R$^g$, —NHCO$_2$R$^g$, —NR$^g$CO$_2$R$^g$ and —OSi(R$^g$)$_3$, wherein each R$^g$ is independently a $C_{1-6}$alkyl. R$^g$ can also be optionally substituted with an aryl. In certain instances, the aryl in R$^g$ can be further substituted with from 1-3 R$^f$. In one embodiment, R$^a$, R$^b$, R$^c$ and R$^d$ are each independently H, $C_{1-6}$alkyl or phenyl-$C_{1-6}$alkyl.

In one group of embodiments of compounds having formula II, $R^6$ is selected from the group consisting of —$X^1$C(O)$R^a$, —$CR^b$=$NOR^c$, —$X^1$NHR$^e$, —$X^1$N(R$^e$)$_2$ and —$X^1$R$^e$. In certain instances, $X^1$ is a bond. In certain other instances, $X^1$ is CH$_2$. In yet certain other instances, R$^e$ is $C_{1-6}$alkyl substituted with from 1-3 R$^f$. In some occasions, R$^e$ is —CH$_2$—R$^f$.

In another group of embodiments of compounds having formula II, $R^6$ is selected from the group consisting of —CH$_2$OH, —CH$_2$OAc, —CH$_2$OC$_{1-6}$alkyl, —CHO, —CH=NOR$^c$, —CH$_2$NHR$^e$, —CH$_2$OSi(R$^e$)$_3$ and —CH$_2$OSi(R$^f$)$_3$. In certain instances, $R^6$ is —CH$_2$OH, —CH$_2$OAc, —CH$_2$OC$_{1-6}$alkyl, —CHO, —CH$_2$OSiTBS, —CH=NOH, —CH$_2$NH—C$_{1-6}$alkyl-aryl and —CH=NOR$^g$. In certain other instances, $R^6$ is selected from the group consisting of —CH$_2$OH, —CH$_2$OAc, —CH$_2$OTBS, —CHO, —CH=NOH and —CH$_2$NHBn.

In formula II, the symbol A is selected from the group consisting of C=Y$^1$, C=NOR$^c$, C=NOC(O)R$^g$, C=NOCO$_2$R$^g$, C=NOC(O)NH$_2$, C=NOC(O)NHR$^g$ and C=NOC(O)N(R$^g$)$_2$ and —CR$^c$R$^h$, wherein Y$^1$ is =O or =S, and R$^h$ is selected from the group consisting of halo, CN, NO$_2$, —OH, —OR$^i$, —OC(O)NHR$^i$, —OC(O)N(R$^i$)$_2$, —OC(O)R$^i$, —OC(O)H, —NH$_2$, —NHR$^i$, —N(R$^i$)$_2$, —SH, —SR$^i$, —S(O)$_2$R$^i$, —SO$_2$NH$_2$, —SO$_2$NHR$^i$, —SO$_2$N(R$^i$)$_2$, —NHS(O)$_2$R$^i$, —NR$^i$S(O)$_2$R$^i$, —C(O)NH$_2$, —C(O)NHR$^i$, —C(O)N(R$^i$)$_2$, —C(O)H, —C(O)R$_i$, —NHC(O)R$^i$, —NR$^i$C(O)R$^i$, —NHC(O)NH$_2$, —NR$^i$C(O)NH$_2$, —NR$^i$C(O)NHR$^i$, —NHC(O)NHR$^i$, —NR$^i$C(O)N(R$^i$)$_2$, —NHC(O)N(R$^i$)$_2$, —COOH, —CO$_2$R$^i$, —NHCO$_2$R$^i$, —NR$^i$CO$_2$R$^i$, —OSi(R$^i$)$_3$, —O—(Z)$_{1-6}$, —S—(Z)$_{1-6}$, —NH(Z)$_{1-6}$ and —NR$^c$(Z)$_{1-6}$, wherein each R$^i$ is independently a $C_{1-6}$alkyl, $C_{1-6}$haloalkyl, $C_{3-6}$cycloalkyl, arylC$_{0-6}$alkyl or —(Z)$_{1-6}$, optionally substituted with from 1-3 R$^f$; —(Z)$_{1-6}$ is a sequence of 1-6 independently selected $C_{4-7}$monosaccharide residues linked together through ether bonds, optionally Z is substituted with from 1-3 $C_{1-6}$alkyl or R$^f$.

In one group of embodiments of compounds having formula II, A is CR$^c$—O(Z)$_{1-6}$. In one instance, Z is independently $C_{4-7}$monosaccharide. In another instance, Z is independently $C_{5-6}$monosacchardide residue. Exemplary $C_{4-7}$monosaccharides include, but are not limited to, erythrose, threose, arabinose, ribose, ribulose, xylose, xylulose, lyxose, allose, altrose, fructose, galactose, glucose, gulose, idose, mannose, sorbose, talose and tagatose, Sedoheptulose. Prefereably, Z is a $C_{5-6}$monosaccharide residue selected from the group consisting of arabinose, ribose, ribulose, xylose, xylulose, lyxose, allose, altrose, fructose, galactose, glucose, gulose, idose, mannose, sorbose, talose, tagatose and each of which is optionally acetylated. In yet another instance, —(Z)$_2$ is selected from the group consisting of:

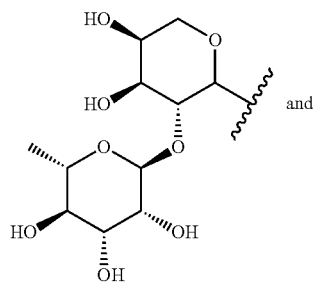

and

-continued

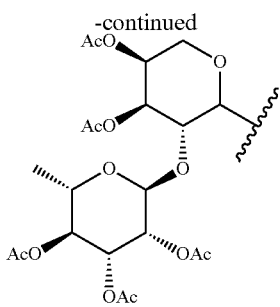

where the wavy line indicates the point of attachment to the rest of the molecule.

In another group of embodiments of compounds having formula II, A is selected from the group consisting of C=O, $CR^CR^h$, $C=NOR^c$, $C=NOC(O)R^g$, $C=NOCO_2R^g$, $C=NOC(O)NH_2$, $C=NOC(O)NHR^g$ and $C=NOC(O)N(R^g)_2$. In one instance, A is selected from the group consisting of C=O, $CR^c$—$OR^d$, $CR^c$—$OC(O)R^i$, $C=NOR^c$, $C=NOC(O)R^g$, $C=NOCO_2R^g$, $C=NOC(O)NH_2$, $C=NOC(O)NHR^g$, $C=NOC(O)N(R^g)_2$, CW—$NH_2$, CW—$NHR^i$, $CR^c$—$OSi(R^i)_3$ and $CR^c$—$N(R^i)_2$. In another instance, A is selected from the group consisting of C=O, $CR^c$-β-OH, $CR^c$—OBn, $CR^c$-OAc, C=NOH, $CR^C$—$NHR^e$ and $CR^c$—SiTBS. In one instance, $R_c$ is H. In certain other instances, A is selected from the group consisting of CH—OH, CHOAc, C=O, C=NOAc, CHO,

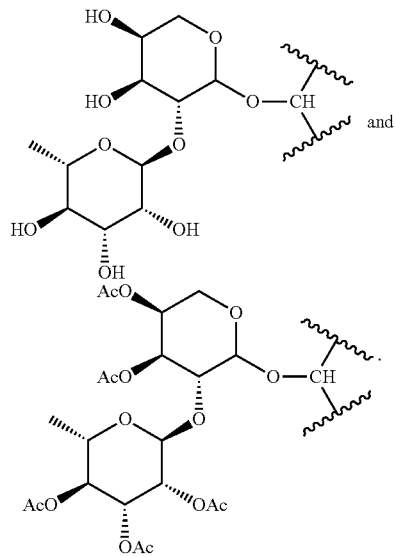

$R^{10}$ is selected from the group consisting of $C_{1-6}$haloalkyl, $C_{3-6}$cycloalkyl, —$X^2$CN, —$X^2NO_2$, —$X^2C(O)R^a$, —$CR^b$=$NOR^c$, —$X^2CO_2R^c$, —$X^2C(O)NR^cR^d$, —$X^2C(NR^cR^d)$=$NR^c$, —$X^2C(O)NR^cS(O)R^d$, —$X^2C(O)NR^cS(O)R^d$, —$X^2OR^a$, —$X^2SR^a$, —$X^2NHR^a$ and —$X^2N(R^a)_2$ and —$X^2R^e$, wherein each $X^2$ is independently a bond or $C_{1-4}$alkylene; wherein the aliphatic portion of each $R^{10}$ substituent is optionally substituted with from 1-3 $R^f$, wherein the two adjacent $R^f$ substituents together with the atoms to which they are attached optionally form a 5-membered heterocyclic ring having from 1-3 heteroatoms selected from N, O or S, wherein the heterocyclic ring is optionally substituted with from 1-3 $R^g$, and the aromatic ring of each $R^{10}$ is optionally substituted with from 1-5 $R^f$.

In one group of embodiments, $R^{10}$ is selected from the group consisting of —$X^2OC(O)R^a$, —$X^2CO_2R^c$, —$X^2C(O)NR^cR^d$, —$X^2R^e$, —$X^2C(O)R^a$ and —$CR^b$=$NOR^c$. In certain instances, $R^{10}$ is selected from the group consisting of —COOH, —$COOR^g$, —$CH_2OH$, —$CH_2OR^g$, —CHO, —$CH_2NHCH_2Ph$ and —CH=$NOR^c$, —$CH_2OAc$, —$CH_2CH_2OH$, —$C_{1-6}$alkylene-OH, $CO_2$—$C_{1-6}$alkylene-OH, —$CH_2CH(OH)$—$CH_2OH$, $CO_2$—$CH_2CH(OH)$—$CH_2OH$, —$C_{1-6}$alkylene-$NH_2$, CONH—$C_{1-6}$alkylene-$NH_2$, —$C(O)NH_2$, —$C(O)NHR^c$ and

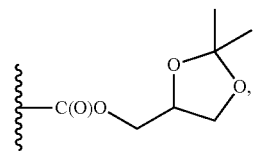

wherein $R^c$ is optionally substituted with —OH or $NH_2$. In certain other instances, $R^{10}$ is selected from the group consisting of —COOH, —$CH_2OH$ and —CH=$NOR^c$. In one occurence, $R^c$ is —H. In another occurrence, $R^{10}$ is selected from the group consisting of —COOH, —COOMe, —COOEt, —$CH_2OH$, —CHO, —CH=NOH, —$CH_2OAc$, —$CH_2CH_2OH$, —$CO_2CH_2CH_2OH$, —$C_{1-6}$alkylene-OH, —$CO_2$—$C_{1-6}$alkylene-OH, —$CO_2CH_2CH_2OH$, —$CH_2CH(OH)$—$CH_2OH$, $CO_2$—$CH_2CH(OH)$—$CH_2OH$, —$C_{1-6}$alkylene-$NH_2$, —$C(O)NH_2$, —$C(O)NHCH_3$, —$C(O)NHCH_2Ph$, —$C(O)NH$—$C_{1-6}$alkylene-OH, —$CONHCH_2CH_2OH$, —$C(O)NH$—$C_{1-6}$alkylene-$NH_2$, —$CONHCH_2CH_2NH_2$ and

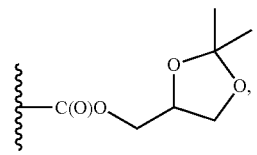

In yet another occurrence, $R^{10}$ is selected from the group consisting of —COOH, —COOMe, —COOEt, —$CH_2OH$, —CHO, —CH=NOH, —$CH_2OAc$, —$CO_2CH_2CH_2OH$, —$CH_2CH_2OH$, —$CO_2CH_2CH(OH)$—$CH_2OH$, —$C(O)NH_2$, —$C(O)NHCH_3$, —$C(O)NHCH_2Ph$, —$C(O)NH$—$CH_2CH_2$—$NH_2$ and

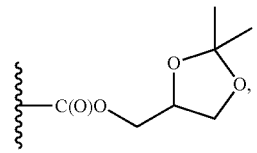

wherein the wavy line indicates the point of attachment to the rest of the molecule.

$R^{11}$ is selected from the group consisting of $C_{1-6}$alkyl, $C_{1-6}$haloalkyl, $C_{3-6}$cycloalkyl, $C_{2-6}$alkenyl, $C_{2-6}$haloalkenyl, C$_{5-6}$cycloalkenyl and C$_{2-6}$epoxyalkyl, optionally substituted with from 1-3 R$^f$. In certain instances, the aryl in R$^f$ can be further substituted with from 1-3 R$^f$ groups.

In one group of embodiments of the compounds having formula (II), R$^{11}$ is selected from the group consisting of C$_{1-6}$alkyl, C$_{2-6}$alkenyl and C$_{2-6}$epoxyalkyl, each of which is optionally substituted with 1-3 R$^f$. In certain instances, R$^{11}$ is C$_{1-6}$alkyl or C$_{2-6}$alkenyl. In certain other instances, R$^{11}$ is ethylene oxide radical, optionally substituted with 1-3 R$^f$. For example, R$^{11}$ is ethylene oxide substituted with from 1-3 C$_{1-6}$alkyl. Exemplary R$^{11}$ include epoxyethyl, epoxypropyl, epoxybutyl, epoxypentyl, epoxyhexyl and the other isomeric forms thereof, such as 1,2-epoxypropyl, 1,2-epoxy-2-propyl, 1,2-epoxy-3-propyl, 1,2-epoxybutyl, 1,2-epoxy-2-butyl, 1,2-epoxy-3-butyl, 2,3-epoxybutyl, and the like. In yet certain other instances, R$^{11}$ is selected from the group consisting of —CH═CH$_2$, —C(CH$_3$)═CH$_2$, —C(CH$_2$OH)═CH$_2$, —CH$_2$CH$_3$, —CH$_2$CH$_2$CH$_3$, —CH(CH$_3$)CH$_3$, epoxyethyl, epoxypropyl, epoxybutyl and 1,2-epoxy-2-propyl. In one occurrence, R$^{11}$ is selected from the group consisting of —C(CH$_3$)═CH$_2$, —C(CH$_2$OH)═CH$_2$ and 1,2-epoxy-2-propyl.

In one group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (IIa):

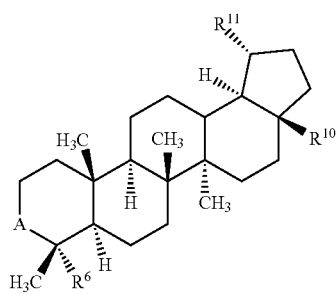

or a pharmaceutically acceptable salt, hydrate, solvate, isomer thereof, with the receptor of PGE2. Exemplar receptors include EP1, EP2 and EP4 receptors.

The substituents R$^6$, R$^{10}$, R$^{11}$ and A in formula (IIa) are as defined above in formula (II). In a group of instances of compounds having formula IIa, A is CR$^c$—OH. In one instance, R$^{10}$ is —COOH. In another group of instances of compounds having formula IIa, R$^6$ is C$_{1-6}$alkyl, haloalkyl or cycloalkyl substituted with 1-3 hydroxyl groups and A is other than CR$^c$—OC(O)C$_{1-6}$alkyl. In yet another group of instances, R$^6$ is C$_{1-6}$alkyl substituted with a hydroxyl group. For example R$^6$ is —CH$_2$OH.

In a second group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (IIa-1):

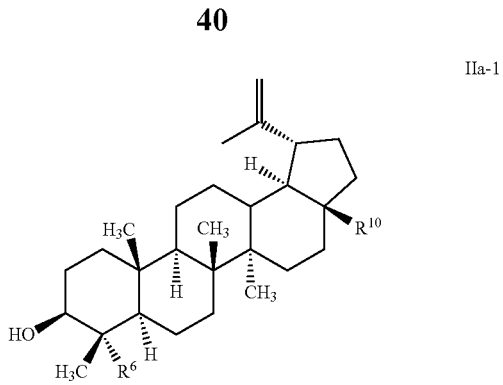

or a pharmaceutically acceptable salt, hydrate, solvate, isomer thereof, with the receptor of PGE2. Exemplar receptors include EP1, EP2 and EP4 receptors. The substituents R$^6$ and R$^{10}$ are as defined above in formulas II or IIa.

In a third group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (IIa-2):

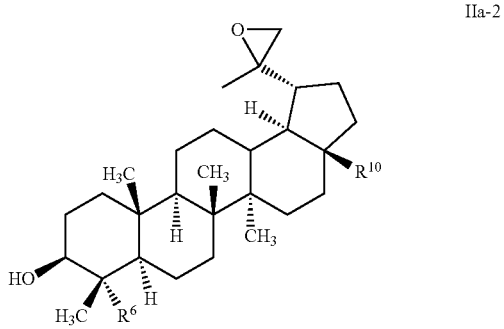

or a pharmaceutically acceptable salt, hydrate, solvate, isomer thereof, with the receptor of PGE2. Exemplar receptors include EP1, EP2 and EP4 receptors. The substituents R$^6$ and R$^{10}$ are as defined above in formulas II or IIa.

In a fourth group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (IIa-3):

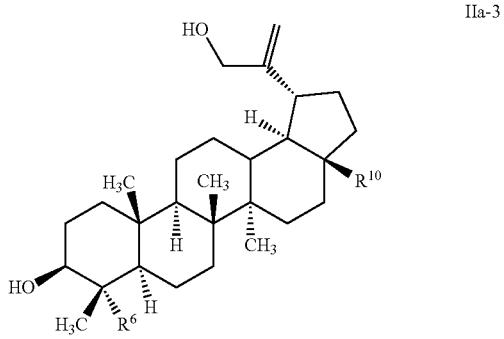

or a pharmaceutically acceptable salt, hydrate, solvate, isomer thereof, with the receptor of PGE2. Exemplar receptors include EP1, EP2 and EP4 receptors. The substituents $R^6$ and $R^{10}$ are as defined in formulas II or IIa.

In a fifth group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (IIa-4):

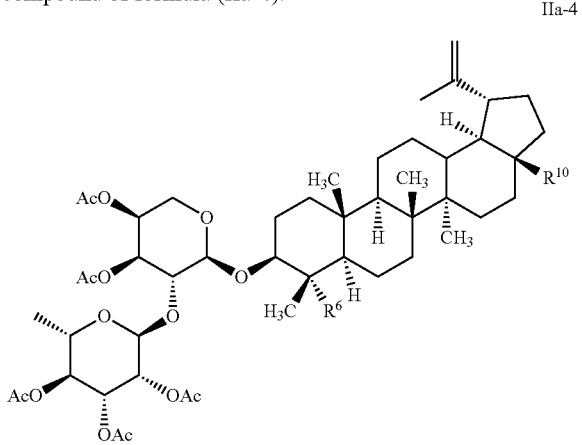

IIa-4 or a pharmaceutically acceptable salt, hydrate, solvate, isomer thereof, with the receptor of PGE2. Exemplar receptors include EP1, EP2 and EP4 receptors. The substituents $R^6$ and $R^{10}$ are as defined above in formulas II or IIa.

In a sixth group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound of formula (IIa-5):

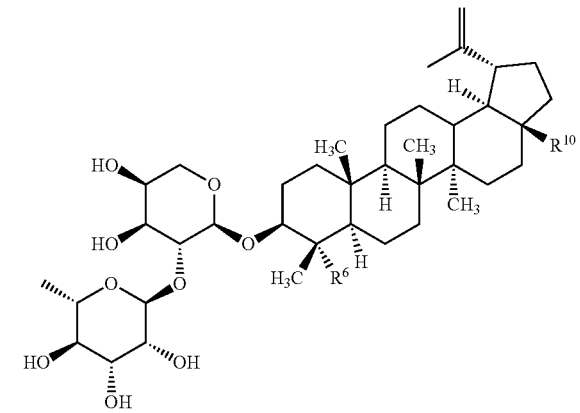

IIa-5 or a pharmaceutically acceptable salt, hydrate, solvate, isomer thereof, with the receptor of PGE2. Exemplar receptors include EP1, EP2 and EP4 receptors. The substituents $R^6$ and $R^{10}$ are as defined above in formulas II or IIa.

In another group of embodiments, the present invention provides a method of inhibiting the activities of PGE2 EP1, EP2 and EP4 receptors activity and a method of inducing CCAAT/enhancer binding protein beta expression for preventing, treating or aliomerating pain or inflammation and/or for regulating acute phase reactions, inflammation and hemopoiesis in a mammal. The method includes contacting a compound having a formula selected from the group consisting of DA001-DA047 or a pharmaceutically acceptable salt, hydrate, solvate, isomer thereof with the receptor of PGE2. Exemplar receptors include EP1, EP2 and EP4 receptors. The compounds DA001-DA047 are set forth in Table 3 below.

TABLE 3

| Compound | A | $R^2$ | $R^6$ | $R^7$ |
|---|---|---|---|---|
| DA001 | (sugar group) | —CH$_2$OH | —COOH | 2-propenyl |

TABLE 3-continued

| Compound | A | R² | R⁶ | R⁷ |
|---|---|---|---|---|
| DA002 | CH—OH | —CH₂OH | —COOH | 2-propenyl |
| DA003 | CH—OH | —CH₂OH | —COOMe | 2-propenyl |
| DA004 | CH—OH | —CH₂OH | —COOEt | 2-propenyl |
| DA005 | CH—OH | —CH₂OH | —COOH | isopropyl |
| DA006 | CH—OAc | —CH₂OAc | —COOH | 2-propenyl |
| DA007 | CH—OAc | —CH₂OH | —COOH | 2-propenyl |
| DA008 | CH—OH | —CH₂OAc | —COOH | 2-propenyl |
| DA009 | CH—OH | —CH₂OH | —COOH | epoxide group |
| DA010 | CH—OH | —CH₂OH | —CH₂OH | 2-propenyl |
| DA011 | CH—OAc | —CH₂OAc | —COOMe | 2-propenyl |
| DA012 | CH—OH | —CH₂OAc | —COOMe | 2-propenyl |
| DA013 | C=O | —CH₂OAc | —COOMe | 2-propenyl |
| DA014 | C=O | —CH₂OH | —COOMe | 2-propenyl |
| DA015 | C=N—OH | —CH₂OH | —COOMe | 2-propenyl |
| DA016 | C=O | —CH₂OAc | —COOH | 2-propenyl |
| DA017 | CH—OH | —CH₂OTBS | —COOH | 2-propenyl |
| DA018 | C=O | —CH₂OH | —COOH | 2-propenyl |
| DA019 | CH=N—OH | —CH₂OH | —COOH | 2-propenyl |
| DA020 | CH—OH | —CH₂OH | —CHO | 2-propenyl |
| DA021 | C=O | —CH₂OH | —CH=NOH | 2-propenyl |
| DA022 | CH—OAc | —CH₂OAc | —CHO | 2-propenyl |
| DA023 | CH—OAc | —CH₂OAc | —CH₂NHCH₂Ph | 2-propenyl |
| DA024 | CH—OH | —CH₂OH | —CH₂NHCH₂Ph | 2-propenyl |
| DA025 | C=N—OAc | —CH₂OAc | —COOMe | 2-propenyl |
| DA026 | CH—OH | —CHO | —COOMe | 2-propenyl |
| DA027 | CH—OH | —CH=NOH | —COOMe | 2-propenyl |
| DA028 | CH—OH | —CH₂NHBn | —COOMe | 2-propenyl |
| DA029 | CH—OH | —CH₂NHBn | —COOH | 2-propenyl |
| DA033 | CH—OH | —CH₂OH | —CH₂OAc | 2-propenyl |
| DA034 | CH—OH | —CH₂OH | —CH₂OAc | epoxide group |
| DA035 | CH—OH | —CH₂OH | —CH₂OAc | epoxide group |
| DA036 | C=O | —CHO | —CH₂OAc | epoxide group |
| DA037 | CH—OH | —CH₂OH | —C(O)OMe | 3-hydroxy-2-propenyl |

TABLE 3-continued
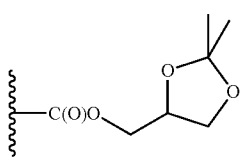
| Compound | A | R² | R⁶ | R⁷ |
|---|---|---|---|---|
| DA038 | CH—OH | —CH₂OH | 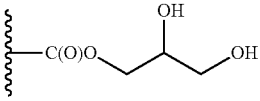 | 2-propenyl |
| DA039 | CH—OH | —CH₂OH | 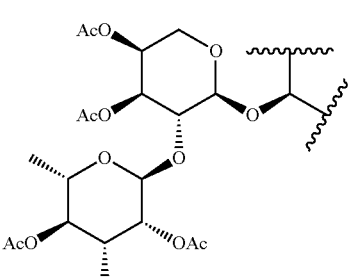 | 2-propenyl |
| DA040 | CH—OH | —CH₂OH | —C(O)O(CH₂)₂OH | 2-propenyl |
| DA041 | CH—OAc | —CH₂OAc | —C(O)NHCH₂Ph | 2-propenyl |
| DA042 | CH—OH | —CH₂OH | —C(O)NHCH₂Ph | 2-propenyl |
| DA043 | 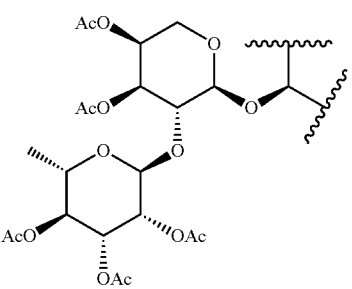 | —CH₂OAc | —C(O)OAc | 2-propenyl |
| DA044 | 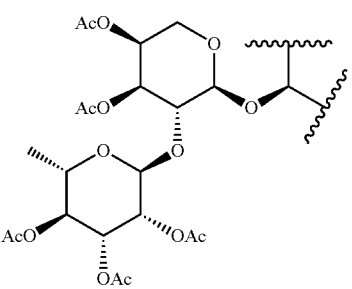 | —CH₂OAc | —C(O)OH | 2-propenyl |
| DA045 | 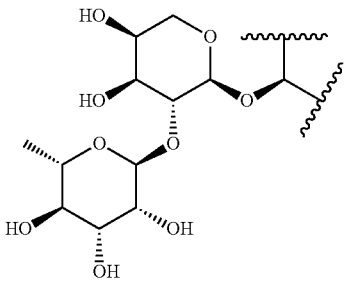 | —CH₂OH | —C(O)NHCH₂Ph | 2-propenyl |

TABLE 3-continued

| Compound | A | R² | R⁶ | R⁷ |
|---|---|---|---|---|
| DA046 | (2,3,4-tri-O-acetyl-rhamnopyranosyl)(1→2)-(3,4-di-O-acetyl-arabinopyranosyl) | —CH₂OAC | —C(O)NH(CH₂)₂NH₂ | 2-propenyl |
| DA047 | α-L-rhamnopyranosyl-(1→2)-α-L-arabinopyranosyl | —CH₂OH | —C(O)NH(CH₂)₂NH₂ | 2-propenyl |

The compounds of any of formulas II, IIa, IIa-1 to IIa-5 and DA001-DA047 are also described in PCT Patent Application No. PCT/CN2008/000348, which is incorporated herein by reference in its entirety. The compounds of any of formulas II, IIa, IIa-1 to IIa-5 and DA001-DA047 can be prepared according to the procedures set forth in PCT Patent Application No. PCT/CN2008/000348, which is incorporated herein by reference. Compound DA001, a triterpene compound 3-O-[α-L-rhamnopyranosyl-(1→2)-α-L-arabinopyranosyl]-3,23-dihydroxy-20(29)-lupen-28-oic acid was isolated from the herb *Pulsatilla Chinensis* (see, Chen et al. "Saponins from *Pulsatilla Chinensis*" *Acta Chimica Sinica* 1990, 48, 501).

In one embodiment, the present invention provides compounds of any of formulas I, IA, Ia, Ib, Ib-1, II, IIa, IIa-1 to IIa-5 and DA001-DA090 or a compound as described herein, which can be used to inhibit the binding of PGE2 receptor ligand to PGE2 receptors in vitro or in vivo. Exemplary receptors of PGE2 include PGE2 EP1, EP2 and EP4 receptors. In general, such methods comprise the step of contacting a PGE2 EP1, EP2 or EP4 receptor with a sufficient amount of one or more PGE2 EP1, EP2 and EP4 receptor antagonist as provided herein, in the presence of PGE2 EP1, EP2 and EP4 receptor ligand in aqueous solution and under conditions otherwise suitable for binding of the ligand to PGE2 EP1, EP2 and EP4 receptors. The PGE2 EP1, EP2 and EP4 receptors may be present in suspension (e.g., in an isolated membrane or cell preparation), or in a cultured or isolated neuron cell.

Preferably, the amount of PGE2, EP1, EP2 and EP4 receptor modulator contacted with the receptor should be sufficient to inhibit binding to PGE2 EP1, EP2 and EP4 receptor in vitro as measured, for example, using whole-cell patch clamp studies, calcium mobilization assay, fluormetric imaging plate reader (FLIPR) assey, or neuronal survival assay as described herein.

In one embodiment, the compounds of any formulas I, IA, Ia, Ib, Ib-1, II, IIa, IIa-1 to IIa-5 and DA001-DA090 or a compound as described herein are used to modulate, preferably inhibit, the activity of a PGE2 EP1, EP2 or EP4 receptor, for example, by contacting one or more compound(s) of any of formulas I, IA, Ia, Ib, Ib-1, II, IIa, IIa-1 to IIa-5 and DA001-DA090 with a a PGE2 EP1, EP2 or EP4 receptor (either in vitro or in vivo) under conditions suitable for binding of the modulator(s) to the receptor. The receptor may be present in solution or suspension, in a cultured or isolated cell preparation or within a patient. Any modulation of the activity may be assessed using patch clamp, FLIPR, or calcium assay techniques by detecting the ion current across the surface of neurons, or by survival assay, or immunocytochemical analysis. In general, an effective amount of a compound of any of formulas I, IA, Ia, Ib, Ib-1, II, IIa, IIa-1 to IIa-5 and DA001-DA090 antagonist(s) in an amount sufficient to modulate a PGE2 EP1, EP2 or EP4 receptor activity in vitro within patch clamp studies and calcium mobilization assays, followed by neuronal survival assays.

In another embodiment, comparative studies are conducted to determine its efficacy in comparison to the known antagonist memantine. The effect of the compound on cognitive functions, such as in treating dementia, improving memory in test subjects is evaluated in animal models using Morris Water Maze task.

In yet another aspect, the present invention provides methods and use of a compound of any of formulas I, IA, Ia, Ib, Ib-1, II, IIa, IIa-1 to IIa-5 and DA001-DA090 or a compound as described herein for the treating, preventing and/or ameliorating pain or inflammation in a mammal in a mammal or human. The methods include administering to the mammal or human a therapeutically effective amount of the compounds of any of formulas I, IA, Ia, Ib, Ib-1, II, IIa, IIa-1 to IIa-5 and DA001-DA090 or a compound as described herein.

In a further aspect, the present invention provides methods and uses of a compound of any of formulas I, IA, Ia, Ib, Ib-1, II, IIa, IIa-1 to IIa-5 and DA001-DA090 or a compound as described herein for inducing CCAAT/enhancer binding protein beta (C/EBP-b) mRNA in cortical neuron cultures. The methods include contacting a compound of any of formulas I, IA, Ia, Ib, Ib-1, II, IIa, Ia-1 to IIa-5 and DA001-DA090 or a compound as described herein with a cell.

In still another aspect, the present invention provides methods and use of a compound of any of formulas I, IA, Ia, Ib, Ib-1, II, IIa, IIa-1 to IIa-5 and DA001-DA090 or a compound as described herein for regulating acute phase reactions, inflammation or hemopoiesis in a mammal. The method includes administering to the mammal a therapeutically effective amount of a compound of any of formulas I, IA, Ia, Ib, Ib-1, II, IIa, IIa-1 to IIa-5 and DA001-DA090 or a compound as described herein.

In another aspect, the present invention provides a use of a compound of any of formulas I, IA, Ia, Ib, Ib-1, II, IIa, IIa-1 to IIa-5 and DA001-DA090 or a compound as described herein for modulating the expression of pro-inflammation proteins in a mammal. The use includes the exogenous treatments with a compound of any of formulas I, IA, Ia, Ib, Ib-1, II, IIa, IIa-1 to IIa-5 and DA001-DA090 or a compound as described herein. The present invention further provides a use of a compound of any of formulas I, IA, Ia, Ib, Ib-1, II, IIa, IIa-1 to IIa-5 and DA001-DA090 or a compound as described herein for improving the symptoms of experimental autoimmune encephalomyelitis in a mammal. The use includes administering to the mammal an effective amount of a compound of any of formulas I, IA, Ia, Ib, Ib-1, II, IIa, IIa-1 to IIa-5 and DA001-DA090 or a compound as described herein. The invention also provides a use of a compound of any of formulas I, IA, Ia, Ib, Ib-1, II, IIa, IIa-1 to IIa-5 and DA001-DA090 or a compound as described herein for decreasing lymphocyte infiltration into the spinal cords of a mammal.

In another aspect, the present invention provides a method of inhibiting the activities of a kainate receptor. The method includes contacting a compound as described herein or a compound of any of formulas I, IA, Ia, Ib, Ib-1, II, IIa, IIa-1 to IIa-5 and DA001-DA090, or a pharmaceutically acceptable salt or solvate thereof, with a kainate receptor.

In yet another aspect, the present invention provides a method of protecting a neuron against amyloid beta peptide excitotoxicity. The method includes contacting a compound as described herein or a compound of any of formulas I, IA, Ia, Ib, Ib-1, II, IIa, IIa-1 to IIa-5 and DA001-DA090, or a pharmaceutically acceptable salt or solvate thereof, with a neuron cell. In one embodiment, the neuron is a cortical neuron. The invention further provides a method of inhibiting the production of amyloid-beta peptides. The method includes contacting a compound as described herein or a compound of any of formulas I, IA, Ia, Ib, Ib-1, II, IIa, IIa-1 to IIa-5 and DA001-DA090, or a pharmaceutically acceptable salt or solvate thereof, with a PGE2 receptor.

In one embodiment, the present invention provides a compound as described herein or a compound of any of formulas I, IA, Ia, Ib, Ib-1, II, IIa, IIa-1 to IIa-5 and DA001-DA090, or a pharmaceutically acceptable salt or solvate thereof, for use as a medicament.

In another embodiment, the present invention provides a compound as described herein or a compound of any of formulas I, IA, Ia, Ib, Ib-1, II, IIa, IIa-1 to IIa-5 and DA001-DA090, or a pharmaceutically acceptable salt or solvate thereof, for use in the treatment of pain and inflammation. In certain instances, the pain includes, but are not limited to, acute pain, chronic pain, visceral pain, inflammatory pain and neuropathic pain and the pain as described herein. In other instances, the inflammation includes chronic inflammation and acute inflammation; inflammation that is categorized in terms of its severity, e.g., mild, moderate, or severe; and inflammation that is a symptom or a result of a disease state or syndrome.

In yet another embodiment, the present invention provides a use of a compound as described herein or a compound of any of formulas I, IA, Ia, Ib, Ib-1, II, IIa, IIa-1 to IIa-5 and DA001-DA090, or a pharmaceutically acceptable salt or solvate thereof, in the manufacture of a medicament for the treatment of pain and inflammation. In certain instances, the pain includes, but are not limited to, acute pain, chronic pain, visceral pain, inflammatory pain and neuropathic pain and the pain as described herein. In other instances, the inflammation includes chronic inflammation and acute inflammation; inflammation that is categorized in terms of its severity, e.g., mild, moderate, or severe; and inflammation that is a symptom or a result of a disease state or syndrome.

Conditions that can be Treated by PGE2 Receptor Antagonists:

The present invention provides treatment, prevention, amelioration, regulation and modulation of pain, inflammation, acute phase reactions and hemopoiesis. As PGE2 receptor antagonists, the compounds of any of formulas I, IA, Ia, Ib, Ib-1, II, IIa, IIa-1 to IIa-5 and DA001-DA090 are useful in the treatment, prevention, amelioration, regulation or modulation of inflammatory diseases and pain conditions. The inflammatory diseases and conditions include all categories of inflammation, including localized manifestations and systemic inflammation; inflammation that is categorized temporally, e.g., allergic inflammation, chronic inflammation and acute inflammation; inflammation that is categorized in terms of its severity, e.g., mild, moderate, or severe; and inflammation that is a symptom or a result of a disease state or syndrome. In some embodiments, the inflammation diseases and conditions include autoimmune disorders. In other embodiments, the inflammation diseases and conditions include inflammatory bowel diseases. In yet other embodiments, the inflammation diseases and conditions include glomerulonephritis, transplant rejection, vasculitis, reperfusion injury, asthma, osteoarthritis, rhinitis, conjunctivitis and dermatitis. The pain conditions that can be treated with the compounds of any of formulas I, IA, Ia, Ib, Ib-1, II, IIa, IIa-1 to IIa-5 and DA001-DA090 include all categories of pain. In some embodiments, the pain conditions include, but are not limited to, acute pain, chronic pain, visceral pain, inflammatory pain, somatic pain or neuropathic pain. Disease states that can be treated using the compounds of any of formulas I, Ia, Ib, Ib-1, II, IIa, IIa-1 to IIa-5 and DA001-DA090 include, but are not limited to, autoimmune disorders, (e.g., rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Beheet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis), inflammatory bowel diseases (e.g., ulcerative colitis, Crohn's disease; chronic prostatitis), glomerulonephritis, transplant rejection, vasculitis, reperfusion injury, asthma, osteoarthritis, rhinitis, conjunctivitis and dermatitis, pain in terms of stimulus or nerve response (e.g., somatic pain and neuropathic pain), chronic pain and acute pain, pain that is a symptom or a result of a disease state or syndrome (e.g., inflammatory pain, cancer pain, AIDS pain, arthropathy, migraine, trigeminal neuralgia, cardiac ischaemia, and diabetic neuropathy), and visceral pain.

In one embodiment of the invention, the compounds of any of formulas I, IA, Ia, Ib, Ib-1, II, IIa, Ia-1 to IIa-5 and DA001-DA090 can be used for regulating acute phase reactions, inflammation or hemopoiesis.

Conditions that can be Treated by NMDA and MC Receptor Antagonists

The present invention also provides neuroprotection as well as improves cognitive deficits. As NMDA and MC receptor antagonists, the compounds of the present invention and the compounds as described herein are useful in the treatment of acute and chronic disorders of CNS, ranging from neuropathological conditions to neurodegenerative diseases and conditions related to excitotoxicity. Disease states that can be treated using the compounds of the present invention and the compounds as described herein include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, celebrovascular, stroke, hydrocephalus, subarachnoid hemorrhage, vascular insufficiency, brain tumor, epilepsy, Parkinson's disease, cerebral microangiopathy, pain medication, chemotherapy, oxygen deprivation, e.g, caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, fetal alcohol syndrome, depression, anxiety, anorexia and cachexia, for example.

Treatment methods provided herein include, in general, administration to a subject, patient or a mammal an effective amount of one or more compounds provided herein, e.g., orally, nasally, parenterally, topically or rectally). Suitable patients include those subjects, patients or mammals suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a subject, patient or a mammal an effective amount of a compound one or more compounds provided herein, for example, compounds of any of formulas I, IA, Ia, Ib, Ib-1, II, IIa, IIa-1 to IIa-5 and DA001-DA090. In a preferred embodiment, the compounds of the invention are preferably administered to a patient (e.g., a human) orally. The effective amount may be an amount sufficient to modulate theNMDA, MC or PGE2 receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit the PGE2 receptor in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

The compounds of the present invention can be administered as frequently as necessary, including hourly, daily, weekly or monthly. Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

The compounds of any of formulas I, IA, Ia, Ib, Ib-1, II, IIa, IIa-1 to IIa-5 and DA001-DA090 or a compound as described herein can also be administered in combination with additional therapeutic agents or diagnostic agents can be administered in combination with the compounds of any of formulas I, IA, Ia, Ib, Ib-1, II, IIa, IIa-1 to IIa-5 and DA001-DA090 or a compound as described herein to bring a desired effect. Selection of additional agents will, in large part, depend on the desired target therapy (see, e.g., Turner, N. et al. *Prog. Drug Res*. (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab*. (1999) 84: 1165-71; United Kingdom Prospective Diabetes Study Group: UKPDS 28, *Diabetes Care* (1998) 21: 87-92; Bardin, C. W. (ed.), Current Therapy In Endocrinology And Metabolism, 6th Edition (Mosby—Year Book, Inc., St. Louis, Mo. 1997); Chiasson, J. et al., *Ann. Intern. Med*. (1994) 121: 928-935; Coniff, R. et al., *Clin. Ther*. (1997) 19: 16-26; Coniff, R. et al., *Am. J. Med*. (1995) 98: 443-451; and Iwamoto, Y. et al., *Diabet. Med*. (1996) 13 365-370; Kwiterovich, P. *Am. J. Cardiol* (1998) 82(12A): 3U-17U). Combination therapy includes administration of a single pharmaceutical dosage formulation which contains a compound having the general structure of any of formulas I, Ia, Ib, Ib-1, II, IIa, IIa-1 to IIa-5 and DA001-DA090 and one or more additional active agents, as well as administration of a compound of any of formulas I, Ia, Ib, Ib-1, II, IIa, IIa-1 to IIa-5 and DA001-DA079 and each active agent in its own separate pharmaceutical dosage formulation.

VI. Methods of Treating Diseases and Disorders Modulated by NMDA and MC Receptors In another aspect, the present invention provides a method of inhibiting the activities of an NMDA receptor and/or an MC receptor, e.g. MC 1 or MC4 receptor for treating and/or preventing CNS disorders. The method includes contacting any of compounds DA048-090, or a pharmaceutical composition thereof with the NMDA receptor or the MC1 or MC4 receptor. Preferably, the NMDA receptor is an activated NMDA receptor.

In one embodiment, the compounds of the present invention are NMDA and/or MC antagonists that can be used to inhibit the binding of NMDA and/or MC receptor ligand (e.g., glutamate) to NMDA receptor in vitro or in vivo. In general, such methods comprise the step of contacting an NMDA receptor or an MC with a sufficient amount of one or more NMDA or MC receptor antagonist as provided herein, in the presence of NMDA or MC receptor ligand in aqueous solution and under conditions otherwise suitable for binding of the ligand to NMDA or MC receptor. The NMDA or MC receptor may be present in suspension (e.g., in an isolated membrane or cell preparation), or in a cultured or isolated neuron cell.

Preferably, the amount of NMDA or MC receptor modulator contacted with the receptor should be sufficient to inhibit NMDA or MC binding to NMDA or MC receptor in vitro as measured, for example, using whole-cell patch clamp studies, calcium mobilization assay, fluormetric imaging plate reader (FLIPR) assey, or neuronal survival assay as described herein.

In one embodiment of the invention, the NMDA or MC receptor antagonists of the invention are used to modulate, preferably inhibit, the activity of an NMDA or MC receptor, for example, by contacting one or more compound(s) of the invention with an NMDA or MC receptor (either in vitro or in vivo) under conditions suitable for binding of the modulator(s) to the receptor. The receptor may be present in solution or suspension, in a cultured or isolated cell preparation or within a patient. Any modulation of the activity may be assessed using patch clamp, FLIPR, or calcium assay techniques by detecting the ion current across the surface of neurons, or by survival assay, or immunocytochemical analysis. In general, an effective amount of NMDA or MC antagonist(s) in an amount sufficient to modulate NMDA or MC receptor activity in vitro within patch clamp studies and calcium mobilization assays, followed by neuronal survival assays.

In another embodiment, comparative studies are conducted to determine its efficacy in comparison to the known antagonist memantine. The effect of the compound on cognitive functions, such as in treating dementia, improving memory in test subjects is evaluated in animal models using Morris Water Maze task.

In yet another aspect, the present invention provides methods and use of ompounds DA048-090 for the preventing and/or treating a neurodegenerative diseases or neuropathological conditions in a mammal or human. The methods include administering to the mammal or human a therapeutically effective amount of any of compounds DA048-DA090 of the present invention.

In a further aspect, the present invention provides methods and uses of compounds DA048-DA090 for enhancing the brain's cognitive function in a mammal or human. The methods include administering to the subject a therapeutically effective amount of any of compounds DA048-DA090 of the present invention.

In still another aspect, the present invention provides methods and use of compounds DA048-DA090 for inhibiting the activities of an MC receptor. The method includes contacting the compound with the MC receptor. In one embodiment, the MC receptor is MC1 or MC4 receptor. In another embodiment, the MC receptor is an MC4 receptor.

In another aspect, the present invention provides methods of treating depression, anxiety and cachexia induced by a chronic disease in a mammal. The method includes administering to the mammal a therapeutically effective amount of any of compounds DA048-DA090. Non-limitaing chronic diseases that can induce cachexia include cancer, AIDS, renal failure, liver failure, congestive heart failure and lung disease.

In another aspect, the present invention provides a method of treating a neurodegenerative disease or neuropathological conditions in a mammal. The method includes administering to the mammal a therapeutically effective amount of any of compounds D048-D090. In one embodiment, the disease is selected from the group consisting of amyotrophic lateral sclerosis, Alzheimer's disease, Parkinson's disease and Huntington's disease. In another embodiment, the condition is selected from the group consisting of neuropathic pain, stroke, brain trauma and epilepsy.

In another aspect, the present invention provides a method of preventing neuronal damage under a stress condition in a mammal. The method includes administering to the mammal a therapeutically effective amount of any of compounds D048-D090. In one embodiment, the stress condition is a stroke.

In another aspect, the present invention provides a method of treating depression, anxiety and cachexia induced by a chronic disease in a mammal. The method includes administering to the mammal a therapeutically effective amount of compounds D048-D090. In one embodiment, the chronic disease is selected from cancer, AIDS, renal failure, liver failure, congestive heart failure and lung diseases.

VII. Examples

The following abbreviations are used in the Examples and throughout the description of the invention:
NMDA: N-methyl-D-aspartic acid
Ac: acetyl
DMSO: dimethylsulfoxide
Bn: benzyl
MC: Melanocortins Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

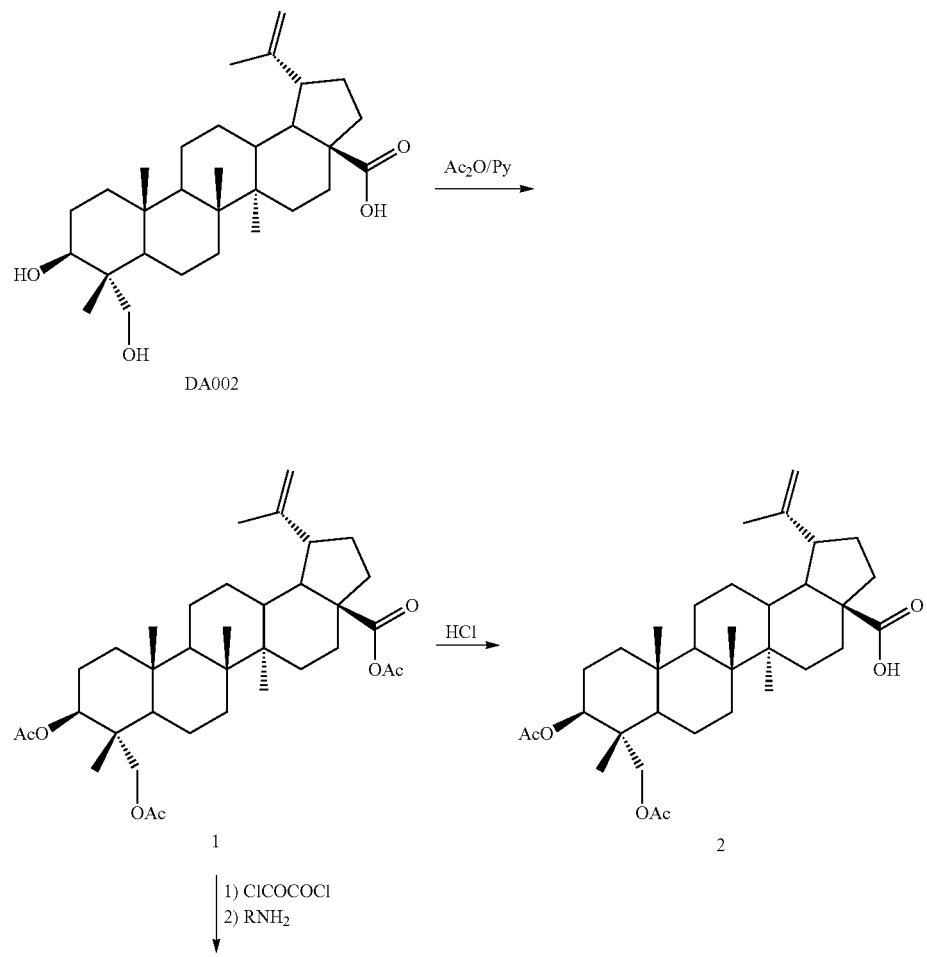

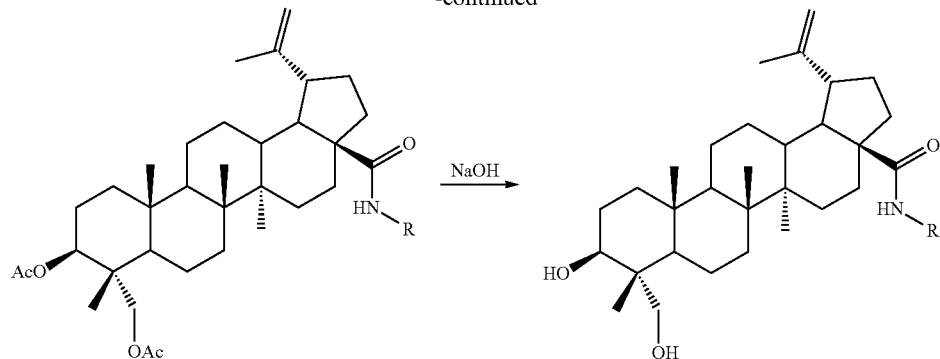

| R | DA# | DA# |
|---|---|---|
| H | DA048 | DA051 |
| HOCH₂CH₂— | DA049 | DA052 |
| CH₃— | DA050 | DA053 |
| NH₂CH₂CH₂— | DA054 | DA057 |
| HO(CH₂)₃— | DA055 | DA058 |
| NH₂(CH₂)₃— | DA056 | DA059 |

Compounds DA048-DA059 were synthesized according to the synthetic approaches outlined in Scheme 3.

Example 1

Preparation of 3,23-Diacetoxy-betulinic amide (DA048)

Synthesis of 3,23-diacetoxy-betulinic acetic anhydride (1)

3,23-Diacetoxy-betulinic acetic anhydride: A mixture of 23-hydroxy-betulinic acid (1.0 g, 2.12 mmoL) in 20 mL of pyridine and 10 mL of acetic anhydride was stirred at room temperature for 48 h. The mixture was diluted with 50 mL of ethyl acetate, washed with 10% HCl (30 mL×3), brine (30 mL×1), dried over sodium sulfate, filtered and concentrated under reduced pressure. The resulting residue was purified by column chromatography on silica gel column, eluting with 1% methanol in methylene chloride to provide the desired product (1.24 g, 2.08 mmoL, 98%) as a white foaming solid. $^1$H NMR (300 MHz, CDCl$_3$) δ 4.77 (dd, J=11.1, 4.5 Hz, 1H), 4.74 (s, 1H), 4.61 (s, 1H), 3.84 (d, J=11.4 Hz, 1H), 3.69 (d, J=11.4 Hz, 1H), 3.03-2.95 (m, 1H), 2.29-2.22 (m, 2H), 2.11 (s, 3H), 2.07 (s, 3H), 2.02 (s, 3H), 2.01-1.95 (m, 1H), 1.68-0.99 (m, 21H), 0.97 (s, 3H), 0.93 (s, 3H), 0.88 (s, 3H), 0.81 (s, 3H). $^{13}$C NMR (75 MHz, CDCl$_3$) δ 182.5, 177.0, 170.9, 170.6, 150.0, 109.6, 74.4, 65.3, 56.3, 50.4, 49.1, 47.9, 46.8, 42.3, 40.6, 40.5, 38.3, 37.9, 37.0, 36.9, 33.9, 32.0, 30.5, 29.6, 25.4, 23.1, 21.1, 20.9 (2), 20.8, 19.3, 17.9, 16.6, 15.9, 14.6, 12.9.

Synthesis of 3,23-Diacetoxy-betulinic amide (DA048)

To a solution of 3,23-diacetoxy-betulinic acetic anhydride (211 mg, 0.35 mmoL) dissolved in 35 mL dry methylene chloride, was added oxalyl dichloride (0.31 mL, 3.52 mmoL) under nitrogen. The mixture was stirred at room temperature for 4 h and then concentrated under reduced pressure. A solution of ammonium saturated in THF (5 mL) and 0.2 mL of triethylamine were added and the mixture was stirred at room temperature overnight. Water was added and the layers were separated. The aqueous layer was extracted with chloroform (×3). The combined organic layer was dried over sodium sulfate, filtered and concentrated. The resulting residue was purified by column chromatography on silica gel column, eluting with 30% ethyl acetate in petroleum ether to give the desired product (196 mg, 100%) as a white solid. $^1$H NMR (300 MHz, CDCl$_3$) δ 5.55 (br s, 1H), 5.39 (br s, 1H), 4.75 (dd, J=11.1, 4.6 Hz, 1H), 4.74 (s, 1H), 4.60 (s, 1H), 3.84 (d, J=11.1 Hz, 1H), 3.68 (d, J=11.1 Hz, 1H), 3.09 (dt, J=11.1, 4.6 Hz, 1H), 2.53-2.40 (m, 1H), 2.06 (s, 3H), 2.04-1.86 (m, 2H), 2.02 (s, 3H), 1.84-0.79 (m, 22H), 1.69 (s, 3H), 0.97 (s, 6H), 0.88 (s, 3H), 0.81 (s, 3H). $^{13}$C NMR (75 MHz, CDCl$_3$) δ 178.69, 170.86, 170.51, 150.59, 109.38, 74.49, 65.42, 55.75, 50.66, 49.83, 48.05, 46.57, 42.50, 40.75, 40.61, 38.38, 38.05, 37.61, 37.02, 34.06, 34.00, 30.76, 29.74, 29.51, 25.58, 23.18, 21.32, 21.03, 19.51, 18.01, 16.71, 16.20, 14.61, 12.99. MS (ESI) m/z 566.45 (M+H$^+$).

Example 2

Preparation of 3,23-diacetoxy-betulinic 2-hydroxyethyl amide (DA049)

To a solution of 3,23-diacetoxy-betulinic acetic anhydride (52 mg, 0.087 mmoL) dissolved in 2 mL dry methylene chloride, was added oxalyl dichloride (76 μL, 0.87 mmoL) under nitrogen. The mixture was stirred at room temperature for 2 h and then concentrated under reduced pressure. A solution of ethanolamine (26 μL, 0.43 mmoL) in 2 mL dry methylene chloride was added and the mixture was stirred at room temperature overnight. Aqueous workup followed by purification by column chromatography on silica gel column, eluting with 50% ethyl acetate in petroleum ether provided the desired product (52 mg, 100%) as a white solid. $^1$H NMR (400 MHz, CDCl$_3$) δ 6.22 (t, J=7.1 Hz, 1H), 4.77 (dd, J=11.4, 4.6 Hz, 1H), 4.74 (s, 1H), 4.60 (s, 1H), 3.84 (d, J=11.4 Hz, 1H), 3.69 (d, J=11.4 Hz, 1H), 3.70 (s, 2H), 3.52-3.33 (m, 2H), 3.19 (br s, 1H), 3.10 (dt, J=11.1, 4.6 Hz, 1H), 2.51-2.39 (m, 1H), 2.10-1.90 (m, 2H), 2.07 (s, 3H), 2.02 (s, 3H), 1.83-0.72

(m, 22H), 1.69 (s, 3H), 0.97 (s, 3H), 0.94 (s, 3H), 0.88 (s, 3H), 0.81 (s, 3H). $^{13}$C NMR (400 MHz, CDCl$_3$) δ 177.80, 170.93, 170.56, 150.57, 109.35, 74.52, 74.44, 65.39, 62.98, 55.63, 50.59, 50.03, 48.00, 46.72, 42.39, 42.25, 40.70, 40.55, 38.38, 37.98, 36.94, 33.96, 33.71, 30.83, 29.37, 25.52, 23.11, 20.97, 19.46, 17.90, 16.58, 12.90. MS (ESI) m/z 600.39 (M+H$^+$)

Example 3

Preparation of 3,23-diacetoxy-betulinic methyl amide (DA050)

To a solution of 3,23-diacetoxy-betulinic acetic anhydride (54 mg, 0.090 mmoL) dissolved in 2 mL dry methylene chloride, was added oxalyl dichloride (78 μL, 0.90 mmoL) under nitrogen. The mixture was stirred at room temperature for 2 h and then concentrated under reduced pressure. A solution of methylamine in ethanol (33% wt, 112 μL, 0.90 mmoL) was added and the mixture was stirred at room temperature overnight. Aqueous workup followed by purification by column chromatography on silica gel column, eluting with 25% ethyl acetate in petroleum ether provided the desired product (51 mg, 100%) as a white solid. $^1$H NMR (400 MHz, CDCl$_3$) δ 5.70 (br s, 1H), 4.77 (dd, J=10.6, 4.6 Hz, 1H), 4.74 (s, 1H), 4.59 (s, 1H), 3.85 (d, J=10.6 Hz, 1H), 3.68 (d, J=10.6 Hz, 1H), 3.14 (dt, J=10.6, 4.6 Hz, 1H), 2.79 (d, J=4.6 Hz, 3H), 2.52-2.40 (m, 1H), 2.07 (s, 3H), 2.05-1.87 (m, 2H), 2.02 (s, 3H), 1.80-0.75 (m, 22H), 1.68 (s, 3H), 0.96 (s, 3H), 0.94 (s, 3H), 0.88 (s, 3H), 0.81 (s, 3H). $^{13}$C NMR (400 MHz, CDCl$_3$) δ 176.64, 170.92, 170.56, 150.76, 109.26, 74.53, 74.46, 65.39, 55.56, 50.61, 50.12, 48.00, 46.74, 42.39, 40.68, 40.56, 38.34, 37.99, 36.95, 34.01, 33.77, 30.84, 29.39, 25.52, 23.12, 20.97, 19.45, 17.93, 16.62, 16.58. MS (ESI) m/z 570.47 (M+H$^+$).

Example 4

Preparation of 3,23-Dihydroxy-betulinic amide (DA051)

To a solution of 3,23-diacetoxy-betulinic amide (22 mg, 0.040 mmoL) dissolved in 1 mL of THF and 2 mL of MeOH, was added aqueous sodium hydroxide solution (20 wt %, 0.2 mL). The resulting mixture was stirred at room temperature overnight. The mixture was concentrated and purified by column chromatography on silica gel column, eluting with 5% methanol in methylene chloride to give the desired product (15 mg, 0.032 mmoL, 80%) as a white solid. $^1$H NMR (400 MHz, CD$_3$OD) δ 4.69 (s, 1H), 4.56 (s, 1H), 3.58 (dd, J=11.3, 5.7 Hz, 1H), 3.50 (d, J=11.3 Hz, 1H), 3.27 (d, J=11.3 Hz, 1H), 3.07 (dt, J=11.3, 5.7 Hz, 1H), 2.59-2.38 (m, 1H), 2.14-0.48 (m, 23H), 1.67 (s, 3H), 0.99 (s, 3H), 0.97 (s, 3H), 0.88 (s, 3H), 0.67 (s, 3H). $^{13}$C NMR (400 MHz, CD$_3$OD) δ 182.11, 152.10, 109.86, 73.90, 67.44, 56.94, 51.95, 51.10, 48.01, 47.94, 43.58, 43.32, 41.87, 39.71, 39.38, 38.07, 35.06, 34.28, 31.81, 30.58, 27.56, 26.94, 22.13, 19.67, 19.09, 17.12, 16.78, 15.08, 12.54. MS (ESI) m/z 943.16 (2M+H$^+$)

Example 5

Preparation of 3,23-Dihydroxy-betulinic 2-hydroxyethyl amide (DA052)

To a solution of 3,23-diacetoxy-betulinic 2-hydroxyethyl amide (44 mg, 0.073 mmoL) dissolved in 1 mL of THF and 2 mL of MeOH, was added aqueous sodium hydroxide solution (20 wt %, 0.5 mL). The resulting mixture was stirred at room temperature overnight. The mixture was concentrated and purified by column chromatography on silica gel column, eluting with 7.5% methanol in methylene chloride to give the desired product (34 mg, 0.066 mmoL, 90%) as a white solid. $^1$H NMR (300 MHz, pyridine-d$_5$) δ 8.26 (t, J=5.4 Hz, 1H), 6.40 (br s, 2H), 5.80 (br s, 1H), 4.93 (br s, 1H), 4.75 (br s, 1H), 4.31-4.13 (m, 2H), 4.12-4.00 (m, 2H), 3.99-3.84 (m, 1H), 3.80-3.55 (m, 3H), 3.14-2.99 (m, 1H), 2.44 (br d, J=13.5 Hz, 1H), 2.32-2.05 (m, 2H), 2.03-0.97 (m, 20H), 1.77 (s, 3H), 1.13 (s, 3H), 1.06 (s, 3H), 1.00 (s, 3H), 0.92 (s, 3H). $^{13}$C NMR (75 MHz, pyridine-d$_5$) δ 177.59, 152.07, 110.01, 73.65, 68.04, 62.27, 56.30, 51.45, 51.09, 49.09, 47.63, 43.37, 43.17, 43.10, 41.53, 39.48, 39.03, 38.09, 37.72, 34.84, 33.98, 31.76, 30.27, 28.25, 26.58, 21.64, 19.92, 18.92, 17.19, 16.88, 15.18, 13.33. MS (ESI) m/z 516.46 (M+H$^+$)

Example 6

Preparation of 3,23-Dihydroxy-betulinic methyl amide (DA053)

To a solution of 3,23-diacetoxy-betulinic methyl amide (48 mg, 0.084 mmoL) dissolved in 1 mL of THF and 2 mL of MeOH, was added aqueous sodium hydroxide solution (20 wt %, 0.3 mL). The resulting mixture was stirred at room temperature overnight. The mixture was concentrated and purified by column chromatography on silica gel column, eluting with 5% methanol in methylene chloride to give the desired product (36 mg, 0.032 mmoL, 88%) as a white solid. $^1$H NMR (300 MHz, pyridine-d$_5$) δ 8.04 (br d, J=4.2 Hz, 1H), 6.35 (br s, 1H), 5.79 (br s, 1H), 4.92 (br s, 1H), 4.75 (br s, 1H), 4.29-4.10 (m, 2H), 3.72 (d, J=9.8 Hz, 1H), 3.68-3.54 (m, 1H), 3.14-2.99 (m, 1H), 2.96 (d, J=4.2 Hz, 3H), 2.37 (d, J=12.7 Hz, 1H), 2.27-0.77 (m, 22H), 1.77 (s, 3H), 1.13 (s, 3H), 1.05 (s, 3H), 1.00 (s, 3H), 0.92 (s, 3H). $^{13}$C NMR (75 MHz, pyridine-d$_5$) δ 177.58, 152.04, 110.03, 73.68, 68.09, 56.21, 51.43, 51.07, 49.10, 47.58, 43.34, 43.09, 41.49, 39.46, 38.99, 38.04, 37.71, 34.91, 33.95, 31.71, 30.27, 28.21, 26.80, 26.55, 21.63, 19.88, 18.92, 17.18, 16.95, 15.16, 13.31. MS (ESI) m/z 485.45 (M+H$^+$).

Example 7

3,23-Diacetoxy-betulinic 2-aminoethyl amide (DA054)

To a solution of 3,23-diacetoxy-betulinic acetic anhydride (47 mg, 0.078 mmoL) dissolved in 2 mL dry methylene chloride, was added oxalyl dichloride (68 μL, 0.78 mmoL) under nitrogen. The mixture was stirred at room temperature for 2 h and then concentrated under reduced pressure. The resulting residue was dissolved in 2 mL dry methylene chloride, and 1,2-diaminoethane (52 μL, 0.78 mmoL) was added. The mixture was stirred at room temperature overnight. Aqueous workup followed by purification by column chromatography on silica gel column, eluting with 7-8% methanol in methylene chloride provided the desired product (47 mg, 100%) as a white solid. $^1$H NMR (300 MHz, CDCl$_3$) δ 6.15 (t, J=5.6 Hz, 1H), 4.77 (dd, J=10.3, 3.8 Hz, 1H), 4.74 (br s, 1H), 4.60 (br s, 1H), 3.84 (d, J=10.3 Hz, 1H), 3.68 (d, J=10.3 Hz, 1H), 3.43-3.19 (m, 2H), 3.13 (dt, J=10.3, 3.8 Hz, 1H), 2.82 (t, J=5.6 Hz, 2H), 2.53-2.39 (m, 1H), 2.07 (s, 3H), 2.05-1.85 (m, 2H), 2.02 (s, 3H), 1.83-0.73 (m, 21H), 1.69 (s, 3H), 0.97 (s, 3H), 0.94 (s, 3H), 0.87 (s, 3H), 0.81 (s, 3H). $^{13}$C NMR (75 MHz, CDCl$_3$) δ 176.44, 170.97, 170.61, 150.82, 109.32, 74.43, 65.34, 55.60, 50.57, 50.02, 47.95, 46.70, 42.35, 41.86, 41.72, 41.58, 40.65, 40.50, 38.37, 37.94, 37.61, 36.89, 33.94, 33.63, 30.82, 29.35, 25.47, 23.05, 21.18, 20.89, 19.39, 17.83, 16.60, 16.11, 14.52, 12.92. MS (ESI) m/z 599.22 (M+H$^+$)

Example 8

Preparation of 3,23-Diacetoxy-betulinic 3-hydroxyl-propyl amide (DA055)

To a solution of 3,23-diacetoxy-betulinic acetic anhydride (47 mg, 0.078 mmoL) dissolved in 2 mL dry methylene chloride, was added oxalyl dichloride (68 μL, 0.78 mmoL) under nitrogen. The mixture was stirred at room temperature for 2 h and then concentrated under reduced pressure. The resulting residue was dissolved in 2 mL dry methylene chloride, and 3-amino-1-propanol (59 μL, 0.78 mmoL) was added. The mixture was stirred at room temperature overnight. Aqueous workup followed by purification by column chromatography on silica gel column, eluting with 50% ethyl acetate in petroleum ether provided the desired product (48 mg, 100%) as a white solid. $^1$H NMR (300 MHz, CDCl$_3$) δ 6.07 (t, J=5.6 Hz, 1H), 4.77 (dd, J=11.2, 4.7 Hz, 1H), 4.74 (s, 1H), 4.61 (br s, 1H), 3.85 (d, J=11.2 Hz, 1H), 3.68 (d, J=11.2 Hz, 1H), 3.62 (br s, 2H), 3.51-3.32 (m, 2H), 3.10 (dt, J=11.2, 4.7 Hz, 1H), 2.53-2.40 (m, 1H), 2.07 (s, 3H), 2.02 (s, 3H), 2.03-1.85 (m, 2H), 1.81-0.85 (m, 23H), 1.69 (s, 3H), 0.97 (s, 3H), 0.95 (s, 3H), 0.88 (s, 3H), 0.81 (s, 3H). $^{13}$C NMR (75 MHz, CDCl$_3$) δ 177.94, 171.05, 170.71, 150.67, 109.45, 74.48, 65.38, 58.99, 55.68, 50.61, 49.96, 47.98, 46.55, 42.37, 40.69, 40.52, 38.66, 37.95, 37.60, 36.91, 35.65, 33.97, 33.68, 32.53, 30.79, 29.40, 25.49, 23.81, 23.05, 21.19, 20.90, 19.43, 17.84, 16.52, 15.99, 14.43, 12.77. MS (ESI) m/z 614.37 (M+H$^+$).

Example 9

Preparation of 3,23-Diacetoxy-betulinic 3-amino-propyl amide (DA056)

To a solution of 3,23-diacetoxy-betulinic acetic anhydride (45 mg, 0.075 mmoL) dissolved in 2 mL dry methylene chloride, was added oxalyl dichloride (66 μL, 0.78 mmoL) under nitrogen. The mixture was stirred at room temperature for 2 h and then concentrated under reduced pressure. The resulting residue was dissolved in 2 mL dry methylene chloride, and 1,3-diaminopropane (63 μL, 0.78 mmoL) was added. The mixture was stirred at room temperature overnight. Aqueous workup followed by purification by column chromatography on silica gel column, eluting with 8% methanol in methylene chloride provided the desired product (46 mg, 100%) as a white solid. $^1$H NMR (300 MHz, CDCl$_3$) δ 6.49 (t, J=5.69 Hz, 1H), 4.77 (dd, J=10.7, 4.8 Hz, 1H), 4.73 (s, 1H), 3.84 (d, J=10.7 Hz, 1H), 3.68 (d, J=10.7 Hz, 1H), 3.47-3.25 (m, 2H), 3.14 (dt, J=10.7, 4.8 Hz, 1H), 2.90-2.69 (m, 2H), 2.59-2.34 (m, 1H), 2.49 (br s, 2H), 2.07 (s, 3H), 2.02 (s, 3H), 2.03-1.86 (m, 2H), 1.80-0.76 (m, 23H), 1.68 (s, 3H), 0.96 (s, 3H), 0.94 (s, 3H), 0.88 (s, 3H), 0.81 (s, 3H). $^{13}$C NMR (75 MHz, CDCl$_3$) δ 176.49, 170.98, 170.62, 150.86, 109.31, 74.43, 65.34, 55.53, 50.58, 49.99, 47.95, 46.65, 42.34, 40.66, 40.50, 39.57, 38.43, 37.93, 37.59, 37.13, 36.89, 33, 95, 33.58, 31.87, 30.82, 29.34, 25.47, 23.05, 21.18, 20.90, 19.38, 17.84, 16.50, 16.13, 14.51, 12.78. MS (ESI) m/z 613.38 (M+H$^+$)

Example 10

3,23-Dihydroxy-betulinic 2-aminoethyl amide (DA057)

To a solution of 3,23-diacetoxy-betulinic 2-aminoethyl amide (42 mg, 0.070 mmoL) dissolved in 1 mL of THF and 2 mL of MeOH, was added aqueous sodium hydroxide solution (20 wt %, 0.3 mL). The resulting mixture was stirred at room temperature overnight. The mixture was concentrated and purified by column chromatography on silica gel column, eluting with 10% methanol in methylene chloride to give the desired product (34 mg, 0.066 mmoL, 94%) as a white solid. $^1$H NMR (300 MHz, pyridine-d$_5$) δ 8.14 (t, J=5.2 Hz, 1H), 4.92 (br s, 1H), 4.75 (s, 1H), 4.28-4.05 (m, 1H), 4.18 (d, J=10.9 Hz, 1H), 3.79-3.36 (m, 3H), 3.72 (d, J=10.9 Hz, 1H), 3.16-2.87 (m, 1H), 3.02 (t, J=5.2 Hz, 2H), 2.44 (d, J=13.0 Hz, 1H), 2.29-2.03 (m, 2H), 2.02-1.86 (m, 2H), 1.85-0.87 (m, 22H), 1.77 (s, 3H), 1.12 (s, 3H), 1.05 (s, 3H), 1.00 (s, 3H), 0.92 (s, 3H). $^{13}$C NMR (75 MHz, pyridine-d$_5$) δ 177.30, 152.04, 110.01, 73.63, 68.02, 56.29, 51.44, 51.05, 49.08, 47.58, 43.35, 43.24, 43.12, 43.08, 41.51, 39.48, 39.05, 38.07, 37.71, 34.89, 33.97, 31.75, 30.26, 28.22, 26.57, 21.65, 19.92, 18.93, 17.20, 16.92, 15.17, 13.32. MS (ESI) m/z 515.33 (M+H$^+$)

Example 11

3,23-Dihydroxy-betulinic 3-hydroxyl-propyl amide (DA058)

To a solution of 3,23-diacetoxy-betulinic 3-hydroxyl-propyl amide (43 mg, 0.070 mmoL) dissolved in 1 mL of THF and 2 mL of MeOH, was added aqueous sodium hydroxide solution (20 wt %, 0.5 mL). The resulting mixture was stirred at room temperature overnight. The mixture was concentrated and purified by column chromatography on silica gel column, eluting with 8% methanol in methylene chloride to give the desired product (23 mg, 0.043 mmoL, 61%) as a white solid. $^1$H NMR (300 MHz, pyridine-d$_5$) δ 8.26 (t, J=5.7 Hz, 1H), 6.34 (br s, 1H), 6.05 (br s, 1H), 5.79 (br s, 1H), 4.92 (br s, 1H), 4.75 (s, 1H), 4.29-4.13 (m, 1H), 4.20 (d, J=9.6 Hz, 1H), 3.98 (t, J=5.7 Hz, 2H), 3.88-3.55 (m, 3H), 3.73 (d, J=9.6 Hz, 1H), 3.13-2.97 (m, 1H), 2.42 (br d, J=11.7 Hz, 1H), 2.29-2.05 (m, 2H), 2.02 (t, J=5.7 Hz, 2H), 1.98-1.86 (m, 2H), 1.86-0.96 (m, 18H), 1.77 (s, 3H), 1.14 (s, 3H), 1.06 (s, 3H), 1.01 (s, 3H), 0.92 (s, 3H). $^{13}$C NMR (75 MHz, pyridine-d$_5$) δ 177.59, 152.03, 110.05, 73.65, 68.05, 60.27, 56.26, 51.46, 51.02, 49.09, 47.56, 43.37, 43.09, 41.54, 39.49, 39.13, 38.09, 37.72, 37.30, 34.90, 34.17, 33.99, 31.75, 30.27, 28.24, 26.59, 21.65, 19.91, 18.93, 17.21, 16.95, 15.17, 13.32. MS (ESI) m/z 530.26 (M+H$^+$).

Example 12

3,23-Dihydroxy-betulinic 3-amino-propyl amide (DA059)

To a solution of 3,23-diacetoxy-betulinic 3-amino-propyl amide (38 mg, 0.062 mmoL) dissolved in 1 mL of THF and 2 mL of MeOH, was added aqueous sodium hydroxide solution (20 wt %, 0.5 mL). The resulting mixture was stirred at room temperature overnight. The mixture was concentrated and purified by column chromatography on silica gel column, eluting with 10% methanol in methylene chloride to give the desired product (27 mg, 0.051 mmoL, 82%) as a white solid. $^1$H NMR (300 MHz, pyridine-d$_5$) δ 8.25 (t, J=6.5 Hz, 1H), 4.93 (br s, 1H), 4.76 (br s, 1H), 4.30-4.15 (m, 1H), 4.20 (d, J=10.8 Hz, 1H), 3.80-3.48 (m, 3H), 3.72 (d, J=10.8 Hz, 1H), 3.15-3.00 (m, 1H), 2.91 (t, J=6.5 Hz, 2H), 2.40 (br d, J=13.0 Hz, 1H), 2.29-2.02 (m, 2H), 1.89-0.79 (m, 22H), 1.77 (s, 3H), 1.15 (s, 3H), 1.06 (s, 3H), 1.01 (s, 3H), 0.92 (s, 3H). $^{13}$C NMR (75 MHz, pyridine-d$_5$) δ 177.14, 152.08, 110.02, 73.66, 68.06, 56.24, 51.47, 51.04, 49.11, 47.57, 43.37, 43.10, 41.55, 40.46, 39.49, 39.13, 38.06, 37.73, 37.50, 34.94, 34.08, 33.98, 31.76, 30.28, 28.25, 26.60, 21.67, 19.92, 18.95, 17.23, 16.98, 15.18, 13.33. MS (ESI) m/z 529.33 (M+H$^+$).

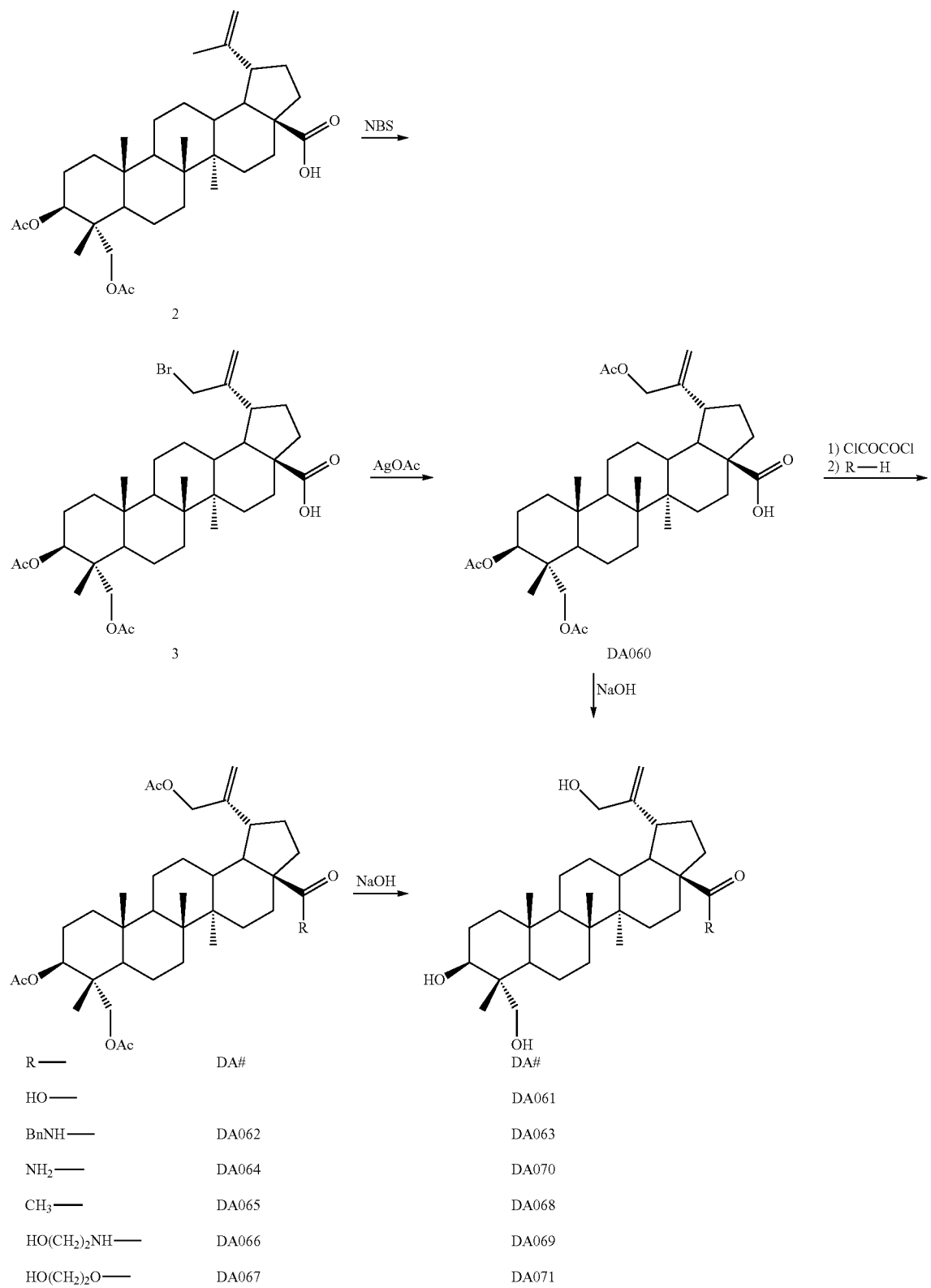
Compounds DA060-DA071 were synthesized according to the synthetic approaches set forth in Scheme 4.

Example 13

Synthesis of 3,23-Diacetoxy-betulinic acid (2)

To a solution of 3,23-diacetoxy-betulinic acetic anhydride (500 mg, 0.84 mmoL) dissolved in 13 mL of MeOH and 3 mL of chloroform, was added 1 mL of aqueous 5% HCl. The mixture was stirred at room temperature overnight. The solvent was removed under reduced pressure. The resulting residue was treated with water and extracted with methylene chloride (×3). The combined organic layer was dried, filtered and concentrated. Purification by column chromatography on silica gel, eluting with 20% ethyl acetate in petroleum ether provided the desired product (380 mg, 0.68 mmoL, 82%) as a white solid. $^1$H NMR (400 MHz, CDCl$_3$, δ ppm): 4.75-4.79 (m, 2H), 4.62 (s, 1H), 3.84 (d, J=11.6 Hz, 1H), 3.69 (d, J=11.6 Hz, 1H), 2.95-3.06 (m, 1H), 2.18-2.29 (m, 2H), 2.07 (s, 3H, CH$_3$), 2.02 (s, 3H, CH$_3$), 1.70 (s, 3H, CH$_3$), 1.02-1.68 (m, 23H) 0.98 (s, 3H, CH$_3$), 0.94 (s, 3H, CH$_3$), 0.88 (s, 3H, CH$_3$), 0.81 (s, 3H, CH$_3$). $^{13}$C NMR (125 MHz, CDCl$_3$) δ 182.0, 179.9, 170.6, 150.2, 109.7, 74.5, 65.4, 56.4, 50.5, 49.2, 48.0, 46.9, 42.4, 40.7, 40.6, 38.4, 38.0, 37.1, 37.0, 34.0, 32.1, 30.6, 29.7, 25.5, 23.2, 21.3, 21.0, 19.4, 18.0, 16.6, 16.1, 14.7, 13.0.

Example 14

Synthesis of 3,23-Diacetoxy-30-bromo-betulinic acid (3)

To a solution of 3,23-diacetoxy-betulinic acid (374 mg, 0.67 mmoL) dissolved in 20 mL of carbon tetrachloride, was added NBS (122 mg, 0.72 mmoL) and AIBN (5 mg, 0.03 mmoL). The resulting mixture was heated to 80 degree C. under nitrogen for 22 h. The reaction was stopped and the mixture was filtered through a plug of celite. The filtrate was concentrated. The resulting residue was purified by column chromatography on silica gel column, eluting with 20% ethyl acetate in petroleum ether. The desired product (242 mg, 0.38 mmoL, 57%) was obtained as a white solid and 25 mg (7%) of starting material was recovered. $^1$H NMR (400 MHz, CDCl$_3$) δ 5.16 (s, 1H), 5.05 (s, 1H), 4.77 (m, 1H), 4.00 (s, 2H), 3.84 (d, J=11.5 Hz, 1H), 3.70 (d, J=11.5 Hz, 1H), 3.02 (m, 1H), 2.30-2.15 (m, 2H), 2.07 (s, 3H), 2.02 (s, 3H), 1.99-1.97 (m, 1H), 1.74-1.01 (m, 22H), 0.99 (s, 3H), 0.93 (s, 3H), 0.88 (s, 3H), 0.81 (s, 3H). $^{13}$C NMR (125 MHz, CDCl$_3$) δ 181.8, 171.0, 170.7, 151.0, 113.4, 74.5, 65.4, 56.4, 50.7, 50.4, 47.9, 42.9, 42.3, 40.6, 40.5, 38.4, 37.9, 37.0, 36.9, 36.7, 33.9, 33.0, 32.0, 29.6, 26.7, 23.1, 21.2, 20.9, 17.9, 16.6, 16.0, 15.6, 12.9.

Example 15

Preparation of 3,23,30-Triacetoxy-betulinic acid (DA060)

To a solution of 3,23-diacetoxy-30-bromo-betulinic acid (242 mg, 0.38 mmoL) in 4 mL of acetic acid, was added silver acetate (635 mg, 3.81 mmoL). The resulting mixture was heated to 120 degree C. under nitrogen for 2 days. The mixture was cooled to room temperature and filtered through a plug of celite, rinsing with methylene chloride. The filtrate was concentrated and purified by column chromatography on silica gel, eluting with 20-25% ethyl acetate in petroleum ether. The desired product (169 mg, 0.28 mmoL, 72%) was obtained as a white solid. $^1$H NMR (300 MHz, CDCl$_3$) δ 4.99 (s, 1H), 4.97 (s, 1H), 4.77 (dd, J=11.2, 4.5 Hz, 1H), 4.57 (m, 2H), 3.85 (d, J=11.4 Hz, 1H), 3.69 (d, J=11.4 Hz, 1H), 2.96 (td, J=11.4, 4.2 Hz, 1H), 2.32-2.29 (m, 1H), 2.11 (s, 3H), 2.07 (s, 3H), 2.02 (s, 3H), 2.18-1.96 (m, 2H), 1.73-1.16 (m, 21H), 0.98 (s, 3H), 0.93 (s, 3H), 0.88 (s, 3H), 0.81 (s, 3H). $^{13}$C NMR (75 MHz, CDCl$_3$) δ 181.8, 171.1, 170.8, 170.7, 149.0, 110.4, 74.3, 66.0, 65.4, 56.3, 50.4, 49.8, 47.9, 43.2, 42.3, 40.6, 40.5, 38.3, 38.0, 36.9, 36.7, 33.9, 31.9, 31.8, 29.6, 26.4, 23.1, 21.2, 21.1, 20.9 (2), 17.8, 16.6, 16.0, 14.6, 12.9. MS (ESI) m/z 637.34 (M+Na$^+$).

Example 16

Preparation of 3,23,30-Trihydroxy-betulinic acid (DA061)

To a solution of 3,23,30-triacetoxy-betulinic acid (23 mg, 0.037 mmoL) in 1 mL of THF and 2 mL of MeOH, was added aqueous sodium hydroxide solution (20%, 0.5 mL). The mixture was stirred at room temperature overnight and concentrated under reduced pressure. The resulting residue was purified by column chromatography on silica gel, eluting with 6% methanol in methylene chloride to give the desired product (16 mg, 0.033 mmoL, 88%) as a white solid. $^1$H NMR (300 MHz, CD$_3$OD) δ 4.96 (d, J=1.2 Hz, 1H), 4.88 (s, 1H), 4.04 (m, 2H), 3.58 (dd, J=10.5, 5.7 Hz, 1H), 3.50 (d, J=10.8 Hz, 1H), 3.27 (d, J=10.8 Hz, 1H), 2.87 (td, J=11.1, 4.2 Hz, 1H), 2.32-2.22 (m, 2H), 2.04-1.08 (m, 22H), 1.01 (s, 3H), 0.96 (s, 3H), 0.88 (s, 3H), 0.67 (s, 3H). $^{13}$C NMR (75 MHz, CD$_3$OD) δ 180.0, 156.3, 107.0, 73.8, 67.3, 65.3, 57.5, 52.0, 51.0, 44.2, 43.6, 43.4, 41.9, 39.8, 39.6, 38.1, 38.0, 35.1, 33.5, 33.3, 30.9, 28.0, 27.6, 22.2, 19.1, 17.1, 16.7, 15.1, 12.6. MS (ESI) m/z 487.49 (M−1, negative mode).

Example 17

Preparation of 3,23,30-Triacetoxy-betulinic benzyl amide (DA062)

To a solution of 3,23,30-triacetoxy-betulinic acid (31 mg, 0.050 mmoL) dissolved in 2 mL dry methylene chloride, was added oxalyl dichloride (44 µL, 0.50 mmoL) under nitrogen. The mixture was stirred at room temperature for 2 h and then concentrated under reduced pressure. The resulting residue was dissolved in 2 mL dry methylene chloride, and triethylamine (70 µL, 0.50 mmoL) and benzylamine (11 µL, 0.10 mmoL) were added. The mixture was stirred at room temperature overnight. Aqueous workup followed by purification by column chromatography on silica gel column, eluting with 25% ethyl acetate in petroleum ether provided the desired product (23 mg, 65%) as a white solid. $^1$H NMR (300 MHz, CDCl$_3$) δ 7.33-7.27 (m, 5H), 5.91 (t, J=5.7 Hz, 1H), 4.98 (1H), 4.94 (d, J=0.9 Hz, 1H), 4.77 (dd, J=11.1, 4.5 Hz, 1H), 4.56 (m, 2H), 4.48 (dd, J=14.7, 5.7 Hz, 1H), 4.35 (dd, J=14.7, 5.7 Hz, 1H), 3.16 (td, J=11.7, 4.2 Hz, 1H), 2.50 (m, 1H), 2.10 (s, 3H), 2.06 (s, 3H), 2.02 (s, 3H), 1.93-1.89 (m, 1H), 1.78-1.00 (m, 22H), 0.96 (s, 3H), 0.91 (s, 3H), 0.88 (s, 3H), 0.81 (s, 3H). $^{13}$C NMR (75 MHz, CDCl$_3$) δ 175.6, 171.0, 170.8, 170.7, 149.6, 139.0, 128.6 (2), 127.7 (2), 127.3, 74.5, 66.1, 65.4, 55.5, 50.8, 50.6, 48.0, 43.3, 43.0, 42.3, 40.7, 40.6, 38.1, 38.0, 37.6, 37.0, 34.0, 33.5, 32.0, 29.3, 26.5, 23.1, 21.2, 21.1 (2), 20.9, 17.9, 16.6, 16.1, 14.5, 12.9. MS (ESI) m/z 704.26 (M+H$^+$).

Example 18

Preparation of 3,23,30-Trihydroxy-betulinic benzyl amide (DA063)

To a solution of 3,23,30-triacetoxy-betulinic benzyl amide (15 mg, 0.021 mmoL) dissolved in 1 mL of THF and 2 mL of MeOH, was added aqueous sodium hydroxide (20%, 0.5 mL). The resulting mixture was allowed to stir overnight at room temperature. The mixture was concentrated and purified by column chromatography on silica gel, eluting with 6% methanol in methylene chloride to provide the desired product (9 mg, 0.016 mmoL, 77%) as a white solid. $^1$H NMR (400 MHz, CD$_3$OD) δ 8.13 (t, J=6.0 Hz, 1H), 7.29-7.21 (m, 5H), 4.95 (d, J=1.2 Hz, 1H), 4.88 (s, 1H), 4.42 (dd, J=14.7, 6.0 Hz, 1H), 4.25 (dd, J=14.7 Hz, 6.0 Hz, 1H), 4.04 (m, 2H), 3.58 (dd, J=11.1, 5.4 Hz, 1H), 3.51 (d, J=11.1 Hz, 1H), 3.26 (d, J=11.1 Hz, 1H), 2.95 (td, J=10.8, 3.9 Hz, 1H), 2.55 (m, 1H), 2.19-2.14 (m, 1H), 2.06-1.05 (m, 22H), 1.01 (s, 3H), 0.88 (s, 3H), 0.87 (s, 3H), 0.67 (s, 3H). $^{13}$C NMR (125 MHz, CD$_3$OD) δ 179.0, 156.7, 141.1, 129.4 (2), 128.6 (2), 128.0, 106.7, 73.9, 67.3, 65.3, 56.9, 52.1 (2), 49.1, 43.9, 43.8, 43.6, 43.4, 42.0, 39.8, 39.2, 38.9, 38.1, 35.2, 34.0, 33.6, 30.6, 28.1, 27.7, 22.3, 19.1, 17.2, 16.9, 15.1, 12.6. MS (ESI) m/z 578.37 (M+H$^+$)

Example 19

Preparation of 3,23,30-Triacetoxy-betulinic amide (DA064)

To a solution of 3,23,30-triacetoxy-betulinic acid (30 mg, 0.049 mmoL) dissolved in 2 mL dry methylene chloride, was added oxalyl dichloride (42 μL, 0.49 mmoL) under nitrogen. The mixture was stirred at room temperature for 2 h and then concentrated under reduced pressure. The resulting residue was dissolved in 2 mL dry methylene chloride, and ammonium (saturated in methanol, 2 mL) was added. The mixture was stirred at room temperature overnight. Aqueous workup followed by purification by column chromatography on silica gel column, eluting with 40% ethyl acetate in petroleum ether provided the desired product (29 mg, 97%) as a white solid. $^1$H NMR (400 MHz, CDCl$_3$) δ 5.59 (br s, 1H), 5.46 (br s, 1H), 4.98 (s, 1H), 4.94 (s, 1H), 4.78 (m, 1H), 4.56 (m, 2H), 3.85 (d, J=11.7 Hz, 1H), 3.68 (d, J=11.7 Hz, 1H), 3.06 (td, J=11.2, 3.7 Hz, 1H), 2.47 (m, 1H), 2.10 (s, 3H), 2.07 (s, 3H), 2.02 (s, 3H), 1.90-1.20 (m, 23H), 0.97 (s, 3H), 0.95 (s, 3H), 0.88 (s, 3H), 0.81 (s, 3H). $^{13}$C NMR (125 MHz, CDCl$_3$) δ 178.7, 170.9, 170.7, 170.6, 149.3, 110.0, 74.5, 66.0, 65.4, 55.6, 50.6, 50.5, 48.0, 42.9, 42.4, 40.7, 40.6, 38.1, 38.0, 37.5, 37.0, 34.0, 33.8, 31.9, 29.4, 26.5, 23.9, 23.1, 21.3, 21.0 (2), 20.9, 18.0, 16.7, 16.2, 14.6, 12.9. MS (ESI) m/z 637.35 (M+Na$^+$).

Example 20

Preparation of 3,23,30-Triacetoxy-betulinic methyl amide (DA065)

To a solution of 3,23,30-triacetoxy-betulinic acid (30 mg, 0.049 mmoL) dissolved in 2 mL dry methylene chloride, was added oxalyl dichloride (42 μL, 0.49 mmoL) under nitrogen. The mixture was stirred at room temperature for 2 h and then concentrated under reduced pressure. The resulting residue was dissolved in 2 mL dry methylene chloride, and methylamine (33% wt in ethanol, 0.2 mL) was added. The mixture was stirred at room temperature overnight. Aqueous workup followed by purification by column chromatography on silica gel column, eluting with 1.5% methanol in methylene chloride provided the desired product (27 mg, 0.043, 88%) as a white solid. $^1$H NMR (400 MHz, CDCl$_3$) δ 5.63 (q, J=4.6 Hz, 1H), 4.98 (s, 1H), 4.93 (s, 1H), 4.77 (dd, J=11.5, 4.6 Hz, 1H), 4.56 (m, 2H), 3.85 (d, J=11.7 Hz, 1H), 3.67 (d, J=11.7 Hz, 1H), 3.14 (td, J=11.5, 3.7 Hz, 1H), 2.79 (d, J=4.6 Hz, 3H), 2.46 (m 1H), 2.10 (s, 3H), 2.07 (s, 3H), 2.02 (s, 3H), 1.90-1.93 (m, 1H), 1.77-1.24 (m, 17H), 1.16-1.13 (m, 2H), 1.06-1.00 (m, 1H), 0.96 (s, 3H), 0.93 (s, 3H), 0.88 (s, 3H), 0.81 (s, 3H). $^{13}$C NMR (125 MHz, CDCl$_3$) δ 176.3, 170.8, 170.6, 170.5, 149.5, 109.9, 74.5, 66.1, 65.4, 55.5, 50.9, 50.6, 48.0, 43.1, 42.3, 40.7, 40.6, 38.1, 38.0, 37.6, 37.0, 34.1, 33.7, 32.1, 29.4, 26.5, 26.2, 23.1, 21.2, 21.1 (2), 21.0, 17.9, 16.6, 16.2, 14.6, 13.0. MS (ESI) m/z 628.33 (M+H$^+$).

Example 21

Preparation of 3,23,30-Triacetoxy-betulinic 2-hydroxyethyl amide (DA066)

To a solution of 3,23,30-triacetoxy-betulinic acid (27 mg, 0.044 mmoL) dissolved in 2 mL dry methylene chloride, was added oxalyl dichloride (38 μL, 0.44 mmoL) under nitrogen. The mixture was stirred at room temperature for 2 h and then concentrated under reduced pressure. The resulting residue was dissolved in 1.5 mL dry methylene chloride, and ethanolamine (13 μL, 0.22 mmoL) was added. The mixture was stirred at room temperature overnight. Aqueous workup followed by purification by column chromatography on silica gel column, eluting with 1.5% methanol in methylene chloride provided the desired product (29 mg, 0.044, 100%) as a white solid. $^1$H NMR (400 MHz, CDCl$_3$) δ 6.13 (t, J=5.6 Hz, 1H), 4.98 (s, 1H), 4.94 (s, 1H), 4.76 (dd, J=11, 4.9 Hz, 1H), 4.55 (m, 2H), 3.84 (d, J=11.5 Hz, 1H), 3.71 (m, 2H), 3.68 (d, J=12.0 Hz, 1H), 3.48 (m, 1H), 3.36 (m, 1H), 3.09 (td, J=11, 3.9 Hz, 1H), 2.84 (br s, 1H), 2.45 (m, 1H), 2.10 (s, 3H), 2.07 (s, 3H), 2.02 (s, 3H), 2.00-1.94 (m, 1H), 1.79-1.00 (m, 21H), 0.97 (s, 3H), 0.94 (s, 3H), 0.87 (s, 3H), 0.81 (s, 3H). $^{13}$C NMR (125 MHz, CDCl$_3$) δ 177.5, 170.9, 170.7, 170.5, 149.3, 110.0, 74.4, 66.1, 65.4, 63.1, 55.6, 50.8, 50.6, 48.0, 43.0, 42.4, 42.4, 42.3, 40.7, 40.6, 38.2, 38.0, 37.6, 37.0, 34.0, 33.6, 32.0, 29.4, 26.5, 23.1, 21.3, 21.1 (2), 21.0, 17.9, 16.6, 16.1, 14.6, 13.0. MS (ESI) m/z 658.28 (M+H$^+$).

Example 22

Preparation of 3,23,30-Triacetoxy-betulinic 2-hydroxyethyl ester (DA067)

To a solution of 3,23,30-triacetoxy-betulinic acid (30 mg, 0.049 mmoL) dissolved in 2 mL dry methylene chloride, was added oxalyl dichloride (34 μL, 0.39 mmoL) under nitrogen. The mixture was stirred at room temperature for 2 h and then concentrated under reduced pressure. The resulting residue was dissolved in 2 mL dry methylene chloride, and ethylene glycol (22 μL, 0.39 mmoL) and triethylamine (27 μL, 0.20 mmoL) were added. The mixture was stirred at room temperature overnight. Aqueous workup followed by purification by column chromatography on silica gel column, eluting with 3% methanol in methylene chloride provided the desired product (27 mg, 0.041, 84%) as a white solid. $^1$H NMR (400 MHz, CDCl$_3$) δ 4.96 (s, 1H), 4.93 (s, 1H), 4.74 (m, 1H), 4.53 (m, 2H), 4.20 (m, 2H), 3.80-3.79 (m, 3H), 3.66 (d, J=11.7 Hz, 1H), 2.92 (m, 1H), 2.12-2.28 (m, 2H), 2.07 (s, 3H), 2.03 (s, 3H), 1.98 (s, 3H), 1.84-2.00 (m, 2H), 1.67-1.58 (m, 5H), 1.50-0.98 (m, 19H), 0.94 (s, 3H), 0.89 (s, 3H), 0.84 (s, 3H), 0.78 (s, 3H). $^{13}$C NMR (125 MHz, CDCl$_3$) δ 176.2, 170.9, 170.6, 170.5, 149.0, 110.4, 74.4, 66.2, 65.7, 65.4, 61.5, 56.6, 50.5, 50.1, 48.0, 43.1, 42.3, 40.7, 40.6, 38.3, 38.0, 37.0, 36.8, 34.0, 32.0, 31.9, 29.6, 26.6, 23.1, 21.3, 21.1 (2), 21.0, 17.9, 16.6, 16.0, 14.7, 13.0. MS (ESI) m/z 681.51 (M+Na$^+$).

Example 23

Preparation of 3,23,30-Trihydroxy-betulinic methyl amide (DA068)

To a solution of 3,23,30-triacetoxy-betulinic methyl amide (23 mg, 0.037 mmoL) dissolved in 1 mL of THF and 2 mL of MeOH, was added aqueous sodium hydroxide (20%, 0.5 mL). The resulting mixture was allowed to stir overnight at room temperature. The mixture was neutralized with aqueous HCl and concentrated. The resulting residue was purified by column chromatography on silica gel, eluting with 5% methanol in methylene chloride to provide the desired product (9 mg, 0.018 mmoL, 49%) as a white solid. $^1$H NMR (400 MHz, CD$_3$OD/CDCl$_3$) δ 7.43 (q, J=4.4 Hz, 1H), 4.94 (s, 1H), 4.85 (s, 1H), 4.03 (m, 2H), 3.57 (dd, J=10.7, 5.1 Ha, 1H), 3.51 (d, J=11 Hz, 1H), 3.27 (d, J=11 Hz, 1H), 2.94 (td, J=11, 3.9 Hz, 1H), 2.69 (d, J=4.4 Hz, 3H), 2.49 (m, 1H), 2.07 (m, 1H), 1.96 (m, 1H), 1.77-1.22 (m, 18H), 1.15-1.03 (m, 3H), 0.99 (s, 3H), 1.94 (s, 3H), 0.87 (s, 3H), 0.68 (s, 3H). $^{13}$C NMR (125 MHz, CD$_3$OD/CDCl$_3$) δ 179.3, 156.2, 106.4, 64.2, 67.9, 65.1, 56.6, 51.8, 51.7, 43.5, 43.3, 43.1, 41.7, 39.5, 39.0, 38.7, 37.9, 34.9, 33.9, 33.4, 30.4, 27.8, 27.4, 26.4, 22.1, 19.0, 17.1, 16.7, 15.1, 12.4. MS (ESI) m/z 502.36 (M+H$^+$).

Example 24

Preparation of 3,23,30-Trihydroxy-betulinic 2-hydroxyethyl amide (DA069)

To a solution of 3,23,30-triacetoxy-betulinic 2-hydroxyethyl amide (22 mg, 0.033 mmoL) dissolved in 1 mL of THF and 3 mL of MeOH, was added aqueous sodium hydroxide (20%, 0.5 mL). The resulting mixture was allowed to stir overnight at room temperature. The mixture was neutralized with aqueous HCl and concentrated. The resulting residue was purified by column chromatography on silica gel, eluting with 7-8% methanol in methylene chloride to provide the desired product (18 mg, 0.033 mmoL, 100%) as a white solid. $^1$H NMR (300 MHz, CD$_3$OD/CDCl$_3$) δ 4.94 (d, J=1.5 Hz, 1H), 4.86 (s, 1H), 4.53 (br s, 1H), 4.03 (m, 2H), 3.59-3.54 (m, 3H), 3.51 (d, J=10.8 Hz, 1H), 3.38-3.18 (m, 2H), 2.91 (td, J=11.4, 4.2 Hz, 1H), 2.49 (m, 1H), 2.12-2.08 (m, 1H), 1.98 (m, 1H), 1.82-1.17 (m, 20H), 0.99 (s, 3H), 0.94 (s, 3H), 0.86 (s, 3H), 0.69 (s, 3H). $^{13}$C NMR (125 MHz, CD$_3$OD/CDCl$_3$) δ 180.0, 156.1, 106.4, 74.3, 67.9, 65.1, 61.9, 56.7, 51.8, 51.7, 43.5, 43.3, 43.1, 42.4, 41.7, 39.5, 38.0, 38.6, 37.9, 34.9, 33.9, 33.4, 30.4, 27.8, 27.3, 22.1, 19.0, 17.1, 16.7, 15.1, 12.4. MS (ESI) m/z 532.28 (M+H$^+$).

Example 25

Preparation of 3,23,30-Trihydroxy-betulinic amide (DA070)

To a solution of 3,23,30-triacetoxy-betulinic amide (25 mg, 0.041 mmoL) dissolved in 1 mL of THF and 2 mL of MeOH, was added aqueous sodium hydroxide (20%, 0.5 mL). The resulting mixture was allowed to stir overnight at room temperature. The mixture was neutralized with aqueous HCl and concentrated. The resulting residue was purified by column chromatography on silica gel to provide the desired product (15 mg, 0.031 mmoL, 76%) as a white solid. $^1$H NMR (400 MHz, CD$_3$OD/CDCl$_3$) δ 4.97 (s, 1H), 4.89 (s, 1H), 4.06 (m, 2H), 3.61-3.55 (m, 1H), 3.56 (d, J=10.6 Hz, 1H), 3.32 (d, J=10.6 Hz, 1H), 2.91 (m, 1H), 2.49 (m, 1H), 2.11-2.02 (m, 2H), 1.85 (dd, J=11.8, 7.4 Hz, 1H), 1.72-1.18 (m), 1.01 (s, 3H), 0.97 (s, 3H), 0.88 (s, 3H), 0.75 (s, 3H). $^{13}$C NMR (125 MHz, CD$_3$OD/CDCl$_3$) δ 181.4, 155.6, 106.3, 75.0, 69.2, 64.9, 56.4, 51.4, 51.2, 43.1, 43.0, 42.6, 41.4, 39.2, 38.7, 38.2, 37.7, 34.7, 33.9, 33.1, 30.2, 27.4, 26.9, 21.8, 18.9, 17.0, 16.5, 15.0, 12.1. MS (ESI) m/z 488.34 (M+H$^+$).

Example 26

Preparation of 3,23,30-Trihydroxy-betulinic 2-hydroxyethyl ester (DA071)

To a solution of 3,23,30-triacetoxy-betulinic 2-hydroxyethyl ester (23 mg, 0.035 mmoL) dissolved in 1 mL of THF and 2 mL of MeOH, was added aqueous sodium hydroxide (20%, 0.5 mL). The resulting mixture was allowed to stir overnight at room temperature. The mixture was neutralized with aqueous HCl and concentrated. The resulting residue was purified by column chromatography on silica gel, eluting with 5-6% methanol in methylene chloride to provide the desired product (15 mg, 0.033 mmoL, 81%) as a white solid. $^1$H NMR (400 MHz, CD$_3$OD) δ 4.96 (s, 1H), 4.91 (s, 1H), 4.13 (m, 2H), 4.04 (br s, 2H), 3.72 (t, J=5.1 Hz, 2H), 3.58 (dd, J=10.8, 4.9 Hz, 1H), 3.50 (d, J=11 Hz, 1H), 3.27 (d, J=11 Hz, 1H), 2.88 (td, J=11, 4.2 Hz, 1H), 2.31-2.21 (m, 2H), 2.02-1.87 (m, 2H), 1.77 (t, J=11.4 Hz, 1H), 1.69-1.07 (m, 19H), 1.01 (s, 3H), 0.94 (s, 3H), 0.91 (s, 3H), 0.88 (s, 3H), 0.67 (s, 3H). $^{13}$C NMR (125 MHz, CD$_3$OD) δ 177.4, 156.1, 107.0, 73.8, 67.3, 66.3, 65.2, 61.1, 57.9, 51.9, 51.2, 44.0, 43.6, 43.4, 41.9, 39.7, 39.6, 38.1, 37.7, 35.0, 33.4, 33.0, 30.9, 28.0, 27.6, 22.1, 19.1, 17.1, 16.7, 15.2, 12.6. MS (ESI) m/z 1087.31 (2M+Na$^+$).

Scheme 5

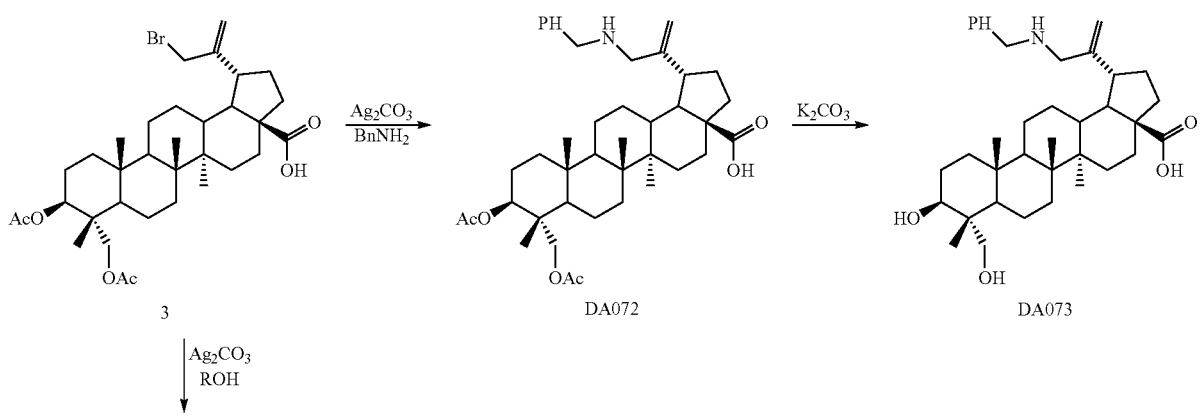

-continued

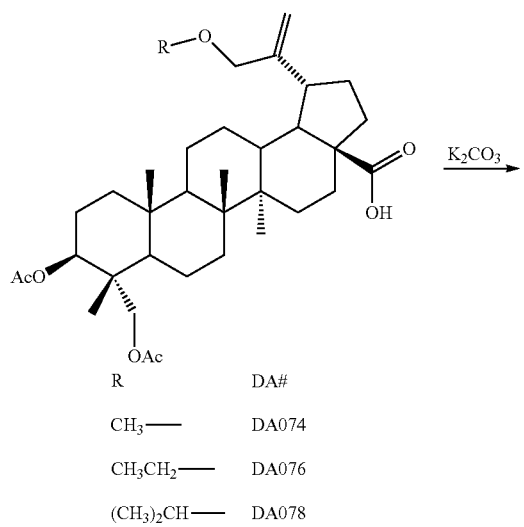 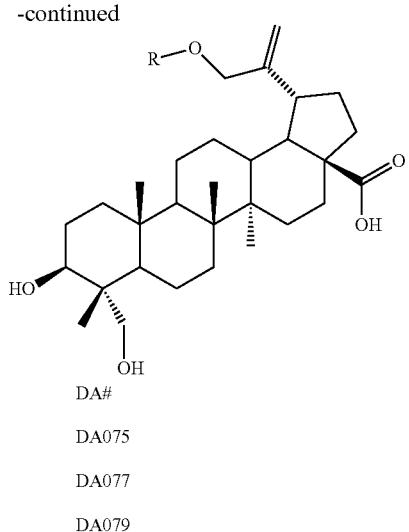

| R | DA# | | DA# |
|---|---|---|---|
| CH₃— | DA074 | | DA075 |
| CH₃CH₂— | DA076 | | DA077 |
| (CH₃)₂CH— | DA078 | | DA079 |

Compounds DA072-DA079 were synthesized according to the synthetic approaches outlined in Scheme 5.

Example 27

Preparation of 30-N-Benzylamino-3,23-diacetoxy-betulinic acid (DA072)

Ag$_2$CO$_3$ (17.1 mg, 62.0 mol) and BnNH$_2$ (10.0 μL, 91.5 μmol) were added to a solution of 3,23-diacetoxy-30-bromo-betulinic acid (22.8 mg, 35.9 μmol) in DMF (1.00 mL). The mixture was stirred for 22 h at room temperature. The reaction mixture was filtered through a short pad of SiO$_2$ eluting with AcOEt. After the organic layer was evaporated, 16.2 mg of residue was purified by column chromatography (CHCl$_3$:MeOH=100:1→60:1→30:1) to obtain 3.20 mg (23%) of the desired compound as a colorless oil. $^1$H NMR (400 MHz, CDCl$_3$) δ 7.40-7.26 (m, 5H), 4.98 (s, 1H), 4.91 (s, 1H), 4.75 (dd, J=11.7, 4.5 Hz, 1H), 4.66 (br s, 1H), 3.95 (d, J=15.1 Hz, 1H), 3.84 (d, J=15.1 Hz, 1H), 3.82 (d, J=11.7 Hz, 1H), 3.68 (d, J=11.7 Hz, 1H), 3.36-3.24 (m, 2H), 2.95 (dt, J=11.7, 4.5 Hz, 1H), 2.30-0.65 (m, 24H), 2.06 (s, 3H), 2.02 (s, 3H), 0.94 (s, 3H), 0.87 (s, 3H), 0.85 (s, 3H), 0.80 (s, 3H). $^{13}$C NMR (125 MHz, CDCl$_3$) δ 180.93, 171.10, 170.77, 152.20, 137.80, 128.73, 127.70, 74.67, 65.59, 56.68, 52.20, 51.37, 50.70, 48.20, 42.58, 40.91, 40.80, 38.44, 38.24, 37.31, 37.17, 34.18, 32.77, 29.93, 27.51, 23.36, 21.50, 21.38, 21.19, 18.16, 16.88, 16.25, 14.81, 13.18, 0.247. MS (ESI) m/z 662 (M+H$^+$).

Example 28

Preparation of 30-N-Benzylamino-23-hydroxy-betulinic acid (DA073)

K$_2$CO$_3$ (4.24 mg, 30.7 μmol) was added to a solution of DA072 (10.7 mg, 16.2 μmol) in MeOH (500 μL). The mixture was stirred for 19.5 h at room temperature. The reaction mixture was diluted with H$_2$O at 0 C and acidified with conc. HCl aq. The mixture was extracted with CHCl$_3$×3 (20.0 mL) and the combined organic layer was dried (Na$_2$SO$_4$) and concentrated. The obtained residue (6.30 mg) was purified by column chromatography (CHCl$_3$:MeOH=10:1) to obtain 3.20 mg (34%) of the desired compound as a white solid. $^1$H NMR (400 MHz, CD$_3$OD) δ 7.56-7.37 (m, 5H), 5.14 (s, 1H), 4.99 (s, 1H), 4.15-4.05 (m, 2H), 3.62 (dd, J=11.0, 4.7 Hz, 1H), 3.54 (d, J=11.0 Hz, 1H), 3.47 (d, J=11.0 Hz, 1H), 3.09-2.98 (m, 1H), 2.50-1.94 (m, 4H), 1.80-0.80 (m, 20H), 1.32 (s, 3H), 1.00 (s, 3H), 0.91 (s, 3H), 0.70 (s, 3H). $^{13}$C NMR (125 MHz, CD$_3$OD) δ 182.50, 151.61, 144.29, 131.28, 130.74, 130.47, 111.10, 74.65, 68.09, 53.83, 53.00, 52.79, 52.47, 46.57, 44.47, 44.25, 42.76, 40.68, 40.26, 39.06, 38.95, 35.98, 34.64, 34.11, 32.85, 31.79, 31.63, 29.16, 28.48, 23.12, 20.00, 16.91, 16.81, 15.98, 13.46. MS (ESI) m/z 578 (M+H$^+$).

Example 29

Preparation of 3,23-Diacetoxy-30-methoxy-betulinic acid (DA074)

Ag$_2$CO$_3$ (12.9 mg, 46.8 μmol) was added to a solution of 3,23-diacetoxy-30-bromo-betulinic acid (17.5 mg, 27.5 μmol) in MeOH (1.00 mL). The mixture was stirred for 5 h at 40 C. The reaction mixture was filtered through a short pad of SiO$_2$ eluting with AcOEt. After the organic layer was evaporated, 14.6 mg of residue was purified by column chromatography (Hexane:AcOEt=6:1) to obtain 11.3 mg (70%) of the desired compound as a colorless oil. $^1$H NMR (400 MHz, CDCl$_3$) δ 4.94 (d, J=2H), 4.76 (dd, J=11.7, 4.5 Hz, 1H), 3.88 (s, 2H), 3.84 (d, J=15.1 Hz, 1H), 3.68 (d, J=15.1 Hz, 1H), 3.36 (s, 3H), 2.89 (dt, J=11.7, 4.5 Hz, 1H), 2.28-0.65 (m, 24H), 2.06 (s, 3H), 2.01 (s, 3H), 0.98 (s, 3H), 0.92 (s, 3H), 0.88 (s, 3H), 0.80 (s, 3H). $^{13}$C NMR (125 MHz, CDCl$_3$) δ 181.42, 171.15, 170.80, 151.17, 109.30, 75.21, 74.68, 70.08, 65.60, 58.55, 56.54, 50.71, 50.03, 48.20, 43.24, 42.57, 40.91, 40.82, 38.60, 38.22, 37.20, 37.08, 34.21, 32.27, 29.94, 29.91, 26.80, 23.36, 21.51, 21.21, 18.15, 16.86, 16.28, 14.84, 13.18. MS (ESI) m/z 585 (M−H$^+$), 1061 (2M−H$^+$).

Example 30

Preparation of 23-Hydroxy-30-methoxy-betulinic acid (DA075)

K$_2$CO$_3$ (6.52 mg, 47.2 μmol) was added to a solution of DA074 (8.50 mg, 14.5 μmol) in MeOH (500 μL). The mixture was stirred for 20 h at room temperature and for 28 h at 50 C.

The reaction mixture was diluted with H$_2$O at 0 C and acidified with conc. HCl aq. The mixture was extracted with CHCl$_3$×3 (20.0 mL) and the combined organic layer was dried (Na$_2$SO$_4$) and concentrated. The obtained residue (7.20 mg) was purified by column chromatography (CHCl$_3$:MeOH=50:1) to obtain 6.30 mg (86%) of the desired compound as a white solid. $^1$H NMR (400 MHz, CDCl$_3$) δ 4.95 (br s, 2H), 4.62 (br s, 1H), 3.93 (s, 2H), 3.62 (dd, J=11.1, 5.6 Hz, 1H), 3.54 (d, J=11.1 Hz, 1H), 3.37 (s, 3H), 2.96 (dt, J=11.1, 3.9 Hz, 1H), 2.37-2.23 (m, 2H), 2.13-0.85 (m, 22H), 1.05 (s, 3H), 1.00 (s, 3H), 0.92 (s, 3H), 0.71 (s, 3H). $^{13}$C NMR (125 MHz, CDCl$_3$) δ 153.63, 110.57, 76.98, 74.66, 68.12, 59.39, 58.37, 52.77, 51.88, 50.14, 45.41, 44.47, 44.24, 42.75, 40.61, 40.50, 35.96, 34.15, 34.10, 31.75, 28.92, 28.49, 23.10, 19.99, 17.98, 17.59, 15.98, 13.46. MS (ESI) m/z 501 (M−H$^+$), 1003 (2M−H$^+$).

Example 31

Preparation of 3,23-Diacetoxy-30-ethoxy-betulinic acid (DA076)

Ag$_2$CO$_3$ (28.1 mg, 102 μmol) was added to a solution of 3,23-diacetoxy-30-bromo-betulinic acid (21.7 mg, 34.1 μmol) in EtOH (1.00 mL). The mixture was stirred for 6 h at 40 degree C. The reaction mixture was filtered through a short pad of SiO$_2$ eluting with AcOEt. After the organic layer was evaporated, 18.3 mg of residue was purified by column chromatography (Hexane:AcOEt=10:1) to obtain 13.7 mg (67%) of the desired compound as a colorless oil. $^1$H NMR (400 MHz, CDCl$_3$) δ 4.96 (s, 1H), 4.92 (s, 1H), 4.76 (dd, J=11.7, 4.5 Hz, 1H), 3.93 (s, 2H), 3.84 (d, J=15.1 Hz, 1H), 3.78 (d, J=15.1 Hz, 1H), 3.50 (q, J=7.2 Hz, 1H), 2.89 (dt, J=11.7, 4.5 Hz, 1H), 2.35-0.65 (m, 24H), 2.07 (s, 3H), 2.03 (s, 3H), 0.98 (s, 3H), 0.93 (s, 3H), 0.88 (s, 3H), 0.80 (s, 3H). $^{13}$C NMR (125 MHz, CDCl$_3$) δ 181.43, 171.16, 170.81, 151.40, 109.13, 74.68, 73.02, 56.55, 50.73, 49.92, 48.21, 43.38, 42.59, 41.07, 40.91, 40.82, 38.62, 38.23, 37.20, 37.10, 34.21, 32.27, 29.93, 26.71, 24.08, 23.36, 21.51, 21.22, 18.15, 17.75, 17.55, 16.86, 16.28, 15.45, 14.88, 13.17. MS (ESI) m/z 599 (M−H$^+$), 1199 (2M−H$^+$).

Example 32

Preparation of 23-Hydroxy-30-ethoxy-betulinic acid (DA077)

K$_2$CO$_3$ (7.18 mg, 51.9 μmol) was added to a solution of DA076 (10.4 mg, 17.3 μmol) in MeOH (500 μL). The mixture was stirred for 20 h at room temperature and for 8.5 h at 50 C. The reaction mixture was diluted with H$_2$O at 0 C and acidified with conc. HCl aq. The mixture was extracted with CHCl$_3$×3 (20.0 mL) and the combined organic layer was dried (Na$_2$SO$_4$) and concentrated. The obtained residue (8.50 mg) was purified by column chromatography (CHCl$_3$:MeOH=500:1→100:1) to obtain 6.40 mg (72%) of the desired compound as a white solid. $^1$H NMR (400 MHz, CD$_3$OD) δ 4.82 (br s, 2H), 3.85 (s, 2H), 3.48 (dd, J=11.1, 5.5 Hz, 1H), 3.42 (br d, J=11.1 Hz, 1H), 3.40 (q, J=6.9 Hz, 2H), 3.25-3.15 (m, 1H), 2.83 (dt, J=12.0, 5.5 Hz, 1H), 2.23-2.11 (m, 2H), 1.98-1.85 (m, 1H), 1.77 (dd, J=12.4, 8.2 Hz, 1H), 1.69-0.69 (m, 23H), 1.10 (t, J=6.9 Hz, 3H), 0.92 (s, 3H), 0.87 (s, 3H), 0.79 (s, 3H), 0.58 (s, 3H). $^{13}$C NMR (125 MHz, CD$_3$OD) δ 179.88, 153.10, 109.73, 74.16, 73.89, 67.35, 66.99, 57.58, 52.02, 51.03, 44.74, 43.72, 43.47, 41.97, 39.84, 39.76, 38.19, 38.04, 35.18, 33.35, 33.30, 30.98, 30.87, 28.08, 27.72, 22.33, 19.22, 17.21, 16.81, 15.59, 15.26, 12.68; MS (ESI) m/z 1031 (2M−H$^+$).

Example 33

Preparation of 3,23-Diacetoxy-30-isopropyloxy-betulinic acid (DA078)

Ag$_2$CO$_3$ (30.3 mg, 110 μmol) was added to a solution of 3,23-diacetoxy-30-bromo-betulinic acid (23.2 mg, 36.5 μmol) in 2-propanol (1.00 mL). The mixture was stirred for 19 h at 50 C. The reaction mixture was filtered through a short pad of SiO$_2$ eluting with AcOEt. After the organic layer was evaporated, 20.4 mg of residue was purified by column chromatography (Hexane:AcOEt=8:1) to obtain 12.7 mg (57%) of the desired compound as a colorless oil. $^1$H NMR (400 MHz, CDCl$_3$) δ 4.97 (s, 1H), 4.90 (s, 1H), 4.76 (dd, J=11.7, 4.5 Hz, 1H), 3.93 (s, 2H), 3.84 (d, J=15.1 Hz, 1H), 3.68 (d, J=15.1 Hz, 1H), 3.61 (heptet, J=7.2 Hz, 1H), 2.88 (dt, J=11.7, 4.5 Hz, 1H), 2.30-0.70 (m, 24H), 2.06 (s, 3H), 2.03 (s, 3H), 1.18 (br d, J=7.2 Hz, 6H), 0.98 (s, 3H), 0.93 (s, 3H), 0.88 (s, 3H), 0.80 (s, 3H). $^{13}$C NMR (125 MHz, CDCl$_3$) δ 181.40, 171.14, 170.78, 151.95, 108.85, 74.68, 71.42, 70.40, 65.60, 56.57, 50.74, 49.86, 48.22, 43.44, 42.59, 40.91, 40.82, 38.62, 38.23, 37.21, 37.09, 34.21, 32.29, 29.94, 26.67, 23.36, 22.33, 21.50, 21.22, 18.15, 16.87, 16.28, 14.91, 14.38, 13.18, 0.282. MS (ESI) m/z 613 (M−H$^+$), 1227 (2M−H$^+$).

Example 34

Preparation of 23-Hydroxy-30-isopropyloxy-betulinic acid (DA079)

K$_2$CO$_3$ (4.09 mg, 29.6 μmol) was added to a solution of DA078 (9.10 mg, 14.8 μmol) in MeOH (500 μL). The mixture was stirred for 18 h at 50 C. The reaction mixture was diluted with H$_2$O at 0 C and acidified with conc. HCl aq. The mixture was extracted with CHCl$_3$×3 (20.0 mL) and the combined organic layer was dried (Na$_2$SO$_4$) and concentrated. The obtained residue (8.50 mg) was purified by column chromatography (CHCl$_3$:MeOH=500:1) to obtain 4.60 mg (58%) of the desired compound 6d as a white solid. $^1$H NMR (400 MHz, CD$_3$OD) δ 4.83 (br s, 2H), 4.49 (br s, 1H), 3.86 (s, 2H), 3.53 (heptet, J=6.0 Hz, 1H), 3.50 (br s, 1H), 3.42 (d, J=10.6 Hz, 1H), 3.18 (d, J=10.6 Hz, 1H), 2.83 (dt, J=10.6, 3.8 Hz, 1H), 2.25-2.10 (m, 2H), 1.98-1.83 (m, 1H), 1.77 (dd, J=12.0, 8.0 Hz, 1H), 1.70-0.70 (m, 20H), 1.07 (dd, J=6.0, 2.0 Hz, 6H), 0.92 (s, 3H), 0.87 (s, 3H), 0.79 (s, 3H), 0.58 (s, 3H). $^{13}$C NMR (125 MHz, CD$_3$OD) δ 180.04, 153.69, 109.43, 73.92, 72.60, 71.66, 67.39, 57.65, 52.04, 51.04, 44.75, 43.74, 43.48, 41.99, 39.86, 39.76, 38.19, 38.07, 35.20, 33.42, 31.01, 30.88, 28.09, 27.73, 22.53, 22.48, 22.34, 19.24, 17.22, 16.84, 15.31, 12.69. MS (ESI) m/z 529 (M−H$^+$), 1059 (2M−H$^+$).

The syntheses of compounds DA080-DA090 are shown in Schemes 6-9. The 3,23-dihydroxyl groups of 23-hydroxyl-betulinic acid could be protected as acetates or bis-TBS ethers if required. Modifications of C$_{2-8}$ carboxylic acid involved formation of esters, reduction of the resulting esters to the alcohol and reaction of the alcohol to form different ethers or esters. Modification of the C20-C29 olefin region involved reaction with mCPBA to form epoxide, or reaction with NBS to form 3-bromo-2-propenyl. The bromo could be replaced with acetoxyl by reacting with silver acetate to form 3-acetoxyl-2-propenyl, which could be de-protected to give 3-hydroxyl-2-propenyl.

Scheme 6

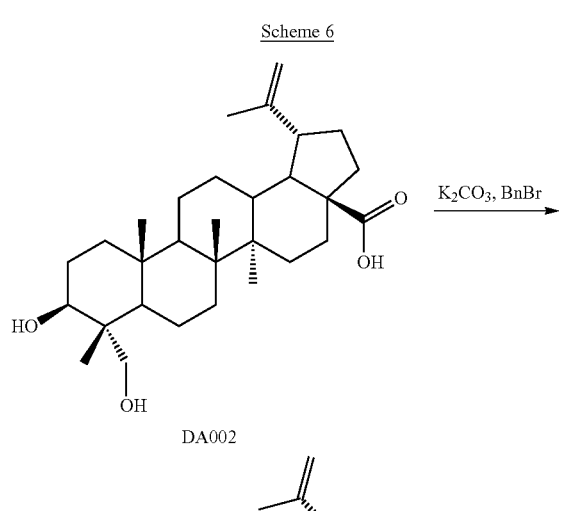

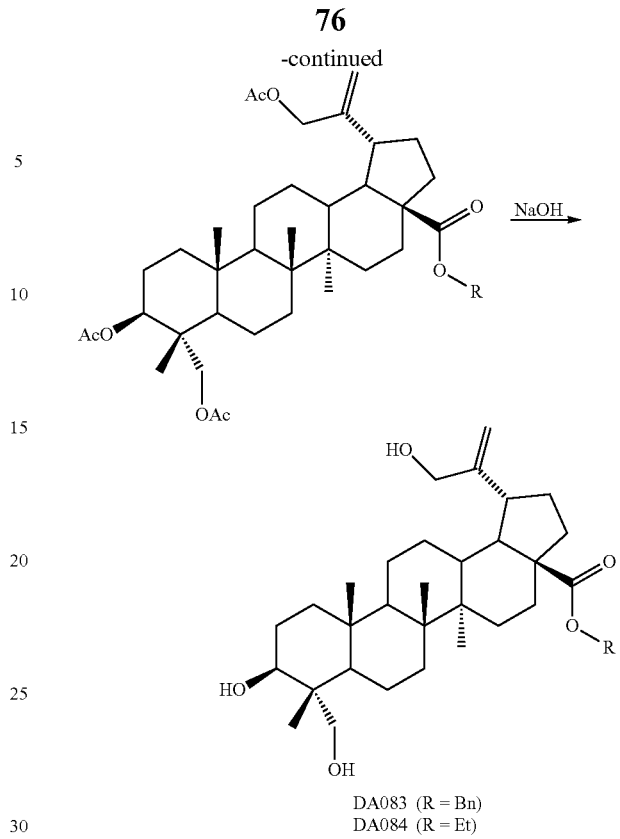

Compounds DA080-DA084 were synthesized according to the synthetic approaches set forth in Scheme 6.

Example 35

Preparation of 23-Hydroxyl-betulinic acid benzyl ester (DA080)

A mixture of 23-hydroxyl-betulinic acid (325 mg, 0.69 mmoL), benzyl bromide (0.12 mL, 1.03 mmoL) and potassium carbonate (190 mg, 1.38 mmoL) in DMF (3.5 mL) was stirred at room temperature for 24 h under nitrogen. After the reaction was completed as indicated by TLC, ice water (~20 mL) was added. The resulting white precipitate was collected by filtration. Purification by column chromatography on silica gel, eluting with 2-4% methanol in dichloromethane, provided the desired benzyl ester as a white solid (351 mg, 0.62 mmoL, 90%). $^1$H NMR (400 MHz, CDCl$_3$): 7.35-7.36 (m, 5H), 5.15 (d, J=12.2 Hz, 1H), 5.09 (d, J=12.2 Hz, 1H), 4.72 (s, 1H), 4.59 (s, 1H), 3.70 (d, J=10.3 Hz, 1H), 3.60 (m, 1H), 3.40 (d, J=10.5 Hz, 1H), 3.01 (m, 1H), 2.28 (m, 1H), 2.18 (m, 1H), 1.84-1.93 (m, 2H), 1.67 (s, 3H), 1.55-1.65 (m, 6H), 1.20-1.32 (m, 12H), 0.98-1.12 (m, 2H), 0.93 (s, 3H), 0.86 (s, 3H), 0.84 (s, 3H), 0.76 (s, 3H). $^{13}$CNMR (100 MHz, CDCl$_3$): 175.6, 150.3, 136.2, 128.3 (2), 128.0 (2), 127.9, 109.5, 76.3, 71.4, 65.6, 56.4, 50.4, 49.8, 49.3, 46.8, 42.3, 41.7, 40.6, 38.4, 38.1, 37.0, 36.9, 34.0, 32.0, 30.5, 29.5, 26.7, 25.5, 20.8, 19.3, 18.3, 16.5, 15.8, 14.7, 11.4. ESI-MS: 1125.70 (2M+1).

Example 36

Preparation of 23-Hydroxy-20:29-epoxy-betulinic acid benzyl ester (DA081)

To a solution of 23-hydroxyl-betulinic acid benzyl ester (122 mg, 0.22 mmoL) dissolved in dry THF (4 mL), was added mCPBA (73 mg, 0.33 mmoL). The resulting mixture was stirred at room temperature for 24 h. The reaction was quenched with 10% $Na_2S_2O_3$ and extracted with dichloromethane. Purifications by column chromatography on silica gel provided the desired product as a white solid (101 mg, 0.17 mmoL, 79%). $^1$H NMR (400 MHz, $CDCl_3$): 7.32-7.34 (m, 5H), 5.09 (m, 2H), 3.69 (d, J=10.2 Hz, 1H), 3.61 (m, 1H), 3.39 (d, J=10.2 Hz, 1H), 2.61-3.64 (m, 2H), 2.26-2.30 (m, 1H), 2.09-2.17 (m, 2H), 1.26-1.95 (m, 21H), 1.24 (s, 3H), 1.05 (m, 1H), 0.92 (s, 3H), 0.84 (s, 3H), 0.83 (s, 3H), 0.74 (s, 3H). $^{13}$CNMR (100 MHz, $CDCl_3$): 175.3, 136.1, 128.3 (2), 128.1 (2), 127.9, 76.3, 71.4, 65.7, 60.1, 56.7, 56.4, 50.3, 50.0, 49.8, 45.3, 42.3, 41.7, 40.5, 38.4, 37.2, 37.0, 36.7, 33.9, 31.9, 29.2, 27.0, 26.8, 26.6, 20.9, 18.3 (2), 16.4, 15.8, 14.6, 11.4. ESI-MS: 579.75 (M+1), 1157.76 (2M+1).

Example 37

Synthesis of 3,23,30-Triacetoxy-betulinic acid benzyl ester

A mixture of 3,23,30-triacetoxy-betulinic acid (DA060, 15 mg, 0.024 mmoL), potassium carbonate (7 mg, 0.05 mmoL) and benzyl bromide (0.004 mL, 0.036 mmoL) in DMF (0.5 mL) was stirred at room temperature for 18 h under nitrogen. After the reaction was completed as shown by TLC, water was added. The mixture was extracted with ethyl acetate (×3). The combined extract was dried, filtered and concentrated. The resulting residue was purified by column chromatography on silica gel, eluting with 15% ethyl acetate in petroleum ether to give the desired benzyl ester product (14 mg, 0.02 mmoL, 83%). $^1$H NMR (300 MHz, $CDCl_3$): 7.31-7.38 (m, 5H), 5.15 (d, J=12.3 Hz, 1H), 5.08 (d, J=12.3 Hz, 1H), 4.96 (d, J=7.5 Hz, 2H), 4.70-4.78 (m, 1H), 4.54 (s, 2H), 3.83 (d, J=11.7 Hz, 1H), 3.68 (d, J=11.6 Hz, 1H), 2.93-3.00 (m, 1H), 2.28-2.32 (m, 1H), 2.13-2.22 (m, 1H), 2.09 (s, 3H), 2.06 (s, 3H), 2.02 (s, 3H), 1.88-1.97 (m, 2H), 1.00-1.75 (m, 20H), 0.94 (s, 3H), 0.85 (s, 3H), 0.80 (s, 3H), 0.75 (s, 3H). $^{13}$CNMR (75 MHz, $CDCl_3$): 175.6, 171.1, 170.8, 170.7, 149.2, 136.3, 128.5 (2), 128.2 (2), 128.1, 110.2, 74.4, 66.0, 65.8, 65.4, 56.5, 50.5, 50.0, 47.9, 43.1, 42.3, 40.6, 40.5, 38.1, 38.0, 36.9, 36.6, 33.9, 31.9, 31.8, 29.5, 26.5, 23.1, 21.2, 21.1, 20.9, 17.9, 16.6, 15.8, 14.6, 12.9.

Example 38

Preparation of 23,30-Dihydroxyl-betulinic acid benzyl ester (DA083)

A mixture of 3,23,30-triacetoxyl-betulinic acid benzyl ester (14 mg, 0.02 mmoL) dissolved in THF/MeOH (0.5 mL/1 mL) was added sodium hydroxide (20% in water, 0.3 mL). After stirring at room temperature for 5 h, the reaction was quenched with saturated ammonium chloride and extracted with dichloromethane (×3). The combined extract was concentrated and the resulting residue was purified by column chromatography on silica gel to give the desired product as a white solid (7 mg, 0.012 mmoL, 61%). $^1$H NMR (300 MHz, $CDCl_3/CD_3OD$): 7.36-7.39 (m, 5H), 5.15 (d, J=12.3 Hz, 1H), 5.09 (d, J=12.2 Hz, 1H), 4.97 (s, 1H), 4.89 (s, 1H), 3.54-3.62 (m, 3H), 3.31-3.36 (m, 1H), 2.84 (m, 1H), 2.27-2.31 (m, 1H), 2.10-2.18 (m, 1H), 1.86-1.96 (m, 2H), 1.03-1.75 (m, 21H), 0.95 (s, 3H), 0.84 (s, 3H), 0.81 (s, 3H), 0.74 (s, 3H). $^{13}$CNMR (75 MHz, $CDCl_3/CD_3OD$): 175.8, 154.3, 136.0, 128.3, 128.0, 127.9, 105.8, 75.7, 70.4, 65.6, 64.2, 56.3, 50.2, 49.7, 49.4, 42.3, 42.1, 41.4, 40.4, 38.1, 37.9, 36.7, 36.4, 33.7, 32.0, 31.7, 29.3, 26.4, 26.0, 18.0, 16.1, 15.5, 14.3, 11.0. ESI-MS: 1157.43 (2 M+1), 1180.32 (2 M+Na).

Example 39

Preparation of 3,23,30-Triacetoxyl-betulinic acid ethyl ester 3,23,30-Triacetoxyl-betulinic acid ethyl ester was prepared from DA060 using the same procedure described for the preparation of the benzy ester, by replacing benzyl bromide with ethyl bromide. The yield was 89%. $^1$H NMR (300 MHz, $CDCl_3$): 4.98 (s, 1H), 4.95 (s, 1H), 4.77 (dd, J=10.8, 4.2 Hz, 1H), 4.56 (m, 2H), 4.08-4.19 (m, 2H), 3.84 (d, J=11.6 Hz, 1H), 3.70 (d, J=11.6 Hz, 1H), 2.94-3.00 (m, 1H), 2.18-2.28 (m, 2H), 2.11 (s, 3H), 2.07 (s, 3H), 2.02 (s, 3H), 1.87-1.98 (m, 2H), 1.01-1.70 (m, 23H), 0.97 (s, 3H), 0.92 (s, 3H), 0.88 (s, 3H), 0.81 (s, 3H). $^{13}$CNMR (75 MHz, $CDCl_3$): 175.9, 171.1, 170.8, 170.7, 149.3, 110.2, 74.4, 66.1, 65.4, 59.9, 56.3, 50.5, 50.0, 48.0, 43.2, 42.3, 40.7, 40.6, 38.1, 38.0, 36.9, 36.7, 33.9, 31.9, 31.8, 29.5, 26.5, 23.1, 21.2, 21.1, 21.0 (2), 17.9, 16.6, 15.9, 14.6, 14.3, 12.9.

Example 40

Preparation of 3,30-Dihydroxyl-betulinic acid ethyl ester (DA084)

DA084 was prepared from 3,23,30-triacetoxyl-betulinic acid ethyl ester by base hydrolysis using the same procedure described for the synthesis as DA083. The yield was 81%. $^1$H NMR (300 MHz, $CDCl_3/CD_3OD$): 4.97 (s, 1H), 4.90 (s, 1H), 4.08-4.16 (m, 4H), 3.55-3.64 (m, 2H), 3.35 (d, J=10.4, 1H), 2.82-2.92 (m, 1H), 2.17-2.27 (m, 2H), 1.83-2.06 (m, 2H), 1.04-1.74 (m, 23H), 0.97 (s, 3H), 0.91 (s, 3H), 0.85 (s, 3H), 0.83 (s, 3H). $^{13}$CNMR (75 MHz, $CDCl_3/CD_3OD$): 176.3, 154.6, 106.1, 76.1, 91.1, 64.5, 59.8, 56.3, 50.3, 49.9, 49.7, 42.4, 42.2, 41.5, 40.5, 38.3, 38.0, 36.9, 36.7, 33.9, 32.2, 31.9, 29.5, 26.6, 26.2, 20.8, 18.2, 16.3, 15.8, 14.5, 14.1, 11.2. ESI-MS: 1033.32 (2M+1), 1055.20 (2M+Na).

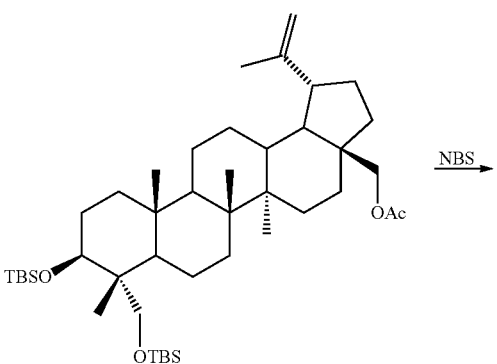

Scheme 7

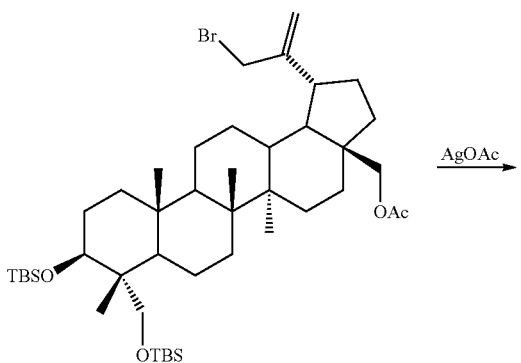

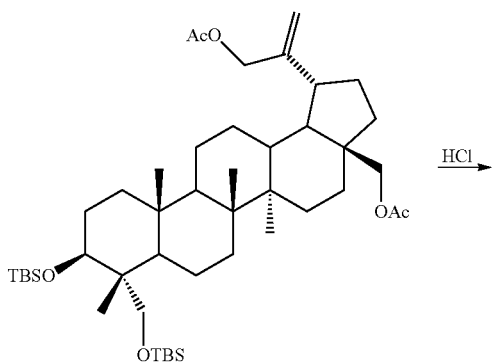

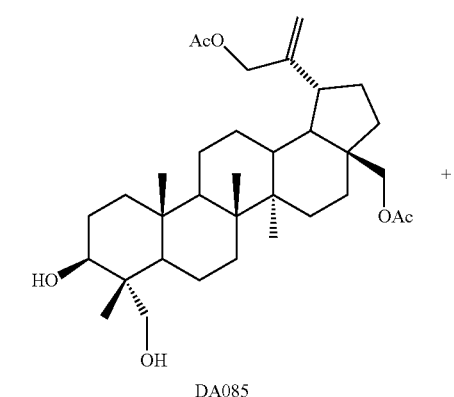

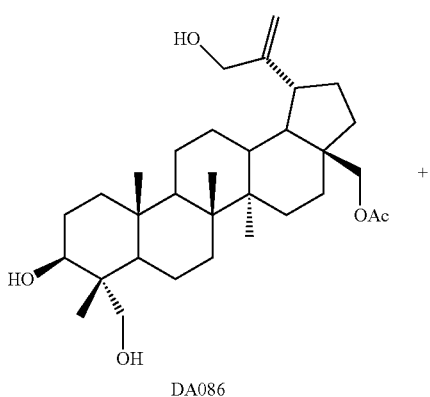

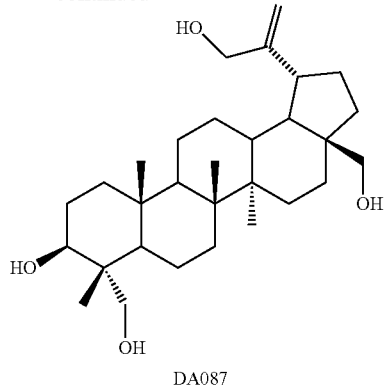

DA087

Compounds DA085-DA087 were synthesized according to the synthetic approaches set forth in Scheme 7.

Example 41

Preparation of 28-Acetoxyl-30-bromo-3,23-di-(tert-butyldimethylsiloxyl)-20(29)-lupene To a solution of 28-acetoxyl-3,23-di-(tert-butyldimethylsiloxyl)-20(29)-lupene (207 mg, 0.28 mmoL) dissolved in carbon tetrachloride (7 mL), was added NBS (53 mg, 0.30 mmoL) and AIBN (2 mg, 0.014 mmoL). The resulting mixture was heated to 80 degree Celsius under nitrogen for 3 h. After checking with TLC, more NBS (10 mg) and AIBN (1 mg) were added and the reaction was continued at 80 degree Celsius for 2 h and room temperature overnight. The reaction was filtered and rinsed with carbon tetrachloride. The filtrate was concentrated and purified by column chromatography on silica gel, eluting with 2% ethyl acetate in petroleum ether. A mixture of the desired product contaminated with un-reacted starting material was obtained, which was used directly in the next step without further purifications.

Example 42

Preparation of 28,30-Diacetoxyl-3,23-di-(tert-butyldimethylsiloxyl)-20(29)-lupene The mixture obtained from the previous bromination reaction (186 mg, 0.23 mmoL) was dissolved in acetic acid (5 mL) and silver acetate (77 mg, 0.46 mmoL) was added. The resulting mixture was heated at 120 degree Celsius for 18 h. The reaction was stopped and the solvent was removed under reduced pressure. Aqueous workup and purification by column chromatography on silica gel, eluting with 3-5% ethyl acetate in petroleum ether provided the desired product (105 mg, 0.13 mmoL, 58%). $^1$H NMR (300 MHz, CDCl$_3$): 4.93 (s, 1H), 4.92 (s, 1H), 4.53 (s, 2H), 4.20 (d, J=11.0 Hz, 1H), 3.83 (d, J=11.1 Hz, 1H), 3.65 (dd, J=10.7, 4.9 Hz, 1H), 3.33 (d, J=9.7 Hz, 1H), 3.12 (d, J=9.7 Hz, 1H), 2.36 (m, 1H), 2.08 (s, 3H), 2.05 (s, 3H), 1.06-1.85 (m, 24H), 1.00 (s, 3H), 0.92 (s, 3H), 0.90 (s, 9H), 0.84 (s, 9H), 0.81 (s, 3H), 0.53 (s, 3H), 0.00 (s, 12H). $^{13}$CNMR (75 MHz, CDCl$_3$): 171.6, 170.7, 148.7, 110.4, 71.6, 65.9, 63.8, 62.4, 50.4, 49.3, 46.2, 46.1, 43.8, 43.3, 42.6, 40.8, 38.3, 37.5, 36.5, 34.3, 33.6, 31.0, 29.7, 27.4, 26.9, 26.6, 26.0 (3), 25.9 (3), 21.0, 20.8, 18.0 (2), 17.8, 16.3, 16.1, 14.5, 12.3, −3.7, −5.0, −5.4, −5.9.

81

Example 43

Preparation of 28,30-diacetoxyl-3,23-dihydroxyl-20(29)-lupene (DA085)

To a solution of 28,30-diacetoxyl-3,23-di-(tert-butyldimethylsiloxyl)-20(29)-lupene (37 mg, 0.047 mmoL) dissolved in THF/MeOH (1.2 mL/1.2 mL), was added aqueous hydrochloric acid (37%, 8 drops), and the resulting mixture was stirred for 2.5 h. The reaction was neutralized with saturated sodium bicarbonate and the volatiles was removed under reduced pressure. Water was added and the mixture was extracted with dichloromethane (×5). Purification by column chromatography on silica gel, eluting with 3-6% methanol in dichloromethane provided three major products 28,30-diacetoxyl-3,23-dihydroxyl-20(29)-lupene (DA085, 6 mg, 23%), $^1$H NMR (300 MHz, CDCl$_3$): 4.94 (s, 1H), 4.93 (s, 1H), 4.54 (s, 2H), 4.23 (d, J=10.8 Hz, 1H), 3.82 (d, J=11.0 Hz, 1H), 3.71 (d, J=10.5 Hz, 1H), 3.58-3.63 (m, 1H), 3.41 (d, J=10.2 Hz, 1H), 2.37 (m, 1H), 2.10 (s, 3H), 2.07 (s, 3H), 1.05-1.87 (m, 23H), 1.03 (s, 3H), 0.97 (s, 3H), 0.86 (s, 6H). $^{13}$CNMR (75 MHz, CDCl$_3$): 171.7, 170.8, 148.7, 110.6, 76.7, 72.0, 65.9, 62.4, 50.3, 49.8, 49.4, 46.3, 43.9, 42.7, 41.9, 40.8, 38.4, 37.4, 37.0, 34.3, 33.9, 31.0, 29.7, 27.0 (2), 26.5, 21.1 (2), 20.8, 18.4, 16.4, 16.0, 14.8, 11.2. ESI-MS: 581.37 (M+Na), 1117.25 (2M+1).

Example 43

Preparation of 28-Acetoxyl-3,23,30-trihydroxyl-20(29)-lupene (DA086)

DA086 (yield 7 mg, 29%) was prepared similarly. $^1$H NMR (300 MHz, CDCl$_3$): 4.95 (s, 1H), 4.89 (s, 1H), 4.22 (d, J=12.3 Hz, 1H), 4.10 (s, 2H), 3.82 (d, J=11.0 Hz, 1H), 3.70 (d, J=10.2 Hz, 1H), 3.58-3.63 (m, 1H), 3.40 (d, J=10.2 Hz, 1H), 2.28-2.33 (m, 1H), 2.08-2.10 (m, 1H), 2.06 (s, 3H), 1.60-1.86 (m, 10H), 1.05-1.41 (m, 13H), 1.02 (s, 3H), 0.96 (s, 3H), 0.86 (s, 6H). $^{13}$CNMR (75 MHz, CDCl$_3$): 171.7, 154.1, 107.1, 76.6, 71.9, 64.9, 62.4, 50.3, 49.8, 49.3, 46.3, 43.3, 42.6, 41.8, 40.8, 38.4, 37.4, 37.0, 34.3, 33.9, 31.5, 29.7, 27.0, 26.9, 26.6, 21.0, 20.8, 18.4, 16.4, 16.0, 14.7, 11.2. ESI-MS: 1033.29 (2M+1).

Example 44

Preparation of 3,23,28,30-Tetrahydroxyl-20(29)-lupene (DA087)

3,23,28,30-Tetrahydroxyl-20(29)-lupene (DA087, 6 mg, 27%). $^1$H NMR (300 MHz, CDCl$_3$/CD$_3$OD): 4.86 (s, 1H), 4.79 (s, 1H), 3.92-4.02 (m, 2H), 3.63-3.67 (m, 2H), 3.16-3.30 (m, 3H), 2.16 (m, 1H), 2.01 (m, 1H), 1.82 (m, 2H), 0.98-1.58 (m, 21H), 0.94 (s, 3H), 0.89 (s, 3H), 0.77 (s, 3H), 0.74 (s, 3H). $^{13}$CNMR (75 MHz, CDCl$_3$/CD$_3$OD): 154.8, 106.6, 75.7, 70.2, 64.5, 59.7, 50.7, 49.7, 49.6, 48.0, 43.8, 43.0, 42.1, 41.2, 38.8, 37.6, 37.3, 34.2, 34.1, 32.0, 29.5, 27.3, 27.0, 26.6, 21.3, 18.6, 16.7, 16.2, 14.9, 11.7. ESI-MS: 971.30 (2 M+1).

82

Scheme 8

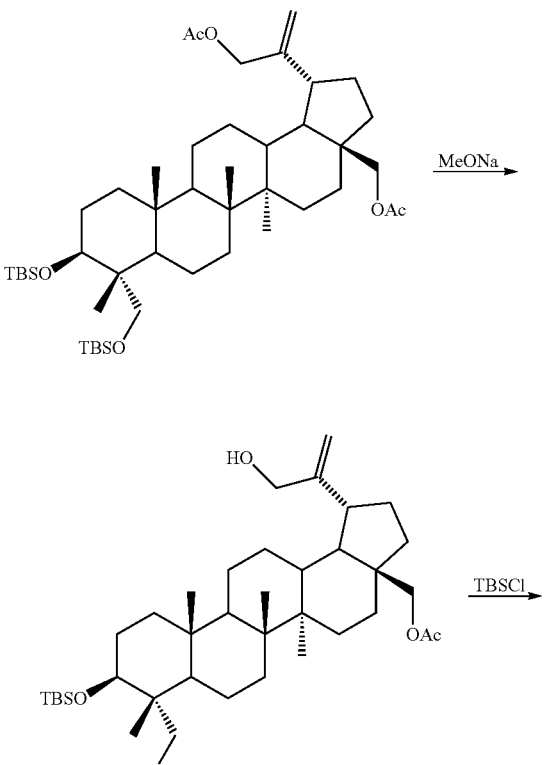

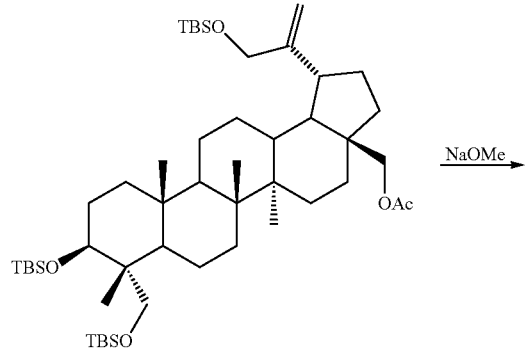

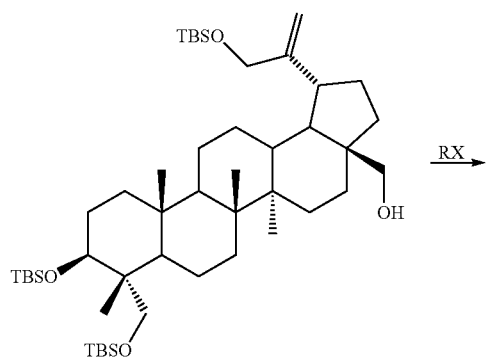

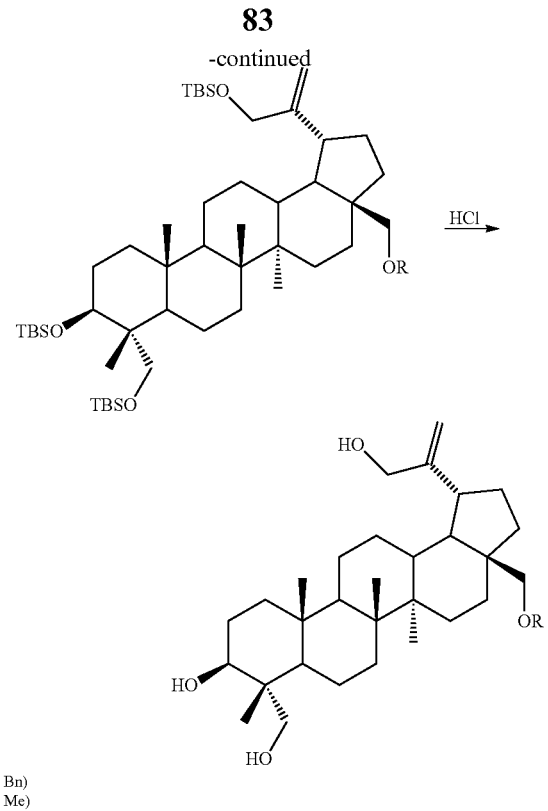

(R = Bn)
(R = Me)

Compounds DA088 and DA090 were synthesized according to the synthetic approaches set forth in Scheme 8.

Example 45

Preparation of 28-Acetoxyl-30-hydroxyl-3,23-di-(tert-butyldimethylsiloxyl)-20(29)-lupene To a mixture of 28,30-diacetoxyl-3,23-di-(tert-butyldimethylsiloxyl)-20(29)-lupene (110 mg, 0.14 mmoL) dissolved in MeOH/THF (10 mL/2 mL), was added a solution of sodium methoxide (0.5 M in MeOH, 0.2 mL). The reaction was stirred at room temperature for 6 h and quenched with saturated ammonium hydroxide. The volatiles were removed under reduced pressure. Water was added and the mixture was extracted with dichloromethane (×3). The extract was dried, filtered and concentrated. Purification by column chromatography on silica gel provided the desired product (78 mg, 0.11 mmoL, 75%). $^1$H NMR (300 MHz, CDCl$_3$): 4.93 (s, 1H), 4.87 (s, 1H), 4.19 (d, J=11.0 Hz, 1H), 4.09 (m, 2H), 3.84 (d, J=10.5 Hz, 1H), 3.63-3.66 (m, 1H), 3.33 (d, J=9.7 Hz, 1H), 3.11 (d, J=9.7 Hz, 1H), 2.30 (m, 1H), 2.04 (s, 3H), 2.03 (m, 1H), 1.06-1.85 (m, 23H), 1.00 (s, 3H), 0.92 (s, 3H), 0.90 (s, 9H), 0.84 (s, 9H), 0.81 (s, 3H), 0.53 (s, 3H), 0.00 (s, 12H). $^{13}$CNMR (75 MHz, CDCl$_3$): 171.6, 154.2, 107.0, 71.6, 64.9, 63.8, 62.5, 50.4, 49.4, 46.2, 46.1, 43.3, 42.6, 40.8, 38.3, 37.5, 36.5, 34.3, 33.6, 31.5, 29.7, 27.4, 26.9, 26.8, 26.0 (3), 25.9 (3), 21.0, 20.9, 18.0 (2), 17.8, 16.3, 16.1, 14.5, 12.3, −3.7, −5.0, −5.3, −5.9.

Example 46

Preparation of 28-Hydroxyl-3,23,30-tri-(tert-butyldimethylsiloxyl)-20(29)-lupene To a solution of 28-acetoxyl-30-hydroxyl-3,23-di-(tert-butyldimethylsiloxyl)-20(29)-lupene (58 mg, 0.078 mmoL) dissolved in dichloromethane (1 mL), was added imidazole (18 mg, 0.16 mmoL) and TBSCl (18 mg, 0.12 mmoL). The resulting mixture was stirred at room temperature overnight under nitrogen. The reaction was quenched with saturated ammonium chloride and extracted with dichloromethane (×3). The extract was dried, filtered and concentrated. The resulting residue was dissolved in THF (5 mL) and a solution of sodium methoxide in methanol (0.5 M, 5 mL) was added. The mixture was stirred at room temperature overnight. After neutralized with saturated ammonium chloride, the volatiles were removed under reduced pressure. Water was added and the mixture was extracted with dicholomethane (×3). The extract was dried, filtered and concentrated. Purification by column chromatography on silica gel provided the desired product (46 mg, 0.056 mmoL, 72% for 2 steps). $^1$H NMR (400 MHz, CDCl$_3$): 4.93 (s, 1H), 4.80 (s, 1H), 4.03-4.09 (m, 2H), 3.76 (d, J=10.8 Hz, 1H), 3.66 (dd, J=11.2, 4.9 Hz, 1H), 3.33 (d, J=9.5 Hz, 1H), 3.27 (d, J=10.8 Hz, 1H), 3.12 (d, J=9.5 Hz, 1H), 2.14 (m, 1H), 2.04 (m, 1H), 1.80-1.92 (m, 2H), 1.03-1.70 (m, 21H), 0.99 (s, 3H), 0.92 (s, 3H), 0.90 (s, 18H), 0.84 (s, 9H), 0.81 (s, 3H), 0.53 (s, 3H), 0.05 (s, 6H), 0.00 (s, 12H). $^{13}$CNMR (100 MHz, CDCl$_3$): 153.8, 106.2, 71.7, 65.5, 63.9, 60.3, 50.5, 49.4, 47.8, 46.2, 43.4, 42.7, 40.9, 38.4, 37.3, 36.6, 33.8, 33.7, 32.0, 29.2, 27.5, 27.0, 26.9, 26.0 (m), 21.0, 18.5, 18.2, 18.1, 18.0, 16.4, 16.1, 14.6, 12.5, −3.6, −4.9, −5.2, −5.3 (2), −5.7.

Example 47

Preparation of 28-Benzyloxyl-3,23,30-trihydroxyl-20(29)-lupene (DA088)

To a solution of 28-hydroxyl-3,23,30-tri-(tert-butyldimethylsiloxyl)-20(29)-lupene (26 mg, 0.032 mmoL) dissolved in THF (1.5 mL) under nitrogen, was added benzyl bromide (0.016 mL, 0.12 mmoL) and sodium hydride (60% in mineral oil, 10 mg). The resulting mixture was heated to 70 degree Celsius overnight. The reaction was quenched with saturated ammonium chloride and extracted with dichloromethane (×3). The extract was dried, filtered and concentrated.

The resulting residue was dissolved in THF/MeOH (0.5 mL/0.5 mL), concentrated hydrochloride (3 drops) was added. The mixture was stirred at room temperature for 5 h and quenched with 20% NaOH (4 drops). The volatiles were removed under reduced pressure. Water was added and the resulting mixture was extracted with dichloromethane (×3). The combined extract was dried, filtered and concentrated. Purification by column chromatography on silica gel, eluting with 5% methanol in chloromethane provided the desired product (11 mg, 0.02 mmoL, 61% for 2 steps). $^1$H NMR (300 MHz, CDCl$_3$): 7.33 (m, 5H), 4.92 (s, 1H), 4.86 (s, 1H), 4.56 (d, J=12.5 Hz, 1H), 4.45 (d, J=12.5 Hz, 1H), 4.08 (m, 2H), 3.70 (d, J=10.2 Hz, 1H), 3.57-3.62 (m, 1H), 3.48 (d, J=8.6 Hz, 1H), 3.40 (d, J=10.3 Hz, 1H), 3.07 (d, J=8.6 Hz, 1H), 2.25 (m, 1H), 1.96-2.03 (m, 3H), 0.97-1.64 (m, 21H), 0.93 (s, 3H), 0.86 (s, 3H), 0.83 (s, 6H). $^{13}$CNMR (75 MHz, CDCl$_3$): 154.6, 138.9, 128.3 (2), 127.5 (3), 106.8, 76.6, 73.4, 72.1, 67.7, 64.9, 50.2, 49.8, 49.4, 47.2, 43.6, 42.5, 41.8, 40.8, 38.3, 37.2, 37.0, 34.7, 33.9, 31.9, 29.9, 27.0, 26.9, 26.6, 20.9, 18.4, 16.4, 15.7, 14.8, 11.2. ESI-MS: 1129.29 (2 M+1).

Example 48

Preparation of 28-Methoxyl-3,23,30-trihydroxyl-20(29)-lupene (DA090)

28-Methoxyl-3,23,30-trihydroxyl-20(29)-lupene (DA090) was prepared using the similar procedures described as DA088, using the same starting material, but replacing benzyl bromide with methyl iodide in the first step. $^1$H NMR (400 MHz, CDCl$_3$): 4.95 (s, 1H), 4.89 (s, 1H), 4.10 (m, 2H), 3.70 (d, J=10.4 Hz, 1H), 3.58-3.64 (m, 1H), 3.47 (d, J=9.1 Hz, 1H), 3.40 (d, J=10.4 Hz, 1H), 3.35 (s, 3H), 3.03 (d, J=9.1 Hz, 1H), 2.26-2.31 (m, 1H), 2.06-2.13 (m, 1H), 1.05-1.96 (m, 23H), 1.03 (s, 3H), 0.97 (s, 3H), 0.87 (s, 6H). $^{13}$CNMR (100 MHz, CDCl$_3$): 154.6, 106.8, 76.7, 72.0, 71.1, 64.9, 59.7, 50.3, 49.9, 49.4, 47.1, 43.6, 42.6, 41.8, 40.9, 38.4, 37.3, 37.0, 34.5, 33.9, 31.9, 29.9, 27.2, 26.8, 26.7, 20.9, 18.4, 16.4, 16.0, 14.8, 11.3. ESI-MS: 977.23 (2M+1).

Scheme 9

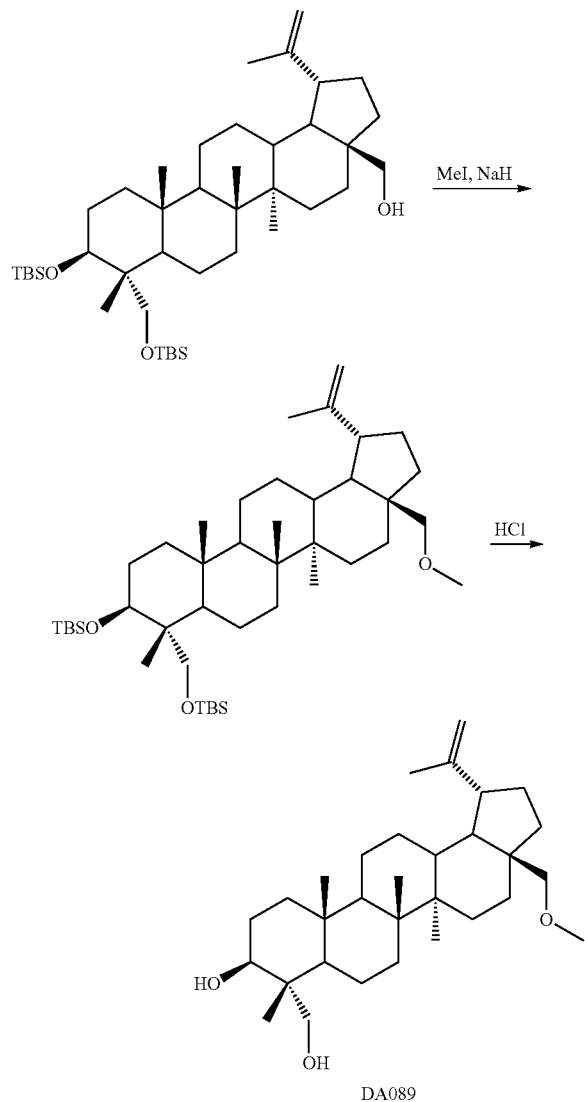

DA089

Compound DA089 was synthesized according to the synthetic approaches set forth in Scheme 9.

Example 49

Preparation of 28-Methoxyl-3,23-dihydroxyl-20(29)-lupene (DA089)

28-Methoxyl-3,23-dihydroxyl-20(29)-lupene (DA089) was prepared from 28-hydroxyl-3,23-di-(tert-butyldimethyl-siloxyl)-20(29)-lupene and iodomethane in two steps using the similar procedure as described as DA088. $^1$H NMR (300 MHz, CDCl$_3$): 4.68 (s, 1H), 4.57 (s, 1H), 3.71 (d, J=10.1 Hz, 1H), 3.59-3.64 (m, 1H), 3.48 (d, J=9.1 Hz, 1H), 3.41 (d, J=10.2 Hz, 1H), 3.35 (s, 3H), 3.05 (s, J=9.1 Hz, 1H), 2.39-2.41 (m, 1H), 1.85-1.96 (m, 3H), 1.68 (s, 3H), 1.14-1.64 (m, 21H), 1.04 (s, 3H), 0.96 (s, 3H), 0.87 (s, 6H). $^{13}$CNMR (75 MHz, CDCl$_3$): 150.7, 109.6, 76.8, 72.1, 71.3, 59.7, 50.3, 49.9, 48.8, 47.9, 47.1, 42.7, 41.8, 40.8, 38.3, 37.4, 37.0 (2), 34.7, 33.9, 29.9, 27.2, 26.9, 25.1, 20.8, 19.0, 18.4, 16.4, 16.0, 14.8, 11.2. ESI-MS: 964.67 (2 M+1).

Example 50

Materials and Methods

1. Experimental Autoimmune Encephalomyelitis (EAE) Induction

On day 0, six-week old male C57BL/6 mice (Hong Kong University of Science and Technology, Animal Care facility) were immunized with 100 µg of myelin oligodendrocyte glycoprotein peptide (MOG$_{35-55}$)/complete Freund's Adjuvant (CFA) emulsion kit (Hooke Laboratories) was injected subcutaneously at both sides of the tail base. 250 ng of pertussis toxin (PTX) (Hooke Laboratories) was injected intraperitoneally on the day of immunization and again 24 h later. Albumin/CFA kit (100 µg, Hooke Laboratories) was used as an immunization control group. Animals were fed either H$_2$O (vehicle control) for DA001 at 100 mg/kg or DA021 at 100 mg/kg daily via oral administration. The animals were also weighed and the neurological impairment was quantified daily based on the previously published criteria.

2. Primary Splenocytes Cultures

On day 21, EAE mice were sacrificed by cervical dislocation and spleens were removed aseptically. The removed spleens were then cut with sterilized scissors and strained through 70 µM mesh (BD Bioscience) with a plunger of 5 mL syringe (BD Bioscience) in 9 mL of RPMI 1640 (Invitrogen) with 100 U/mL penicillin and 100 µg/mL streptomycin (Sigma). The cell mixture was then added to 9 mL of Lympholyte (Cedarlane Laboratories) for gradient separation of splenocytes from red bloods cells by centrifugation at 1500 g for 20 min. After the centrifugation, the lympholyte layer containing splenocytes were carefully removed and washed with 10 mL of RPMI 1640 at 800 g for 10 min for three times. The isolated splenocytes were seeded onto different plate format and cultured with RPMI 1640 medium (Invitrogen) supplement with 10% heat inactivated fetal bovine serum (Invitrogen) and 100 U/mL penicillin and 100 µg/mL streptomycin at 37° C. CO2 incubator.

3. Western Blot Analysis

Splenocytes of EAE mice were cultured at the density of 1×10$^7$ cells in 6-well plates (Falcon) and treated with the absence or presence of the MOG peptide (25 µg/mL) (Hooke Laboratories), DA001, and DA021 (30 µM) for 24 h. After overnight incubation, the splenocytes were lysed with RIPA containing antipain dihydrochloride, trypsin inhibitor, leupeptin, aprotinin, sodium orthovanadate, benzamidine and phenyl methane sulphonyl fluoride. After centrifugation at 14000 rpm for 15 min, 4° C., protein concentrations were determined by D$_c$ Protein Assay kit (Bio-Rad). 20 µg of each sample was subjected to 10% SDS-PAGE with 20 mA for 3 h. Immunoblot analysis was performed by transfer of proteins onto nitrocellulose membranes using a mini trans-blot apparatus (Bio-Rad). After 2 h blocking with milk, the membranes were incubated overnight at 4° C. with specific primary Abs (1:1000): anti-phospho-Stat 3 (Cell signaling), anti-phospho- Stat 4 (BD Bioscience), and anti-phospho-Stat 6 (Cell signaling). Anti-α-tubulin (Sigma) was used as a loading control. After washing, subsequent incubation with anti-rabbit or anti-mouse HRP-conjugated secondary antibody (1:3000) (Cell Signaling) for 1 h at room temperature was carried out. The signal was detected by ECL Western blot detection kit (GE Healthcare).

4. Quantikine™ ELISA Assay

Splenocytes from EAE mice were cultured at the density of $1 \times 10^6$ cells in 12-well plates (Falcon) in the absence or presence of the MOG peptide (25 μg/mL) (Hooke Laboratories), DA001 and DA021 (30 μM) with RPMI 1640 medium (Invitrogen) supplement with 10% heat inactivated fetal bovine serum (Invitrogen) and 100 U/mL penicillin and 100 μg/mL streptomycin (Sigma) for 48 h. After 48 h, the supernatants were collected by pelleting the cells at 300 g for 10 min at 4° C. 50 μL of the each sample was added to the microtiter plate provided by the manufacturer of the Quantikine ELISA assay kit (R and D systems). Additional 50 μL of assay diluents buffer was added and incubated at room temperature for 2 h. After the incubation, the supernatants were discarded and the cells were washed with wash buffer. 100 μL of conjugate was added to the cells and the plate was again incubated at room temperature for 2 h. After another washing, 100 μL of substrate solution was added followed by 30 min incubation at room temperature. Subsequently, 100 μL of stop solution was added to each well and the plate was read in 450 nm wavelength on a microplate reader (Dynex Revelation 2.2).

5. Hematoxyline and Eosin Staining

On day 21, animals were anesthetized intraperitoneally with 4% (w/v) chloral hydrate (BDH) in 0.9% (w/v) saline (USB). Once the anesthetics has set it, the animals were then perfused transcardially (Gilson) with 50 mL of 37° C., 0.005% (w/v) heparinized (Sigma) saline (USB), followed by 80 mL of ice-cold, 4% (w/v) paraformaldehyde (Sigma) in Dulbecco's Phosphate Buffered Saline (GIBCO). The perfused spinal cords were then further fixed in 4% (w/v) paraformaldehyde (Sigma) overnight at 4° C. After overnight incubation, the samples were prepared in an automated tissue processor for dehydration, clearing and paraffin infiltration (Leica EG1150H) followed by paraffin embedding (Leica RM2255). After overnight incubation at room temperature, the blocks were sectioned at 6 μm thickness on microtome (Leica 1250) and laid on Histobond slides (Merienfeld). The slides were incubated at 60 C oven for 24 h before being stained. On the day of staining, the slides were rehydrated in a series of EtOH solutions. The rehydrated slides were then submerged in hematoxyline solution for 20 min at room temperature. The slides were differentiated in acidic solution before being fixed in a series of EtOH solutions then eosin at 20 min in room temperature. The slides were washed in distilled water and dehydrated in a series of EtOH solutions before mounted in DPX mounting media (Sigma) for visualization under a microscope.

6. Evaluation of DA021 in a Murine Model of Lipopolysaccharide-Induced Cytokine Production.

This is a contract research performed by Washington Biotechnology Inc., Columbia, Md., protocol 1077. Swiss-Webster mice (female, Harlan Sprague-Dawley, 5-6 weeks) were weighed and dosed orally with 10 ml/kg water, prednisolone at 10 mg/kg, or DA021 at 30 mg/kg or 100 mg/kg. Thirty minutes after oral dosing, lipopolysaccharides (LPS) at 2 mL/kg was injected. Two hours after LPS injection, the mice were anesthetized and exsanguinated into serum separator micro-container tubes. The blood was processed to serum. The serum samples were assayed for tumor necrosis factor-α (TNFα) concentration by ELISA (Pierce) according to the manufacturer's protocol.

7. Evaluation of DA021 in a Murine Model of Oxazolone-Induced Ear Edema.

This is a contract research performed by Washington Biotechnology Inc., Columbia, Md., protocol 1041. On day 0, 42 BALB/c mice (female, Harlan Sprague-Dawley, 5-6 weeks) were shaved on the ventral surface of the right ear. 100 μl of the 5% oxazolone solution (Sigma) was then applied to the saved ear. The treated mice were then returned to the cage and kept for additional 6 days. On day 7, the mice were weighed and dosed orally with 10 ml/kg water or DA021 at either 30 mg/kg or 100 mg/kg or topically applied on both sides of both ears with 25 μl betamethasone. Thirty minutes after oral dosing, 5 μl of 3% oxazolone was applied to both sides of the right ear and 5 μl of acetone was applied to both sides of the contralateral ear. Twenty-four hours after 3% oxazolone/acetone application, the mice were euthanized, the ears removed and weighed.

8. Evaluation of DA001 in Decreasing the Infarct Size and Edema of Ischemic Brain The MCAO (middle carotid artery occlusion model) was performed to investigate the protective effects of DA001 on the brain when the brain was exposed to transient focal ischemia (or lack of oxygen) such as during a stroke. Hemispheric brain swelling and infarct volume (the area of dead tissue caused by inadequate blood supply) was measured for test subjects treated with the compound 6 hours after ischemia and compared to that of the control group. DA001 effectively reduced infarct volume (the area of dead tissue caused by inadequate blood supply) and the extent of edema during ischemic conditions.

9. Morris Water Maze 6-8 week old outbred male I.C.R. mice, weighing 25-35 g were housed two per cage in a climatically controlled animal room (23-25° C.) under 12 hours light/dark cycling. The animals were allowed access to water and food ad lib. The mice used for the experiment were brought to particular laboratory conditions for two days. All the experiments were conducted between 14:00 and 18:00. Scopolamine hydrobromide (Sigma, USA) was dissolved in saline in 0.1 mg/kg and administered in a volume of 10 ml/kg body weight. The experimental mice were randomly assigned into 4 or 6 groups, each consisting of 12 mice with similar mean body weights and age. The test compound was dissolved in physiological saline before the experiments each day. Scopolamine (0.1-4 mg/kg) was administrated through intraperitoneal injection (i.p.) at 30 minutes before the swimming tasks to induce memory deficit. Oral administrations (p.o.) of the sample (0.1, 0.2, 0.4, 30 and 100 mg/kg), or its saline (0.9% NaCl) was initiated at the first day of the task and administrated according to a volume of 10 ml/kg body weight. Oral administrations were given 45 minutes before the swimming tasks and performed daily for 4 consecutive days until the end of the task.

Each mouse was subjected to 4 trials per day for 5 consecutive days. A trial began when a mouse held facing the pool wall was immersed in the water. The mouse was then allowed 60 seconds to search for the platform. If the mouse failed to escape within this time period, it was guided and placed on the platform. Regardless of whether the mouse found the platform or not, it remained there for 20 seconds. There was a 30 seconds recovery period between trials. The 4 trials were started from the 2 points (north and west) located farthest from the platform. The probe trial (without platform) was assessed within a 60 s period on the fifth day of behavioral testing (one experiment), and the time spent in the southeast quadrant where the escape platform had been set during training was recorded computationally and presented as percentage of spatial bias.

Because both the escape latency and swimming distance of mice in the behavioral experiment showed similar group differences, only the escape latency to find the platform in the water maze was used to evaluate the memory performance in the tested mice. The two-way ANOVA with repeated measures was used to analyze latency values, and calculated as the mean latency periods for each mouse. (Data are expressed as means±S.E.M. by using 2-way ANOVA). One-way ANOVA followed by Duncan's multiple-range test (data expressed as mean±S.E.M. *P<0.05 and **P<0.01 versus scopolamine) was used to analyze group differences of the data collected during probe trials.

RNA Extraction, cDNA Synthesis, and Real-Time Quantitative PCR

Cortical neurons of 11 DIV-12 DIV were pre-incubated with DA001 or DMSO for 24 hours. Cells were washed in Locke's medium without magnesium for 15 min, followed by the treatment of NMDA (20 µM) or water for 20 min. Neurons were incubated with normal growth medium and total RNA were extracted at different time intervals after or without NMDA treatment. Total RNA was extracted using RNeasy Mini kit (Qiagen) according to the manufacturer's protocol, and was reverse-transcribed into single-stranded cDNA with SuperScript II Reverse Transcriptase (Invitrogen) and oligo-dT primers. Real-time Quantitative PCR was performed using Power SYBR Green PCR Master Mix (Applied Biosystems) on the Mx3000P Real-Time PCR System (Stratagene). Thermal cycling was initiated with a 10-min denaturation step at 95° C., followed by 40 cycles of 95° C. for 30 sec, 60° C. for 1 min and 72° C. for 30 sec. The final product was subjected to a Meltcurve detection at the end of the reaction. Regulation of the gene expression was normalized against home gene, hypoxanthine phosphoribosyltransferase 1 (HPRT1) and glyceraldehyde 3-phosphate dehydrogenase (GAPDH). Real-time PCR primers are as follows.

```
                                              (SEQ ID NO: 1)
BDNF Forward: TTGAGCACGTGATCGAAGAG (SEQ ID NO: 2)
BDNF Reverse: CCAGCAGAAAGAGCAGAGGA (SEQ ID NO: 3)
NT-3 Forward: GGGGGATTGATGACAAACAC (SEQ ID NO: 4)
NT-3 Reverse: ACAAGGCACACACACAGGAA (SEQ ID NO: 5)
Bcl-2 Forward: ATAACCGGGAGATCGTGATG (SEQ ID NO: 6)
Bcl-2 Reverse: CAGGCTGGAAGGAGAAGATG (SEQ ID NO: 7)
c-fos Forward: GGAGCCGGTCAAGAACATTA (SEQ ID NO: 8)
c-fos Reverse: TGCTGCATAGAAGGAACCAG (SEQ ID NO: 9)
HPRT1 Forward: TGACACTGGTAAAACAATGCA (SEQ ID NO: 10)
HPRT1 Reverse: GGTCCTTTTCACCAGCAAGCT (SEQ ID NO: 11)
GAPDH Forward: TGCACCACCAACTGCTTAGC (SEQ ID NO: 12)
GAPDH Reverse: GGCATGGACTGTGGTCATGAG (SEQ ID NO: 13)
NGF Forward: CAACAGGACTCACAGGAGCA (SEQ ID NO: 14)
NGF Reverse: GTCCGTGGCTGTGGTCTTAT (SEQ ID NO: 15)
NT-4 Forward: TCCCCTGCGTCAGTACTTCT (SEQ ID NO: 16)
NT-4 Reverse: CGCACATAGGACTGTTTTAGCC (SEQ ID NO: 17)
C/EBPb Forward: ATCGACTTCAGCCCCTACCT (SEQ ID NO: 18)
C/EBPb Reverse: CGTAGTCGGACGGCTTCTT
```

Hippocampal/Cortical Neuron Survival Assay Against NMDA (N-Methyl-D-Aspartate) Excitotoxicity Hippocampal neurons/cortical neurons were prepared from embryonic day 18 Sprague-Dawley rats. After the cortices had been removed from the brain, isolated cells were plated onto Poly d-Lysine (PDL) (P0899, Sigma)-coated 48 well plates (150687, NUNC) at a density of $2 \times 10^5$ cell per well using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Medium was changed to growth medium (Neurobasal Medium with penicillin/streptomycin and B27 supplement) after 3 hours. Half medium was changed with growth medium every 2-3 days to maintain the cells until day 10 in vitro (DIV 10). Serial dilutions of samples were prepared in growth medium and DMSO was used as vehicle control. For pre-treating assay, half of the medium was removed from wells, and equal amount of diluted samples were replaced. Cells were then incubated for 2 hours at 37° C. in a humidified atmosphere of 5% $CO_2$ in air. Culture was subsequently rinsed with Locke's solution (5 mM potassium chloride, 128 mM sodium chloride, 2.7 mM calcium chloride, 1 mM di-sodium hydrogen orthophosphate, 5 mM HEPES and 10 mM Glucose in Milli-Q water), then incubated with Locke's solution in the presence of glycine (10 µM) for 15 minutes before N-Methyl-D-Aspartic Acid (NMDA) (M-3262, Sigma) treatment. NMDA dissolved in Locke's plus glycine solution was then substituted and incubated for 20 minutes at 37° C. For co-treated NMDA assay, serial dilutions of samples were prepared in Locke's solution plus glycine and 20 µM NMDA solution and incubated for 20 minutes at 37° C., 5% $CO_2$. Afterwards, cells were incubated in growth medium for 18-24 hours and detected with Cytotoxicity Detection Kit (1644793, Roche).

Hippocampal/Cortical Neuron Survival Assay Against Glutamate Excitotoxicity

Hippocampal neurons/cortical neurons were prepared from embryonic day 18 Sprague-Dawley rats. After the cortices had been removed from the brain, isolated cells were plated onto Poly d-Lysine (PDL) (P0899, Sigma)-coated 48 well plates (150687, NUNC) at a density of $2 \times 10^5$ cell per well using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Medium was changed to growth medium (Neurobasal Medium with penicillin/streptomycin and B27 supplement) after 3 hours. Half medium was changed with growth medium every 2-3 days to maintain the cells until day 10 in vitro (DIV 10). Serial dilutions of samples were prepared in growth medium and DMSO was used as vehicle control. For pre-treating assay, half of the medium was removed from wells, and equal amount of diluted samples were replaced. Cells were then incubated for 2 hours at 37° C. in a humidified atmosphere of 5% $CO_2$ in air. Culture was subsequently rinsed with Locke's solution (5 mM potassium chloride, 128 mM sodium chloride, 2.7 mM calcium chloride, 1 mM di-sodium hydrogen orthophosphate, 5 mM HEPES and 10 mM Glucose in Milli-Q water), then incubated with Locke's solution in the presence of glycine (10 µM) for 15 minutes before N-Methyl-D-Aspartic Acid (NMDA) (M-3262, Sigma) treatment. Glutamate dissolved in Locke's plus glycine solution was then substituted and incubated for 20 minutes at 37° C. For co-treated glutamate assay, serial dilutions of samples were prepared in Locke's solution plus glycine and glutamate solution and incubated for 20 minutes at 37° C., 5% $CO_2$. Afterwards, cells were incubated in growth medium for 18-24 hours and detected with Cytotoxicity Detection Kit (1644793, Roche).

Cortical Neuron Survival Assay Against Kainate Excitotoxicity

Cortical neurons were prepared from embryonic day 18 Sprague-Dawley rats. After the cortices had been removed from the brain, isolated cells were plated onto Poly d-Lysine (PDL) (P0899, Sigma)-coated 48 well plates (150687, NUNC) at a density of $2\times10^5$ cell per well using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Medium was changed to growth medium (Neurobasal Medium with penicillin/streptomycin and B27 supplement) after 3 hours. Half medium was changed with growth medium every 2-3 days to maintain the cells until day 10 in vitro (DIV 10). Serial dilutions of samples were prepared in growth medium and DMSO was used as vehicle control. For pre-treating assay, half of the medium was removed from wells, and equal amount of diluted samples were replaced. Cells were then incubated for 2 hours at 37° C. in a humidified atmosphere of 5% $CO_2$ in air. Culture was subsequently rinsed with Locke's solution (5 mM potassium chloride, 128 mM sodium chloride, 2.7 mM calcium chloride, 1 mM di-sodium hydrogen orthophosphate, 5 mM HEPES and 10 mM Glucose in Milli-Q water), then incubated with Locke's solution in the presence of glycine (10 µM) for 15 minutes before N-Methyl-D-Aspartic Acid (NMDA) (M-3262, Sigma) treatment. Kainate dissolved in Locke's plus glycine solution was then substituted and incubated for 20 minutes at 37° C. For co-treated kainate assay, serial dilutions of samples were prepared in Locke's solution plus glycine and kainate solution and incubated for 20 minutes at 37° C., 5% $CO_2$. Afterwards, cells were incubated in growth medium for 18-24 hours and detected with Cytotoxicity Detection Kit (1644793, Roche).

Cortical Neuron Survival Assay Against Amyloid Beta Peptide Excitotoxicity

Cortical neurons were prepared from embryonic day 18 Sprague-Dawley rats. After the cortices had been removed from the brain, isolated cells were plated onto Poly d-Lysine (PDL) (P0899, Sigma)-coated 48 well plates (150687, NUNC) at a density of $1\times10^5$ cell per well using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Medium was changed to growth medium (Neurobasal Medium with penicillin/streptomycin and B27 supplement) after 3 hours. Half medium was changed with growth medium every 2-3 days to maintain the cells until day 7 in vitro (7 DIV). Serial dilutions of samples were prepared in growth medium and DMSO was used as vehicle control. For pre-treating part, half of the medium was removed from wells, and equal amount of diluted samples were replaced. Cells were then incubated for 2 hours at 37° C. in a humidified atmosphere of 5% $CO_2$ in air. Cortical neurons were then incubated with DA001 derived compounds (at various concentrations in [µM]) together with $A\beta_{25-35}$ (10 µM, Sigma) for 24 hours. Quantification of living cells are measured by MTT (3-(4,5-Dimethylthiazol-2-yl)-2,5-diphenyltetrazolium bromide, USB) assay performed 24 hours after $A\beta_{25-35}$ treatment. Yellow MTT is reduced to purple formazan in the mitochondria of living cells. A solubilization solution [10% SDS (sodium dodecyl sulfate)/0.01 M hydrochloric acid] is added to dissolve the insoluble purple formazan product into a colored solution which was then quantified at wavelength 570 nm using a spectrophotometer (DYNEX Technologies).

Example 51

DA001 Antagonizes MC1 and MC4 Receptor Activity

Figure 1:
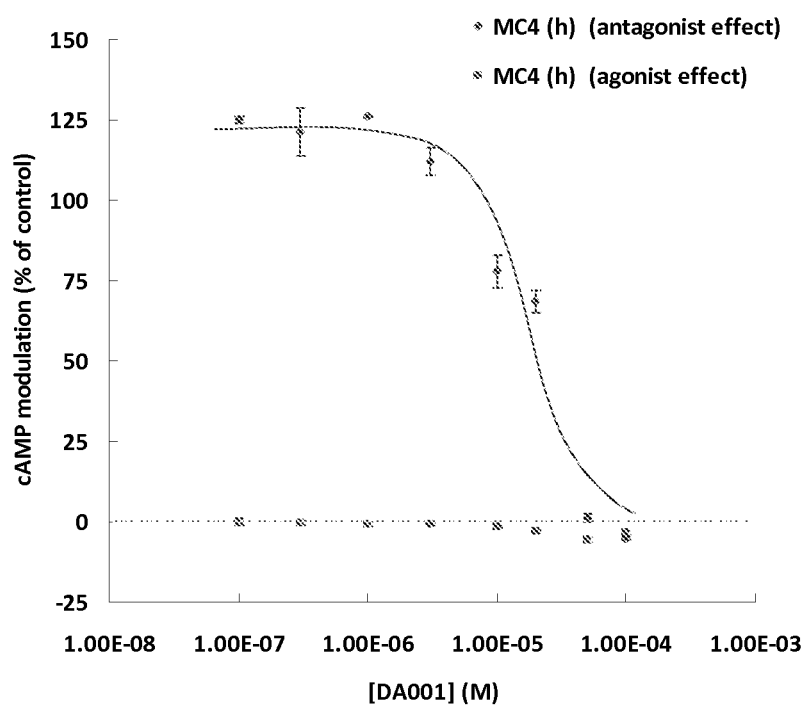
FIG. 1. DA001 shows a dose-dependent inhibitory effect on MC4 receptor by reducing the cAMP increase upon the ligand (NDP-α-MSH) binding (red line). DA001 alone is unable to induce cAMP increase (blue square dots). DA001 shows antagonist effect at the human MC4 receptor with an IC$_{50}$ of 1.7E-05 M.

DA001 inhibits ligand binding to MC1 and MC4 receptors. To determine whether the inhibitory effect is due to agonist or antagonist activity, DA001 was evaluated at 6 or 8 concentrations in cellular assays assessing receptor function. Upon ligand binding, the MC1 or MC4 receptor is activated which leads to an increase in intracellular cyclic AMP. DA001 showed a dose dependent inhibition of cyclic AMP in the presence of the MC1 or MC4 receptor ligand, α-MSH, in cells over-expressing the MC1 or MC4 receptor, while DA001 alone did not induce an increase in cAMP on the MC4 receptor. FIG. 1 illustrates that DA001 shows a dose-dependent inhibitory effect on MC1 and MC4 receptor by reducing the cAMP increase upon the ligand (NDP-α-MSH) binding (red line). DA001 alone is unable to induce cAMP increase (blue square dots). DA001 shows antagonist effect at the human MC1 and MC4 receptor with an $IC_{50}$ of 5.0E-05 M ($K_B$ of 5.3E-06 M) and 1.7E-05 M, respectively. DA001 was further evaluated with MC2 receptor functional assay. Upon ligand binding, the MC2 receptor is activated which leads to an increase in intracellular cyclic AMP. DA001 did not show any effect on MC2 receptor in the presence or absence of the MC2 receptor ligand, adrenocorticotropin [ACTH1-39], in cells over-expressing the MC2 receptor as shown in table belows.

| MC2 receptor | cAMP measurement |
|---|---|
| Agonist effect | 0 |
| Antagonist effect | −8 |

Example 52

DA001 Inhibits E Type Prostaglandins Binding to EP Receptors

DA001 was further evaluated against 32 receptor binding assays. Radioligand competition assays were conducted whereby DA001 was tested at one concentration (10 uM) in duplicate. DA001 significantly inhibits ligand binding of E type prostaglandins ($PGE_2$) to its receptor family EP1, EP2 and EP4, according to the manufacturer's guidelines of a cutoff inhibition at 50%. It could compete with the radioligand [$^3$H] $PGE_2$ binding at the EP1 and EP4 receptors, and weakly competed with the EP2 and FP receptors.

| Binding assay | % inhibition of control specific binding | Target |
| --- | --- | --- |
| EP1 | 52 | $PGE_2$ |
| EP2 | 31 | $PGE_2$ |
| EP4 | 49 | $PGE_2$ |
| FP | 27 | PGF |
| IP | 0 | PGI |
| TP | 17 | Thromoboxanes A |

Example 53

DA001 Antagonizes the EP1 and EP4 Receptors

To determine whether the inhibitory effect of DA001 on the ligand binding to EP receptors results from agonist or antagonist activity, DA001 was evaluated at a single concentration (10 μM) on cellular-specific receptor functional assays. Upon ligand binding, the EP receptors are activated which leads to an increase in intracellular cyclic AMP. DA001 did not show any effect on EP receptors in the absence of the receptor ligand, but antagonized the effect of EP1 and EP4 receptor activity in cells over-expressing these receptors. DA001 showed a 38% and 41% inhibition on cyclic AMP induction in the presence of $PGE_2$ for EP1 and EP4 receptor, respectively, while DA001 alone could not elicit cAMP increase on the these receptors.

TABLE 4

| cAMP measurement | EP1 receptor | EP2 receptor | EP4 receptor |
| --- | --- | --- | --- |
| Agonist effect | 8.1 | −0.8 | −11 |
| Antagonist effect | 38 | 2.2 | 41 |

In Table 4, DA001 exhibits a moderate antagonist effect on the EP1 and EP4 receptor.

DA001 (10 μM) was subjected to ligand binding assay with the human EP1 or EP4 receptor over-expressing CHO cells. Results are expressed as a percent of control specific agonist response [100-(measured specific response/control specific agonist response)×100] obtained in the presence of DA001.

Example 54

DA001 Decreases the Infarct Size and Edema of Ischemic Brain

Figure 2:
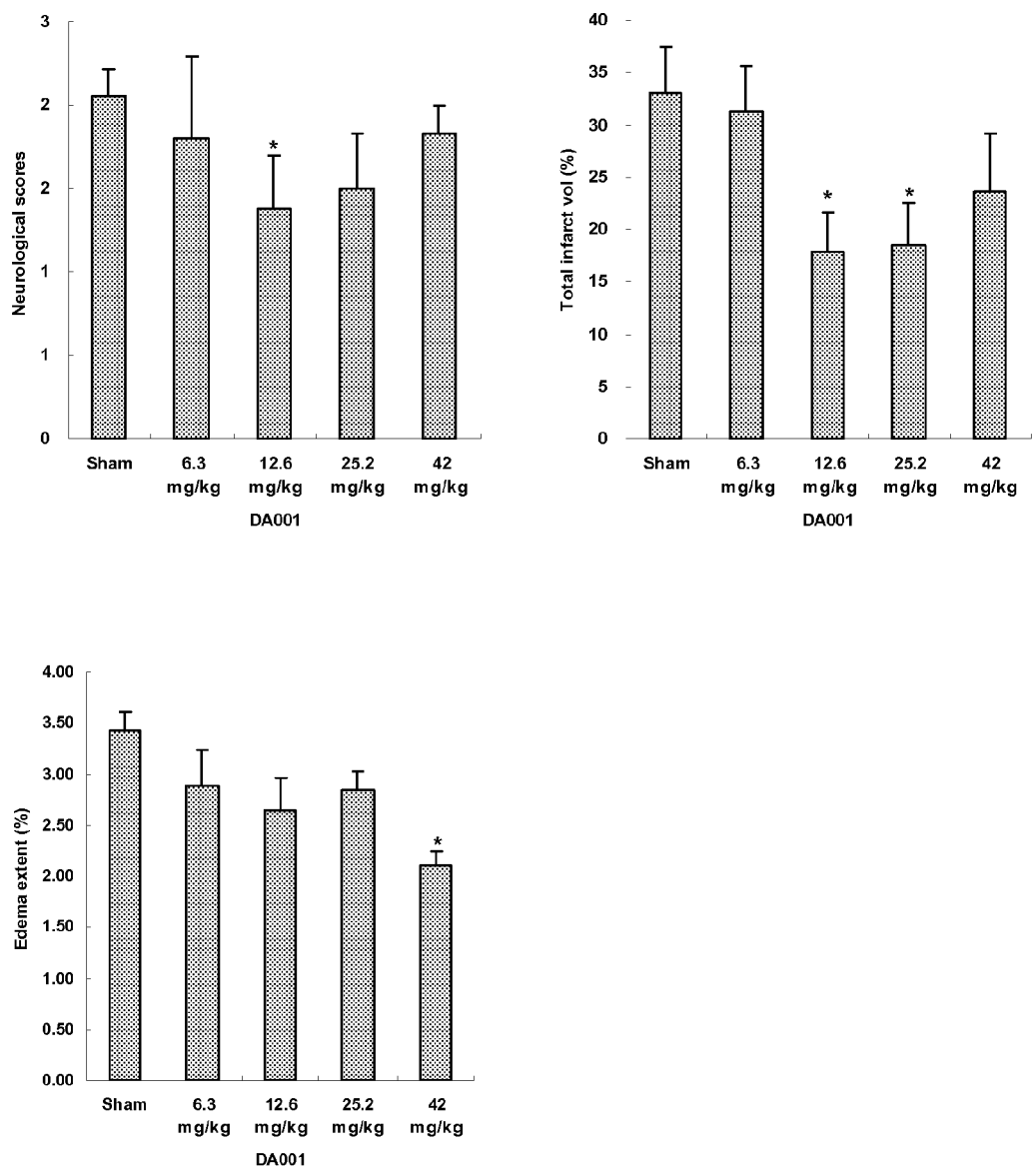
FIG. 2 illustrates that DA001 decreases the infarct size and edema of ischemic brain. DA001 (12.6 mg/kg) orally administered 6 h post-ischemia significantly improved the neurological scores of ischemic rats. DA001 also significantly decrease the total infarction of MCAO rats at the dose 12.6 mg/kg and 25.2 mg/kg, and reduced the extent of edema at a dose of 42 mg/kg.

The MCAO (middle carotid artery occlusion model) was performed to investigate the protective effects of DA001 on the brain when exposed to transient focal ischemia (or lack of oxygen) such as during a stroke. Neurological scores, hemispheric brain swelling and infarct volume (the area of dead tissue caused by inadequate blood supply) was measured in test subjects treated with the compound 6 hours after ischemia and compared to that of the control group. DA001 effectively attenuated neurological deficits, reduced infarct volume (the area of dead tissue caused by inadequate blood supply), especially in brain slices number 3 to 5, and the extent of edema during ischemic conditions as shown in FIG. 2.

DA001 (12.6 and 25.2 mg/kg) orally administered 6 h post-ischemia significantly improved the neurological scores of ischemic rats. DA001 also significantly decreased the total infarction of MCAO rats at the dose 12.6 mg/kg and 25.2 mg/kg, and reduced the extent of edema at a dose of 42 mg/kg.

Example 55

DA001 Induces NGF, BDNF, NT-3 and NT-4 Expression Following NMDA Treatment

Figure 3:
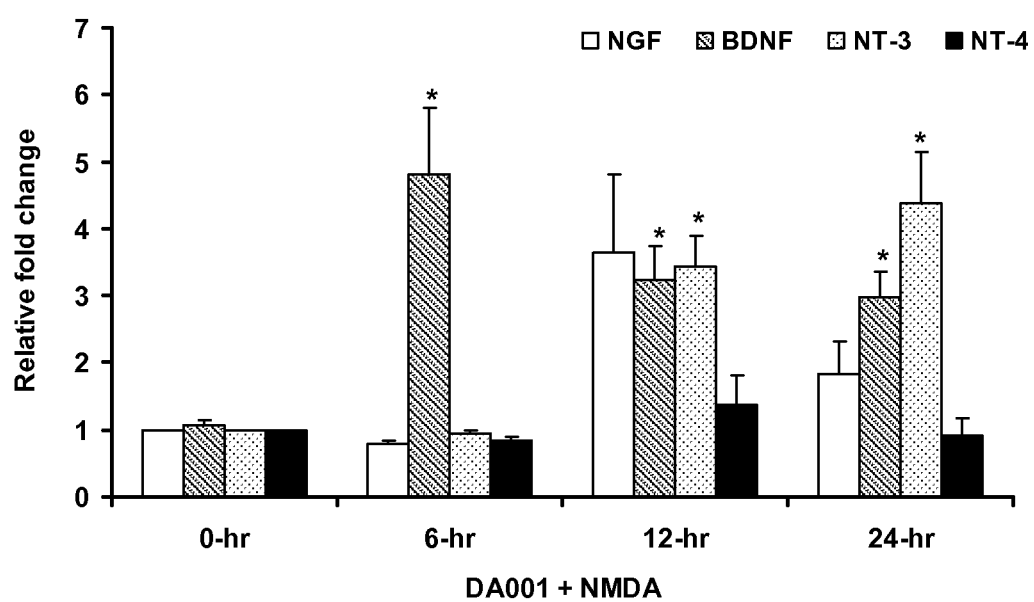
FIG. 3. Pre-treatment of DA001 increases neutrophins expression in cortical neutrons followed by co-treatment with NMDA.

Cortical neurons were pre-treated with DA001 after which the cells were subjected to NMDA insult. The expression of neurotrophins was measured at three different time intervals. DA001 induced NGF, BDNF and NT-3 expression but not NT-4 under the same conditions. FIG. 3 illustrates that cortical neurons were incubated with DA001 or the DMSO control for 24 hrs, followed by treatment with NMDA (20 μM) or water for 20 min. Gene expression was normalized against the house-keeping gene, hypoxanthine phosphoribosyltransferase 1 (HPRT1) and glyceraldehyde 3-phosphate dehydrogenase (GAPDH) and compared to the control (DMSO) with NMDA treatment. Relative changes in gene expression induced by DA001+NMDA was compared with DMSO+NMDA.

Cortical neurons were incubated with DA001 or the DMSO control for 24 hrs, followed by treatment with NMDA (20 μM) or water for 20 min. Gene expression was normalized against the house-keeping gene, hypoxanthine phosphoribosyltransferase 1 (HPRT1) and glyceraldehyde 3-phosphate dehydrogenase (GAPDH) and compared to the control (DMSO) with NMDA treatment. Relative changes in gene expression induced by DA001+NMDA was compared with DMSO+NMDA.

Example 56

DA001 Induces CEBPb mRNA in Cortical Neurons

Cortical neurons were treated with DA001 at different time intervals. The expression of CCAAT/enhancer binding protein beta (C/EBP-b) and c-fos was measured at three different time intervals by real-time PCR. DA001 induced C/EBP-b expression after a 2-day treatment but did not affect expression of c-fos under similar conditions. As shown in FIG. 4, DA001 induces CEBPb mRNA in cortical neurons. Cortical neurons were incubated with DA001 or the DMSO control for 3 different time intervals. Gene expression was normalized against the house-keeping gene, hypoxanthine phosphoribosyltransferase 1 (HPRT1) and glyceraldehyde 3-phosphate dehydrogenase (GAPDH) and compared to the control (DMSO) treatment. Relative change in gene expression induced by DA001 was compared with DMSO. Asterisk represents $P < 0.05$.

Example 57

DA001 Protects Neurons Against Differing Concentrations of Kainate

Cortical neurons were treated with DA001 and subsequently subjected to varying concentrations of kainate. Survival assays were then conducted to determine the ability of DA001 to effectively protect neuronal cells from kainate-induced excitotoxicity. As indicated in FIG. 5, there was a significant reduction in cell death upon treatment with DA001 compared to the DMSO control at high concentrations of kainate.

FIG. 5 illustrates that DA001 protects neurons against differing concentrations of kainate. Cortical neurons were incubated with DA001 (40 μM) or control (DMSO) for 24 hrs, followed by co-treatment with different concentrations of kainate (KA, 5-500 μM) for 20 min. LDH release into the medium was then measured.

Example 58

DA021 enhance learning and memory in in vivo studies

The therapeutic effect of the novel compounds on spatial learning and memory in mice was demonstrated using the Morris water maze task, the favoured test to study hippocampal-dependant learning and memory.

For the compound DA021, the test subjects in the control group (oil/saline) took ~30 seconds to detect the platform after 5 days of training. In contrast, the scopolamine-induced memory-impaired group required almost twice the amount of time to locate the platform after an identical training period. DA021 significantly reversed the increased escape latency induced by scopolamine on day 4 and day 5. FIG. 6 illustrates that DA021 reduces the escape latency in Morris Water Maze model. Scopolamine (SCOP; 4 mg/kg) was first administered intra-peritoneally to mice to impair their memories. Scopolamine-induced memory impaired mice were then orally administered DA021 (10 mg/kg) and subject to the Morris water maze over a period of 5 days. On each day, the time taken for the mice to detect the hidden platform in the water maze was measured, in seconds. Measurements were calculated as the mean latency periods for each mouse, n=12 per group. Data are expressed as mean±s.e.m. and compared to Oil/SCOP group. Doses are represented in mg/kg.

Example 59

DA021 Inhibits Particular Prostanoid and Melatonin Receptors

To determine the targets of DA compounds, the compound was assessed in binding assays for the family of prostanoid receptors. Both compounds were tested at a single concentration (10 μM) in duplicate. DA001 and DA021 inhibit the ligand binding of prostaglandin E2 receptors EP1, EP2 and EP4 and moderately to prostaglandin (PGF) to its receptor (FP), but not prostaglandin I (PGI2), thromoboxane A and prostaglandin D2 to their receptors.

| Binding assay | % inhibition of control specific binding | | Target |
|---|---|---|---|
| | DA001 | DA021 | |
| EP1 | 52 | 31 | $PGE_2$ |
| EP2 | 31 | 42 | $PGE_2$ |
| EP3 | TBD | −3 | PGE2 |
| EP4 | 49 | 36 | $PGE_2$ |
| FP | 27 | 52 | PGF |
| IP | 0 | 9 | PGI |
| TP | 17 | 17 | Thromoboxanes A |
| DP | TBD | 0 | PGD |

Example 60

DA021 and DA034 Protect Neurons Against Differing Concentrations of Glutamate

Cortical neurons were pre-treated with DA021 or DA034 and subsequently subjected to varying concentrations of glutamate (10-200 μM). Glutamate is the neurotransmitter which activates NMDA receptors. Survival assays were then conducted to determine the ability of DA021 or DA034 to effectively protect neuronal cells from excitotoxicity. As indicated in FIG. 7, there was a significant reduction in cell death upon pre-treatment with DA021 or DA034 compared to the DMSO control at high concentrations of glutamate. FIG. 7 illustrates that DA021 and DA034 protect neurons against differing concentrations of glutamate. Cortical neurons were incubated with DA021(30 μM), DA034 (30 μM) or control (DMSO) for 24 hrs, followed by treatment with different concentrations of glutamate (10-200 μM) for 20 min. LDH release into the medium was then measured.

Example 61

DA021 and DA034 Protect Neurons Against Differing Concentrations of Kainate

Cortical neurons were treated with DA021 or DA034 and subsequently subjected to varying concentrations of kainate. Survival assays were then conducted to determine the ability of DA021 or DA034 to effectively protect neuronal cells from kainate-induced excitotoxicity. FIG. 8 illustrates that DA021 and DA034 protect neurons against differing concentrations of Kainate. Cortical neurons were incubated with DA021 (30 μM), DA034 (30 μM) or control (DMSO) for 24 hrs, followed by co-treatment with different concentrations of Kainate (KA, 5-500 μM) for 20 min. LDH release into the medium was then measured.

Example 62

DA021 and DA034 Protect Neurons Against Differing Concentrations of NMDA

Cortical neurons were treated with DA021 or DA034 and subsequently subjected to varying concentrations of NMDA. Survival assays were then conducted to determine the ability of DA021 or DA034 to effectively protect neuronal cells from NMDA-induced excitotoxicity. As indicated in FIG. 9, there was a significant reduction in cell death upon treatment with DA021 or DA034 compared to the DMSO control at high concentrations of NMDA. FIG. 9 illustrates that DA021 and DA034 protect neurons against differing concentrations of NMDA. Cortical neurons were incubated with DA021 (30 μM), DA034 (30 μM) or control (DMSO) for 24 hrs, followed by co-treatment with different concentrations of NMDA (10-200 μM) for 20 min. LDH release into the medium was then measured.

Example 63

DA021 Protect Neurons Against Differing Concentrations of NMDA in Hippocampal Neurons Hippocampal neurons were treated with DA021 and subsequently subjected to varying concentrations of NMDA. Survival assays were then conducted to determine the ability of DA021 to effectively protect neuronal cells from NMDA-induced excitotoxicity. FIG. 10 illustrates that DA021 protects neurons against differing concentrations of NDMA. Hippocampal neurons were incubated with DA021 (30 µM) or control (DMSO) for 24 hrs, followed by co-treatment with different concentrations of NMDA (10-200 µM) for 20 min. LDH release into the medium was then measured.

Example 64

DA021 Protect Neurons Against Differing Concentrations of Glutamate in Hippocampal Neurons Hippocampal neurons were treated with DA021 and subsequently subjected to varying concentrations of glutamate. Survival assays were then conducted to determine the ability of DA021 to effectively protect neuronal cells from glutamate-induced excitotoxicity. FIG. 11 illustrates that DA021 protects neurons against differing concentrations of glutamate in hippocampal neurons. Hippocampal neurons were incubated with DA021 (30 µM) or control (DMSO) for 24 hrs, followed by treatment with different concentrations of glutamate (10-200 µM) for 20 min. LDH release into the medium was then measured.

Example 65

Derivatives of DA001 Protect Cortical Neurons Against NMDA Excitotoxicity

A total of 90 derivatives of DA001 were synthesized, and survival data for them on NMDA survival assay are shown in FIG. 12. Compounds with strong protective effect (>80% survival) against NMDA excitotoxicity are prototype DA001, derivatives DA010, DA021, DA034, DA040, DA081 and DA088. Those with moderate effect are DA002, DA005, DA007, DA008, DA017, DA032, DA035, DA036, DA042 and DA046. FIG. 12 illustrates that derivatives of DA001 rescue the cortical neurons from NMDA excitotoxicity. Cortical neurons were treated with compounds derived from of DA001 (30 µM or otherwise indicated in brackets) 24 hours prior to NMDA treatment. LDH released into the medium were measured 24 hours after NMDA treatment. Data are expressed as averaged percentage of cell survival (±s.e.m) calculated against solvent control (DMSO) and compared to no NMDA control (set as 100% survival). Solid bars represent compounds with strong protective effect (<80%) while shaded bars represent compounds with moderate effects (50-80%), open bars represent compounds without or with effect less than 50%. All the strong and moderate neuroprotective compounds exhibited a significant increase in cell survival as measured by Student T-test, P<0.05.

Example 66

DA001 Dose-Dependently Antagonizes EP2 and EP4 Receptor Activity

As shown in FIG. 13, DA001 inhibits EP2 and EP4 receptors activity upon PGE2 ligand binding. DA001 was evaluated at 6 concentrations in cellular assays assessing receptor function. Upon ligand binding, the EP2 and EP4 receptor is activated which leads to an increase in intracellular cyclic AMP. DA001 showed a dose dependent inhibition of cyclic AMP in the presence of the PGE2 in cells over-expressing the EP2 or EP4 receptor.

Example 67

DA021 Antagonizes EP1 Receptor Activity

DA021 inhibits PGE2 ligand binding to EP1, EP2 and EP4 receptors. To determine whether the inhibitory effect is due to agonist or antagonist activity, DA021 was evaluated and compared at 1 concentration (30 uM) in cellular assays assessing receptor function. Upon ligand binding, the EP receptors are activated which leads to an increase in intracellular cyclic AMP. DA021 showed a strong antagonizing effect on EP1 receptor in the presence of the PGE2 while DA021 alone did not elicit any responses on all these receptors.

| cAMP measurement | EP1 receptor | EP2 receptor | EP4 receptor |
| --- | --- | --- | --- |
| Agonist effect | 9 | −3 | TBD |
| Antagonist effect | 87 | 4 | 18 |

Example 68

Derivatives of DA001 Protect Cortical Neurons Against Amyloid Beta Peptide Excitotoxicity A total of 90 derivatives of DA001 were synthesized, and their effect on cortical neurons survival against amyloid beta peptide ($A\beta_{25-35}$) excitotoxicity was examined. Data for these compounds are shown in FIG. 14. Compounds marked with asterisks significantly protected primary neurons against $A\beta_{25-35}$-induced cell death. Compounds with strong protective effect are DA002, DA005, DA007, DA016, DA018, DA019, DA042, DA044, DA060 and DA072.

Example 69

DA001 Improves the Behavioral Scores of Mice with Experimental Autoimmune Encephalomyelitis The experimental autoimmune encephalomyelitis (EAE) model is a widely-used study that exhibits multiple sclerosis (MS)-like inflammation in the CNS and spinal cord. It is induced by stimulating an immune response directed against CNS antigen, the myelin oligodendrocyte glycoprotein (MOG). It is a transmembrane protein that is expressed on the surface of oligodendrocytes in the CNS. It is used as a target antigen in facilitating demyelination which leads to MS-like symptoms that are observed in mice.

The efficacy of DA001 in improving the symptoms of EAE was examined. C57BL/6 mice were immunized with MOG and performed as described in "Materials and Methods". Upon introduction of MOG, symptomatic manifestation takes anywhere between 9 to 10 days. The clinical scores were given on a point score scale based on the previously published literature, "Active induction of experimental allergic encephalomyelitis (2006:1(4):1810-1818, *Nature Protocol*). MOG-injected mice showed significant deficits in scores (the higher the scores, the more severe the deficits) starting from day 11 and persistent to day 21. In contrast to MOG-injected mice, albumin-injected mice showed no symptoms of deficits and behaved normal as usual. Due to the nature of the axonal damages occur during this particular type of EAE model, limited numbers of therapeutic agents are known to be effective in improving the symptoms of EAE. Oral administration of DA001 at 100 mg/kg which was dissolved in water (Vehicle) showed a marked decrease in EAE scores compared to the vehicle-treated EAE mice, demonstrating the effectiveness of DA001 in successfully alleviating the symptoms of EAE. The studies are illustrated in FIG. 15

Example 70

Improvement in Experimental Autoimmune Encephalomyelitis Scores by DA002

DA002 is the aglycon of DA001. The efficacy of DA002 in ameliorating the symptoms of EAE mice was examined (see EAE mice were generated as described in "Material and Methods". As shown in FIG. 16, DA002 at 100 mg/kg showed significant decrease in the EAE scores when compared to vehicle-treated group.

Example 71

Improvement in Experimental Autoimmune Encephalomyelitis Scores by DA021

DA021 is one of the structural analogs of DA002. The efficacy of DA021 in alleviating the symptoms of EAE mice was examined. EAE mice were generated as described in "Material and methods". As shown in FIG. 17, DA021 at 100 mg/kg showed marked decrease in the EAE scores when compared to vehicle-treated control.

Example 72

DA001 and DA021 Decrease the Expression of Phosphorylated STAT 3, STAT 4, and STAT 6 Nuclear Proteins in Splenocytes Isolated from the Spleen of Vehicle-Treated EAE Mice The efficacy of DA compounds in modulating the expression of pro-inflammation proteins was examined. Western blot analysis was performed on cultured splenocytes isolated from the spleen of EAE mice and the expression of signal transducers and activators of transcription (STAT) proteins was examined in response to exogenous treatments of MOG (25 μg/mL), DA001 (30 μM) and DA021 (30 μM). Exogenous addition of MOG [MOG (Ex)] to EAE splenocytes is shown to robustly increase the phosphorylation of STAT3, STAT4, and STAT6.

As indicated in FIG. 18, upon exogenous treatments with DA001 and DA021 at 30 μM, MOG-induced STAT3 and STAT4 phosphorylation were significantly decreased when compared to the vehicle treated control. There was also a marked decrease in STAT6 phosphorylation upon DA021 treatment demonstrating the effectiveness of DA compounds in reducing the STAT protein expressions which are believed to be one of key molecular events in EAE molecular pathology. In contrast, splenocytes from albumin-injected mice did not respond to MOG stimulation and served as a negative control.

As shown in FIG. 18, Splenocytes from the spleen of vehicle-treated EAE mice were cultured with RPMI 1640 medium supplement with 10% heat inactivated fetal bovine serum and treated with MOG peptide (25 μg/mL, Ex) (Hooke Laboratories) in the presence of DA001, and DA021 (30 μM, Ex). Western blot analysis was performed as described in the methodology.

Example 73

DA001 and DA021 Decrease MOG-Induced IFN-γ Level in Primary Splenocytes Isolated from the Spleen of Vehicle-Treated EAE Mice Cytokines are believed to be one of the key signaling molecules in disease progression of EAE. Autoimmune response observed in the EAE model is believed to be mediated via the Th1 pathway, and interferon-gamma (IFN-γ) is the hallmark cytokine of the Th1 immune response. Therefore, it is critical to examine the efficacy of the compounds in modulating the levels of cytokines in EAE mice. To this end, splenocytes isolated from the spleens of EAE mice were cultured and treated with exogenous MOG peptide and the amount of IFN-γ was measured in response to exogenous DA001 and DA021 (30 μM) treatments using ELISA. In FIG. 19, the IFN-γ level in splenocytes was dramatically increased in response to exogenous MOG treatment. Interestingly, exogenous addition of DA001 and DA021 was found to inhibit the level of MOG-induced IFN-γ when compared to the vehicle control. Treatment of DA001 and DA021 resulted in 71% and 62% reduction, respectively, in the amount of MOG-induced IFN-γ, highlighting the effectiveness of the both DA compounds in successfully reducing the de novo synthesis of IFN-γ in response to exogenous MOG treatment in in vitro splenocytes.

As shown in FIG. 19, splenocytes were prepared from the spleen of vehicle-treated EAE mice. The cells were cultured in RPMI 1640 medium supplement with 10% heat inactivated fetal bovine serum and penicillin/streptomycin, in the absence or presence of MOG (25 μg/mL, Ex) with or without DA001 or DA021 (30 μM, Ex). Supernatants were collected after 48 hrs and IFN-γ Quantikine ELISA assay kit (R and D systems) was used according to the manufacturer's protocol. The amount of IFN-γ was calculated based on the standard curve established during the assay. The graph presented is the composite of two separate trials with duplicate samples in each trial. *=p≤0.0001, =p≤0.001, *=p≤0.01.

Example 74

DA001 Decreases MOG-Induced IFN-γ in Primary Splenocytes Isolated from the Spleens of DA001-Treated EAE Mice Similar studies were performed as the above but using DA001-treated EAE mice. Splenocytes isolated from the spleen of DA001-treated EAE mice were cultured and treated with exogenous MOG peptide and the amount of IFN-γ was measured in response to exogenous DA001 (30 μM) treatment. MOG+DA001 indicates the group of mice which have been immunized with MOG and received daily dose of DA001 (100 mg/kg) dissolved in water (Vehicle) via oral administration. As shown in FIG. 20, splenocytes of DA001-treated EAE mice showed an increase in the IFN-γ level in response to exogenous MOG treatment. However the level of IFN-γ was significantly lower than that in the splenocytes of vehicle-treated EAE mice, 105 pg/ml vs 623 pg/ml (Table 5), demonstrating the effectiveness of DA001 in decreasing the de novo synthesis of IFN-γ. In addition, the amount of IFN-γ in splenocytes of DA001-treated EAE mice also markedly decreased by 91% in response to the exogenous DA001 treatment.

TABLE 5

| Treatment | Reduction in IFN-γ (pg/mL) | | |
|---|---|---|---|
| | Average | p-Value | % Reduction |
| MOG + Vehicle | 623.2 ± 149.8 | — | — |
| MOG + DA001 | 105.7 ± 5.1 | 0.02 | 83.1 |
| MOG + DA021 | 135.3 ± 12.3 | 0.03 | 78.3 |

As shown in FIG. 20, splenocytes were prepared from the spleen of DA001-treated EAE mice. Cells were cultured in RPMI 1640 medium supplement with 10% heat inactivated fetal bovine serum and penicillin/streptomycin, in the absence or presence of MOG (25 μg/mL) with or without DA001 (30 μM). Supernatants were collected after 48 hrs and IFN-γ Quantikine ELISA assay kit (R and D systems) was used according to the manufacturer's protocol. The amount of IFN-γ was calculated based on the standard curve established during the assay. The graph presented is the composite of two separate trials with duplicate samples in each trial. ***=p≤0.0001.

Example 75

DA021 Decreases MOG-Induced IFN-γ in Primary Splenocytes Isolated from the Spleens of DA021-Treated EAE Mice Similar studies were performed as the above but using DA021-treated EAE mice. Splenocytes isolated from the spleens of DA021-treated EAE mice were cultured and treated with exogenous MOG (25 μg/ml) and the level of IFN-γ was measured in response to DA021 (30 μM) treatment. MOG+DA021 represents the group of mice which have been immunized with MOG and received daily dose of DA021 (100 mg/kg) dissolved in water (Vehicle) via oral administration. As seen in FIG. 21, splenocytes of DA021-treated EAE mice showed an increase in the IFN-γ level in response to exogenous MOG treatment. The level of IFN-γ was again significantly lower than that in the splenocytes of vehicle-treated EAE mice, 135 pg/ml vs 623 pg/ml (Table), demonstrating the effectiveness of DA021 in decreasing the de novo synthesis of IFN-γ. In addition, the amount of IFN-γ in splenocytes of DA021-treated EAE mice was then markedly decreased by 78% in response to the exogenous DA021 treatment.

As shown in FIG. 21, splenocytes were prepared from the spleen of DA021-treated EAE mice. Cells were cultured in RPMI 1640 medium supplement with 10% heat inactivated fetal bovine serum and penicillin/streptomycin, in the absence or presence of MOG (25 μg/mL, Ex) with or without DA021 (30 μM, Ex). Supernatants were collected after 48 hrs and IFN-γ Quantikine ELISA assay kit (R and D systems) was used according to the manufacturer's protocol. The amount of IFN-γ was calculated based on the standard curve established during the assay. The graph presented is the composite of two separate trials with duplicate samples in each trial. ***=p≤0.0001.

Example 76

DA001 and DA021 Decrease MOG-Induced IL-6 Level in Primary Splenocytes Isolated from Spleens of Vehicle-Treated EAE Mice Interleukin-6 (IL-6) is one of the key cytokines in the acute phase of proinflammatory reaction in immune response. IL-6 activates JAK-STAT pathway and is believed to be one of the co-affectors in T helper 17 (Th17) differentiation along with transforming growth factor-β (TGF-β) and interleukin-23 (IL-23), which mediates the T-cell autoimmune responses seen in diseases such as EAE and MS. Therefore, it is of key interest to examine the effects of the DA compounds on Th17 pathway related cytokines. In FIG. 22, IL-6 level in splenocytes of EAE mice was dramatically increased in response to exogenous MOG treatment. Interestingly, exogenous addition of DA001 and DA021 was found to inhibit the level of MOG-induced IL-6 when compared to the vehicle control. Treatment of DA001 and DA021 resulted in a 73% and 79% reduction, respectively, in the amount of MOG-induced IL-6, highlighting the effectiveness of both DA compounds in successfully reducing the de novo synthesis of IL-6 in response to exogenous MOG treatment in in vitro splenocytes. Based on the results obtained thus far, decrease in the level of IL-6 in DA001 and DA021-treated splenocytes may act as a key step in the downregulation of phosphorylation of STAT3. This presents another key piece of evidence in demonstrating the efficacy of DA compounds as potential drug candidates for treating autoimmune diseases.

As shown in FIG. 22, splenocytes were prepared from the spleens of vehicle-treated EAE mice. Cells were cultured in RPMI 1640 medium supplement with 10% heat inactivated fetal bovine serum and penicillin/streptomycin, in the absence or presence of MOG (25 μg/mL, Ex) with or without DA001 or DA021 (30 μM, Ex). Supernatants were collected after 48 hrs and IL-6 Quantikine ELISA assay kit (R and D systems) was used according to the manufacturer's protocol. The amount of IL-6 was calculated based on the standard curve established during the assay. The graph presented is the composite of two separate trials with duplicate samples in each trial. *=p≤0.0001, =p≤0.001.

Example 77

DA001 Decreases MOG-Induced IL-6 in Primary Splenocytes Isolated from the Spleens of DA001-Treated EAE Mice Similar studies were performed as the above but using DA001-treated EAE mice. Splenocytes isolated from the spleens of DA001-treated EAE mice were cultured and treated with exogenous MOG peptide and the amount of IL-6 were measured in response to exogenous DA001 (30 μM) treatment. MOG+DA001 indicates the group of mice immunized with MOG and which received a daily dose of DA001 (100 mg/kg) dissolved in water (Vehicle) via oral administration. As shown in FIG. 23, splenocytes of DA001-treated EAE mice showed an increase in the IL-6 level in response to exogenous MOG treatment. Interestingly, the amount of IL-6 in splenocytes of DA001-treated EAE mice was then markedly decreased by exogenous DA001 treatment.

As shown in FIG. 23, splenocytes were prepared from the spleens of DA001-treated EAE mice. Cells were cultured in RPMI 1640 medium supplement with 10% heat inactivated fetal bovine serum and penicillin/streptomycin, in the absence or presence of MOG (25 μg/mL, Ex) with or without DA001 (30 μM, Ex). Supernatants were collected after 48 hrs and IL-6 Quantikine ELISA assay kit (R and D systems) was used according to the manufacturer's protocol. The amount of IL-6 was calculated based on the standard curve established during the assay. The graph presented is the composite of two separate trials with duplicate samples in each trial. ***=p≤0.0001, *=p≤0.01.

Example 78

DA021 Decreases MOG-Induced IL-6 in Primary Splenocytes Isolated from the Spleens of DA001-Treated EAE Mice

Similar studies were performed as the above but using DA021-treated EAE mice. Splenocytes isolated from spleens of DA021-treated EAE mice were cultured and treated with exogenous MOG peptide, and the amount of IL-6 was measured in response to exogenous DA021 (30 µM) treatment. MOG+DA021 indicates the group of mice which were immunized with MOG and which received a daily dose of DA021 (100 mg/kg) dissolved in water (Vehicle) via oral administration. As indicated in FIG. 24, splenocytes of DA021-treated EAE mice showed an increase in the IL-6 level in response to exogenous MOG treatment. Interestingly, the amount of IL-6 in splenocytes of DA021-treated EAE mice was then markedly decreased by exogenous DA021 treatment.

As shown in FIG. 24, splenocytes were prepared from the spleens of DA021-treated EAE mice. Cells were cultured in RPMI 1640 medium supplement with 10% heat inactivated fetal bovine serum and penicillin/streptomycin, in the absence or presence of MOG (25 µg/mL, Ex) with or without DA021 (30 µM, Ex). Supernatants were collected after 48 hrs and IL-6 Quantikine ELISA assay kit (R and D systems) was used according to the manufacturer's protocol. The amount of IL-6 was calculated based on the standard curve established during the assay. The graph presented is the composite of two separate trials with duplicate samples in each trial. *=$p \leq 0.0001$, =$p \leq 0.001$.

Example 79

DA001 and DA021 Decrease MOG-Induced IL-17 Level in Primary Splenocytes Isolated from Spleens of Vehicle-Treated EAE Mice

Interleukin-17 (IL-17) is one of the most important effector cytokines involved in Th17 pathway and mediated autoimmune response. The initiation of Th17 differentiation is believed to involve TGF-β and IL-6 which in turn activate the transcriptions responsible for tissue inflammation and autoimmune responses.

Efficacy of DA001 and DA021 in modulating IL-17 production in exogenous MOG-treated splenocytes isolated from the spleen of EAE mice was investigated. As shown in FIG. 25, robust amount of IL-17 was observed in response to exogenous MOG treatment. As it was observed for both IFN-γ and IL-6, there was 65% and 68% reduction in the amount of IL-17 in response to DA001 and DA021 (30 µM) treatments, respectively. This demonstrates the effectiveness of the DA compounds in reducing the amount of IL-17 which is one of the primary cytokines involved in Th17 mediated immune response in the EAE model.

As shown in FIG. 25, splenocytes were prepared from the spleen of vehicle-treated EAE mice. Cells were cultured in RPMI 1640 medium supplement with 10% heat inactivated fetal bovine serum and penicillin/streptomycin, in the absence or presence of MOG (25 µg/mL, Ex) with or without DA001 or DA021 (30 µM, Ex). Supernatants were collected after 48 hrs and IL-17 Quantikine ELISA assay kit (R and D systems) was used according to the manufacturer's protocol. The amount of IL-17 was calculated based on the standard curve established during the assay. The graph presented is the composite of two separate trials with duplicate samples in each trial. *=$p \leq 0.0001$, =$p \geq 0.001$.

Example 80

DA001 Decreases MOG-Induced IL-17 Level in Primary Splenocytes Isolated from Spleens of DA001-Treated EAE Mice

Similar studies were performed as the above but using DA001-treated EAE mice. Splenocytes isolated from spleens of DA001-treated EAE mice were cultured and treated with exogenous MOG peptide and the amount of IL-17 was measured in response to exogenous DA001 (30 µM) treatment. MOG+DA001 indicates the group of mice which were immunized with MOG and which received a daily dose of DA001 (100 mg/kg) dissolved in water (Vehicle) via oral administration. As indicated in FIG. 26, splenocytes of DA001-treated EAE mice showed an increase in the IL-17 level in response to exogenous MOG treatment. The amount of IL-17 from exogenous MOG treatment in splenocytes of DA001-treated EAE mice was significantly decreased by 51% in response to the exogenous DA001 treatment.

As shown in FIG. 26, splenocytes were prepared from the spleen of DA001-treated EAE mice. Cells were cultured in RPMI 1640 medium supplement with 10% heat inactivated fetal bovine serum and penicillin/streptomycin, in the absence or presence of MOG (25 µg/mL, Ex) with or without DA001 (30 µM, Ex). Supernatants were collected after 48 hrs and IL-17 Quantikine ELISA assay kit (R and D systems) was used according to the manufacturer's protocol. The amount of IL-17 was calculated based on the standard curve established during the assay. The graph presented is the composite of two separate trials with duplicate samples in each trial. *=$p \leq 0.0001$, =$p \geq 0.001$.

Example 81

DA021 Decreases MOG-Induced IL-17 in Primary Splenocytes Isolated from the Spleens of DA021-Treated EAE Mice

Similar studies were performed as the above but using DA021-treated EAE mice. Splenocytes isolated from spleens of DA021-treated EAE mice were cultured and treated with exogenous MOG peptide and the amount of IL-17 was measured in response to exogenous DA021 (30 µM) treatment. MOG+DA021 indicates the group of mice which were immunized with MOG and which received a daily dose of DA021 (100 mg/kg) dissolved in water (Vehicle) via oral administration. As indicated in FIG. 27, splenocytes of DA021-treated EAE mice showed an increase in the IL-17 level in response to exogenous MOG treatment. The amount of IL-17 from exogenous MOG treatment in splenocytes of DA021-treated EAE mice was significantly decreased by 89% in response to the exogenous DA021 treatment.

As shown in FIG. 27, splenocytes were prepared from the spleen of DA021-treated EAE mice. Cells were cultured in RPMI 1640 medium supplement with 10% heat inactivated fetal bovine serum and penicillin/streptomycin, in the absence or presence of MOG (25 µg/mL, Ex) with or without DA021 (30 µM, Ex). Supernatants were collected after 48 hrs and IL-17 Quantikine ELISA assay kit (R and D systems) was used according to the manufacturer's protocol. The amount of IL-17 was calculated based on the standard curve established during the assay. The graph presented is the composite of two separate trials with duplicate samples in each trial. ***=p≤0.0001

Example 82

DA001 Decreases the Lymphocyte Infiltrates in Spinal Cord of EAE Mice

Lymphocyte infiltration into the spinal cords is believed to be one of the reasons for extensive axonal damages observed in EAE model. Histological characterization of lumber sections of spinal cords from EAE mice were carried out in order to ascertain the extent of lymphocyte infiltration and the effects of DA001 in minimizing the degree of infiltration. To this end, the hematoxyline and eosin (H&E) stain technique was used to stain the spinal cords from EAE mice treated with vehicle or DA001. H&E staining is a commonly used histological technique to show the degree of lymphocyte infiltration in spinal cords in EAE. In the pictures presented, lymphocytes observed in the spinal cords of EAE mice were stained bright red or purple granules with blue cytoplasm. There was significantly more cytoplasm with purple granules in the lateral furniculus (framed in red rectangle) of vehicle-treated EAE mice than of DA001-treated EAE mice. There was also an increase in the lymphocytes surrounding axons which facilitated hyper-immune responses as a result of MOG treatment and this reaction was dramatically reduced in the tissues of DA001-treated mice.

As shown in FIG. 28, spinal cords from EAE mice (day 15) were transcardially perfused with 4% paraformaldehyde and were postfixed overnight. Fixed spinal cords were then embedded in paraffin and sections were cut at 6 μm and mounted onto Histobond™ glass slides (Merienfeld, Germany). After overnight incubation in an oven, the slides were rehydrated and stained with hematoxylin and eosin (H&E) as described in the methodology section. The photos were taken using a Leica microscope at both 10× and 20× fields. All the spinal cords presented are from between L-3 and L-5 lumbar sections of the EAE mice.

Example 83

DA021 Decreases *E-coli* Lipopolysaccharide-Induced Tumor Necrosis Factor-α in Mice Evaluation of the efficacy and potency of orally administered DA021 to inhibit the lipopolysaccharide (LPS)-induced release of tumor necrosis factor-α (TNF-α) in mice was carried out. LPS is a widely used endotoxin, isolated from the bacteria, *E. coli* in inducing acute inflammation in an organism. Prednisolone is a synthetic corticosteroid drug that is commonly used in inflammatory reactions. It is a broad range immunosuppressant. Based on FIG. 29, there was a marked increase in the amount of TNF-α in serum upon LPS treatment in mice. More interestingly, DA021 at 30 mg/kg and 100 mg/kg significantly decreased LPS-induced TNF-α in blood serum of mice demonstrating anti-inflammatory effects exerted by DA021 in this model. Thirty minute pretreatment with orally administered DA021 resulted in a 73% and 77% inhibition of the LPS response at 30 mg/kg and 100 mg/kg, respectively. Prednisolone, a positive control, at 10 mg/kg treatment dramatically decreased the LPS-induced TNF-α level in response to LPS.

As shown in FIG. 29, thirty minutes after oral dosing of prednisolone (PNS, mg/kg) or DA021 (mg/kg) in mice, lipopolysaccharide (LPS, 10 mg/kg) was injected intraperitoneally to induce inflammation. Two hours after LPS injection, the serum was collected from the mice. The serum samples were assayed for tumor necrosis factor-α (TNFα) concentration by ELISA (Pierce) according to the manufacturer's protocol. N=10, significance was calculated versus LPS+vehicle using the Student's T-test, *=p≤0.05, #=p≤1×10$^{-4}$.

Example 84

DA021 Inhibits Ear Edema in Mice in Response to Oxazolone Treatment

To evaluate the efficacy and potency of DA021 in acute inflammation, an oxazolone-induced ear edema model was carried out in mice. Oxazolone-induced ear edema model is a commonly used skin inflammatory animal model. Oxazolone (OA) is an allergen that induces immunological responses that lead to surface edema. The amount of weight in the ear caused by the build-up of fluid in edema is significantly increased after OA treatment. As shown in FIG. 30, DA021 significantly reduced the OA-induced ear edema in mice as revealed by the reduction in ear weight. DA021 at 30 mg/kg and 100 mg/kg significantly inhibited 31.7% and 52.9%, respectively (Table 6) in the ear weight in response to oxazolone treatment, demonstrating the efficacy as a potential anti-inflammatory agent in skin inflammation. Betamethasone (BMS) which was used as a positive control, is a corticosteroid that is used as an anti-itching cream and other anti-inflammatory remedies. BMS showed a 75.4% reduction in the weight amount of ear.

TABLE 6

| Treatment | Change in Ear Weight (mg) | | | |
| --- | --- | --- | --- | --- |
|  | Average | SD | p-value | % Inhibition |
| Vehicle | 70.7 | 5.1 | N/A | N/A |
| Betamethasone | 17.4 | 4.9 | 5 × 10$^{-15}$ | 75.4 |
| DA021, po |  |  |  |  |
| 30 mg/kg | 48.3 | 5.7 | 3 × 10$^{-8}$ | 31.7 |
| 100 mg/kg | 33.3 | 3.9 | 1 × 10$^{-12}$ | 52.9 |

As shown in FIG. 30, oxazolone (OA) solution was applied to the shaved mice ear to induce edema. Mice were then treated with betamethasone (BMS, mg, topical) or DA021 (mg/kg, p.o.) and the ears were removed and weighed. N=10 per group, significance (p-value) was calculated versus OA+vehicle using the Student's T-test, *=P≤1×10$^{-7}$, #=P≤1×10$^{-12}$.

Example 85

DA001 Inhibits Melanocortin Binding to MC1 and MC4 Receptors

DA001 was evaluated against 109 receptor binding assays and 17 enzyme assays, comprising of selective, central and peripheral therapeutically-relevant targets. Radioligand competition assays were conducted whereby DA001 was tested at one concentration (10 μM) in duplicate. DA001 significantly inhibits melanocortin binding to melanocortin-1 (MC1) and melanocortin-4 (MC4) receptors (based on the manufacturer's guidelines for a cutoff at 50% inhibition). It could compete with the radioligand [$^{125}$I-NDP-alpha-melanocyte-stimulating hormone (α-MSH)] binding for MC1 and MC4 but not MC3 and MC5 nor the related family, the melanin concentrating hormone receptors (MCH1 and MCH2). Moderate to mild inhibition of DA001 was also observed for kainate, melatonin ($MT_1$) and serotonin ($5-HT_{1D}$ subtype) receptors.

| Binding assay | % inhibition of control specific binding | Target |
|---|---|---|
| MC1 | 64 | Melanocortin |
| MC3 | 12 | Melanocortin |
| MC4 | 59 | Melanocortin |
| MC5 | 11 | Melanocortin |
| MCH1 | −9 | Melanin concentrating hormone |
| MCH2 | −12 | Melanin concentrating hormone |
| Kainate | 35 | Kainate |
| MT1 | 28 | Melatonin |
| 5-HT1D | 30 | Serotonin |

To determine the $IC_{50}$ for DA001 to inhibit α-MSH binding on MC1 and MC4 receptor, the compound was further characterized by a dose-dependent study. DA001 was evaluated with 8 concentrations on MC1 and MC4 receptor binding assays. DA001 showed an $IC_{50}$ of 10 μM and 6.8 μM, for MC1 and MC4, respectively.

|  | $IC_{50}$ (M) | $K_i$ (M) | $n_H$ |
|---|---|---|---|
| MC1 | 1.00E−05 | 5.20E−06 | 0.9 |
| MC4 | 6.80E−06 | 6.30E−06 | 1.3 |

FIG. 31 shows the competition curves obtained with DA001 at the human MC1 or MC4 receptor. The specific ligand binding to the receptors is defined as the difference between the total binding and the nonspecific binding determined in the presence of an excess of unlabelled ligand. The results are expressed as a percent of control specific binding [(measured specific binding/control specific binding)×100] and as a percent inhibition of control specific binding {100−[(measured specific binding/control specific binding)×100]} obtained in the presence of DA001. The $IC_{50}$ values (concentration causing a half-maximal inhibition of control specific binding) and Hill coefficients (nH) were determined by non-linear regression analysis of the competition curves generated with mean replicate values using Hill equation curve fitting (Y=D+[(A−D)/(1+(C/C50)nH)], where Y=specific binding, D=minimum specific binding, A=maximum specific binding, C=compound concentration, C50=$IC_{50}$, and nH=slope factor). This analysis was performed using a software developed at Cerep (Hill software) and validated by comparison with data generated by the commercial software SigmaPlot® 4.0 for Windows® (© 1997 by SPSS Inc.).

Example 86

Investigation to Determine Anti-Inflammatory Properties of Novel Compounds

The novel compounds exhibit anti-inflammatory properties. Additional in vitro and in vivo studies are undertaken to evaluate the therapeutic effect of the novel compounds on inflammation. The studies aim to determine if there is a reduction in proinflammatory cytokines
Method:
In Vitro Studies
Animal Model and Treatment Male ICR mice weighing 30-40 g were used for this study. Animals were housed in cages with food and water ad libitum. The light cycle was controlled automatically (on at 7:00 a.m. and off at 7:00 p.m.), and room temperature was thermostatically regulated to 22±1° C. Prior to experiments, animals were housed under these conditions for 3-4 days to become acclimatized. Mice were divided into groups consisting of five mice each. Animals were slightly anaesthetized with isoflurane, and 1 mg/kg lipopolysaccharide (LPS) (from Escherichia coli O111:B4, Sigma, Deisenhofen, Germany) dissolved in saline was injected intraperitoneally (0.5 mL per mouse). The test compound was administered orally at different time intervals before LPS injection (0.25 mL per mouse). Control groups received an equal volume of saline, respectively. Mice were sacrificed by decapitation during anaesthesia with isoflurane 1, 2 or 6 h after LPS injection. Blood was collected in EDTA tubes and centrifuged at 4000 rpm for 10 min at 4° C. Plasma was obtained and stored at −20° C. until used. Heart, lungs, kidneys and liver were quickly removed, frozen in liquid nitrogen and stored at −80° C. until use.
RNA Extraction and Reverse Transcription Total RNA from heart, lung, kidney and liver was isolated RNAeasy column (Invitrogen) following the manufacturer's instructions and was quantified spectrophotometrically. Reverse transcription was performed according to standard protocols in a total volume of 22 uL containing 2 ug of total RNA, 0.5 mg/mL oligo(dT) 15 primer (Promega, Madison, USA), 20 U of RNAsin (Promega, Madison, USA), 2.5 mM dNTP (Promega, Madison, USA), 200 U of superscript II (Invitrogen) and manufacturer's 5 RT Buffer. cDNA was stored at −20° C. until use.
Real-Time PCR Analysis Expression of TNFα, IL-1β, IFNγ and β-actin mRNA was evaluated by real-time PCR using Fast 7500 System (ABI). All PCRs were performed in a total volume of 20 uL using the ABI DNA SYBR Green I Kit (ABI). Each reaction contained 2 uL of cDNA, 3.0 uM (TNFα, IL-1β, β-actin) or 5.0 uM (IFNγ) $MgCl_2$, 1 uL each of sense and antisense primer (10 pmol/uL) and 2 uL of Mix (containing buffer, dNTPs, SYBR Green and hotstart Taq polymerase). After an initial denaturation step at 95° C. for 10 min, temperature cycling with a total of 40 cycles was initiated. Each cycle consisted of a denaturation phase at 95° C. for 10 s, an annealing phase at 58° C. for 7 s and an elongation phase at 72° C. for 18 s. Amplification was followed by melting curve analysis to verify the correctness of the amplicon. A negative control with water instead of cDNA was run within every PCR to assess specificity of the reaction. To verify the accuracy of the amplification, PCR products were further analysed on ethidium bromide-stained 2% agarose gel. Results are given as a ratio of the amount of TNFα, IL-1β, IFNγ to that of β-actin mRNA.

The following primers were used: TNFα (NM_013693) sense: CCC GG CTC AGC CTC TTC TCA TTC (SEQ ID NO:19), antisense: GGA TCC GGT GGT TTG CTA CGA CGT (SEQ ID NO:20) (201 bp); IL-1β (NM_008361) sense: TCT CGC AGC AGC ACA TCA (SEQ ID NO:21), antisense: CAC ACA CCA GCA GGT TAT (SEQ ID NO:22) (197 bp); IFNγ (NM_008337) sense: CAC AGT CAT TGA AAG CCT (SEQ ID NO:23), antisense: AGA CTT CAA AGA CTC TGA (SEQ ID NO:24) (169 bp); βactin (NM_007393) sense: CCG CCC TAG GCA CCA GGG TG (SEQ ID NO:25), antisense: GGC TGG GGT GTT GAA GGT CTC AAA (SEQ ID NO:26)(285 bp).
Protein Extraction and Determination Tissues were homogenized in phosphate buffered saline (Sigma, Deisenhofen, Germany) using an ultraturrax for 60 s in an ice-cold water bath. The homogenates were then centrifuged for 10 min at 10,000 rpm at 4° C. to remove debris. The supernatants were collected and protein levels were measured by the bicinchoninic acid (BCA) assay kit (Sigma, Deisenhofen, Germany) using bovine serum albumin (BSA) as standard Assay for Cytokines TNFα, IL-1β and IFNγ levels in tissues were assayed by using enzyme-linked immunosorbent assay kits according to the manufacturer's instructions.

In Vivo Studies

Sprague-Dawley rats (250-300 g) are anaesthetised with thiopentone (40 mg/kg; i.p.), and arthritis is induced by a single unilateral injection of 125 μl Freund's complete adjuvant (FCA; containing 125 μg *Mycobacterium tuberculosis*) into synovial cavities of the rat knee; the contralateral knee is injected with 125 μl physiological saline to serve as an internal control. This procedure produces joint oedema after day 1 and histological changes from day 3 onwards. The rats are monitored over a period of 21 days.

General Procedure:

On day 0, rats are anaesthetized and induced with monoarthritis as described above. To investigate the effects of drugs on development of the arthritis symptoms, drugs are administered to 3 cohorts of 8 rats by the oral route on days 0, 1, 2, 4, 7, 11, 14, and 18. Another cohort of 8 rats received paralleled administration of vehicle to act as vehicle control, and a further cohort of 8 rats received paralleled administration of 10 mg/kg indomethacin to act as positive control.

The knee extension angle that provoked struggling behavior, sizes of the knee joints, and body weight of the rats are measured on day 0 prior to induction of arthritis, and on days 1, 2, 4, 7, 11, 14, 18, and day 21 after induction of arthritis, to provide indexes of allodynia, oedema, and drug toxicity respectively. Hyperanemia is assessed by measurement of the knee joint blood flow prior to termination of the animals at the end of the experiment on day 21, and after that, the knee joints are excised and processed for histological examination to provide scores on the extent of immune cell infiltration, tissue proliferation, and cartilage erosion, which served as additional indexes of the arthritis condition.

Assessment of Analgesic Effect

The method is modified from that described by Yu et al (2002). The conscious rat is restrained gently. While the thigh is fixed by holding it with the thumb and the second finger of one hand, the leg is extended by the fingers of the other hand to determine the knee extension angle at which the rat showed struggling behaviour (allodynia). The extension angle is directly measured using a protractor by holding the thigh at the pivot. Each joint is measured three times at 3 minute intervals and the average of the three is taken as the final value.

Assessment of Knee Joint Oedema

The method was previously described by Lam et al (2004). In the anesthetized rat, a digital micrometer (Mitutoyo, Japan) is placed across the medial aspect of the knee joint holding the muscles on either side at an appropriate strength so that it touches but not pressing on these muscles. The reading on the micrometer is then noted. Each joint is measured three times and the average of the three is taken as the final value.

Assessment of Knee Joint Hyperaemia

The method of laser Doppler perfusion imaging (LDI) is used to measure knee joint blood flow. In the anesthetized rat, the skin over the knee joint is removed to expose the anteromedial aspect of the joint capsule. For the exposed surface, 0.1 ml saline is added every 5 minutes to prevent tissue dehydration. A laser Doppler perfusion imager (Moor Instruments, England), which is placed 28 cm above the joint, directs a helium-neon laser (633 nm) to the tissue and scans the joint surface in a square pattern of 2×2 cm in approximately 20 s. Each joint is scanned three times with 2-min intervals. A colour-coded perfusion image is then generated and displayed on the monitor. The actual flux values at each point in the image are stored on disc and can be utilized for calculation of the mean flux value within a given area using an image processing software (Moor Instrument). The area selected is based on the criterion that it should include most of the articular tissue with minimal inclusion of the relatively less well-perfused muscle around the joint.

Assessment of Morphological Changes

The anesthetized rats are exsanguinated, their knee joints dissected, freed from muscles, and fixed in 10% formalin. The joints are decalcified, embedded in wax, sectioned and stained with haematoxylin and eosin. Histological analysis is carried out by a (blinded) observer, focusing especially on polymorphonuclear cell infiltration, tissue proliferation, and cartilage erosion. The severity of the lesions is classified into four grades: 0=no change; 1=mild change; 2=moderate change; and 3=marked change.

Although the foregoing invention has been described in some detail by way of illustration and example for purposes of clarity of understanding, one with skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound having the following formula:

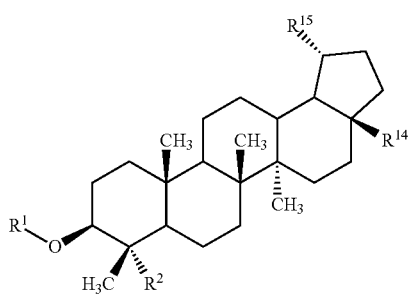

or a pharmaceutically acceptable salt, hydrate, or solvate thereof; wherein:

$R^1$ is —H or alkyl-C(O)—;

$R^2$ is selected from the group consisting of hydroxy-$C_{1-4}$ alkyl, alkoxy-$C_{1-4}$alkyl, aryloxy-$C_{1-4}$alkyl, alkyl-C(O)O—$C_{1-4}$alkyl and arylalkyl-C(O)O—$C_{1-4}$alkyl;

$R^{14}$ is selected from the group consisting of $R^{12}$ and —C(O)$R^3$;

$R^{15}$ is selected from the group consisting of $R^{13}$ and —C(=$CH_2$)($R^4$);

$R^3$ is selected from the group consisting of —$NH_2$, —$NHR^a$, —N($R^a$)$_2$, —OH, OMe, O($CH_2$)$_2$OH, and OEt, wherein $R^a$ is alkyl; wherein the aliphatic portion of the $R^a$ substituent is substituted with from 1-2 $R^c$ substituents independently selected from —OH, —$NH_2$; or optionally any two adjacent $R^c$ substituents together with the atoms to which they are attached form a 5- or 6-membered heterocyclic ring having from 1-3 heteroatoms selected from N, O or S, wherein the heterocyclic ring is optionally substituted with 1-2 $C_{1-8}$alkyl;

$R^4$ is $C_{1-4}$alkyl, haloalkyl, hydroxyalkyl, alkyl-C(O)O—$C_{1-4}$alkyl, arylalkyl-NH—$C_{1-4}$alkyl or alkoxyalkyl;

wherein the aromatic portion of the $R^3$ or $R^4$ group is optionally substituted with from 1-2 $R^d$ substituents independently selected from the group consisting of halo, —CN, —NO$_2$, —OH, —$R^e$, —O$R^e$, —OC(O)NH$R^e$, —OC(O)N($R^e$)$_2$, —OC(O)$R^e$, —OC(O)H, —NH$_2$, —NH$R^e$, —N($R^e$)$_2$, —S(O)$_2R^e$, —SO$_2$NH$_2$, —SO$_2$NH$R^e$, —SO$_2$N($R^e$)$_2$, —NHS(O)$_2R^e$, —N$R^e$S(O)$_2R^e$, —C(O)NH$_2$, —C(O)NH$R^e$, —C(O)N($R^e$)$_2$, —C(O)H, —C(O)$R^e$, —NHC(O)$R^e$, —N$R^e$C(O)$R^e$, —CO$_2R^e$, —NHCO$_2R^e$ and —N$R^e$CO$_2R^e$, wherein each $R^e$ is independently a $C_{1-8}$alkyl;

with the proviso when $R^1$ is —H or CH$_3$C(O)—, $R^2$ is —CH$_2$OH or —CH$_2$OC(O)CH$_3$ and $R^4$ is —CH$_3$ or HOCH$_2$—, then $R^3$ is other than —OH, —OMe, —OEt, —NHCH$_2$Ph, —O(CH$_2$)$_2$OH, —CH$_2$CH(OH)CH$_2$(OH) or 2,2-dimethyl-1,3-dioxolan-4-yl-methyl;

$R^{12}$ is selected from the group consisting of hydroxyalkyl, alkyl-OC(O)—, aryl-$C_{1-4}$alkyl-OC(O)—, alkyl-C(O)O-alkyl, aryl-$C_{1-4}$alkyl-C(O)O-alkyl, aryl-$C_{1-4}$alkoxy or alkoxyalkyl, wherein the aryl moiety of which is optionally substituted with from 1-3 members selected from halogen, alkyl, aryl-$C_{1-4}$alkyl, hydroxyalkyl, alkoxy, aryl-$C_{1-4}$alkoxy, alkyl-OC(O)—, alkyl-C(O)O—, aryl-$C_{1-4}$alkyl-C(O)O—, aryl-$C_{1-4}$alkyl-OC(O)O—, alkoxyalkyl or aryl-$C_{1-4}$alkoxy-alkyl; and $R^{13}$ is $C_{2-6}$alkenyl or $C_{2-6}$epoxyalkyl, each of which is optionally substituted with from 1-3 members selected from —OH, —OC$_{1-6}$alkyl, aryl-$C_{1-4}$alkyl, alkyl-C(O)O— or aryl-$C_{1-4}$alkyl-C(O)O—; and provided that the compound is not

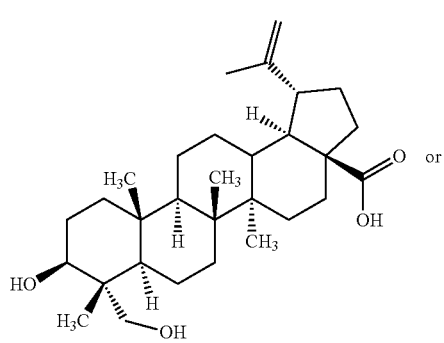

or

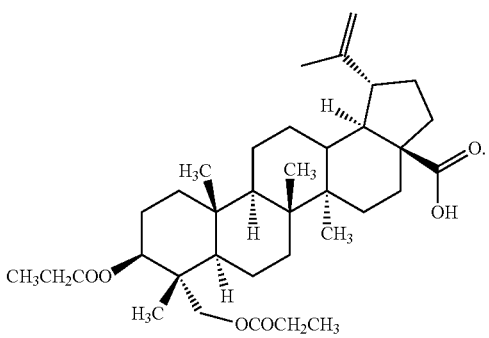

2. The compound of claim 1, having formula (Ia):

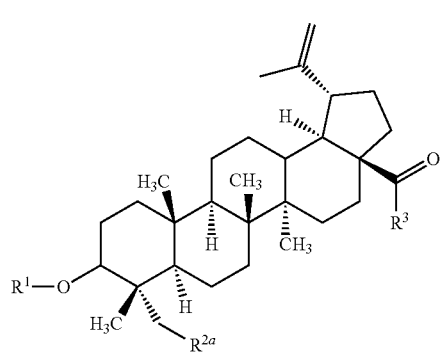

Ia wherein $R^{2a}$ is —OH, alkoxy or alkyl-C(O)O.

3. The compound of claim 2, wherein $R^{2a}$ is —OH or —OAc.

4. The compound of claim 2, wherein $R^1$ is —H or CH$_3$C(O)—.

5. The compound of claim 1, having formula (Ib):

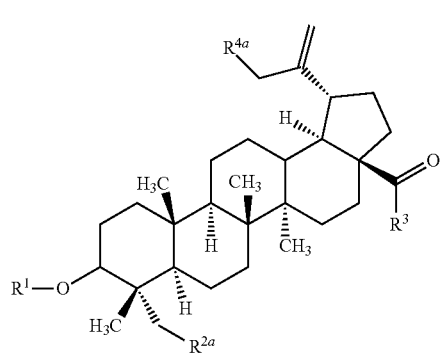

Ib wherein $R^{2a}$ is —OH, alkoxy or alkyl-C(O)O and $R^{4a}$ is —H, —OH, alkoxy, alkyl-C(O)— or arylalkyl-NH—.

6. The compound of claim 5, wherein $R^1$ is —H or CH$_3$C(O)—.

7. The compound of claim 5, wherein $R^{4a}$ is —OH or CH$_3$C(O)—.

8. The compound of claim 5, wherein $R^{4a}$ is alkoxy or arylalkyl-NH.

9. The compound of claim 1, wherein $R^1$ is —H or CH$_3$C(O)—.

10. The compound of claim 1, wherein $R^2$ is hydroxy-$C_{1-4}$alkyl, alkoxy-$C_{1-4}$alkyl or alkyl-C(O)O—$C_{1-4}$alkyl.

11. The compound of claim 10, wherein $R^2$ is hydroxymethyl, CH$_3$OCH$_2$— or CH$_3$C(O)OCH$_2$—.

12. The compound of claim 1, wherein $R^3$ is —OH, —NH$_2$, HO(CH$_2$)$_n$—NH—, NH$_2$(CH$_2$)$_m$NH— or NH$_2$(CH$_2$)$_p$—O—, wherein the script m, n or p are each independently an integer of from 1-4.

13. The compound of claim 2, wherein $R^3$ is —NH$_2$, —NH$R^a$ or —N($R^a$)$_2$, wherein $R^a$ is alkyl; wherein the aliphatic portion of the $R^3$ substituent is substituted with from 1-2 $R^c$ substituents independently selected from —OH, —NH$_2$.

14. The compound of claim 13, wherein $R^a$ is selected from the group consisting of HOCH$_2$CH$_2$—, NH$_2$CHCH$_2$CH$_2$—, HO(CH$_2$)$_3$— and NH$_2$(CH$_2$)$_3$—.

15. The compound claim 1, wherein $R^3$ is —OH, HO(CH$_2$)NH— or HO(CH$_2$)$_2$O—.

16. The compound of claim 1, wherein R⁴ is haloCH₂—, alkyl, hydroxyalkyl, alkyl-C(O)—C$_{1-4}$alkyl, arylalkyl-NH—C$_{1-4}$alkyl or alkoxyalkyl.

17. The compound of claim 16, wherein R⁴ is ClCH₂—, BrCH₂—, methyl, ethyl, isopropyl, HOCH₂—, hydroxyethyl, hydroxypropyl, hydroxylbutyl, CH₃C(O)CH₂—, CH₃C(O) C$_{1-4}$alkyl, benzyl-NHCH₂—, benzyl-NH—C$_{1-4}$alkyl, C$_{1-4}$alkyoxymethyl, CH₃OCH₂—, CH₃CH₂OCH₂— or (CH₃)₂CHOCH₂—.

18. The compound of claim 1, wherein the compound is a member selected from the group consisting of:

DA049
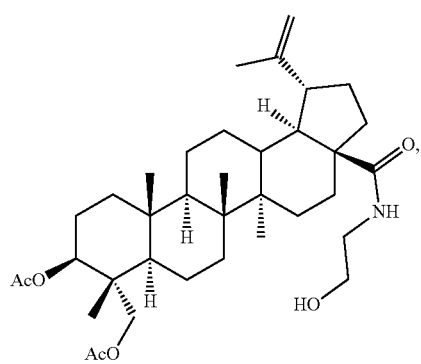

DA052
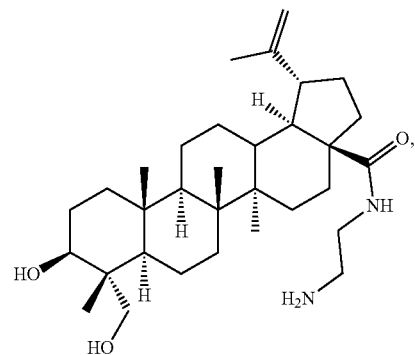

DA054
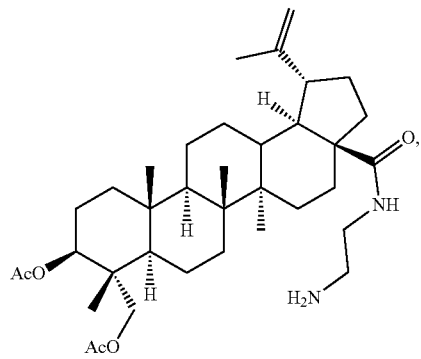

DA055
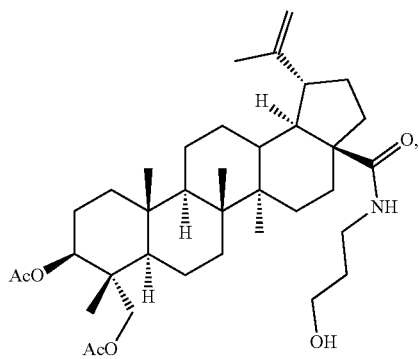

DA057
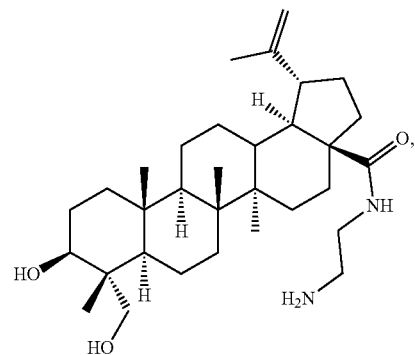

DA058
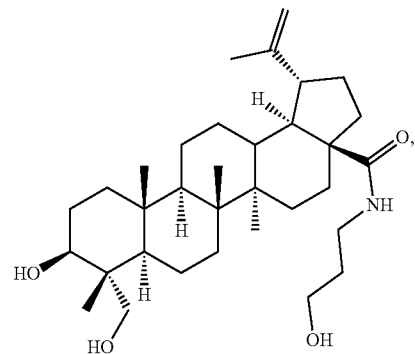

DA059
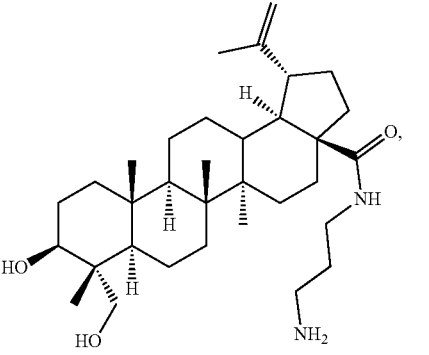

DA060
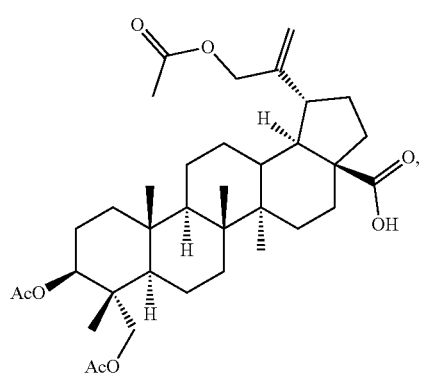
DA061
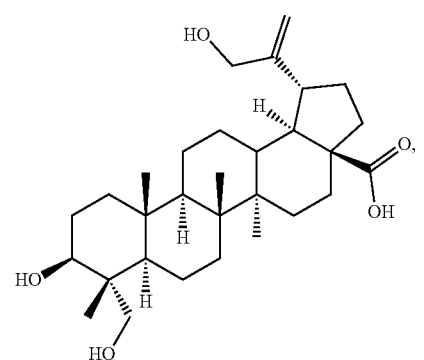
DA066
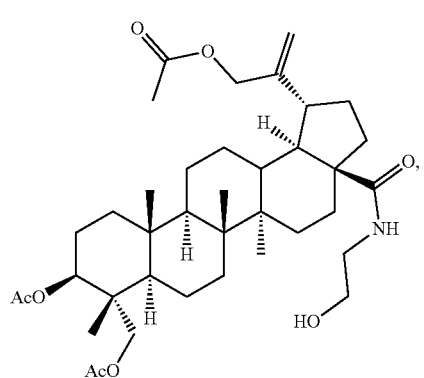
DA067
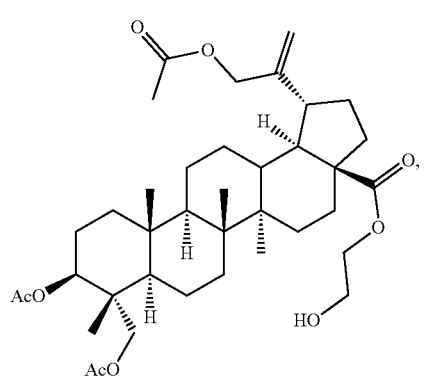
DA069
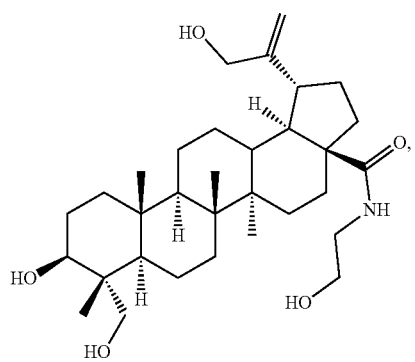
DA071
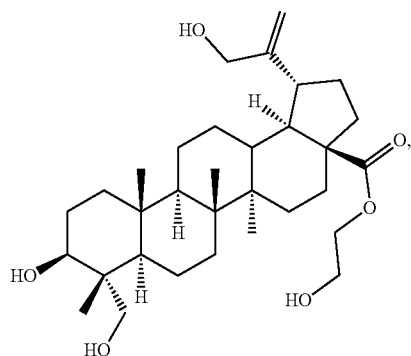
DA072
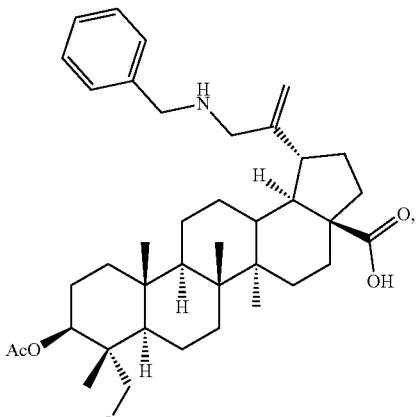
DA073
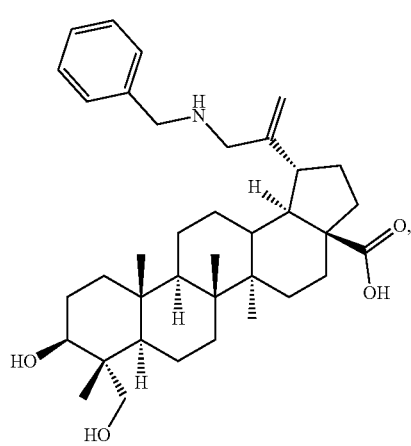

-continued
DA074
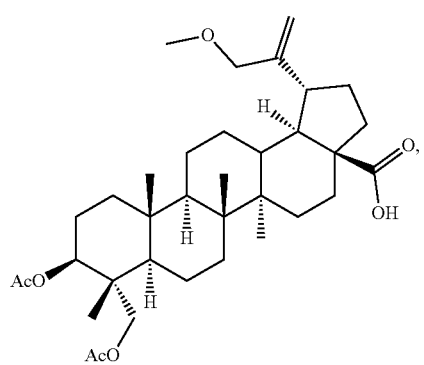
DA075
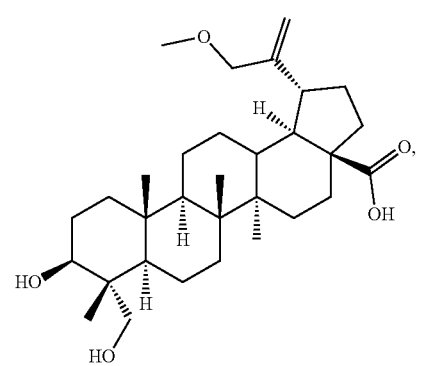
DA076
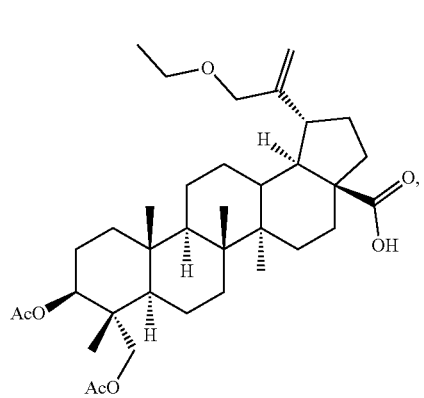
DA077
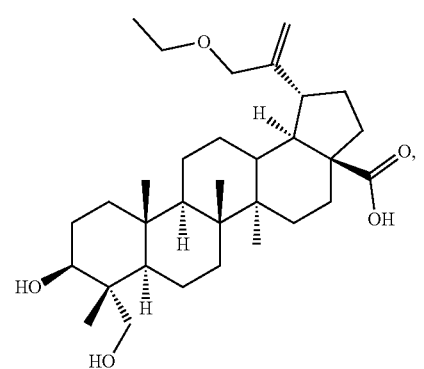
-continued
DA078
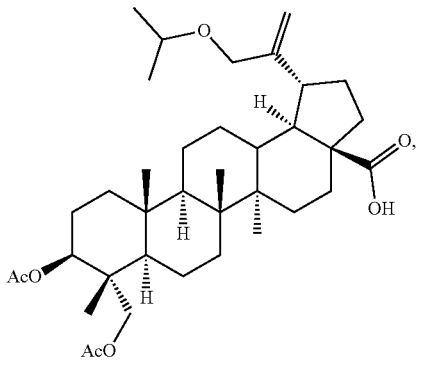
DA079
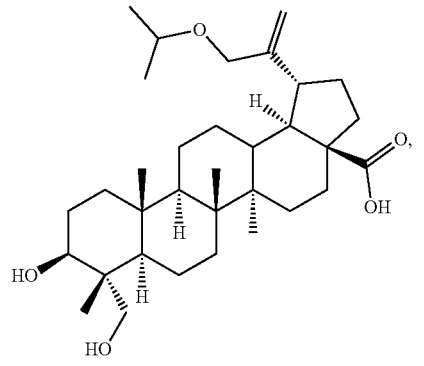
DA084
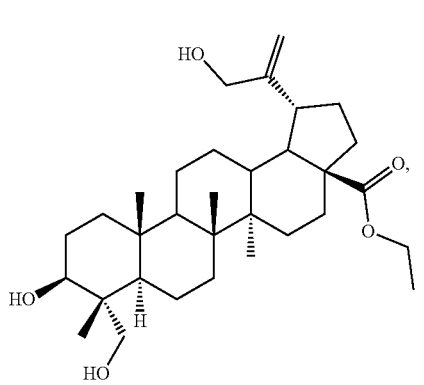
DA085
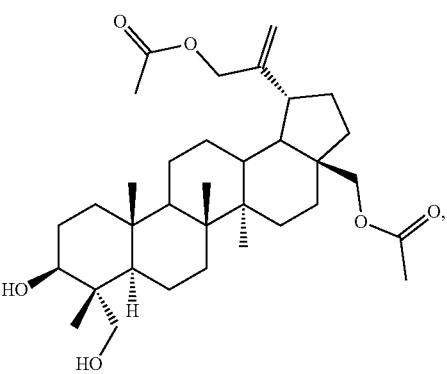

DA086

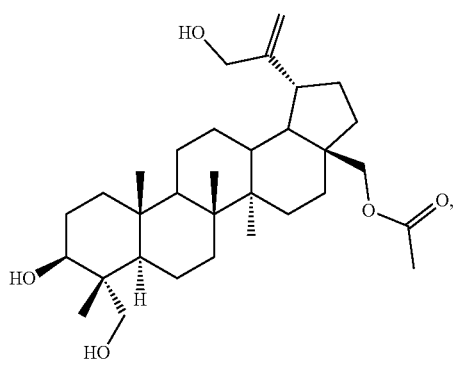

DA087

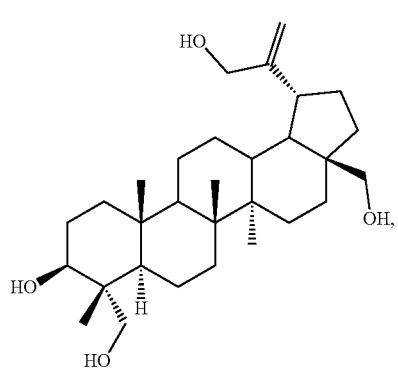

DA088

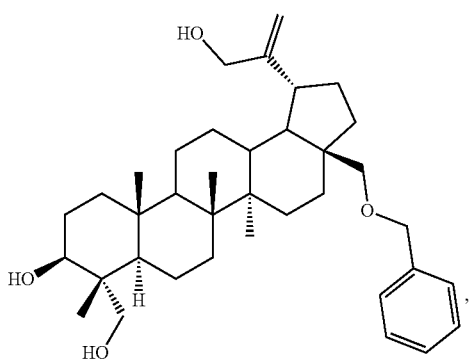

DA089

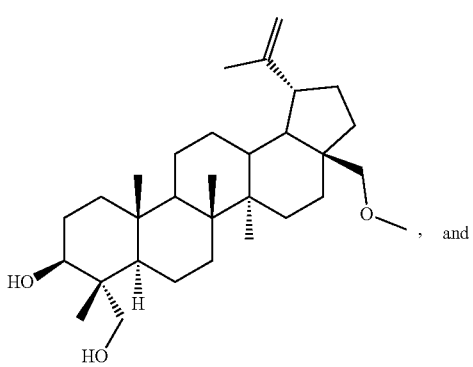

DA090

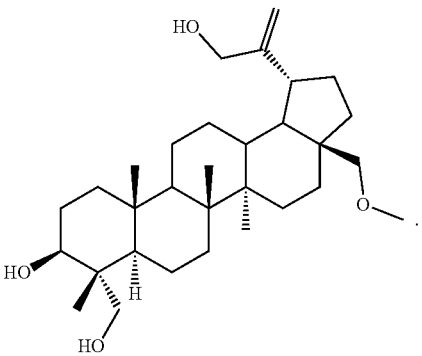

19. The compound of claim 1, having a formula:

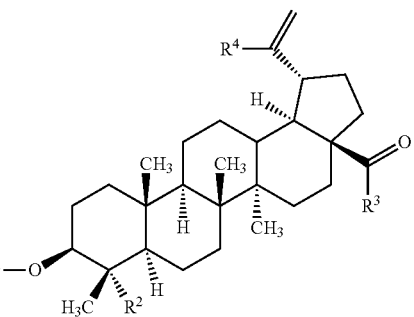

or a pharmaceutically acceptable salt, hydrate, or solvate thereof.

20. The compound of claim 19, wherein $R^{12}$ is hydroxyalkyl, alkyl-OC(O)—, aryl-$C_{1-4}$alkyl-OC(O)—, alkyl-C(O)O-alkyl, aryl-$C_{1-4}$alkyl-C(O)O-alkyl, aryl-$C_{1-4}$alkoxy or alkoxyalkyl, wherein the aryl moiety of which is optionally substituted with from 1-3 members selected from Cl, Br, F, $C_{1-6}$alkyl, benzyl, OHCH$_2$—, CH$_3$O—, CH$_3$C(O)O—, $C_{1-4}$alkyl-O—C(O)— or benzyloxy.

21. The compound of claim 20, wherein $R^{12}$ is benzyloxycarbonyl, $C_{1-6}$alkyl-OC(O)—, CH$_3$C(O)OCH$_2$—, HOCH$_2$—, benzyloxymethyl or CH$_3$OCH$_2$—.

22. The compound of claim 19, wherein $R^{13}$ is 2-propenyl, 3-hydroxy-2-propenyl, 3-acetoxy-2-propenyl or 2-methyl-2-oxiranyl.

23. A pharmaceutical composition comprising: a compound of claim 1 and a pharmaceutically acceptable carrier or excipient.

24. A pharmaceutical composition comprising: a compound selected from the group consisting of:

-continued
DA001
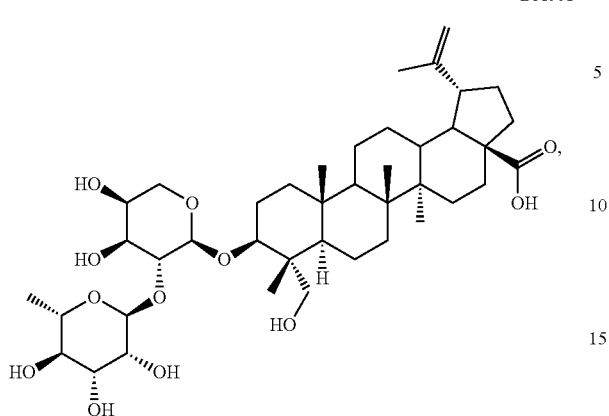
DA002
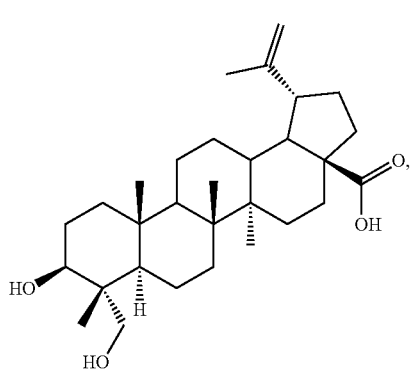
DA003
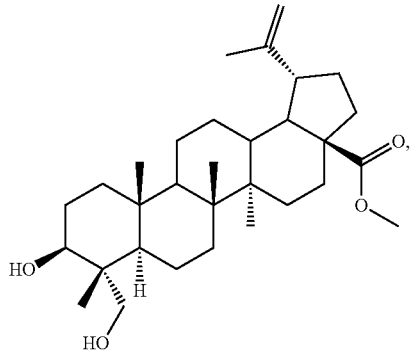
DA004
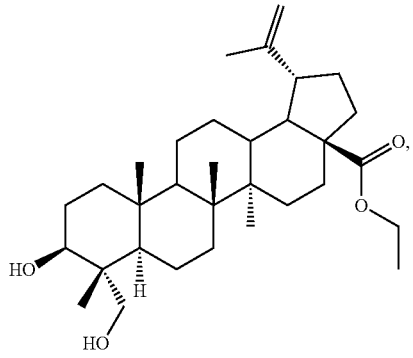
DA005
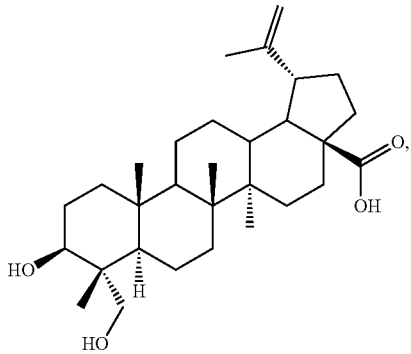
DA006
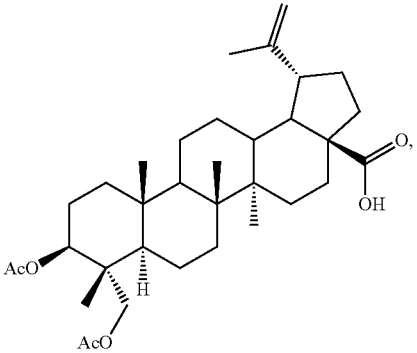
DA007
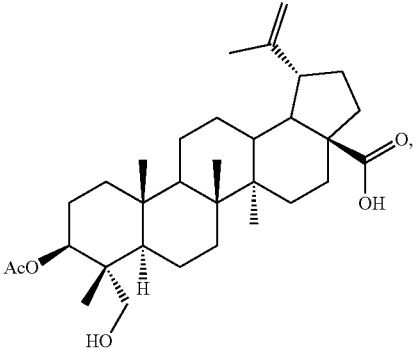
DA008
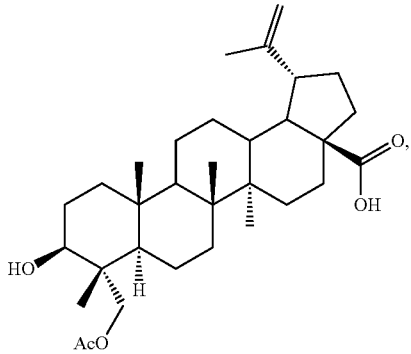

DA009
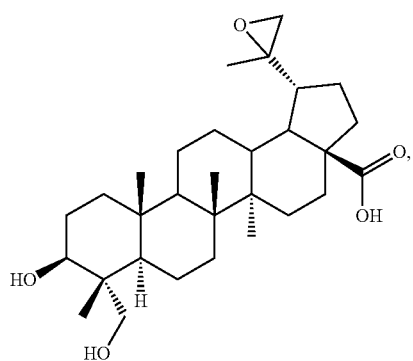
DA010
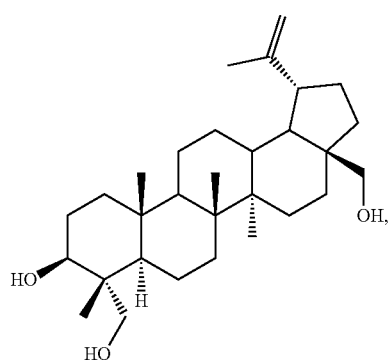
DA011
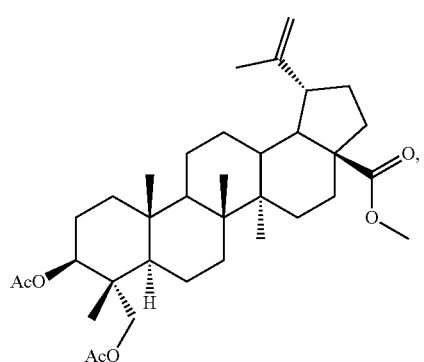
DA012
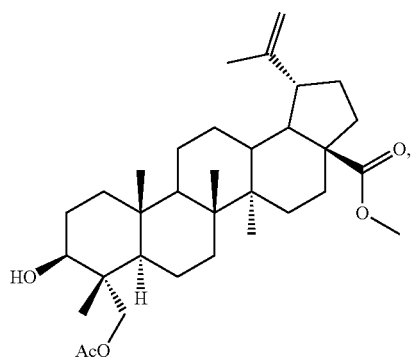
DA013
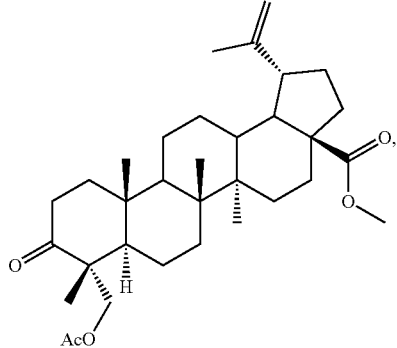
DA014
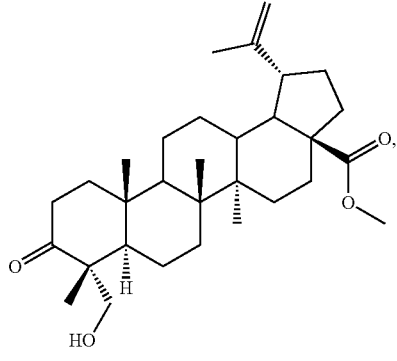
DA015
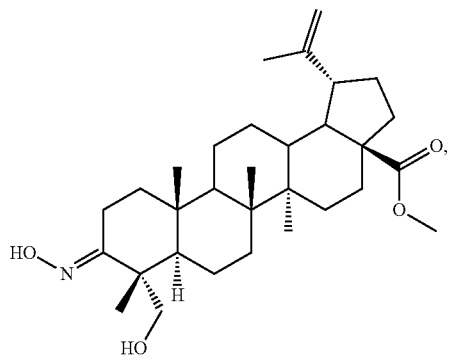
DA016
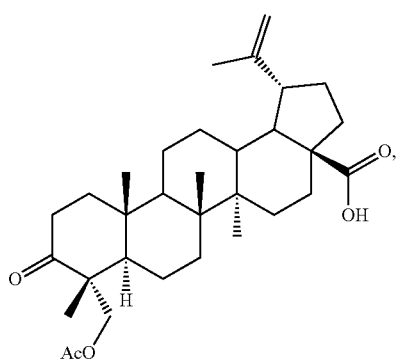

-continued
DA017
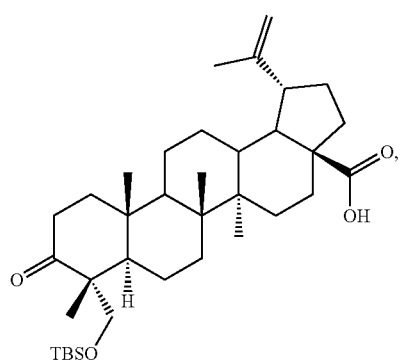
DA018
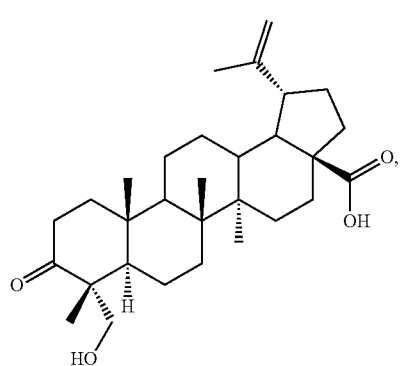
DA019
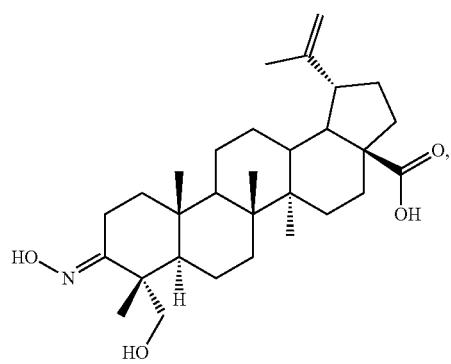
DA020
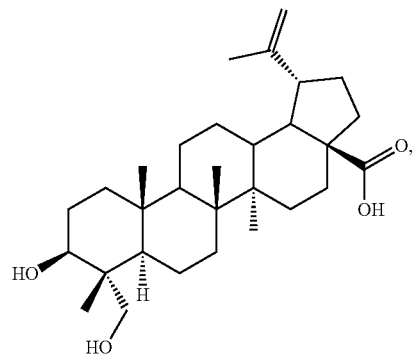
-continued
DA021
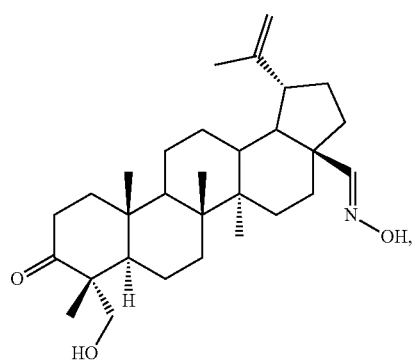
DA022
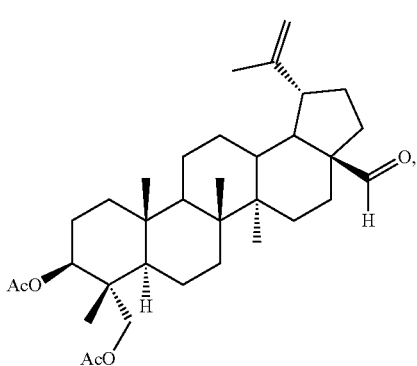
DA023
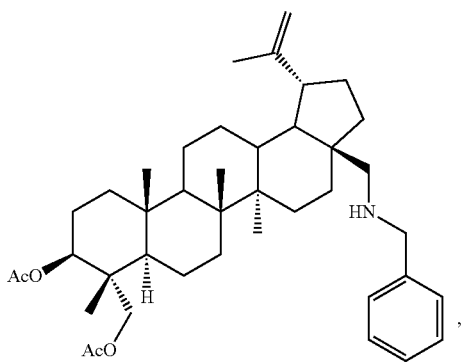
DA024
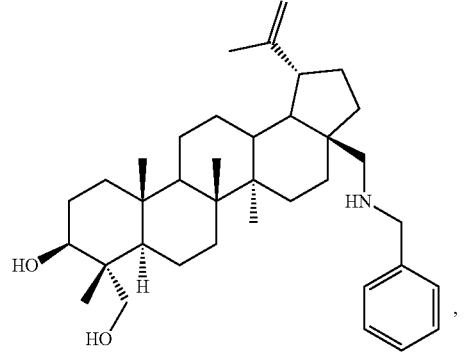

DA025
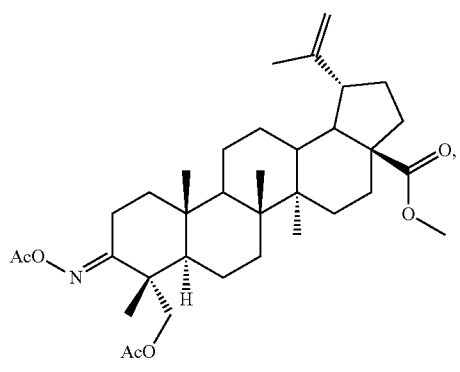
DA026
DA029
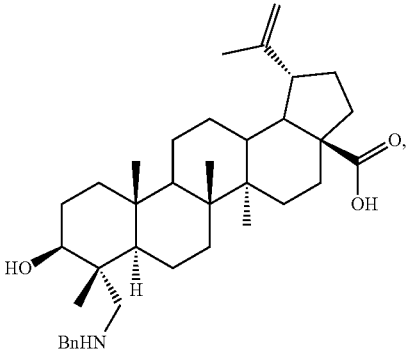
DA030
DA027
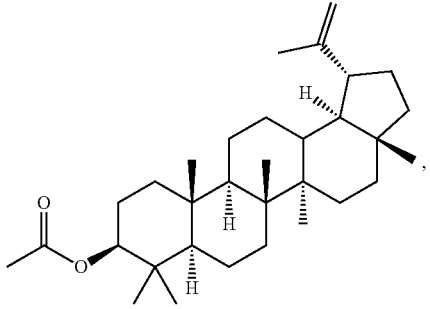
DA031
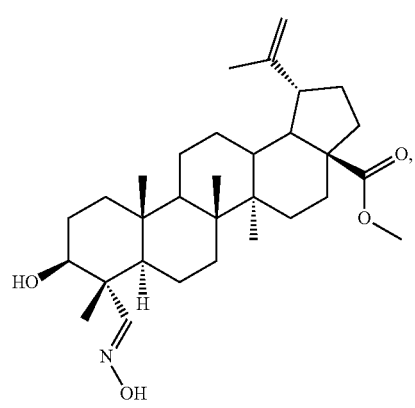
DA028
DA032
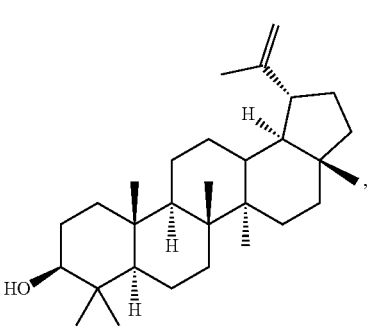
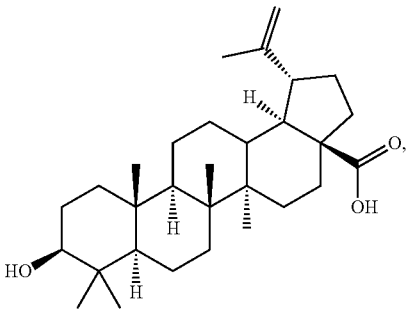

DA033
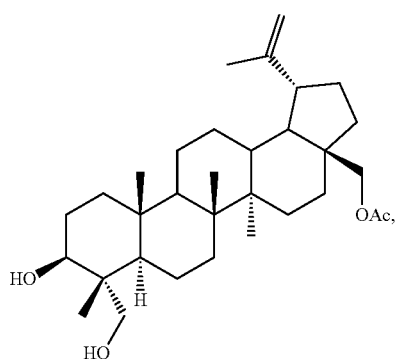
DA037
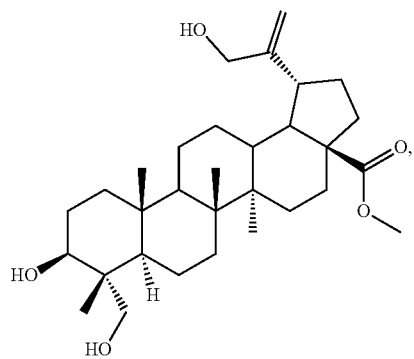
DA034
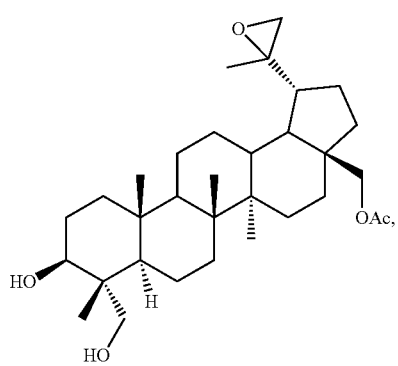
DA038
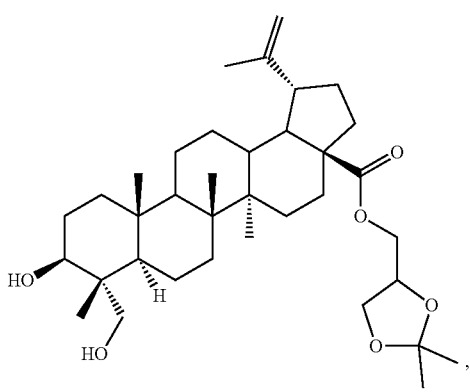
DA035
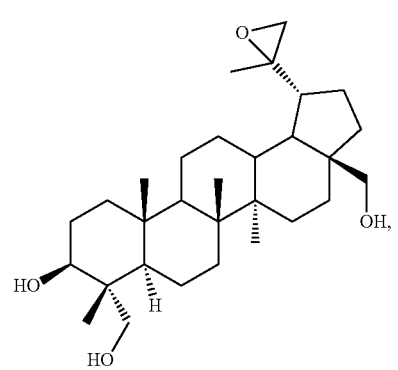
DA039
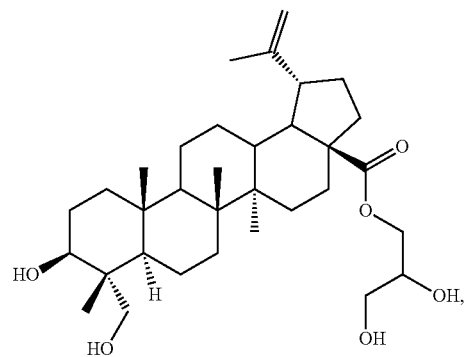
DA036
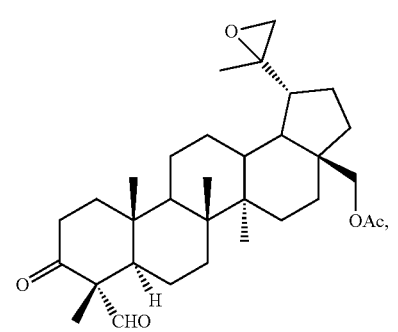
DA040
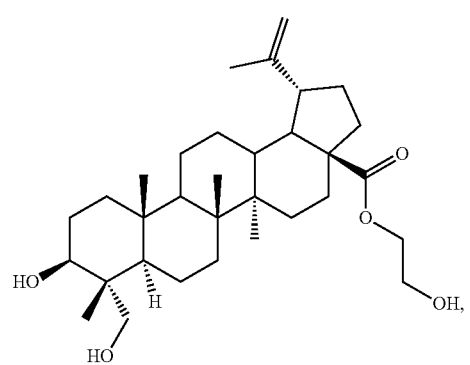

DA041
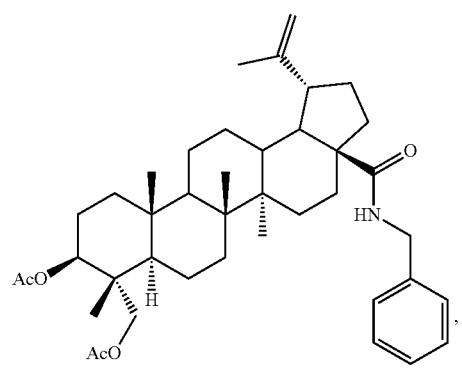
DA042
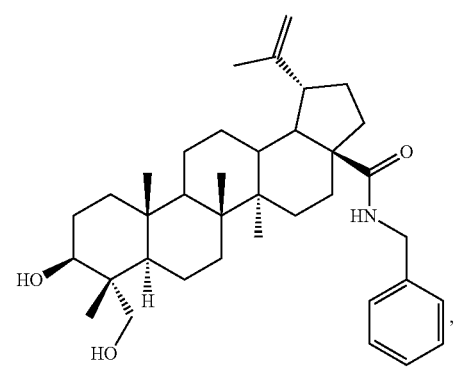
DA043
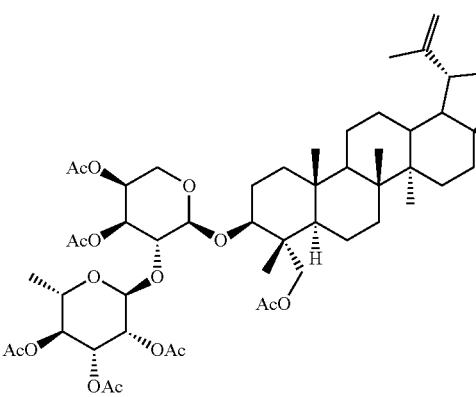
DA044
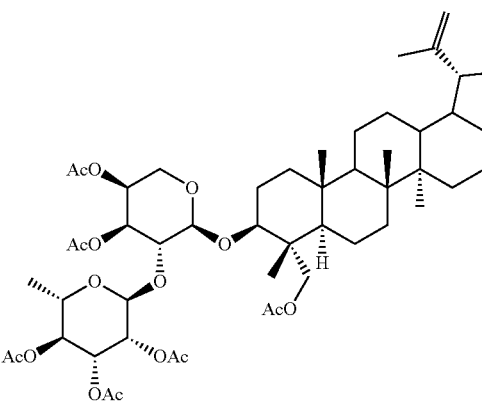
DA045
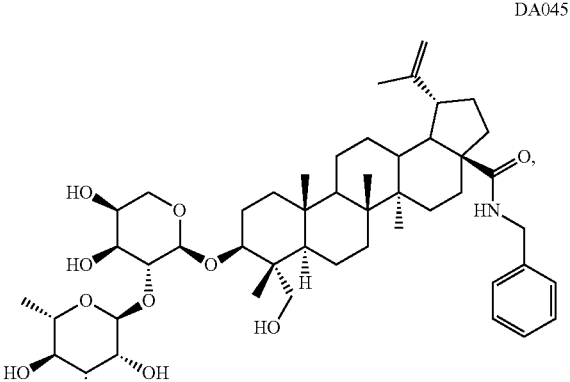
DA046
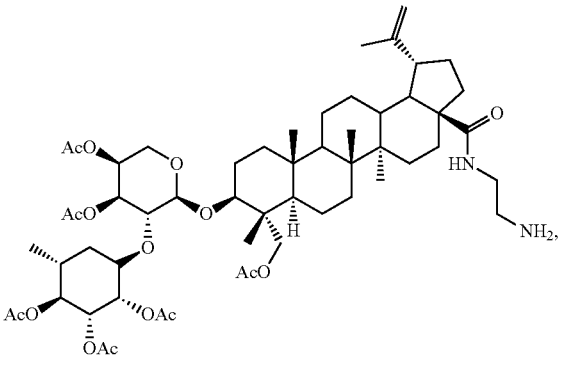
DA047
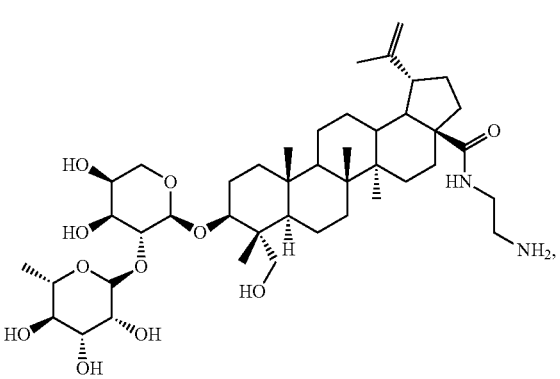
DA048
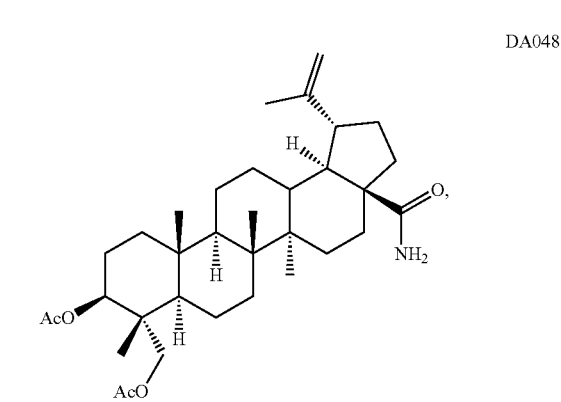

-continued
DA049
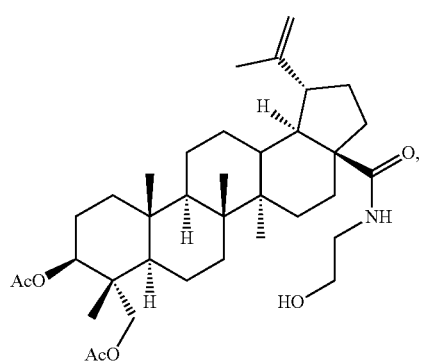
DA050
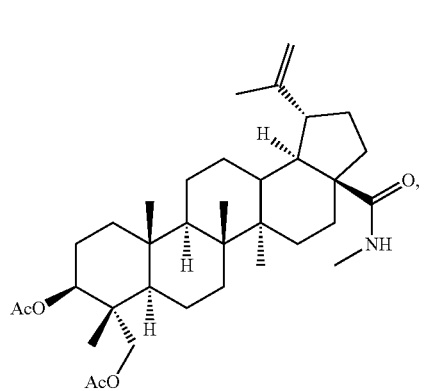
DA051
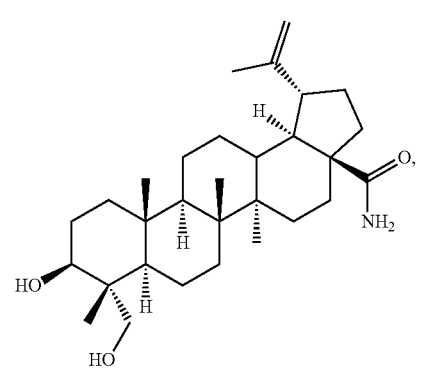
DA052
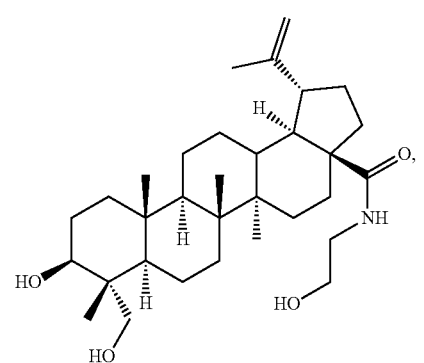
-continued
DA053
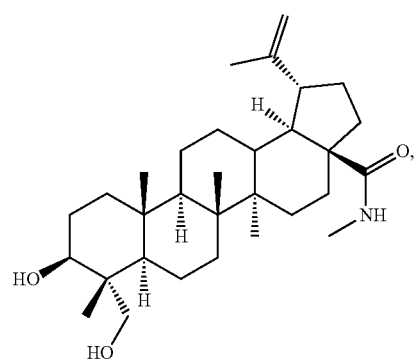
DA054
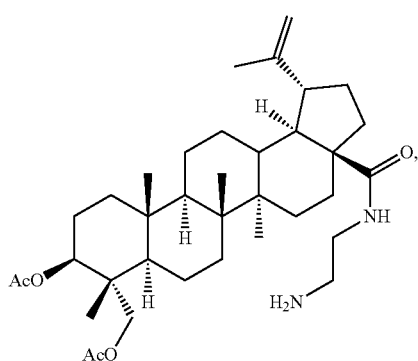
DA055
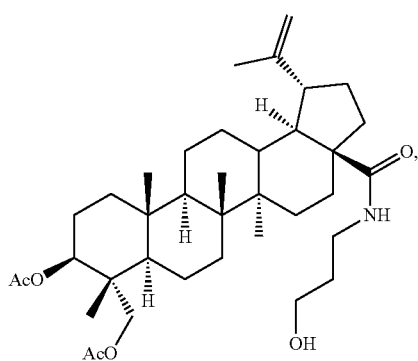
DA056
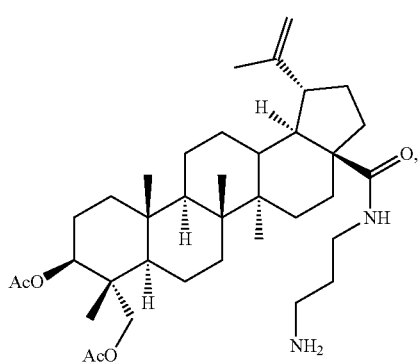

-continued
DA057
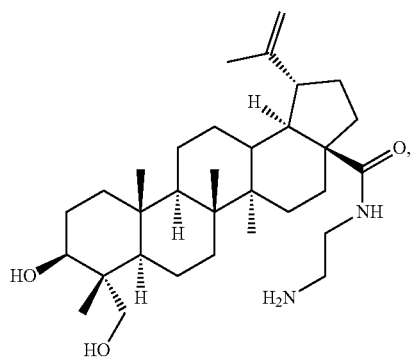
DA058
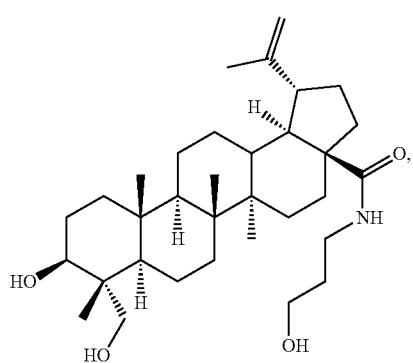
DA059
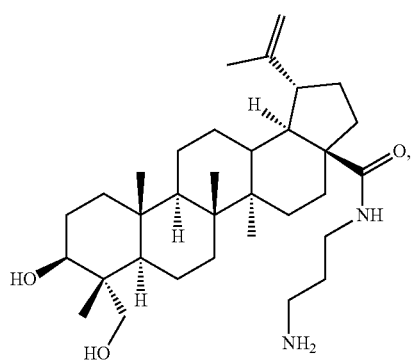
DA060
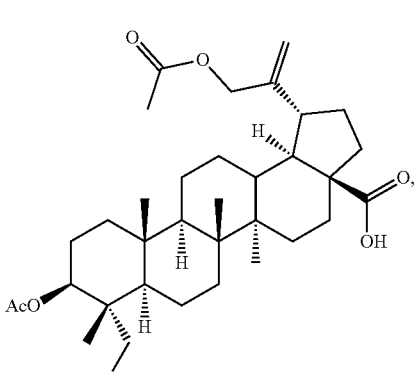
-continued
DA061
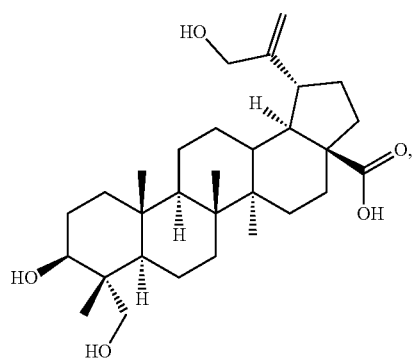
DA062
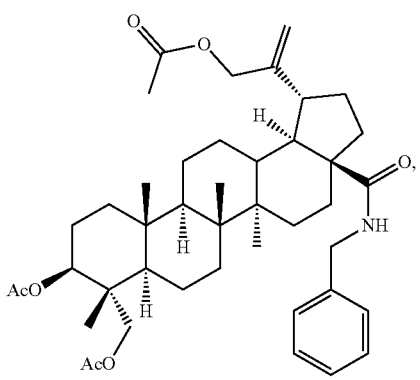
DA063
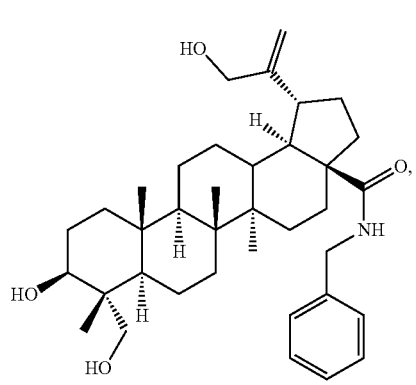
DA064
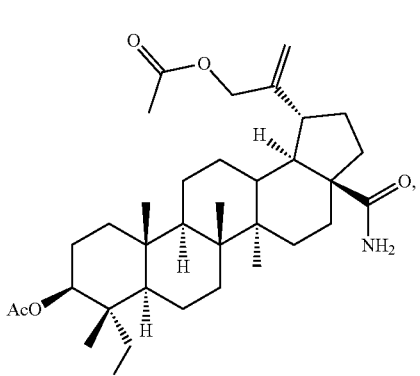

DA065
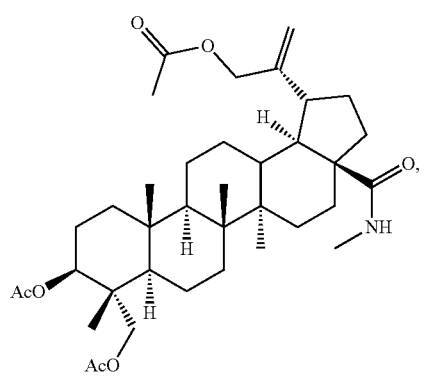
DA069
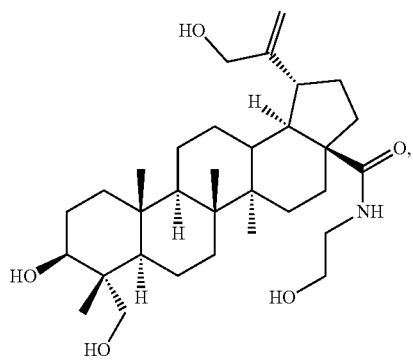
DA066
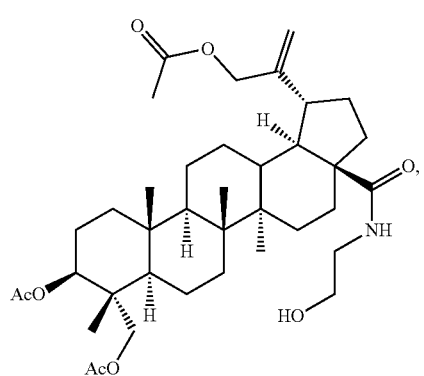
DA070
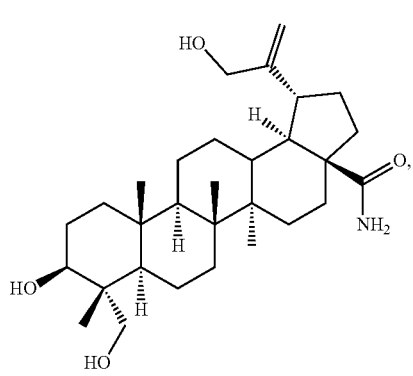
DA067
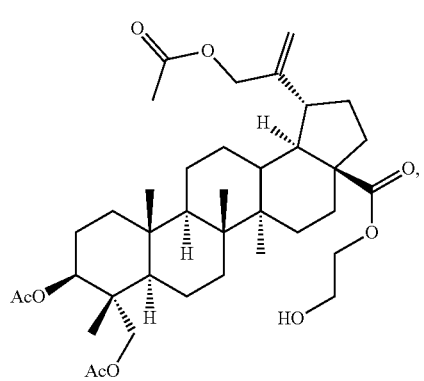
DA071
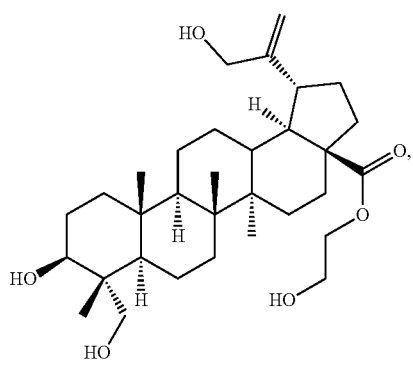
DA068
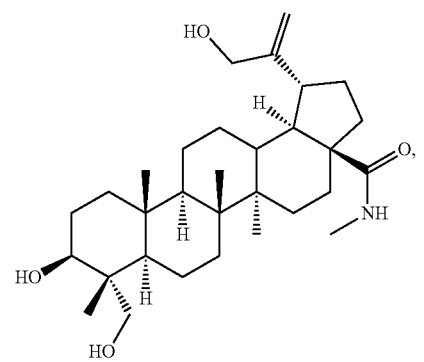
DA072
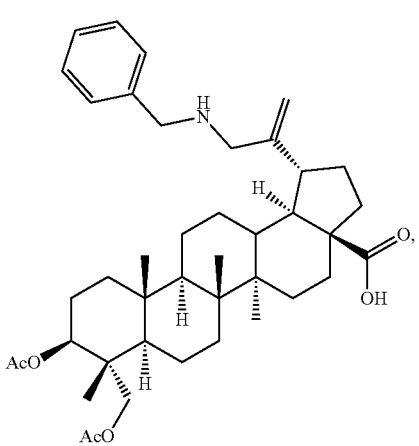

DA073
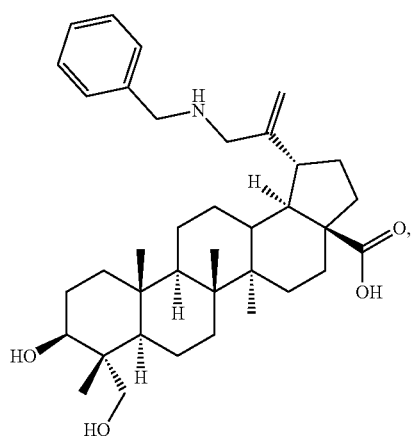
DA074
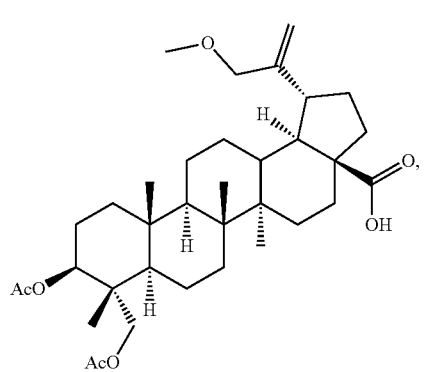
DA075
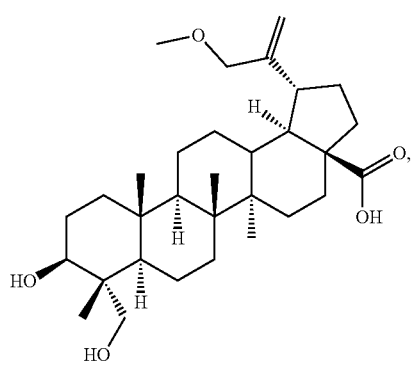
DA076
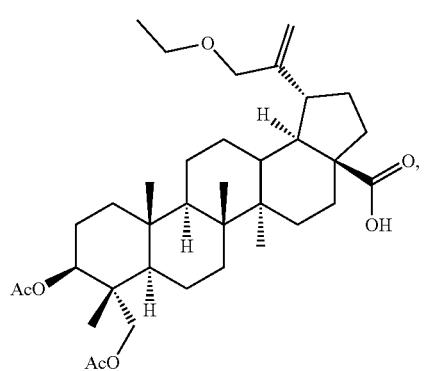
DA077
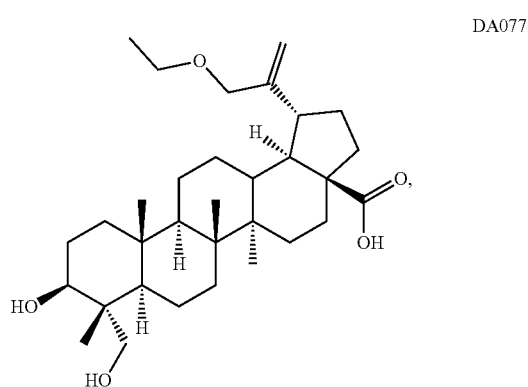
DA078
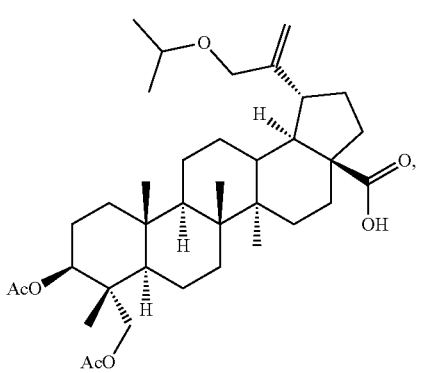
DA079
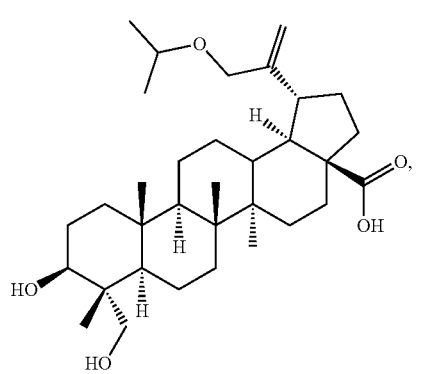
DA080
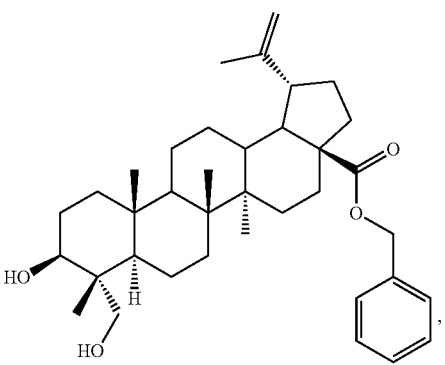

DA081
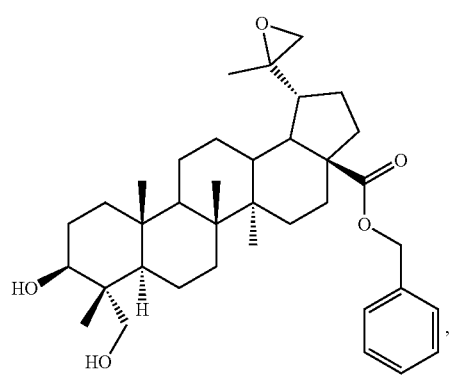
DA082
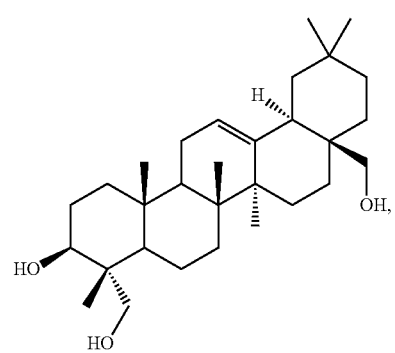
DA083
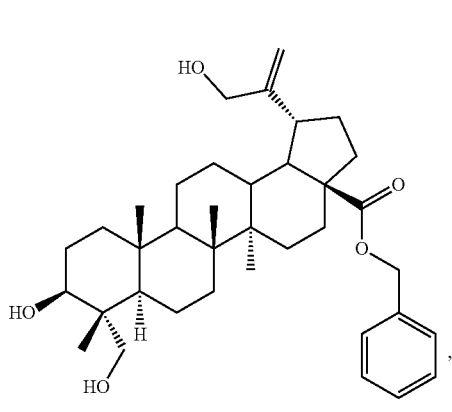
DA084
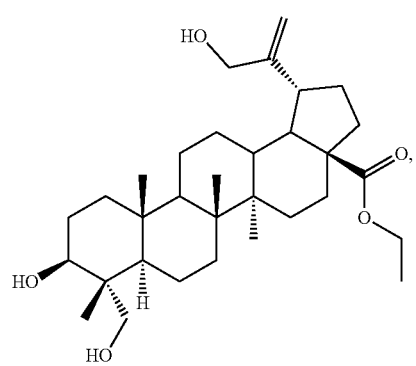
DA085
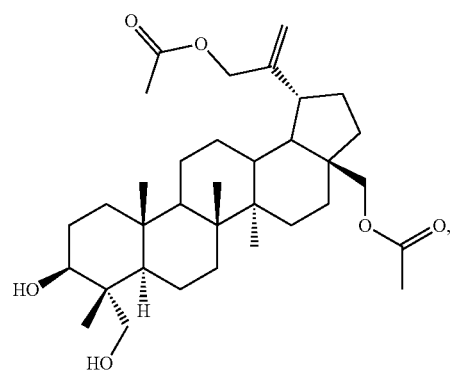
DA086
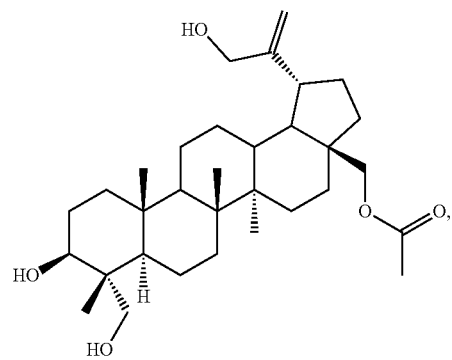
DA087
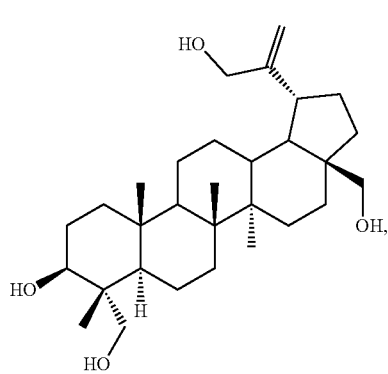
DA088
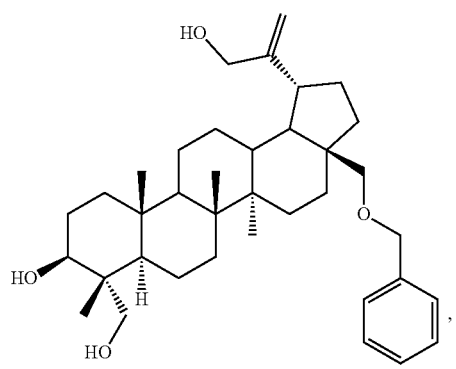

-continued

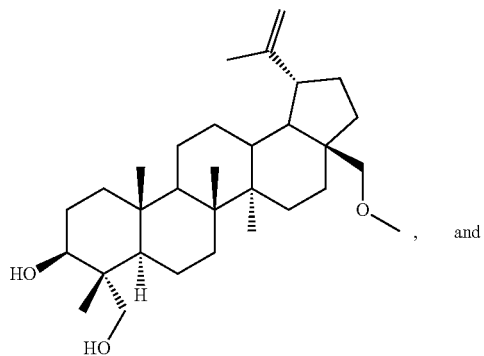
DA089

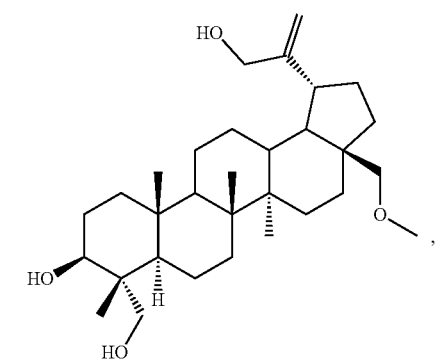
DA090 and a pharmaceutically acceptable carrier or excipient.

25. A method of inhibiting a receptor selected from the group consisting of a PGE receptor, an NMDA receptor and a melanocortin (MC) receptor, said method comprising: contacting a compound of claim 1 with the receptor.

26. A method of inhibiting a receptor of PGE2, said method comprising: contacting a compound of claim 1 with the receptor of PGE2.

27. The method of claim 26, wherein the receptor of PGE2 is an EP1, EP2 or EP4 receptor.

28. A method of treating pain or inflammation caused by endotoxin or arthritis in a mammal, said method comprising: administering to said mammal a therapeutically effective amount of a compound of claim 1.

29. A method of inhibiting a receptor of PGE2, said method comprising: contacting with the receptor of PGE2 a compound selected from the group consisting of:

DA001

-continued

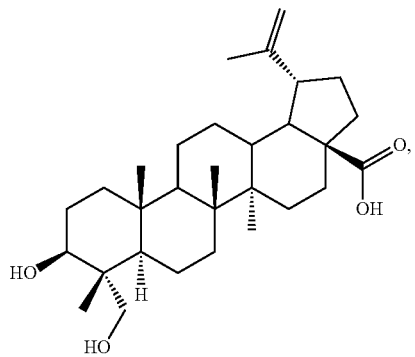
DA002

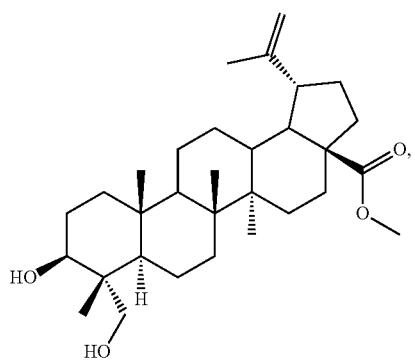
DA003

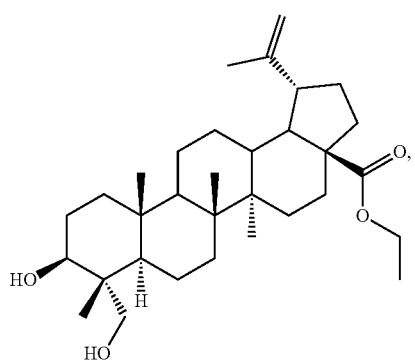
DA004

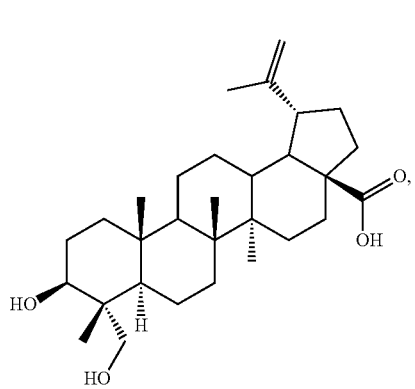
DA005

DA006
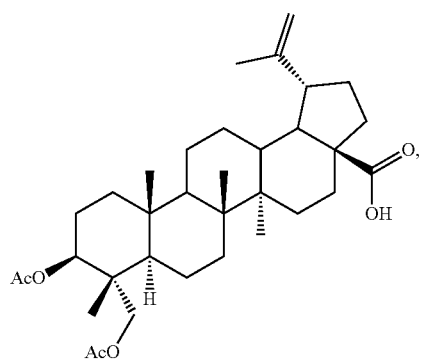
DA007
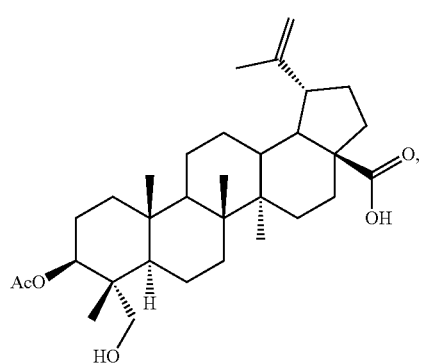
DA008
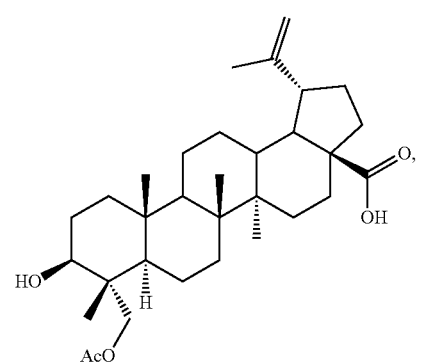
DA009
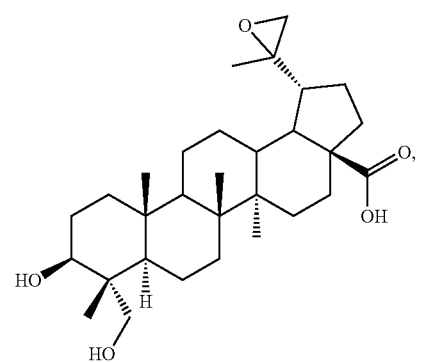
DA010
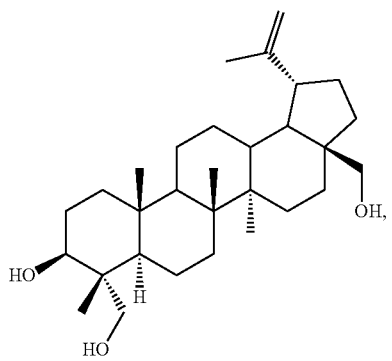
DA011
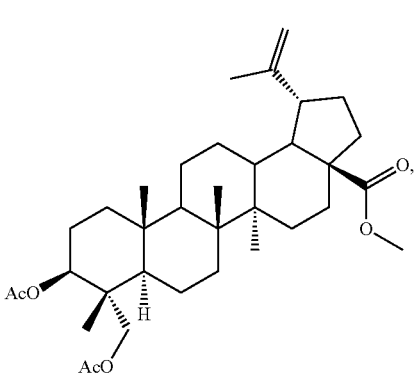
DA012
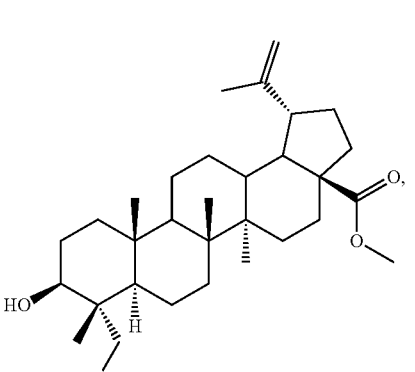
DA013
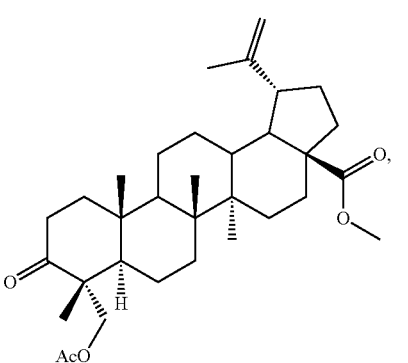

-continued
DA014
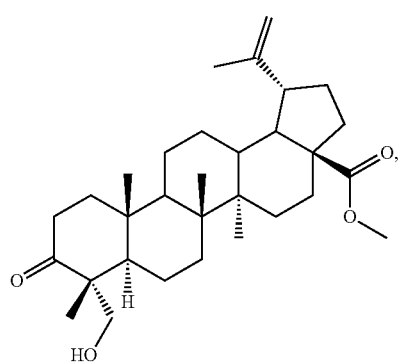
DA018
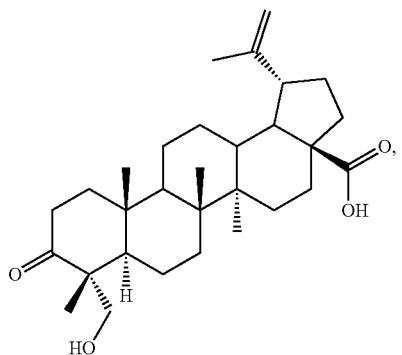
DA015
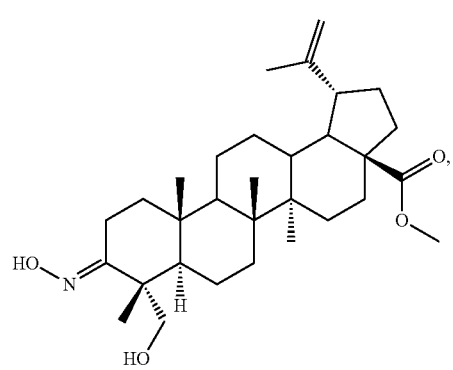
DA019
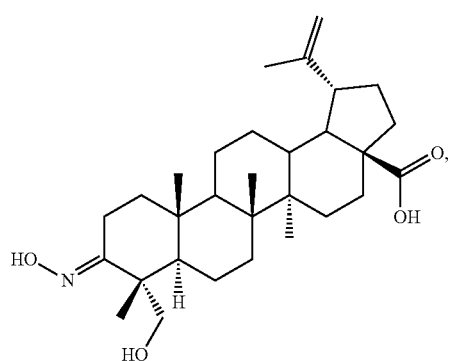
DA016
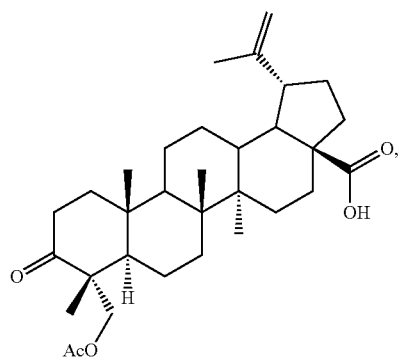
DA020
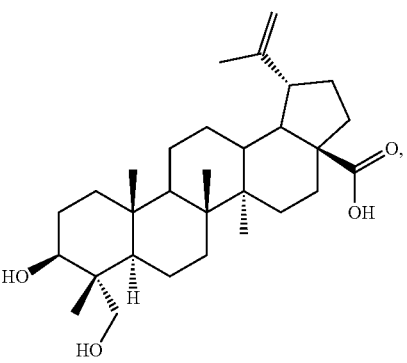
DA017
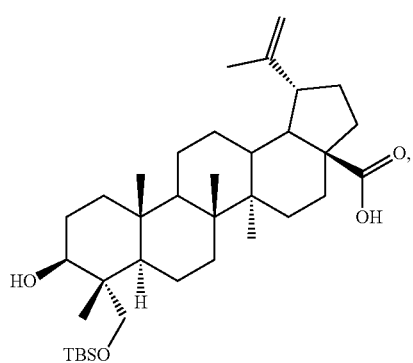
DA021
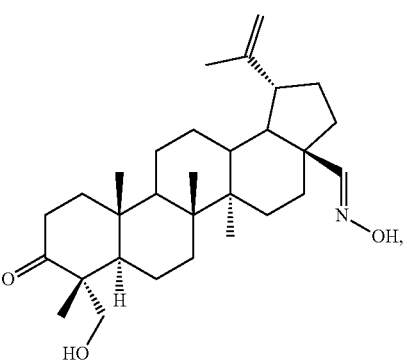

DA022
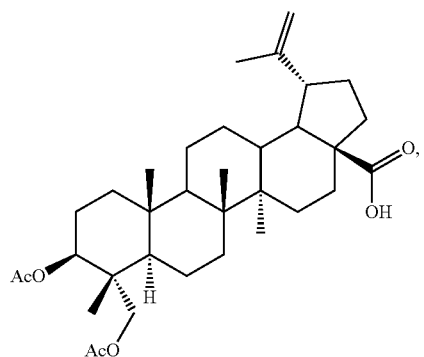
DA023
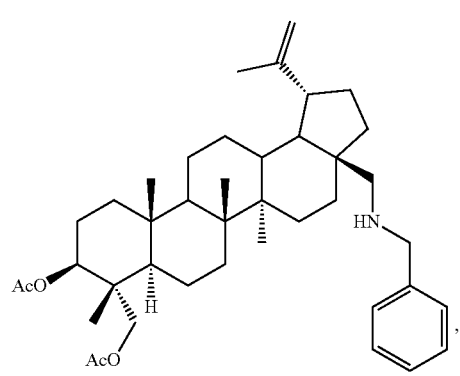
DA024
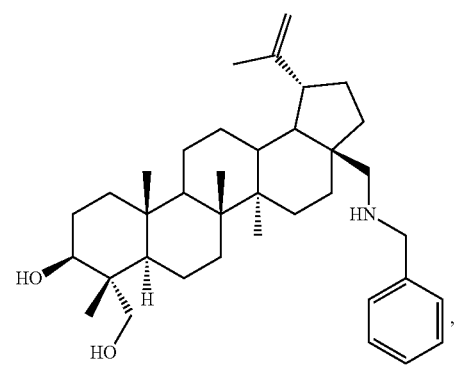
DA025
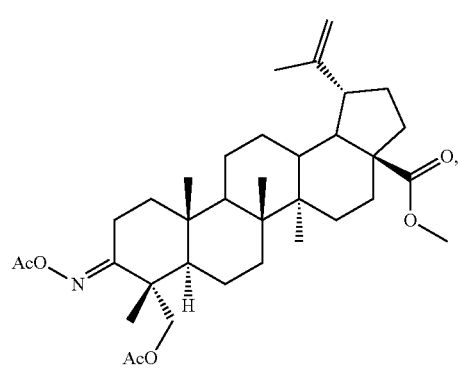
DA026
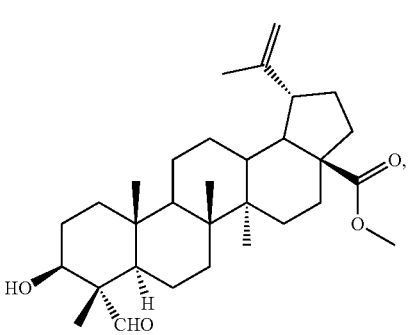
DA027
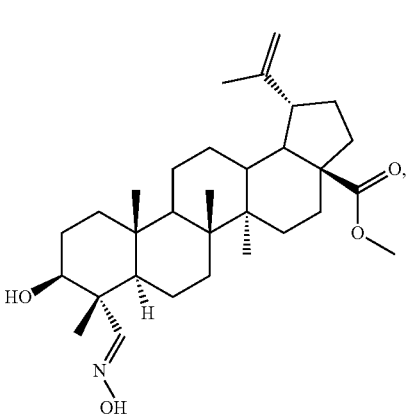
DA028
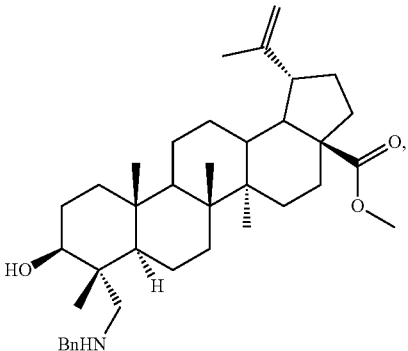
DA029
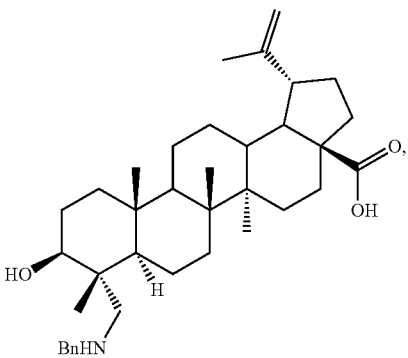

-continued
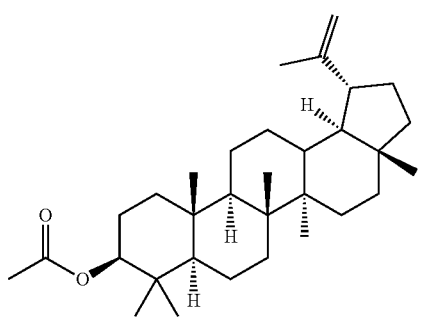
DA030
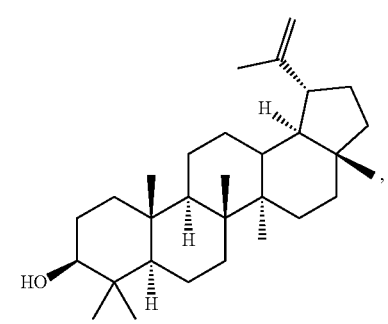
DA031
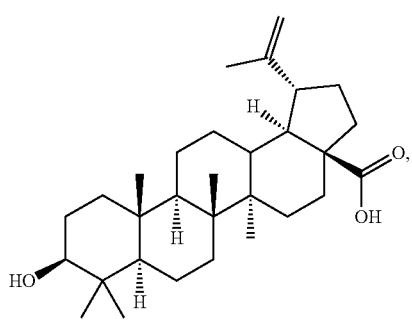
DA032
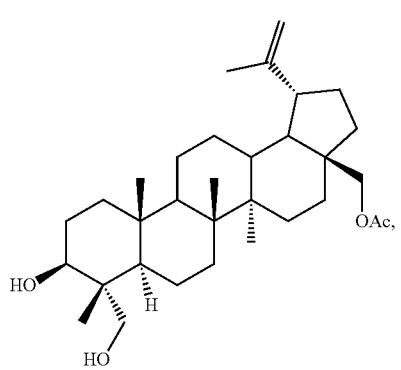
DA033
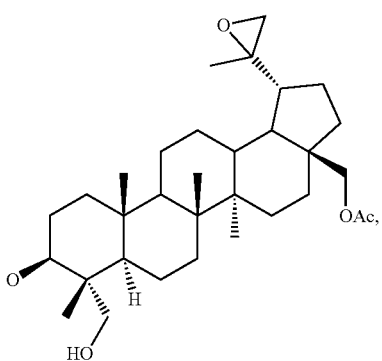
DA034
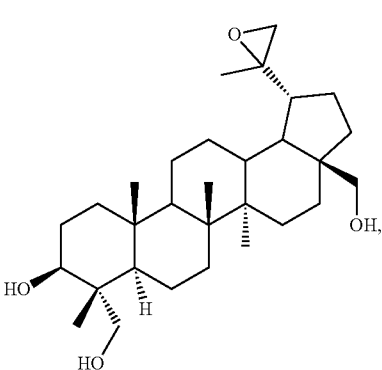
DA035
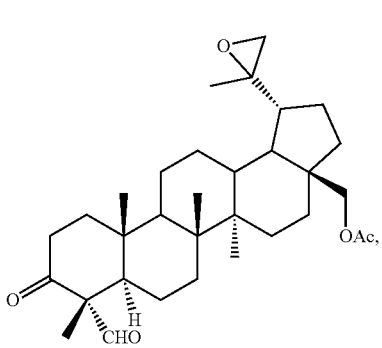
DA036
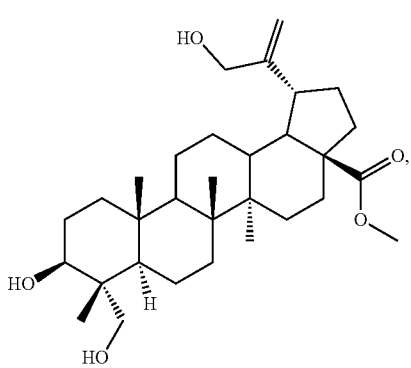
DA037

DA038
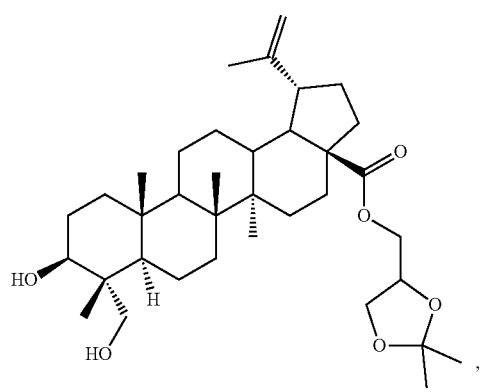
DA039
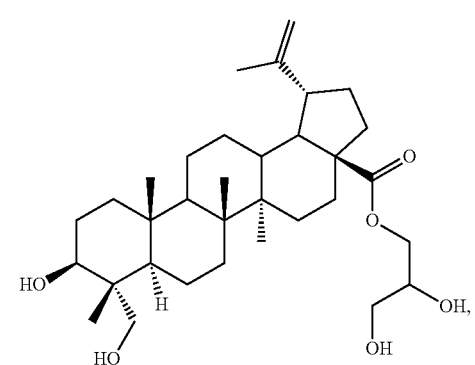
DA040
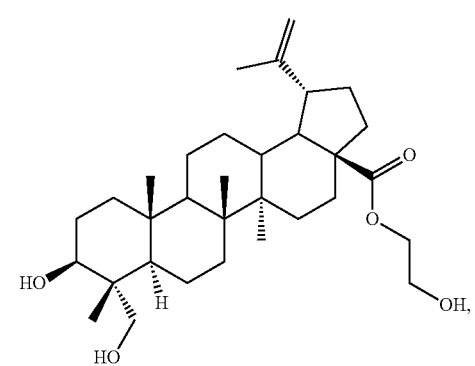
DA041
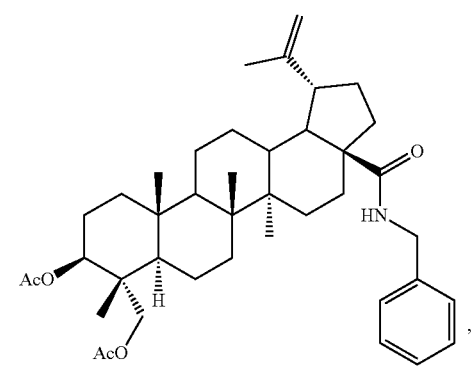
DA042
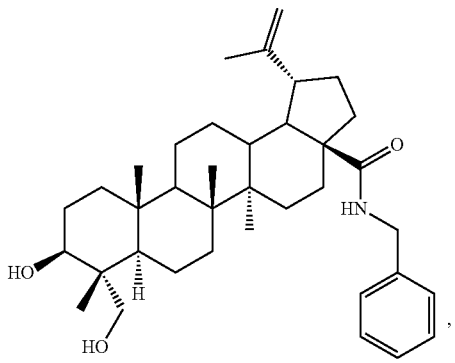
DA043
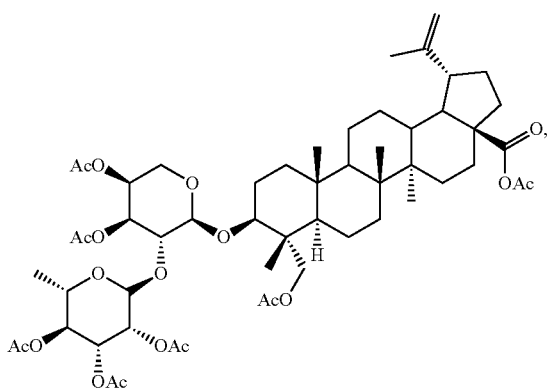
DA044
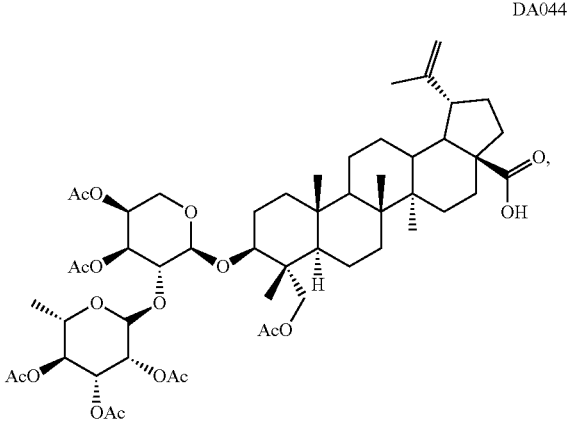
DA045
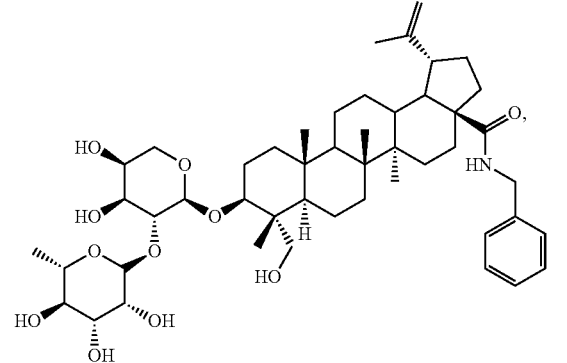

DA046
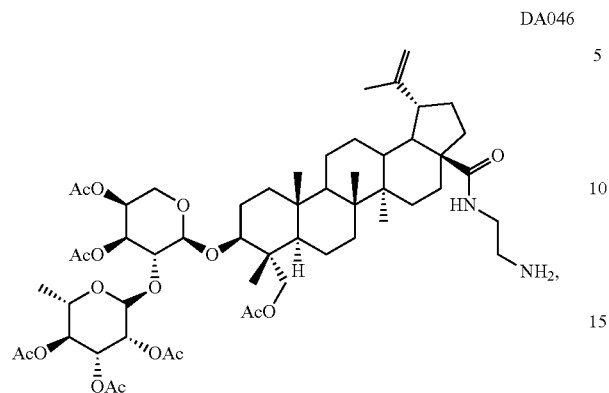
DA047
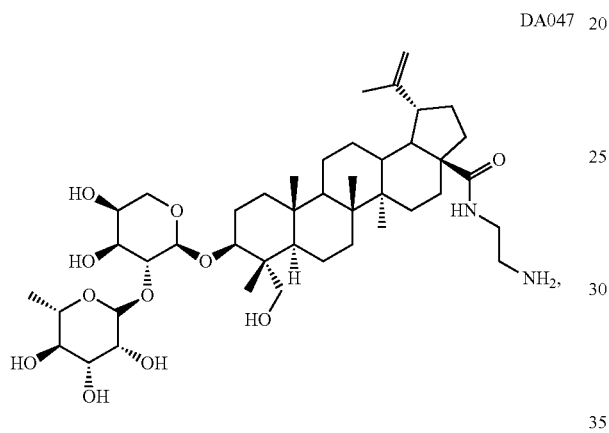
DA048
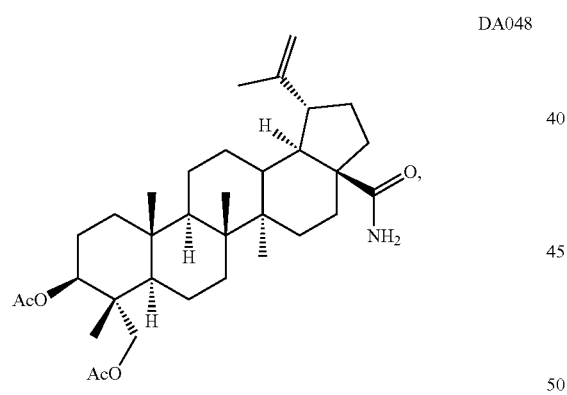
DA049
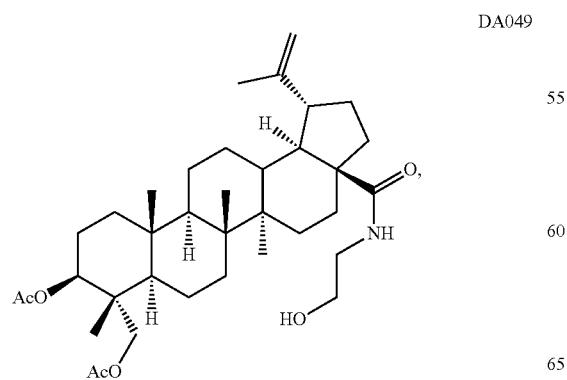
DA050
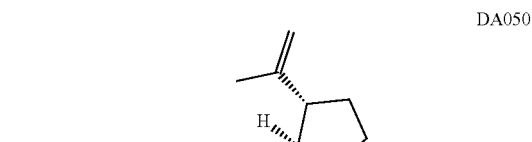
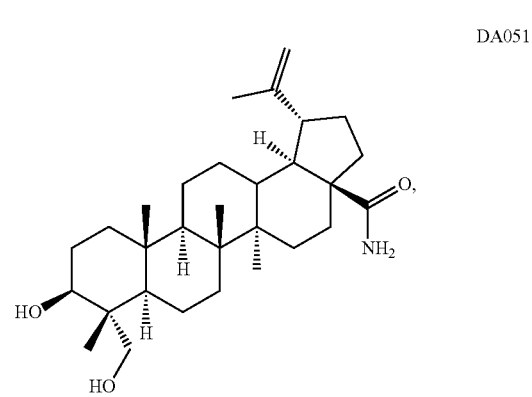
DA051
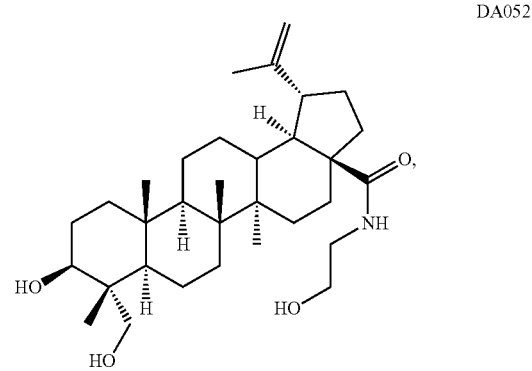
DA052
DA053
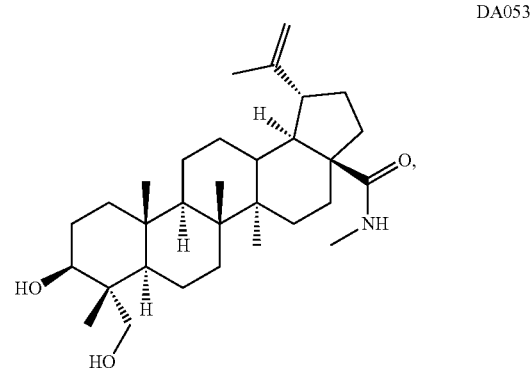

-continued

DA054

DA055

DA056

DA057

DA058

DA059

DA060

DA061

-continued
DA062
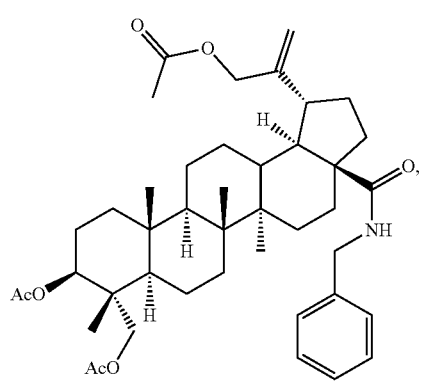
DA063
DA064
DA065
-continued
DA066
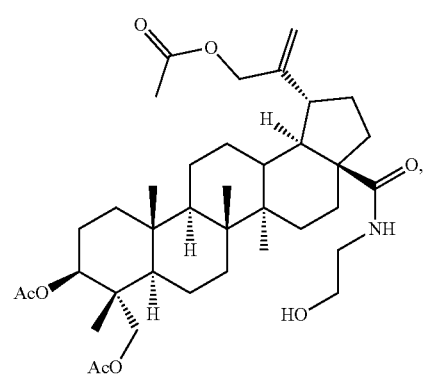
DA067
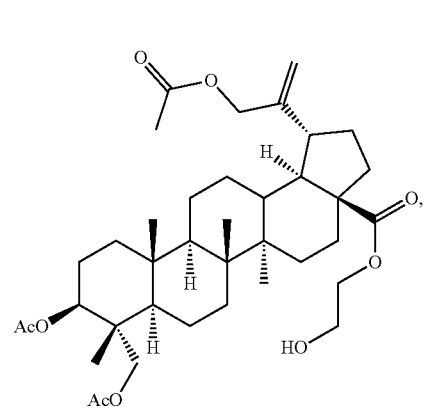
DA068
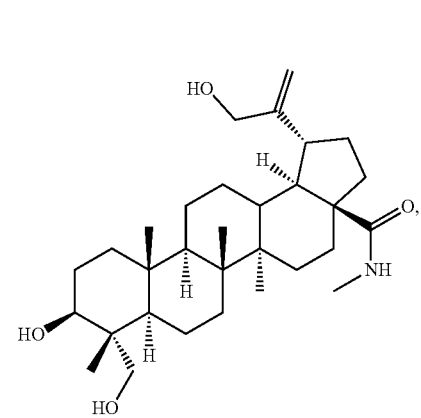
DA069
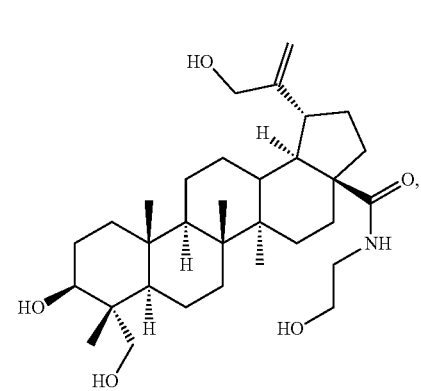

DA070
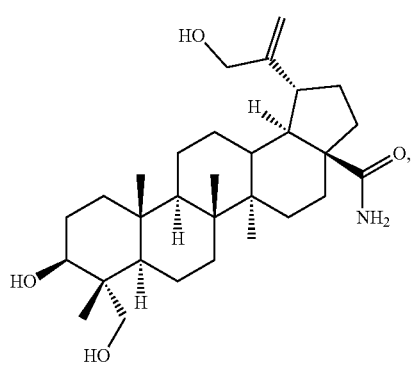
DA071
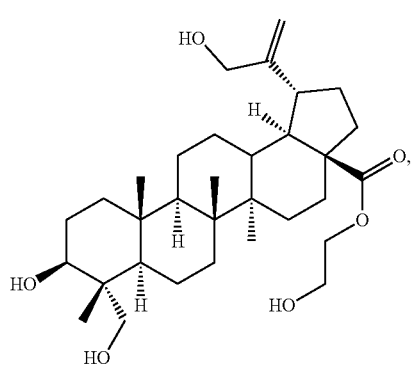
DA072
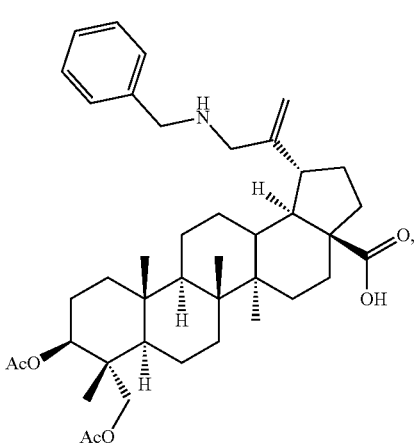
DA073
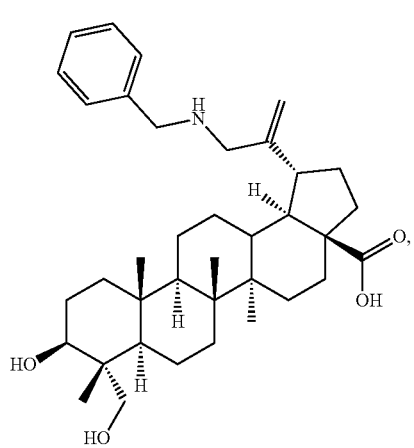
DA074
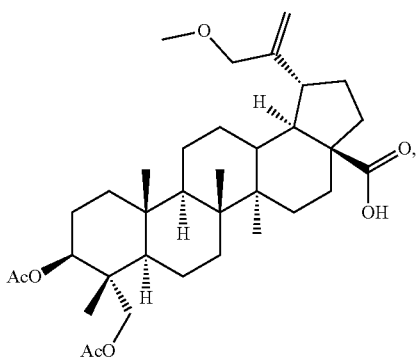
DA075
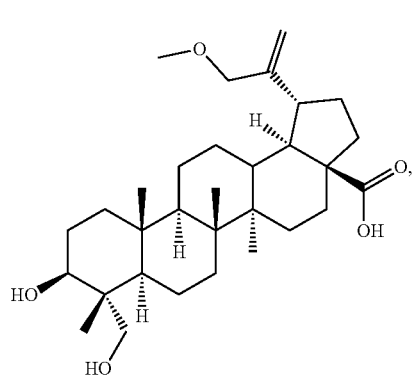
DA076
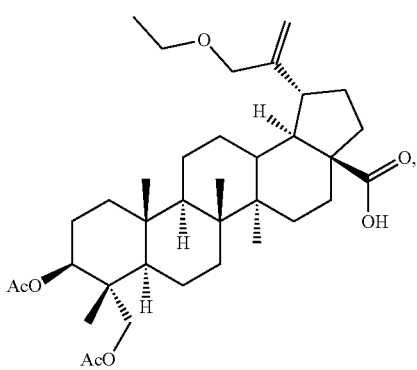
DA077
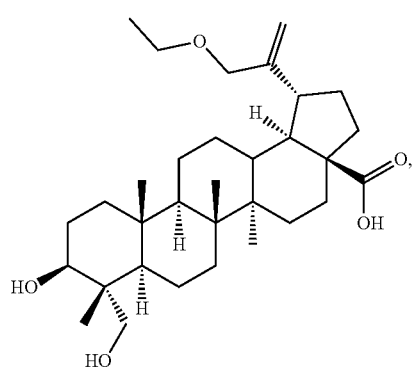

DA078
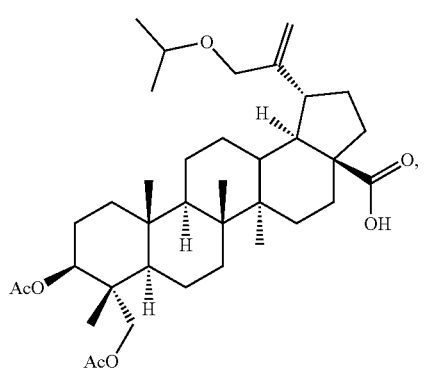
DA082
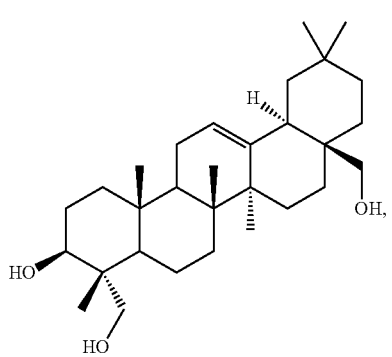
DA079
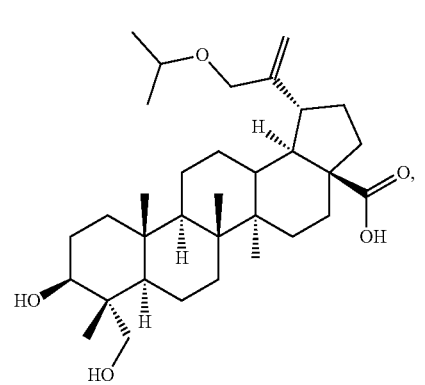
DA083
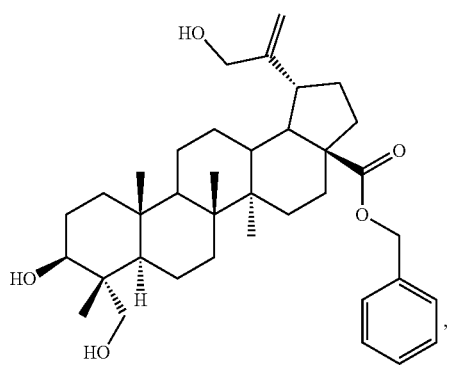
DA080
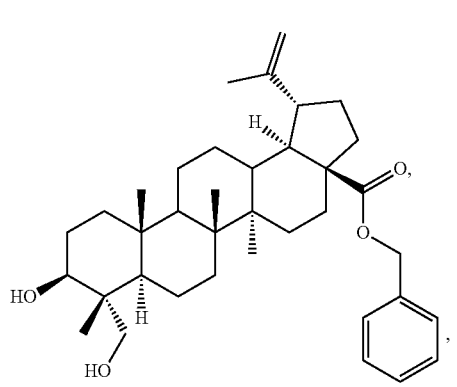
DA084
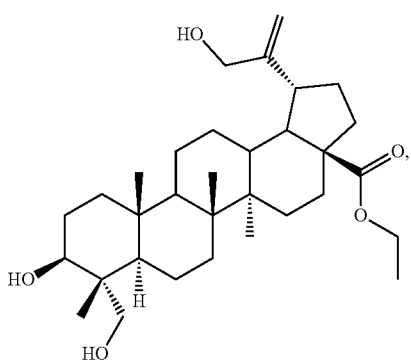
DA081
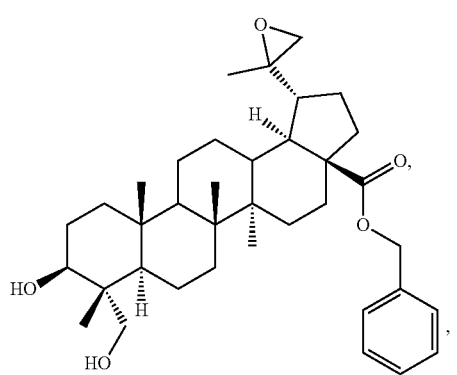
DA085
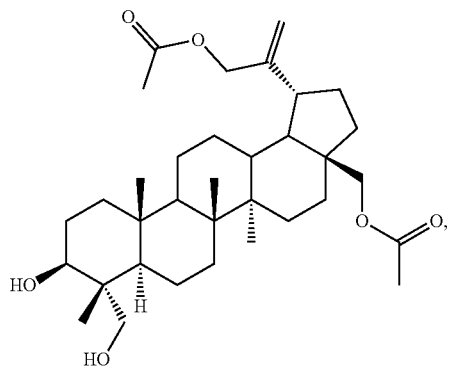

DA086
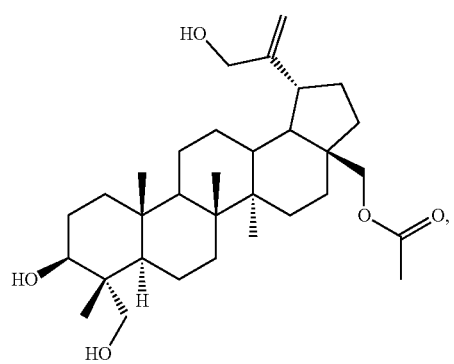
DA087
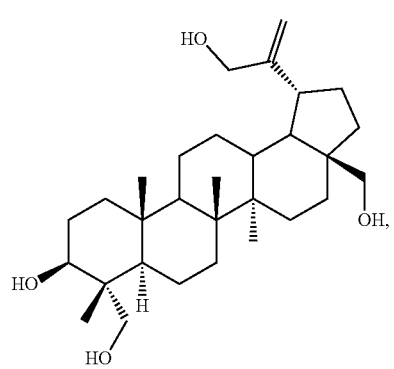
DA088
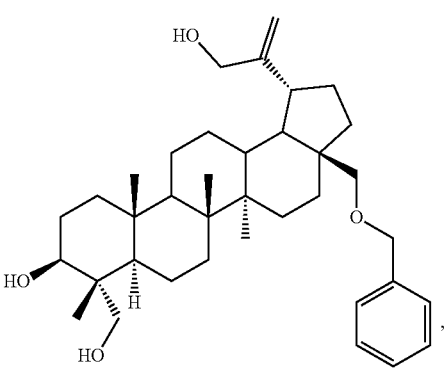
DA089
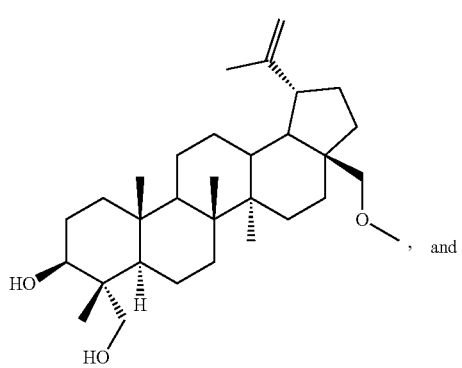
DA090
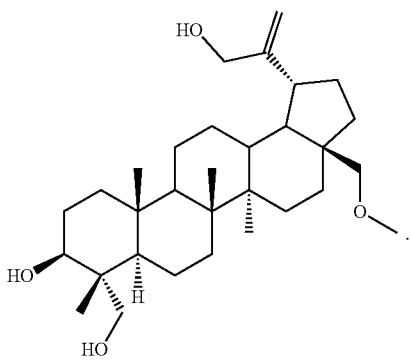
30. The method of claim 29, wherein the receptor of PGE2 is an EP1, EP2 or EP4 receptor.
31. A method of treating pain or inflammation due to arthritis in a mammal, said method comprising: administering to said mammal in need of such treatment a therapeutically effective amount of a compound selected from the group consisting of:
DA001
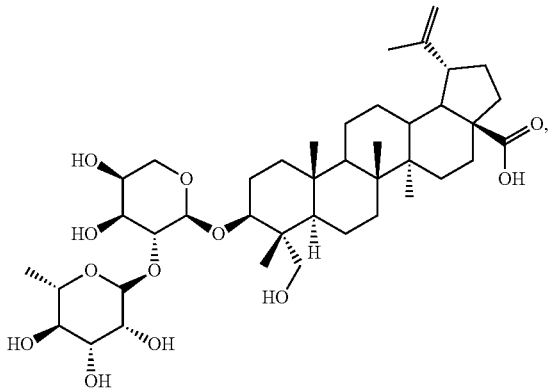
DA002
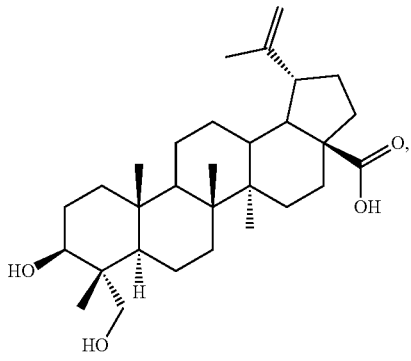

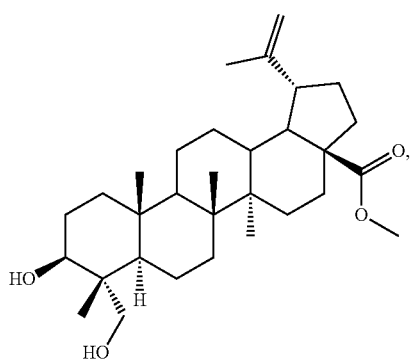
DA003
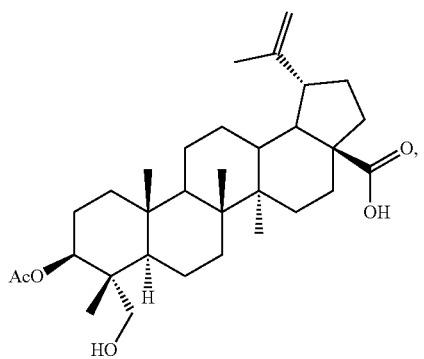
DA007
DA004
DA008
DA005
DA009
DA006
DA010

-continued
DA011
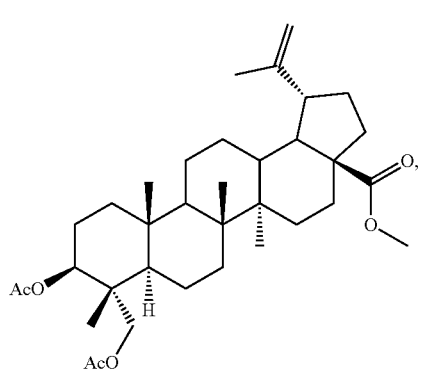
DA012
DA013
DA014
-continued
DA015
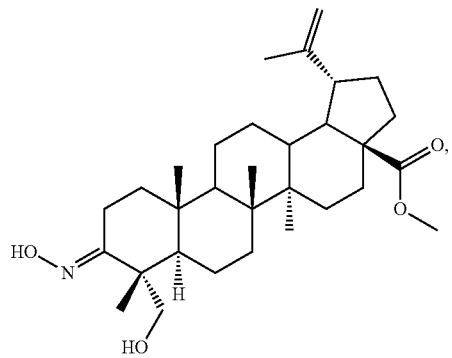
DA016
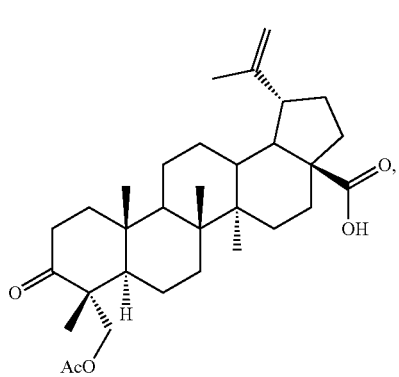
DA017
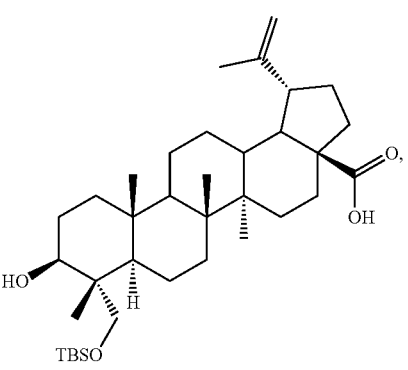
DA018
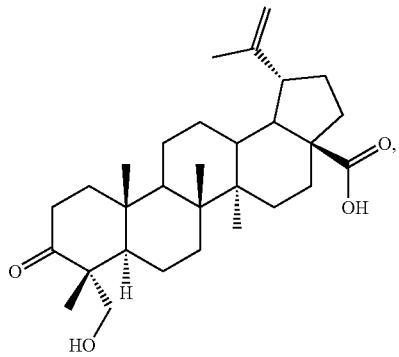

DA019
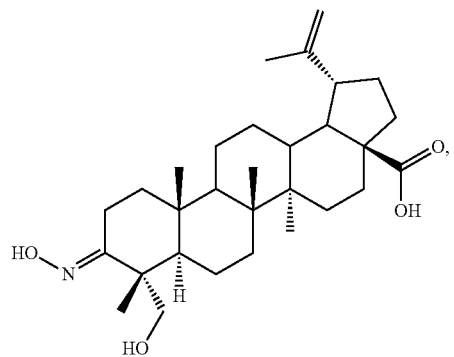
DA020
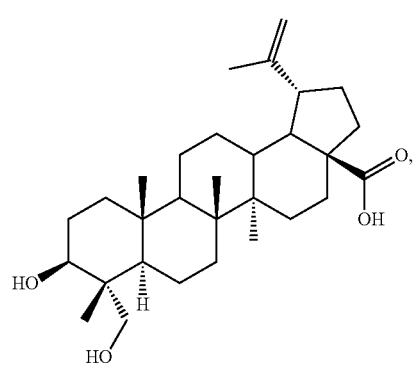
DA021
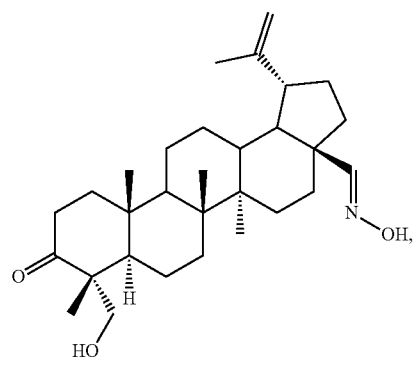
DA022
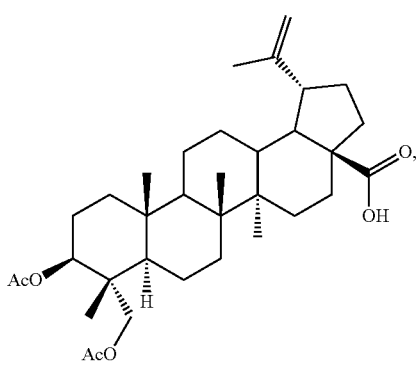
DA023
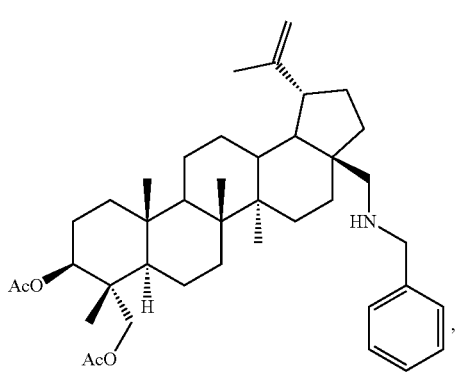
DA024
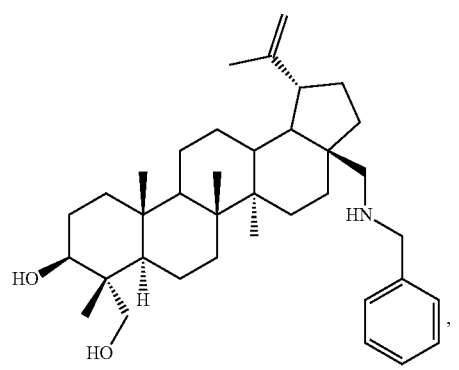
DA025
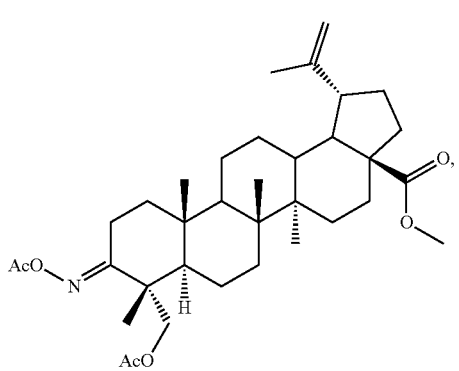
DA026
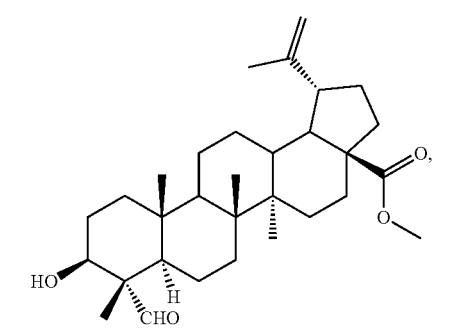

DA027
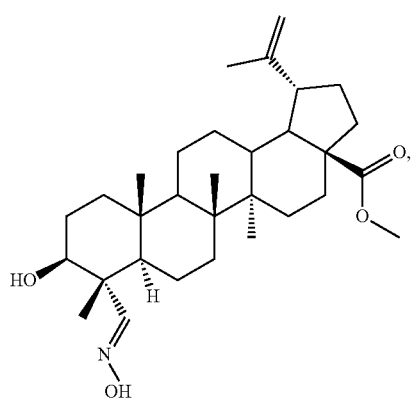
DA028
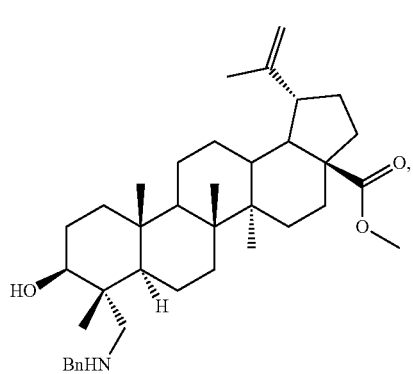
DA029
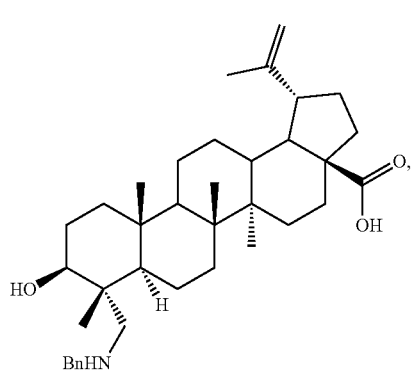
DA030
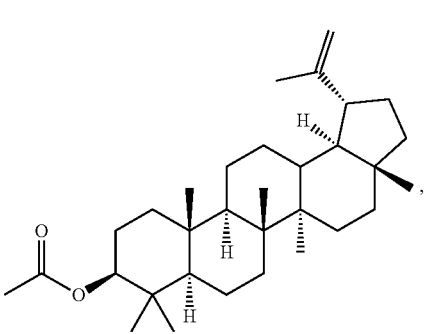
DA031
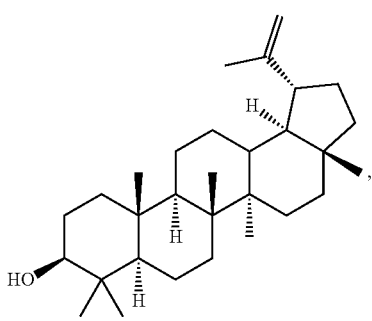
DA032
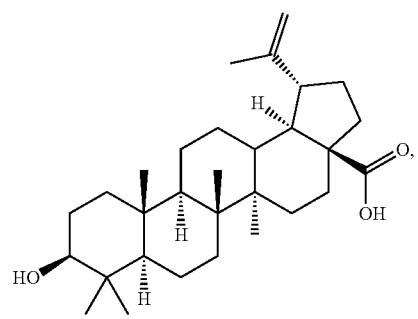
DA033
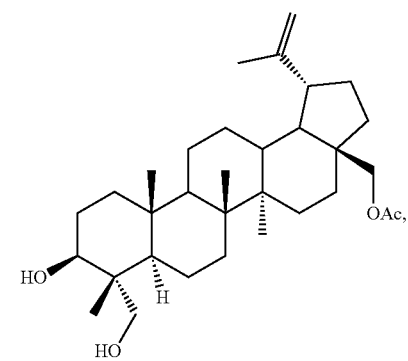
DA034
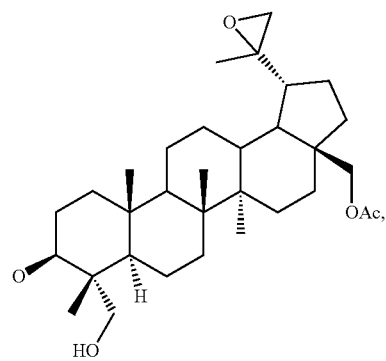

DA035
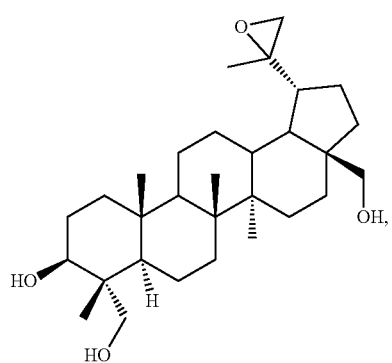
DA036
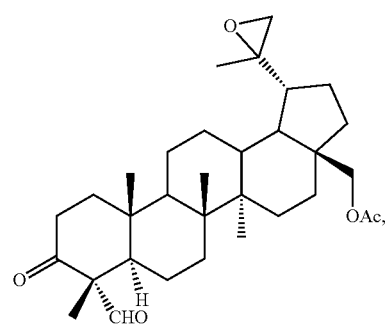
DA037
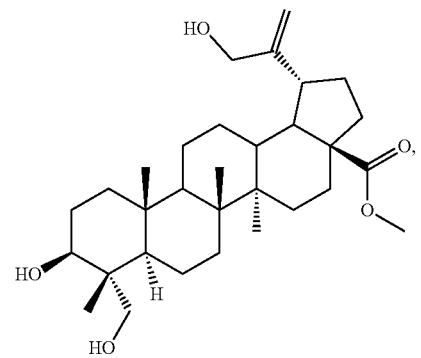
DA038
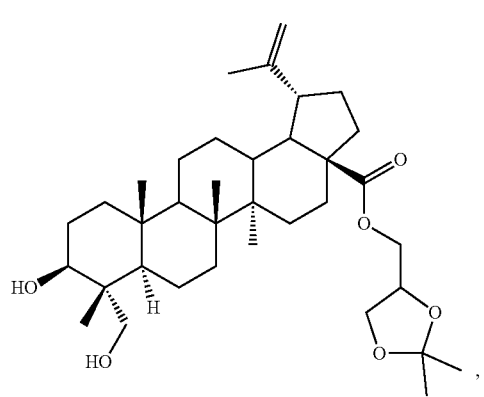
DA039
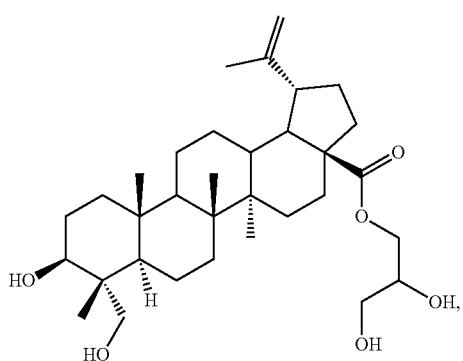
DA040
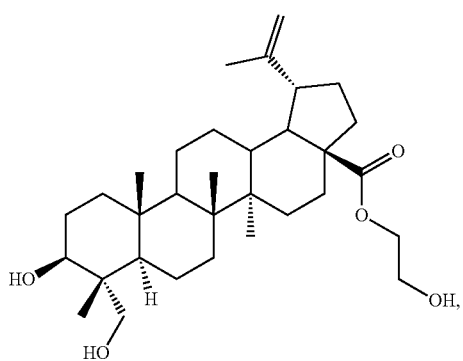
DA041
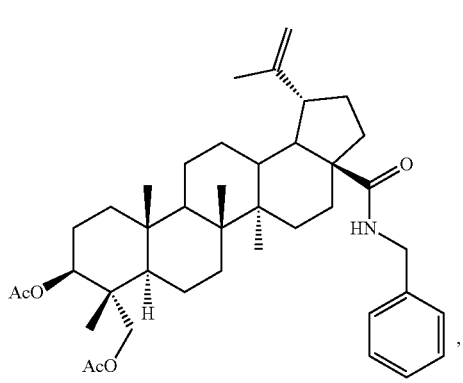
DA042
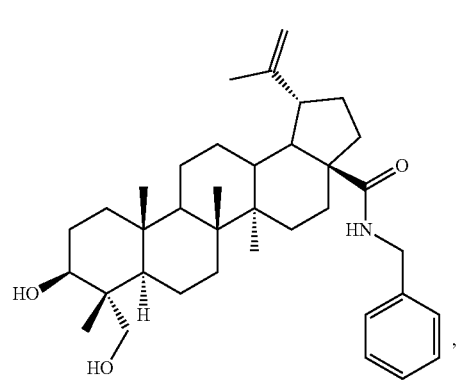

DA043
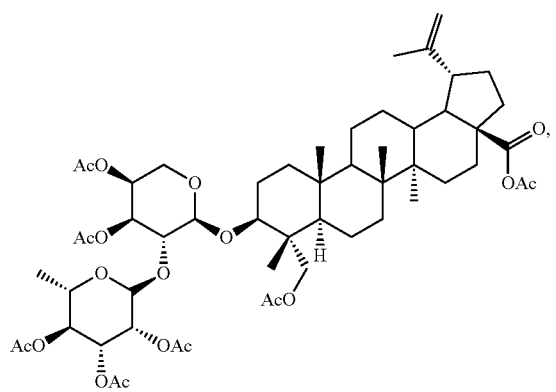
DA044
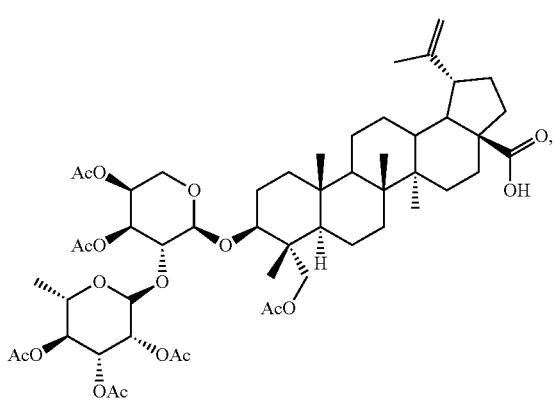
DA045
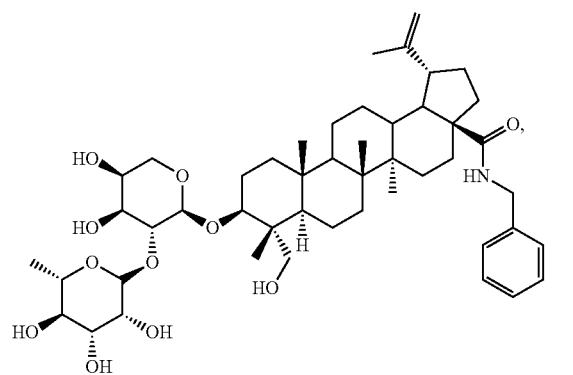
DA046
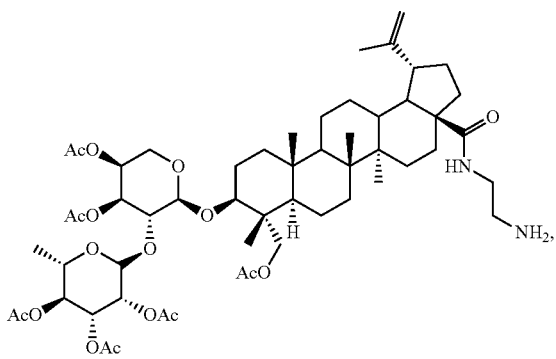
DA047
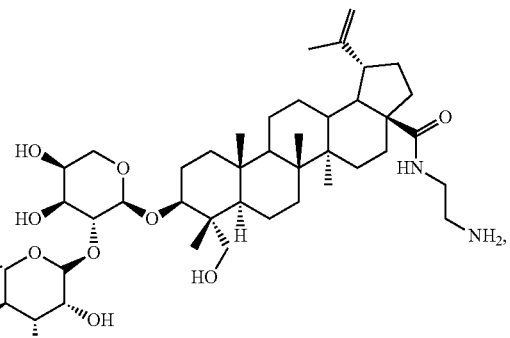
DA048
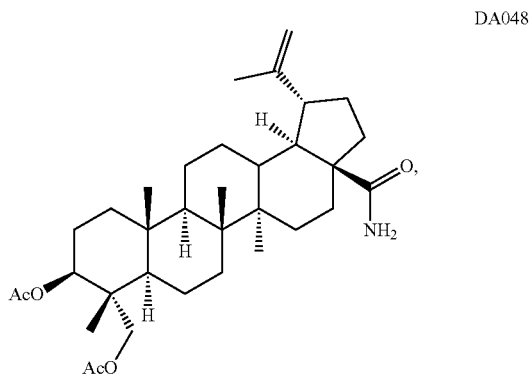
DA049
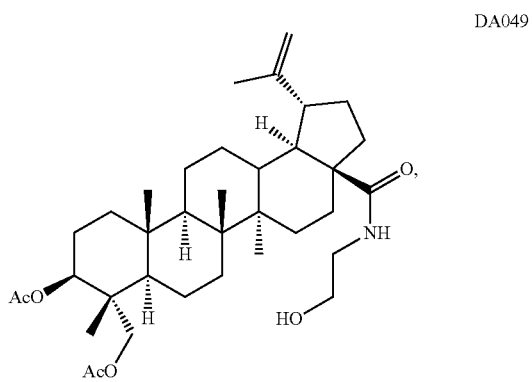
DA050
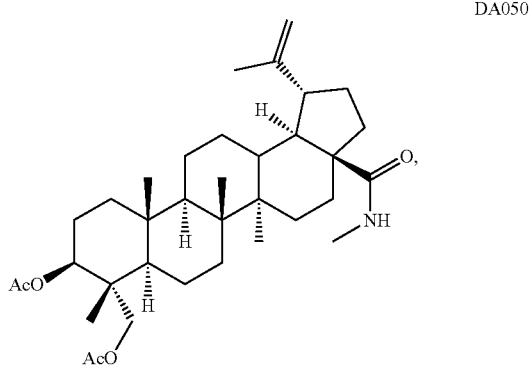

DA051
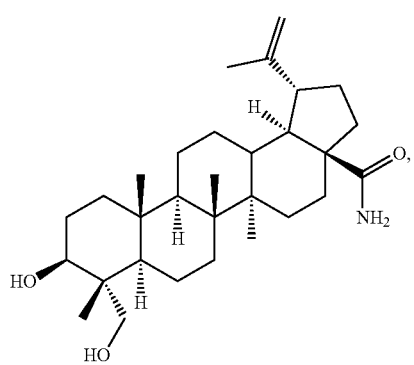
DA052
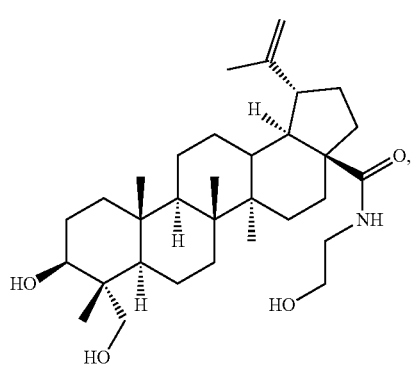
DA053
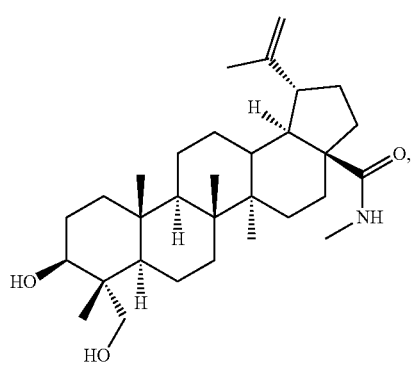
DA054
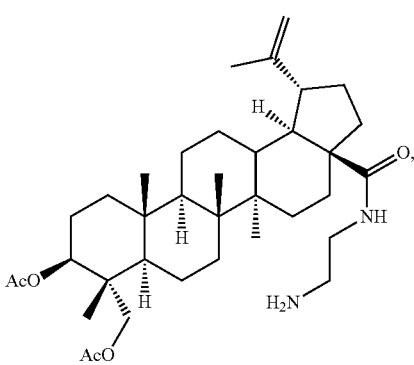
DA055
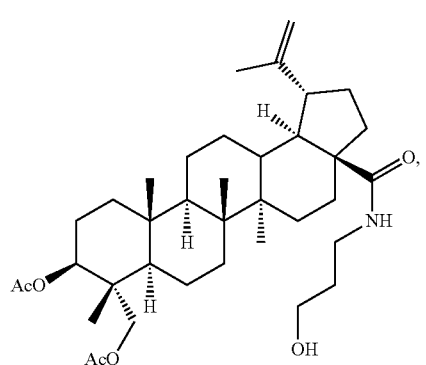
DA056
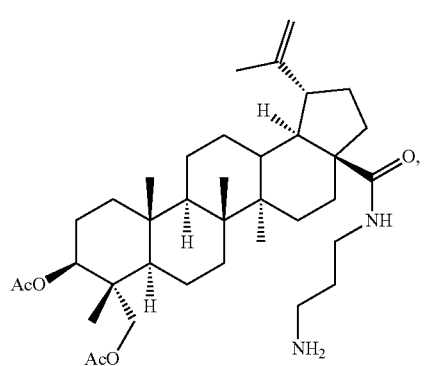
DA057
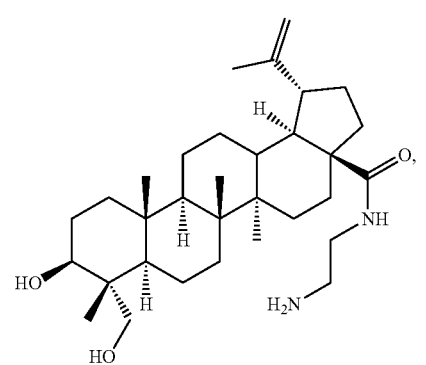
DA058
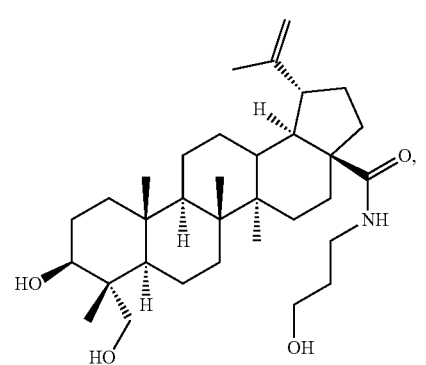

DA059
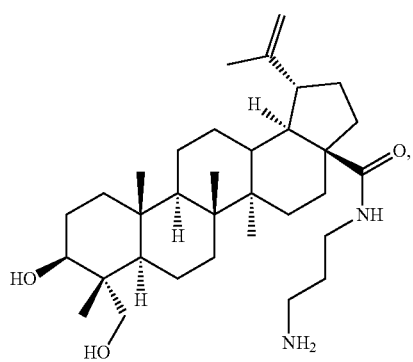
DA063
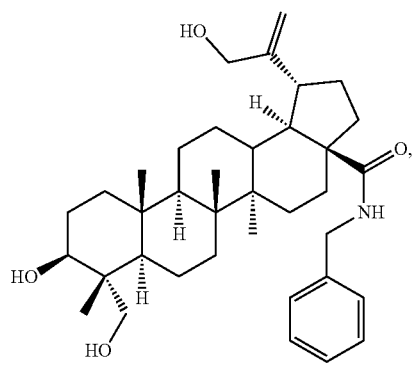
DA060
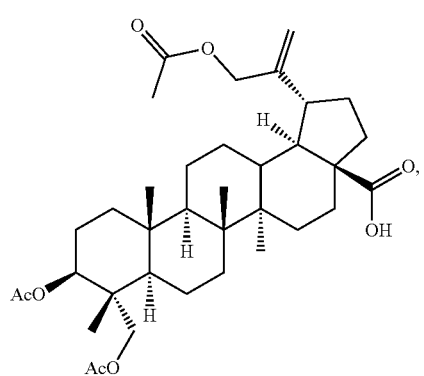
DA064
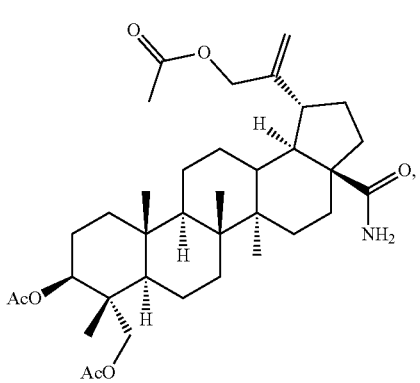
DA061
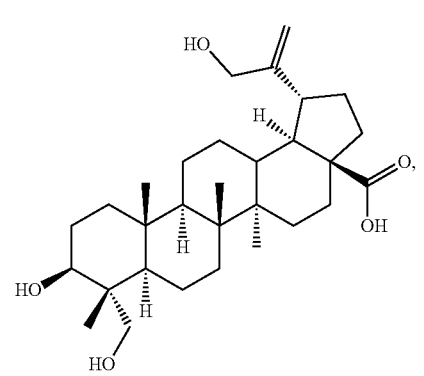
DA065
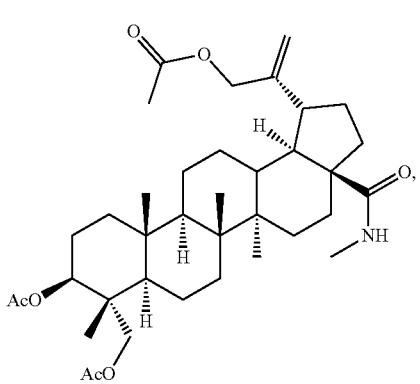
DA062
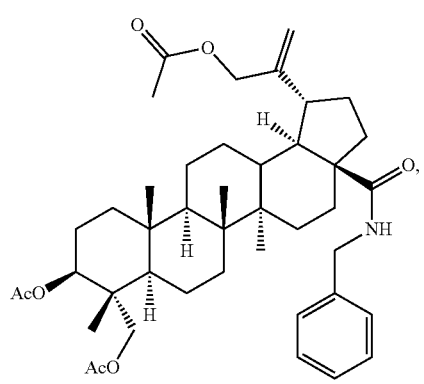
DA066
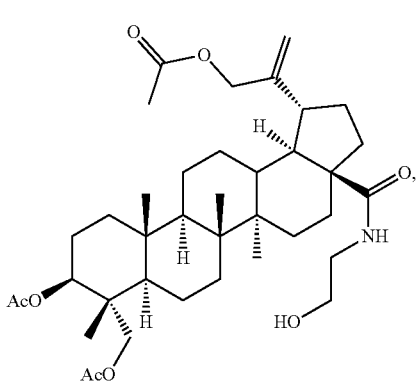

191
-continued
DA067
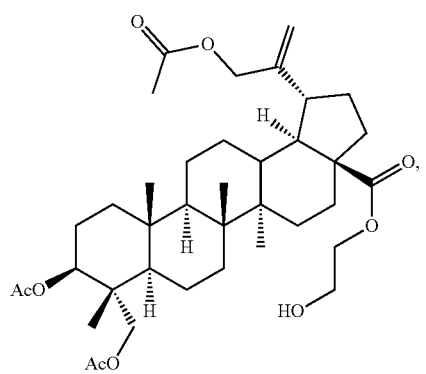
DA068
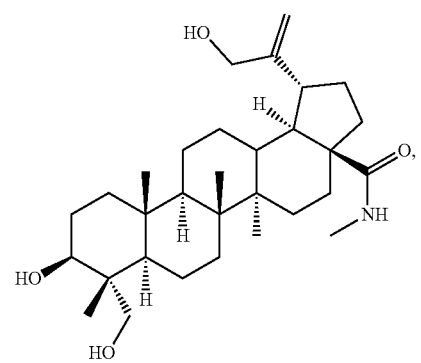
DA069
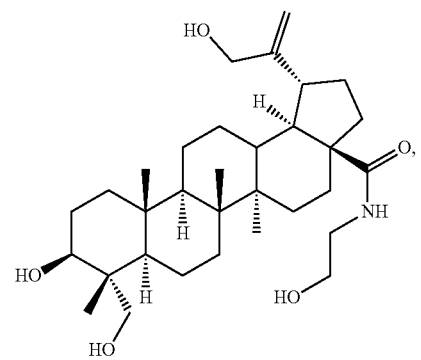
DA070
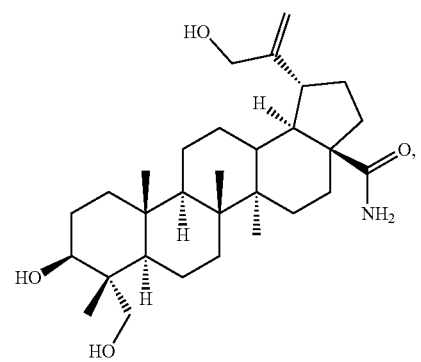
192
-continued
DA071
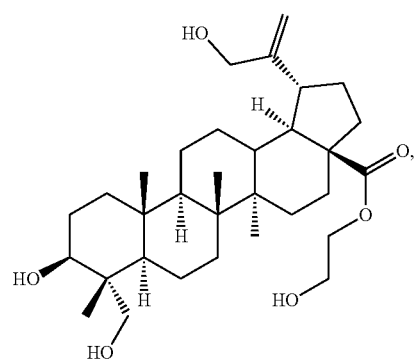
DA072
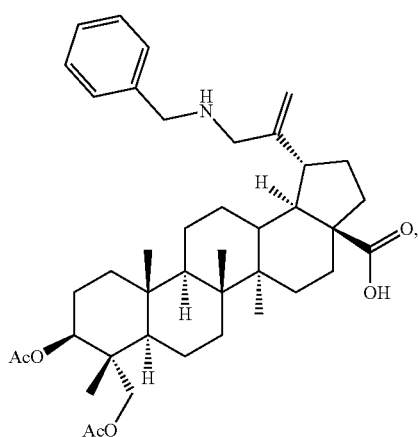
DA073
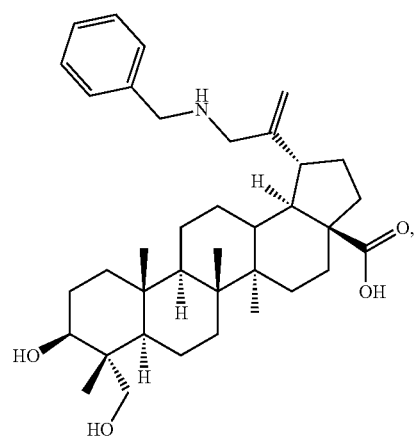
DA074
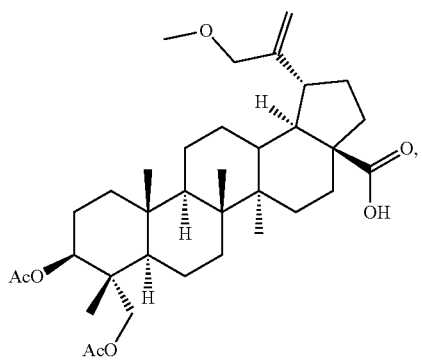

-continued

DA075

DA076

DA077

DA078

DA079

DA080

DA081

DA082

DA083
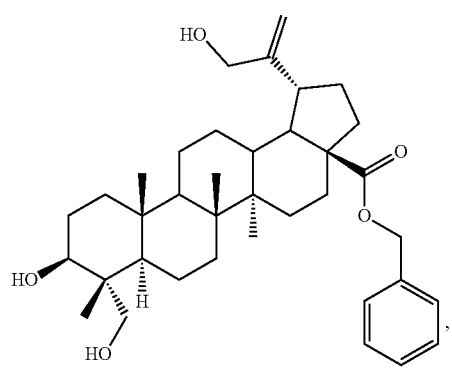
DA084
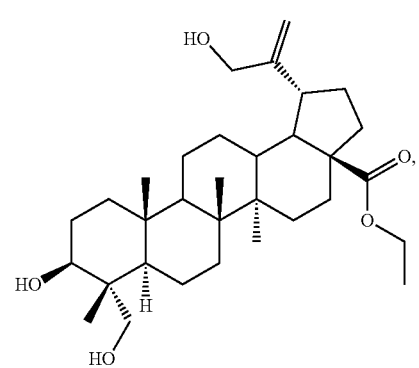
DA085
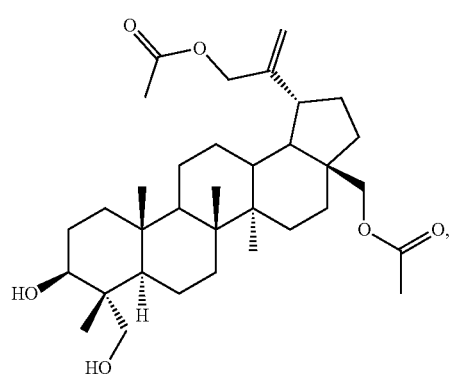
DA086
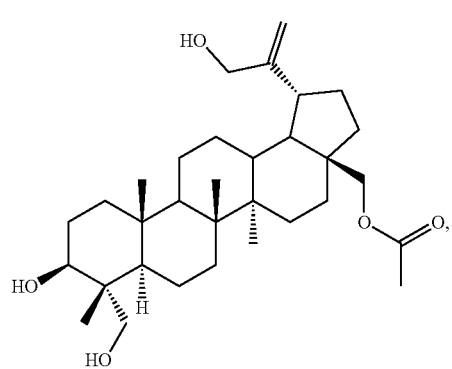
DA087
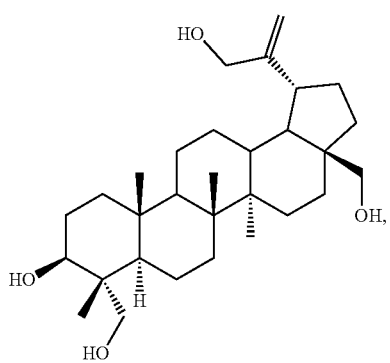
DA088
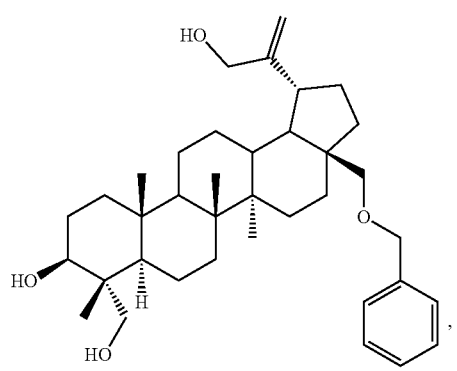
DA089
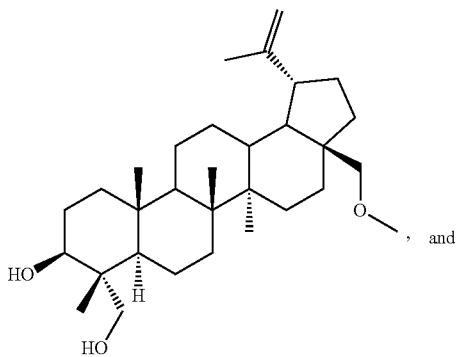
, and
DA090
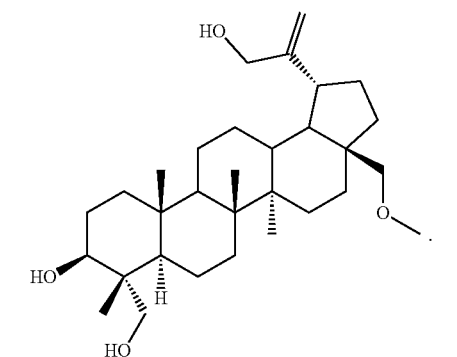
.
32. A method of inhibiting a receptor of PGE2, said method comprising: contacting a compound of formula (II):

(II)

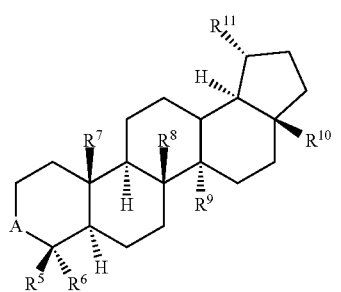

with the receptor of PGE2, wherein:

$R^5$, $R^7$, $R^8$ and $R^9$ are each independently $C_{1-4}$alkyl;

$R^6$ is selected from the group consisting of $C_{1-6}$haloalkyl, $C_{3-6}$cycloalkyl, —$X^1$CN, —$X^1$NO$_2$, —$X^1$C(O)R$^a$, —CR$^b$=NOR$^c$, —$X^1$CO$_2$R$^c$, —$X^1$C(O)NR$^c$R$^d$, —$X^1$C(NR$^c$R$^d$)=NR$^c$, —$X^1$C(O)NR$^c$S(O)R$^d$, —$X^1$C(O)NR$^c$S(O)R$^d$, —$X^1$OR$^e$, —$X^1$SR$^e$, —$X^1$NHR$^e$ and —$X^1$N(R$^e$)$_2$ and —$X^1$R$^e$, wherein each $X^1$ is independently a bond or $C_{1-4}$alkylene, wherein each R$^e$ is independently $C_{1-6}$alkyl, haloalkyl, arylC$_{0-6}$alkyl or cycloalkyl substituted with from 1-3 members of R$^f$, and wherein R$^a$, R$^b$, R$^c$ and R$^d$ are each independently H, $C_{1-6}$alkyl or aryl-$C_{1-6}$alkyl; wherein the aliphatic portion of each R$^6$ substituent is optionally substituted with from 1-3 R$^f$ groups, wherein R$^f$ is selected from the group consisting of halo, CN, NO$_2$, —OH, —R$^g$, —OR$^g$, —OC(O)NHR$^g$, —OC(O)N(R$^g$)$_2$, —OC(O)R$^g$, —OC(O)H, —NH$_2$, —NHR$^g$, —N(R$^g$)$_2$, —SH, —SR$^g$, —S(O)$_2$R$^g$, —SO$_2$NH$_2$, —SO$_2$NHR$^g$, —SO$_2$N(R$^g$)$_2$, —NHS(O)$_2$R$^g$, —NR$^g$S(O)$_2$R$^g$, —C(O)NH$_2$, —C(O)NHR$^g$, —C(O)N(R$^g$)$_2$, —C(O)H, —C(O)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —COOH, —CO$_2$R$^g$, —NHCO$_2$R$^g$, —NR$^g$CO$_2$R$^g$ and —OSi(R$^g$)$_3$, wherein each R$^g$ is independently a $C_{1-6}$alkyl;

A is selected from the group consisting of C=Y$^1$, C=NOR$^c$, C=NOC(O)H, C=NOC(O)R$^g$, C=NOCO$_2$R$^g$, C=NOC(O)NH$_2$, C=NOC(O)NHR$^g$, C=NOC(O)N(R$^g$)$_2$ and —CR$^c$R$^h$, wherein Y$^1$ is =O or =S, and R$^h$ is selected from the group consisting of halo, CN, NO$_2$, —OH, —OR$^i$, —OC(O)NHR$^i$, —OC(O)N(R$^i$)$_2$, —OC(O)R$^i$, —OC(O)H, —NH$_2$, —NHR$^i$, —N(R$^i$)$_2$, —SH, —SR$^i$, —S(O)$_2$R$^i$, —SO$_2$NH$_2$, —SO$_2$NHR$^i$, —SO$_2$N(R$^i$)$_2$, —NHS(O)$_2$R$^i$, —NR$^i$S(O)$_2$ R$^i$, —C(O)NH$_2$, —C(O)NHR$^i$, —C(O)N(R$^i$)$_2$, —C(O)H, —C(O)R$^i$, —NHC(O)R$^i$, —NR$^i$C(O)R$^i$, —NHC(O)NH$_2$, —NR$^i$C(O)NH$_2$, —NR$^i$C(O)NHR$^i$, —NHC(O)NHR$^i$, —NR$^i$C(O)N(R$^i$)$_2$, —NHC(O)N(R$^i$)$_2$, —COOH, —CO$_2$R$^i$, —NHCO$_2$R$^i$, —NR$^i$CO$_2$R$^i$, —OSi(R$^i$)$_3$, —O—(Z)$_{1-6}$, —NH(Z)$_{1-6}$ and —NR$^c$(Z)$_{1-6}$, wherein each R$^i$ is independently a $C_{1-6}$alkyl, arylC$_{0-6}$alkyl or $C_{3-6}$cycloalkyl, optionally substituted with from 1-3 R$^f$ groups; —(Z)$_{1-6}$ is a sequence of 1-6 independently selected $C_{4-7}$monosaccharide residues linked together through ether bonds, optionally each Z is independently substituted with from 1-3 R$^f$ groups;

$R^{10}$ is selected from the group consisting of $C_{1-6}$haloalkyl, $C_{3-6}$cycloalkyl, —$X^2$CN, —$X^2$NO$_2$, —$X^2$C(O)R$^a$, —$X^2$OC(O)R$^a$, —CR$^b$=NOR$^c$, —$X^2$CO$_2$R$^c$, —$X^2$C(O)NR$^c$R$^d$, —$X^2$C(NR$^c$R$^d$)=NR$^c$, —$X^2$C(O)NR$^c$S(O)R$^d$, —$X^2$C(O)NR$^c$S(O)R$^d$, —$X^2$OR$^a$, —$X^2$SR$^a$, —$X^2$NHR$^a$ and —$X^2$N(R$^a$)$_2$, wherein each $X^2$ is independently a bond or $C_{1-4}$alkylene; wherein the aliphatic portion of R$^6$ substituent is optionally substituted with from 1-3 R$^f$ groups, wherein the two adjacent R$^f$ substituents together with the atoms to which they are attached optionally form a 5-membered heterocyclic ring having from 1-3 heteroatoms selected from N, O or S, wherein the heterocyclic ring is optionally substituted with from 1-3 R$^g$ groups, and the aromatic ring of R$^{10}$ is optionally substituted with from 1-5 R$^f$ groups; and $R^{11}$ is selected from the group consisting of $C_{1-6}$alkyl, $C_{1-6}$haloalkyl, $C_{3-6}$cycloalkyl, $C_{2-6}$alkenyl, $C_{2-6}$haloalkenyl, $C_{5-6}$cycloalkenyl and $C_{2-6}$epoxyalkyl, each of which is optionally substituted with from 1-3 R$^f$ groups.

33. The method of claim 32, wherein the receptor of PGE2 is selected from EP1, EP2 or EP4 receptor.

34. A method of reducing inflammation due to arthritis in a mammal, said method comprising: administering to said mammal a therapeutically effective amount of a compound of formula (II):

(II)

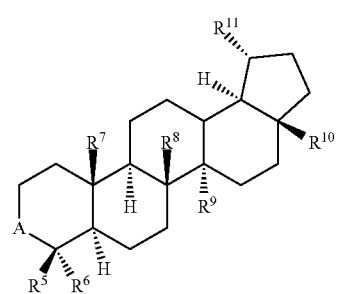

$R^5$, $R^7$, $R^8$ and $R^9$ are each independently $C_{1-4}$alkyl;

$R^6$ is selected from the group consisting of $C_{1-6}$haloalkyl, $C_{3-6}$cycloalkyl, —$X^1$CN, —$X^1$NO$_2$, —$X^1$C(O)R$^a$, —CR$^b$=NOR$^c$, —$X^1$CO$_2$R$^c$, —$X^1$C(O)NR$^c$R$^d$, —$X^1$C(NR$^c$R$^d$)=NR$^c$, —$X^1$C(O)NR$^c$S(O)R$^d$, —$X^1$C(O)NR$^c$S(O)R$^d$, —$X^1$OR$^e$, —$X^1$SR$^e$, —$X^1$NHR$^e$ and —$X^1$N(R$^e$)$_2$ and —$X^1$R$^e$, wherein each $X^1$ is independently a bond or $C_{1-4}$alkylene, wherein each R$^e$ is independently $C_{1-6}$alkyl, haloalkyl, arylC$_{0-6}$alkyl or cycloalkyl substituted with from 1-3 members of R$^f$, and wherein R$^a$, R$^b$, R$^c$ and R$^d$ are each independently H, $C_{1-6}$alkyl or aryl-$C_{1-6}$alkyl; wherein the aliphatic portion of each R$^6$ substituent is optionally substituted with from 1-3 R$^f$ groups, wherein R$^f$ is selected from the group consisting of halo, CN, NO$_2$, —OH, —R$^g$, —OR$^g$, —OC(O)NHR$^g$, —OC(O)N(R$^g$)$_2$, —OC(O)R$^g$, —OC(O)H, —NH$_2$, —NHR$^g$, —N(R$^g$)$_2$, —SH, —SR$^g$, —S(O)$_2$R$^g$, —SO$_2$NH$_2$, —SO$_2$NHR$^g$, —SO$_2$N(R$^g$)$_2$, —NHS(O)$_2$R$^g$, —NR$^g$S(O)$_2$R$^g$, —C(O)NH$_2$, —C(O)NHR$^g$, —C(O)N(R$^g$)$_2$, —C(O)H, —C(O)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —COOH, —CO$_2$R$^g$, —NHCO$_2$R$^g$, —NR$^g$CO$_2$R$^g$ and —OSi(R$^g$)$_3$, wherein each R$^g$ is independently a $C_{1-6}$alkyl;

A is selected from the group consisting of C=Y$^1$, C=NOR$^c$, C=NOC(O)H, C=NOC(O)R$^g$, C=NOCO$_2$R$^g$, C=NOC(O)NH$_2$, C=NOC(O)NHR$^g$, C=NOC(O)N(R$^g$)$_2$ and —CR$^c$R$^h$, wherein Y$^1$ is =O or =S, and R$^h$ is selected from the group consisting of halo, CN, NO$_2$, —OH, —OR$^i$, —OC(O)NHR$^i$, —OC(O)N(R$^i$)$_2$, —OC(O)R$^i$, —OC(O)H, —NH$_2$, —NHR$^i$, —N(R$^i$)$_2$, —SH, —SR$^i$, —S(O)$_2$R$^i$, —SO$_2$NH$_2$, —SO$_2$NHR$^i$, —SO$_2$N(R$^i$)$_2$, —NHS(O)$_2$R$^i$, —NR$^i$S(O)$_2$ R$^i$, —C(O)NH$_2$, —C(O)NHR$^i$, —C(O)N(R$^i$)$_2$, —C(O)H, —C(O)R$^i$, —NHC(O)R$^i$, —NR$^i$C(O)R$^i$, —NHC(O)NH$_2$, —NR$^i$C(O)NH$_2$, —NR$^i$C(O)NHR$^i$, —NHC(O)NHR$^i$, —NR$^i$C(O)N(R$^i$)$_2$, —NHC(O)

N(R$^i$)$_2$, —COOH, —CO$_2$R$^i$, —NHCO$_2$R$^i$, —NR$^i$CO$_2$R$^i$, —OSi(R$^i$)$_3$, —O—(Z)$_{1-6}$, —S—(Z)$_{1-6}$, —NH(Z)$_{1-6}$ and —NR$^c$(Z)$_{1-6}$, wherein each R$^i$ is independently a C$_{1-6}$alkyl, C$_{1-6}$haloalkyl, arylC$_{0-6}$alkyl or C$_{3-6}$cycloalkyl, optionally substituted with from 1-3 R$^f$ groups; —(Z)$_{1-6}$ is a sequence of 1-6 independently selected C$_{4-7}$monosaccharide residues linked together through ether bonds, optionally each Z is independently substituted with from 1-3 R$^f$ groups;

R$^{10}$ is selected from the group consisting of C$_{1-6}$haloalkyl, C$_{3-6}$cycloalkyl, —X$^2$CN, —X$^2$NO$_2$, —X$^2$C(O)R$^a$, —X$^2$OC(O)R$^a$, —CR$^b$═NOR$^c$, —X$^2$CO$_2$R$^c$, —X$^2$C(O)NR$^c$R$^d$, —X$^2$C(NR$^c$R$^d$)═NR$^c$, —X$^2$C(O)NR'S(O) R$^d$, —X$^2$C(O)NR$^c$S(O)R$^d$, —X$^2$OR$^a$, —X$^2$SR$^a$— X$^2$NHR$^a$ and —X$^2$N(R$^a$)$_2$, wherein each X$^2$ is independently a bond or C$_{1-4}$alkylene; wherein the aliphatic portion of R$^6$ substituent is optionally substituted with from 1-3 R$^f$ groups, wherein the two adjacent R$^f$ substituents together with the atoms to which they are attached optionally form a 5-membered heterocyclic ring having from 1-3 heteroatoms selected from N, O or S, wherein the heterocyclic ring is optionally substituted with from 1-3 R$^g$ groups, and the aromatic ring of R$^{10}$ is optionally substituted with from 1-5 R$^f$ groups; and R$^{11}$ is selected from the group consisting of C$_{1-6}$alkyl, C$_{1-6}$haloalkyl, C$_{3-6}$cycloalkyl, C$_{2-6}$alkenyl, C$_{2-6}$haloalkenyl, C$_{5-6}$cycloalkenyl and C$_{2-6}$epoxyalkyl, each of which is optionally substituted with from 1-3 R$^f$ groups.

35. A method of inhibiting an NMDA receptor or MC4 receptor, said method comprising: contacting with an NMDA receptor or MC4 receptor a compound selected from the group consisting of:

DA048

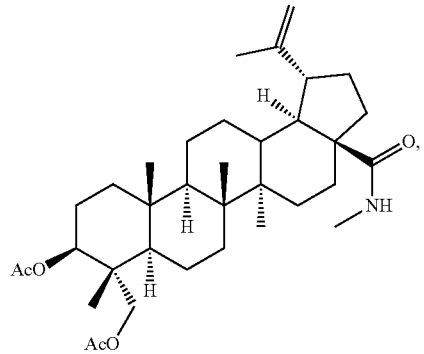

DA050

DA049

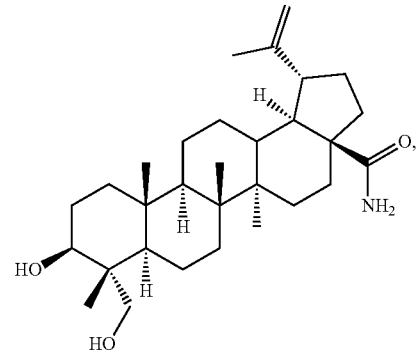

DA051

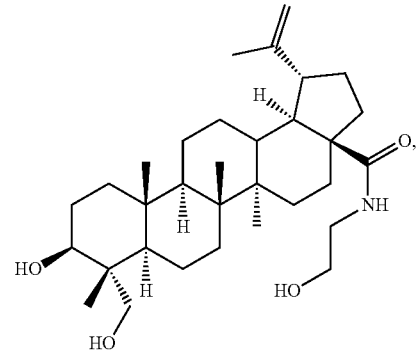

DA052

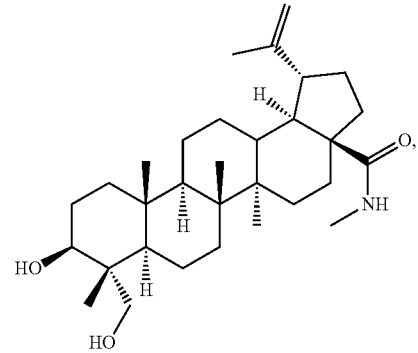

DA053

-continued

DA054, DA055, DA056, DA057, DA058, DA059, DA060, DA061

DA062

DA063

DA064

DA065

DA066

DA067

DA068

DA069

DA070
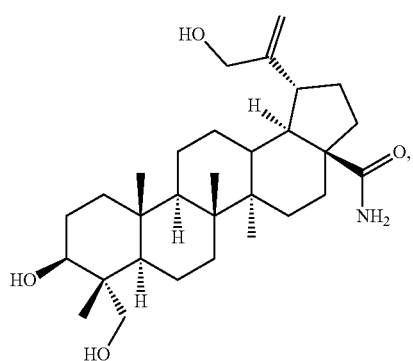
DA071
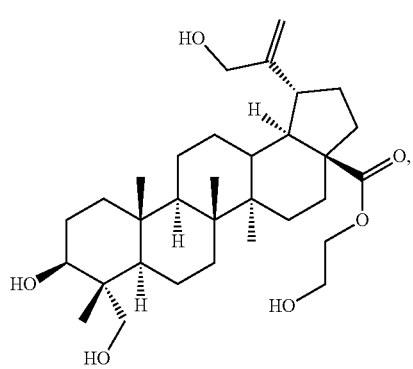
DA072
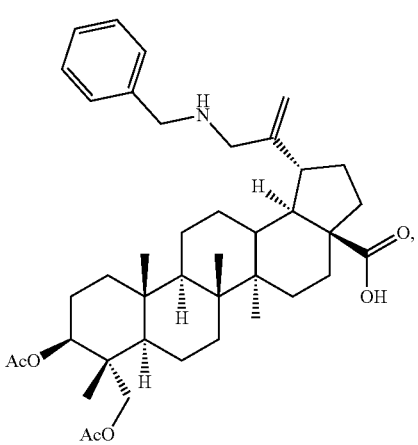
DA073
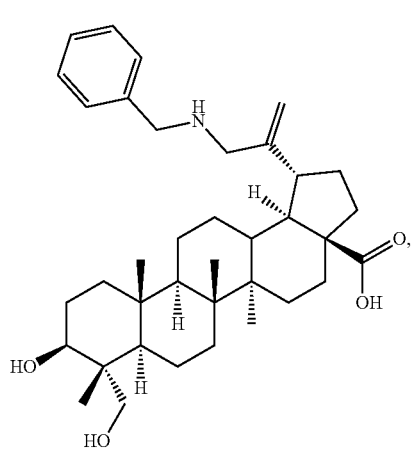
DA074
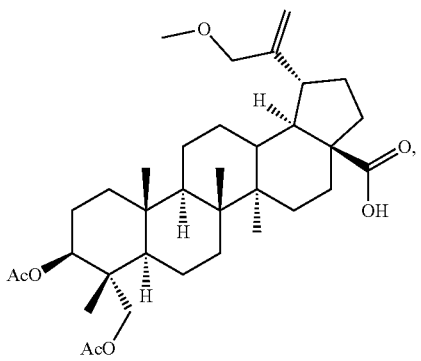
DA075
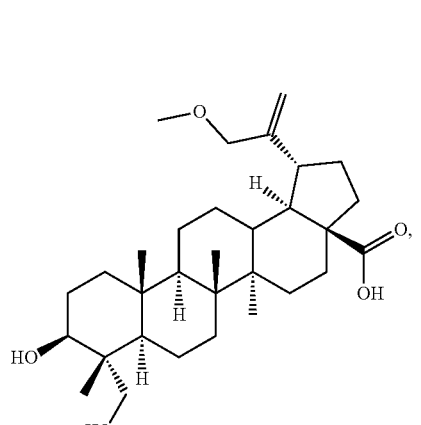
DA076
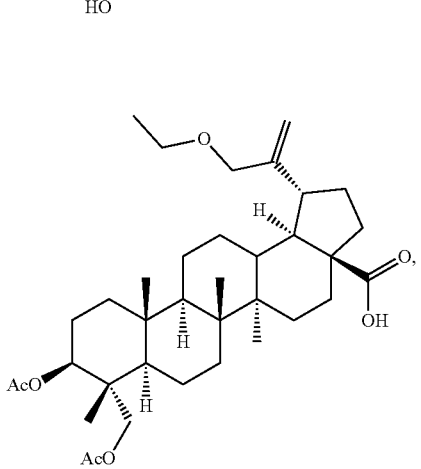
DA077
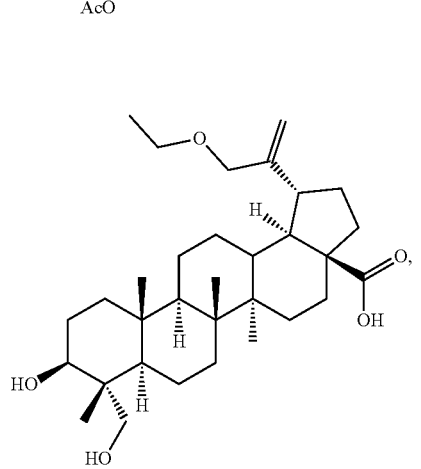

DA078
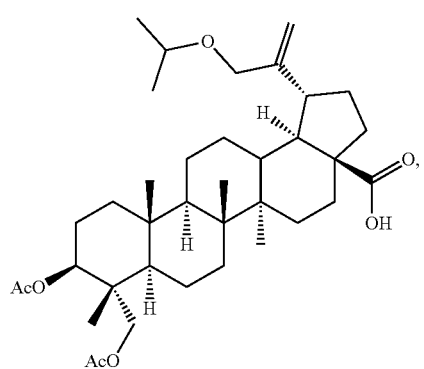
DA082
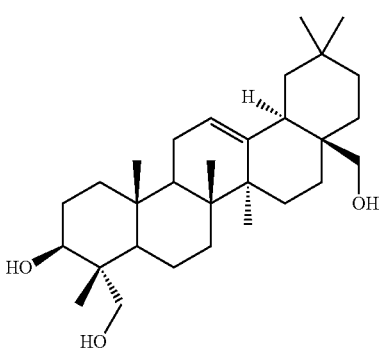
DA079
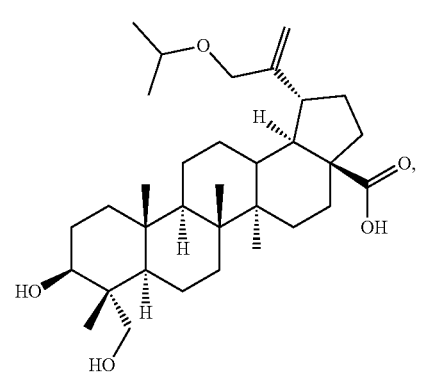
DA083
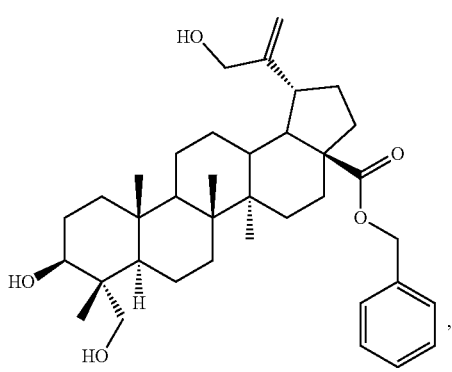
DA080
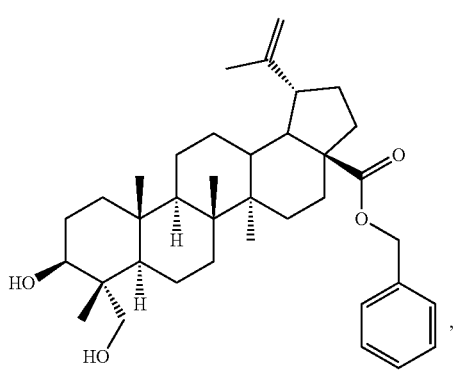
DA084
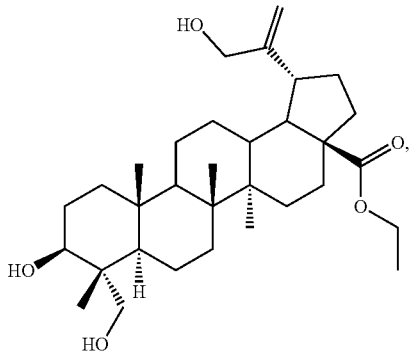
DA081
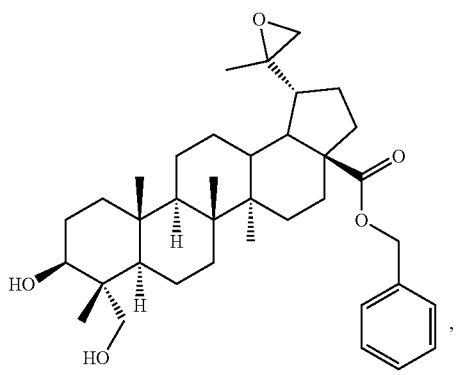
DA085
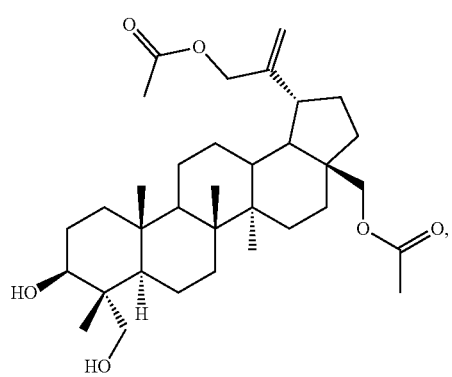

DA086
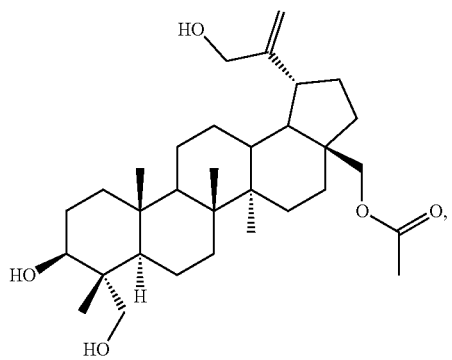
DA087
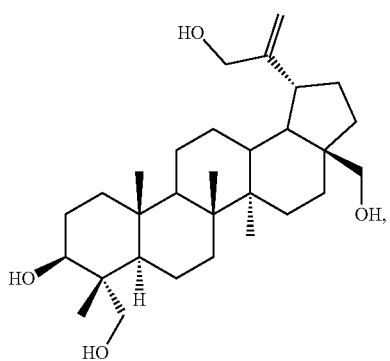
DA088
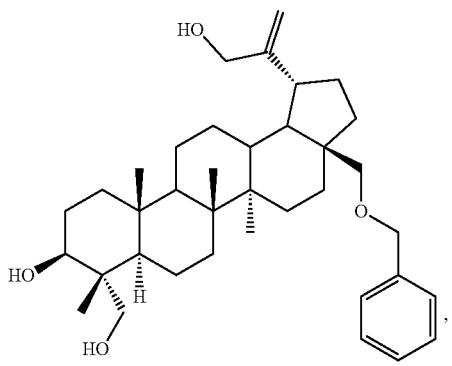
DA089
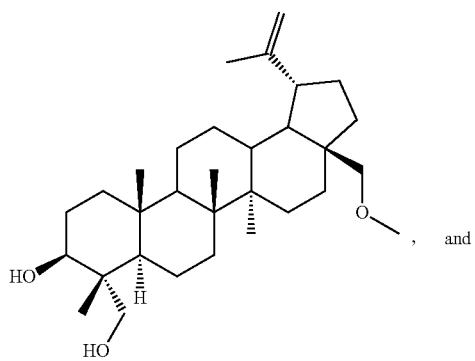
DA090
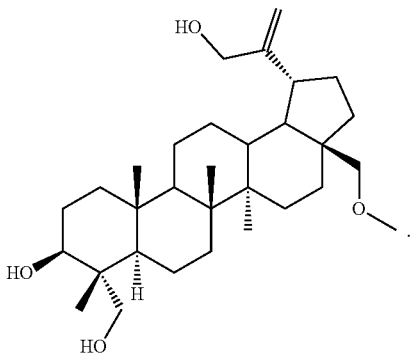
36. A method of reducing neuronal cell death induced or caused by NMDA in a mammal, said method comprising: administering to said mammal a therapeutically effective amount of a compound selected from the group consisting of:
DA048
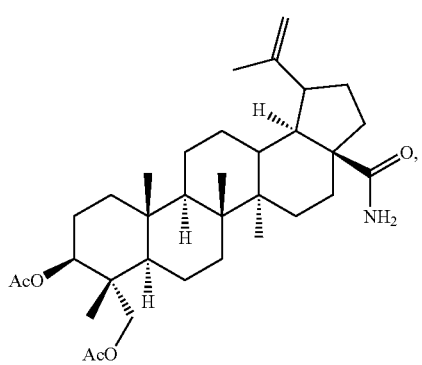
DA049
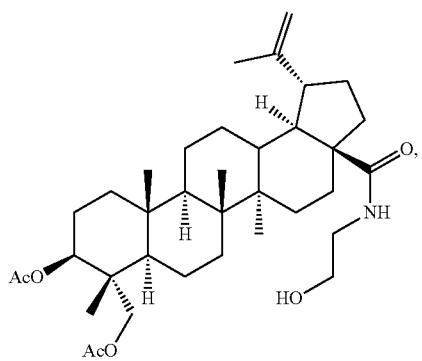
DA050
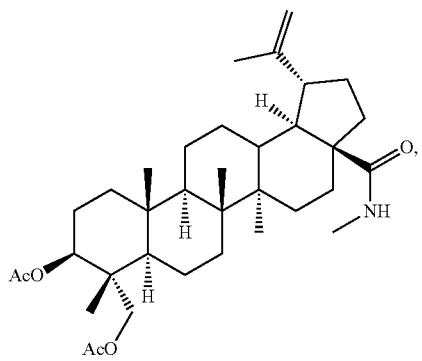

-continued
DA051
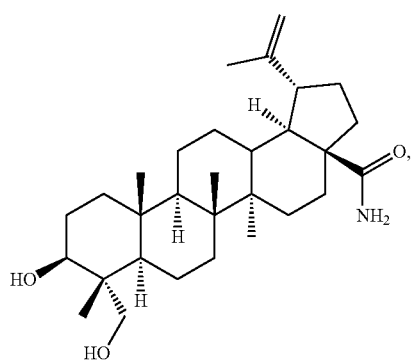
DA052
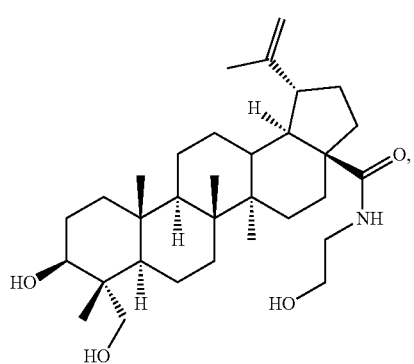
DA053
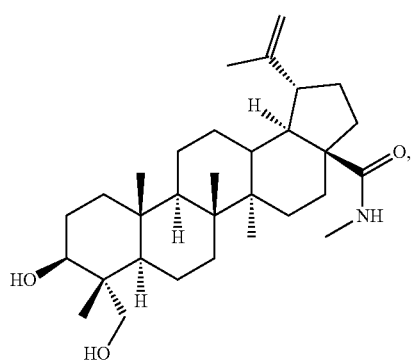
DA054
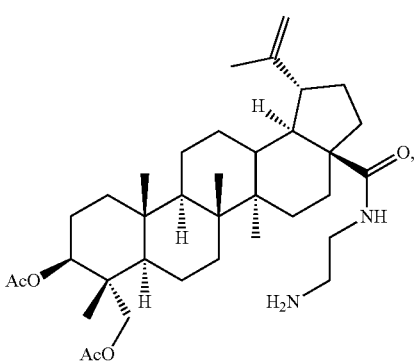
-continued
DA055
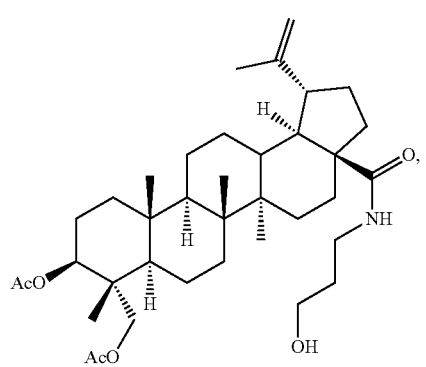
DA056
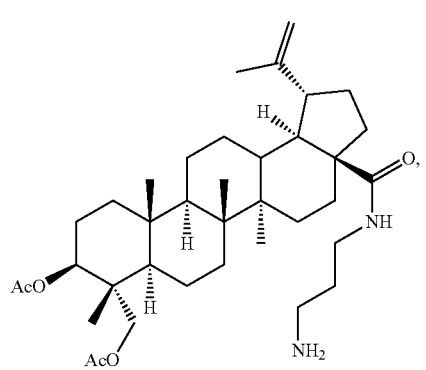
DA057
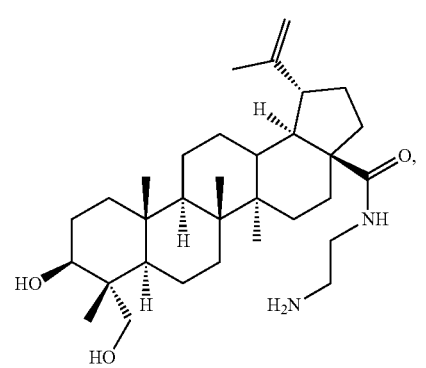
DA058
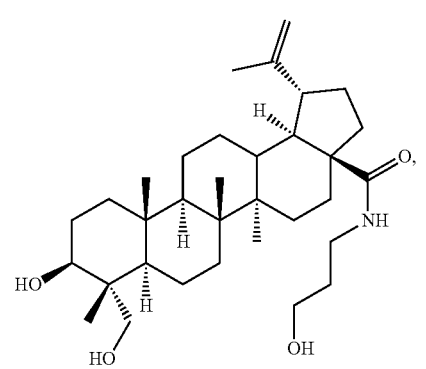

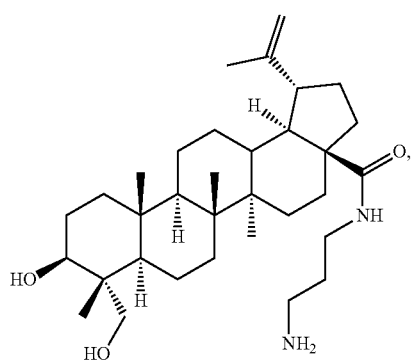
DA059
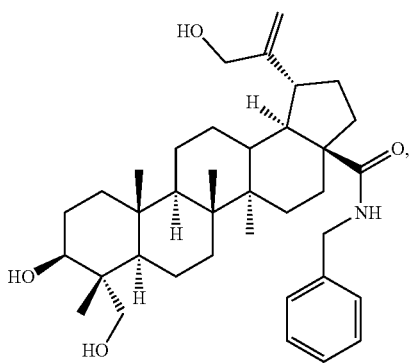
DA063
DA060
DA064
DA061
DA065
DA062
DA066

DA067
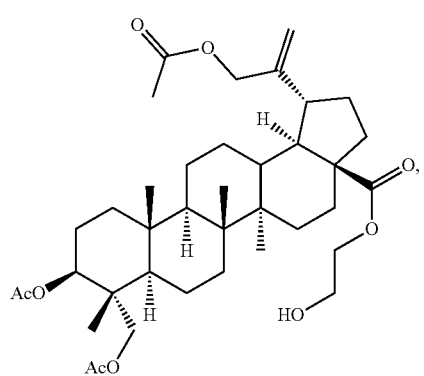
DA068
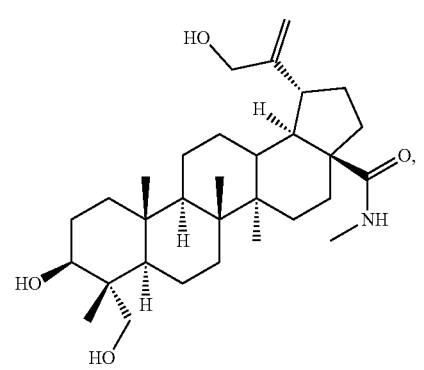
DA069
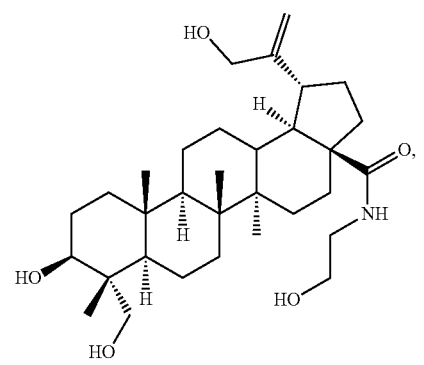
DA070
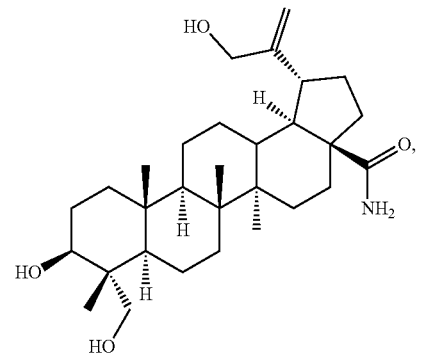
DA071
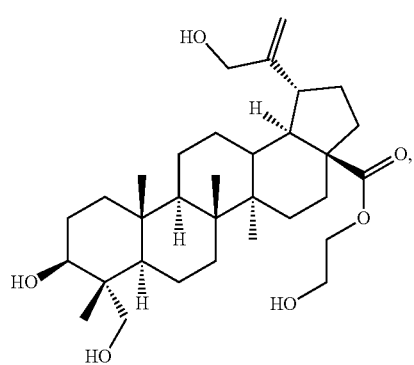
DA072
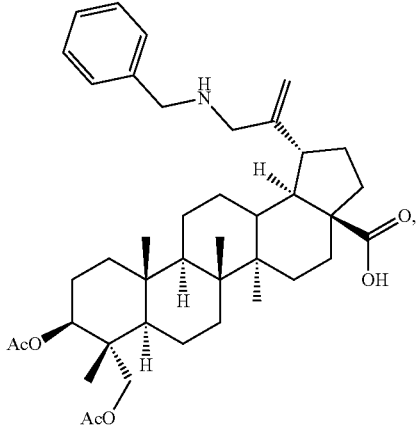
DA073
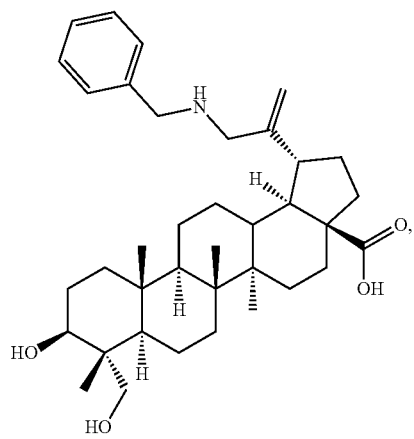
DA074
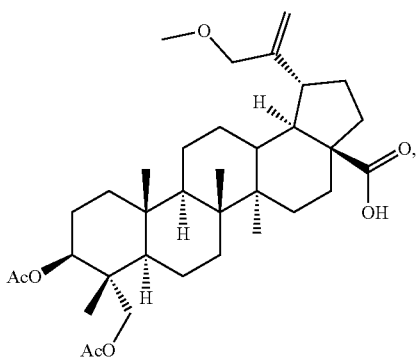

-continued
DA075
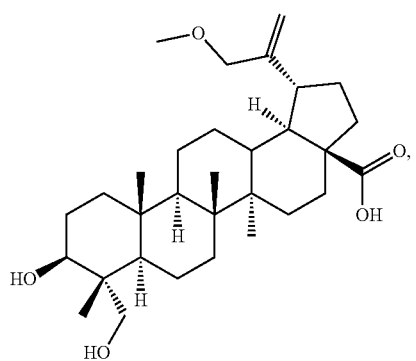
DA076
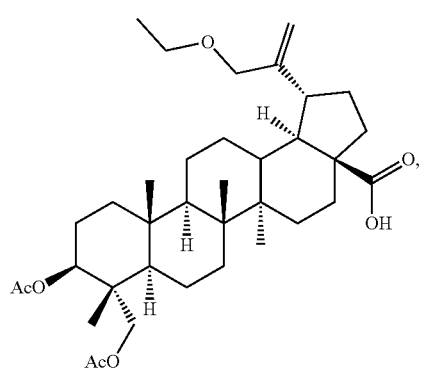
DA077
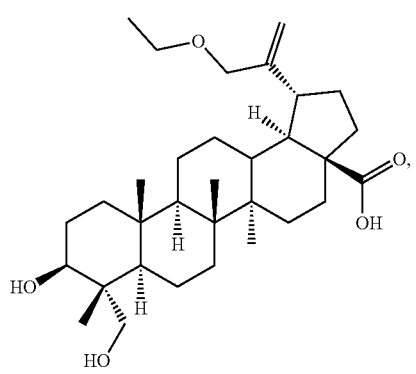
DA078
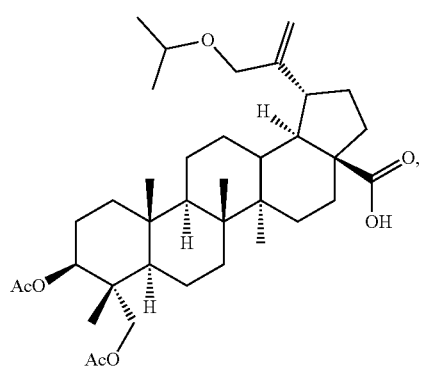
-continued
DA079
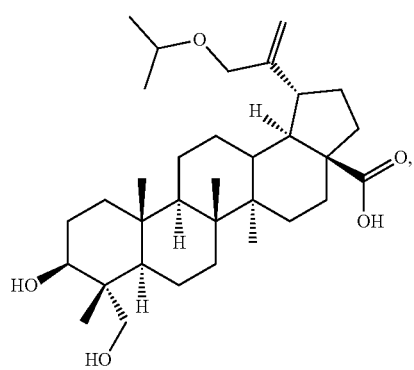
DA080
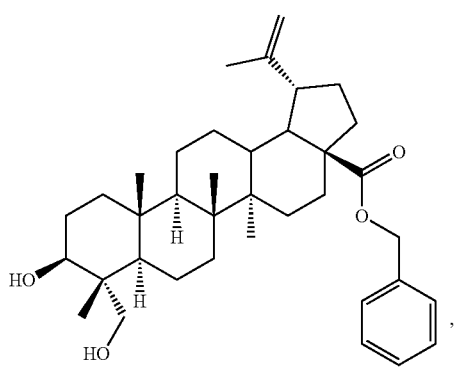
DA081
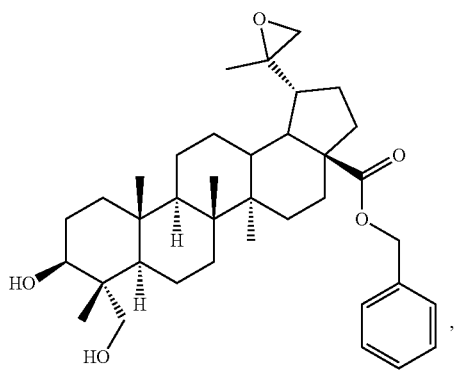
DA082
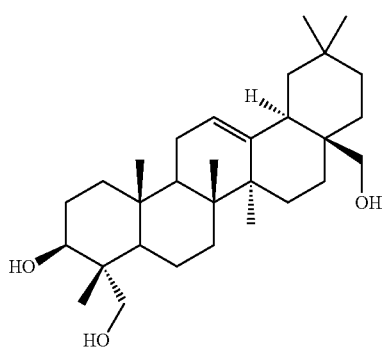

DA083
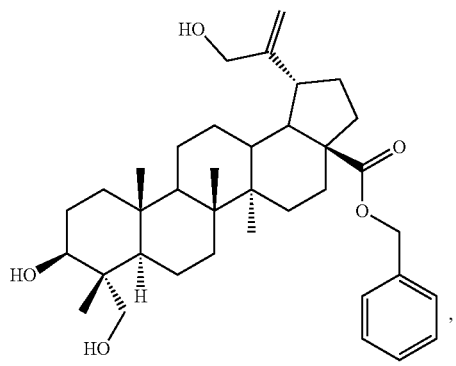
DA084
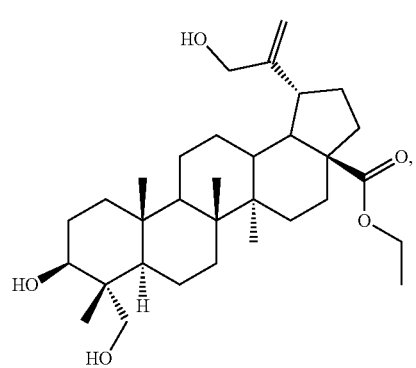
DA085
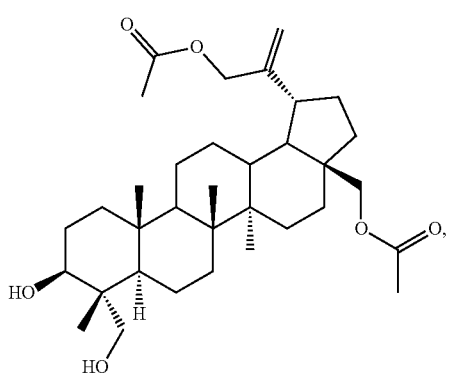
DA086
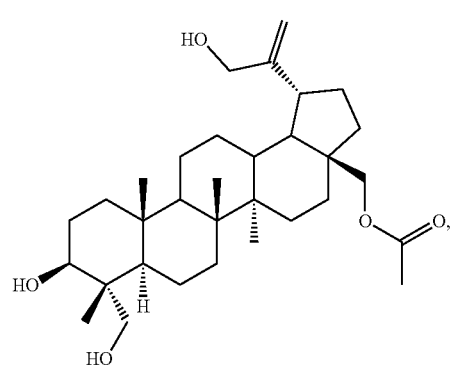
DA087
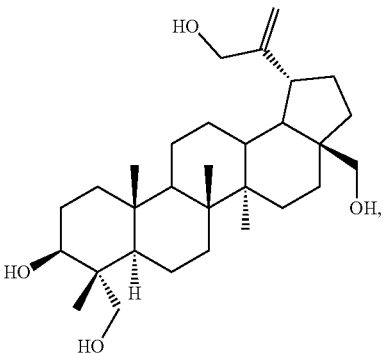
DA088
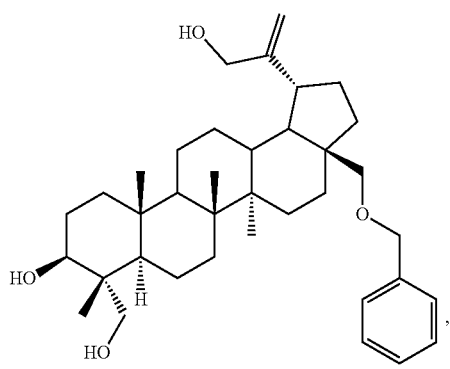
DA089
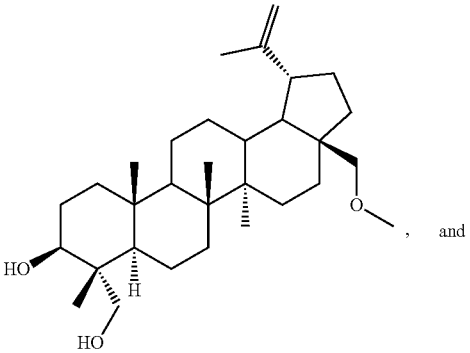
, and
DA090
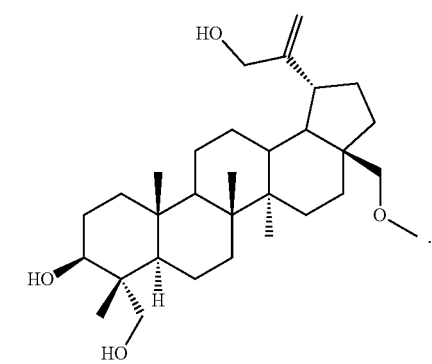
.
37. A method of enhancing the brain's cognitive function in a mammal due to neuronal cell death or cytotoxicity induced or caused by NMDA, said method comprising: administering to said mammal a therapeutically effective amount of a compound selected from the group consisting of:

DA048
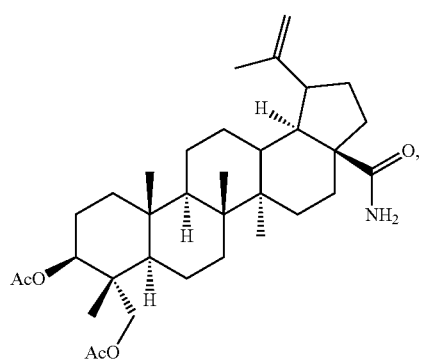
DA049
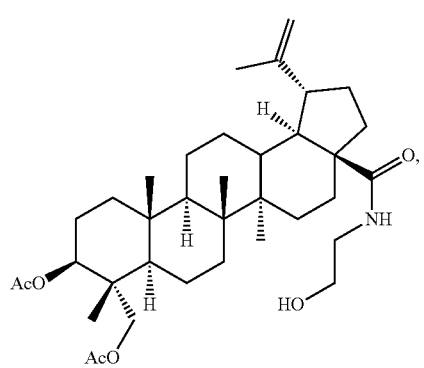
DA050
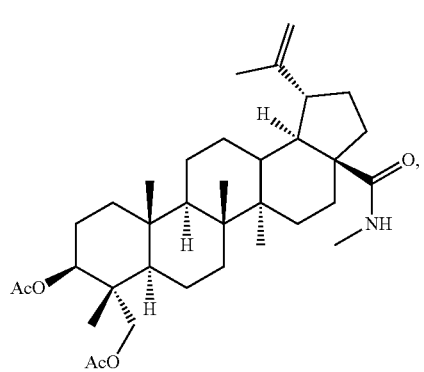
DA051
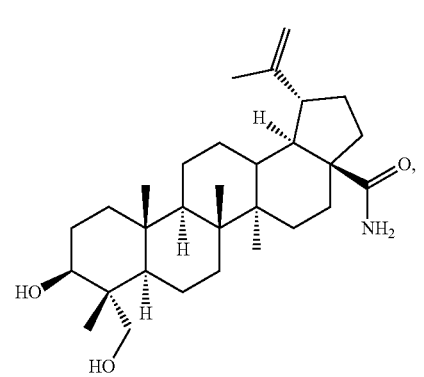
DA052
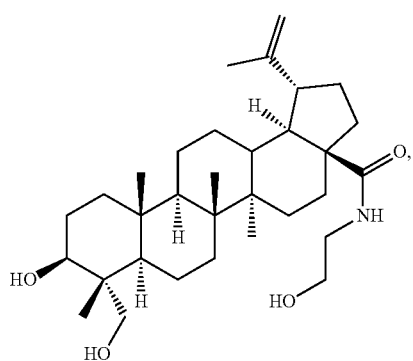
DA053
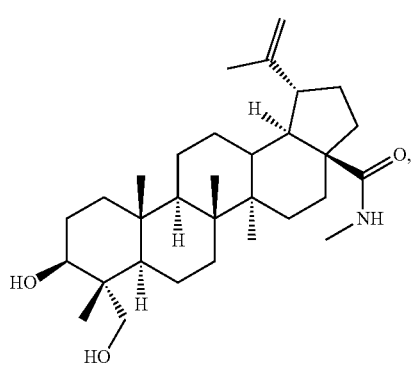
DA054
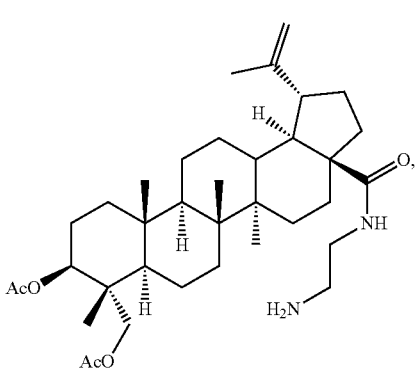
DA055
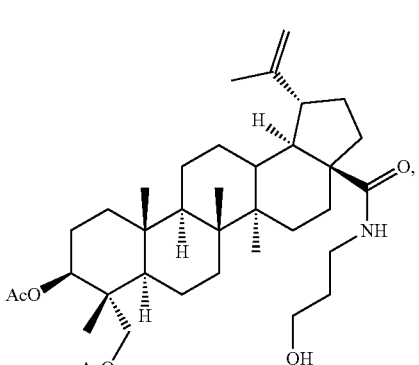

DA056
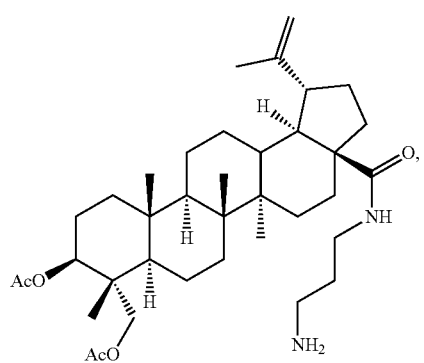
DA057
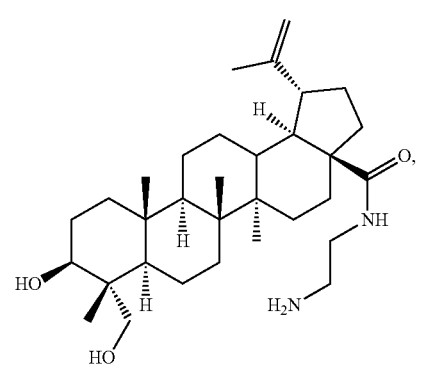
DA058
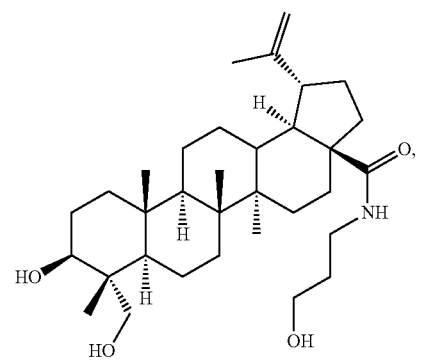
DA059
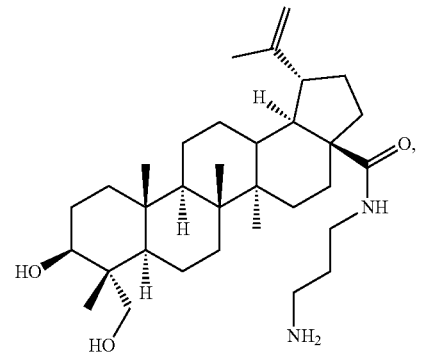
DA060
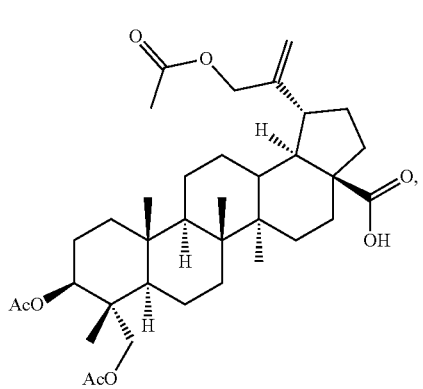
DA061
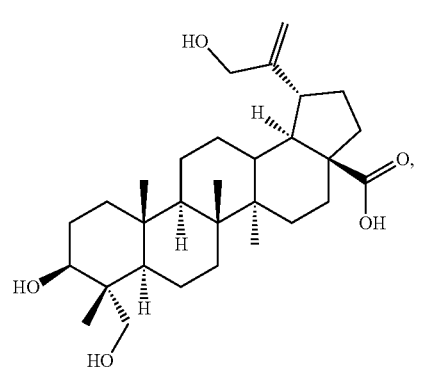
DA062
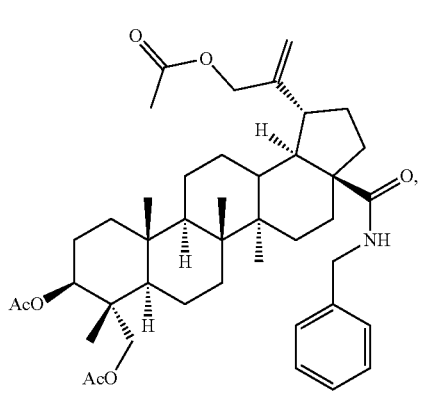
DA063
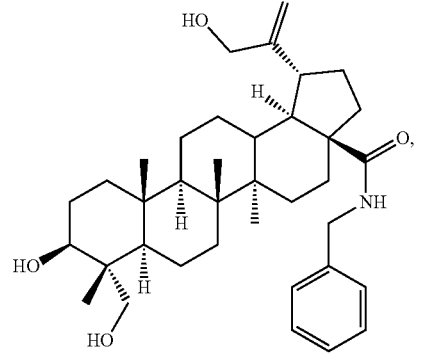

DA064
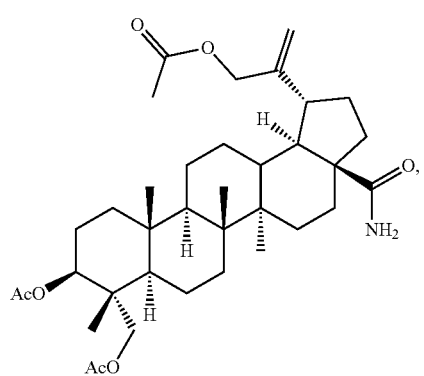
DA065
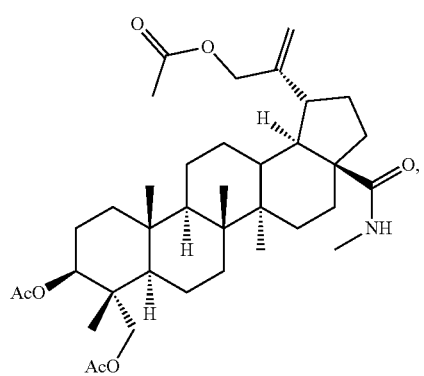
DA066
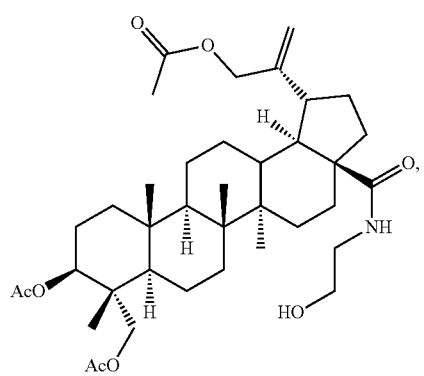
DA067
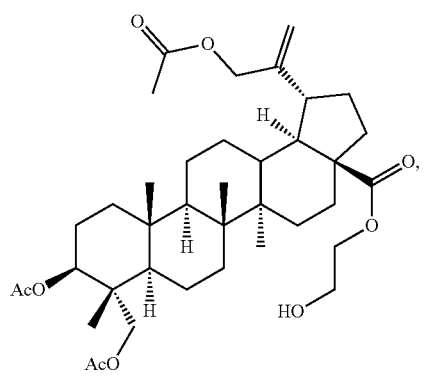
DA068
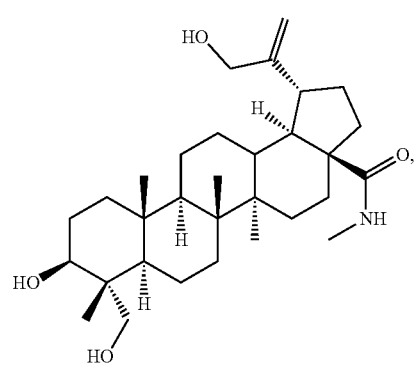
DA069
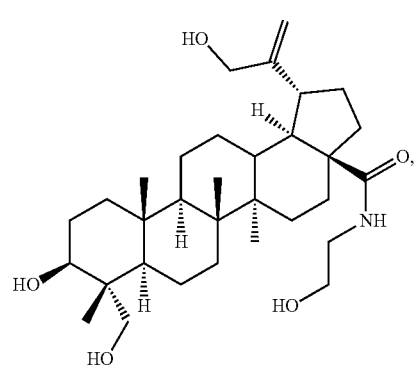
DA070
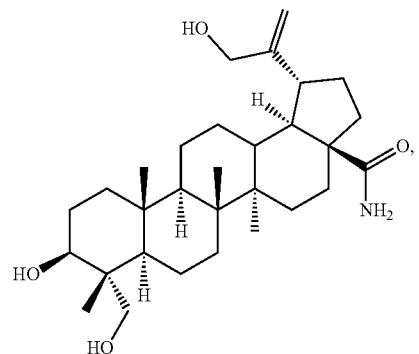
DA071
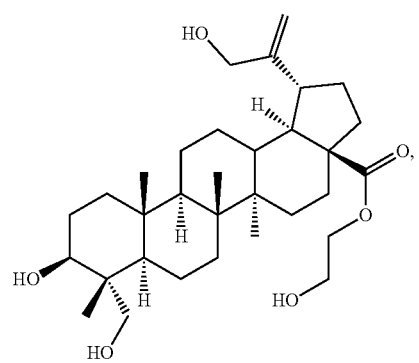

-continued
DA072
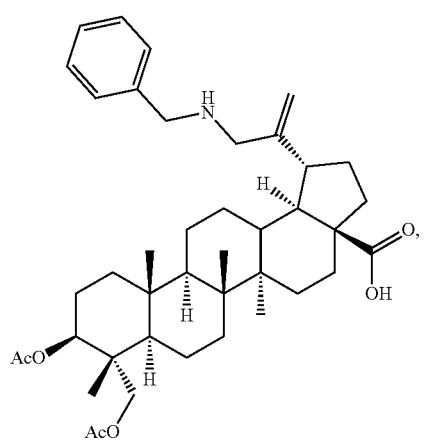
DA073
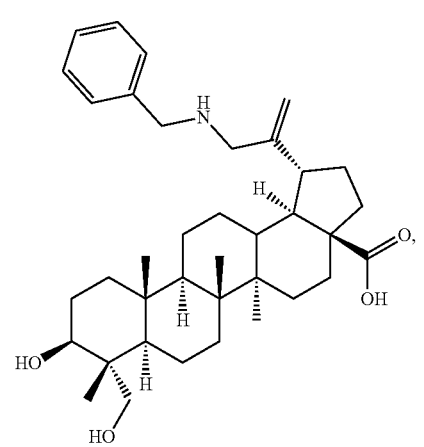
DA074
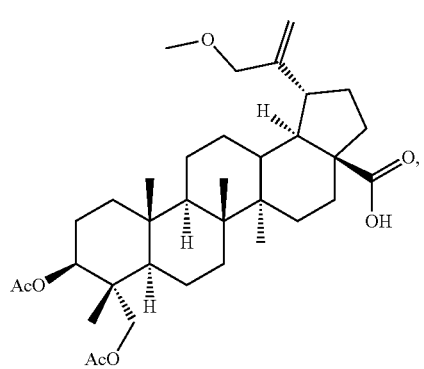
DA075
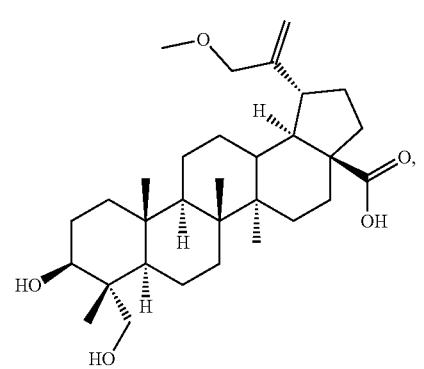
-continued
DA076
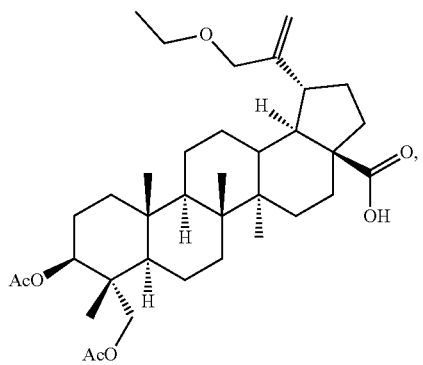
DA077
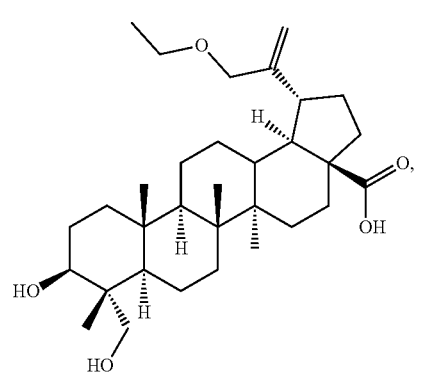
DA078
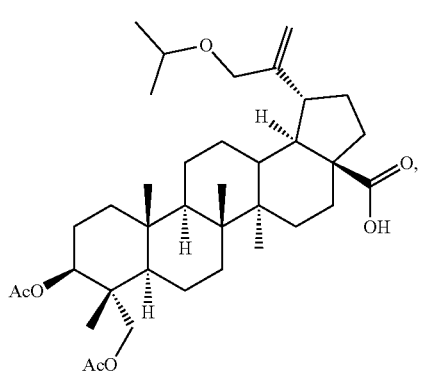
DA079
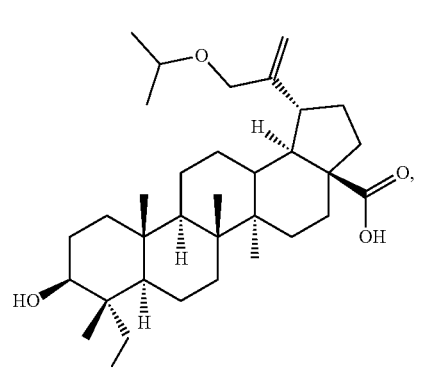

-continued
DA080
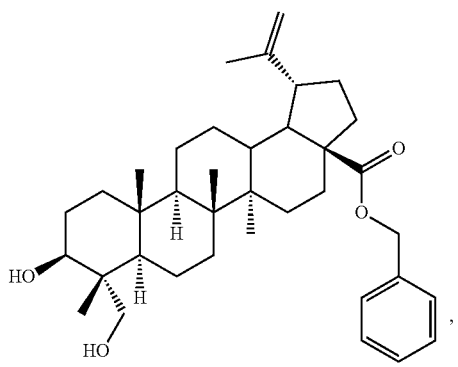
DA081
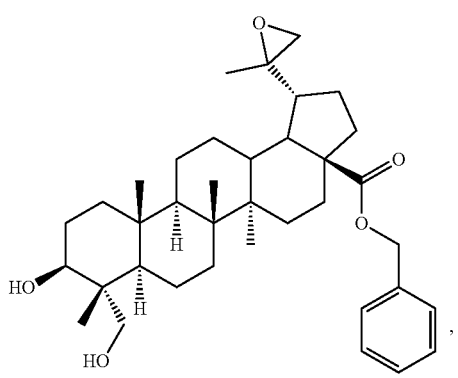
DA082
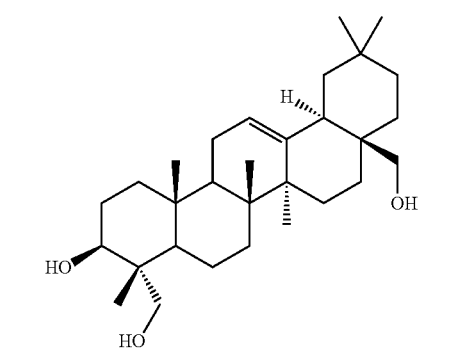
DA083
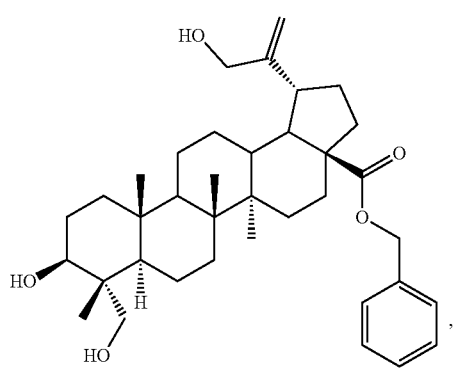
-continued
DA084
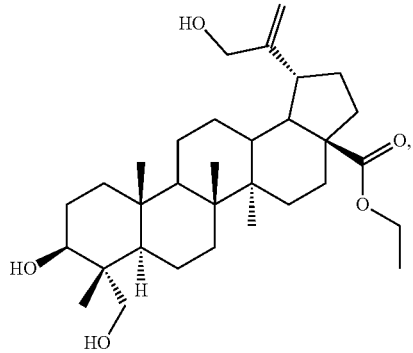
DA085
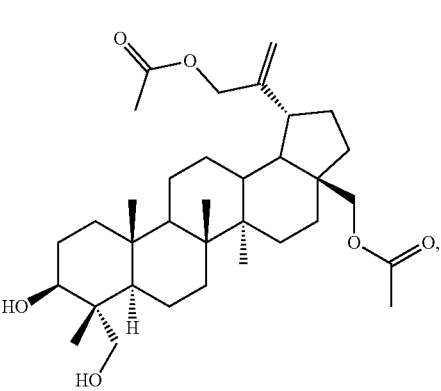
DA086
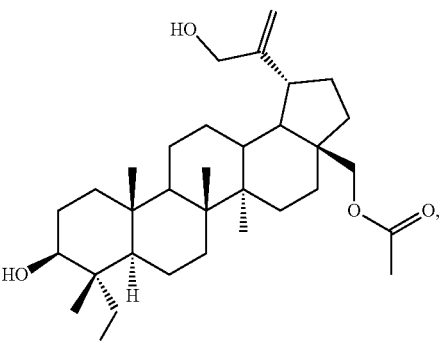
DA087
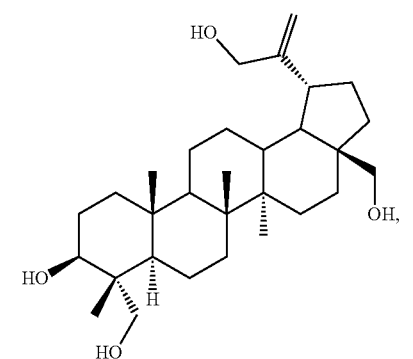

DA088

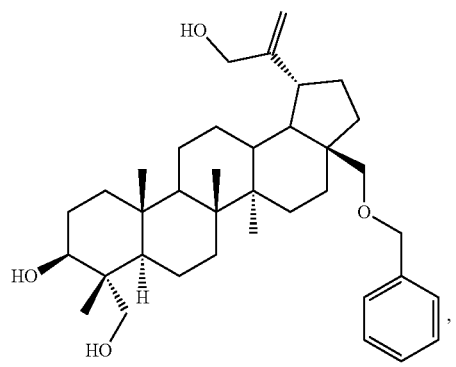

DA089

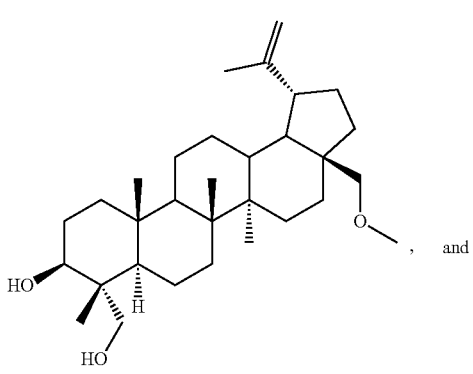
, and

DA090

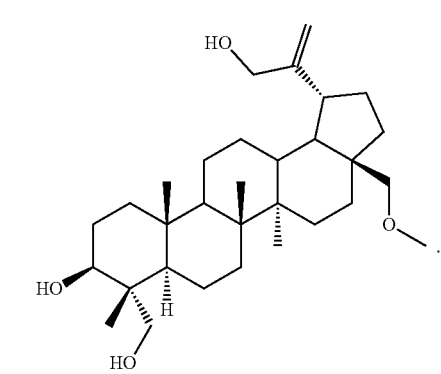
.

38. A method of inhibiting a kainate receptor, said method comprising: contacting a compound of claim 1 with a kainate receptor.

39. A method of protecting a neuron against amyloid beta peptide excitotoxicity, said method comprising: contacting a compound of claim 1 with a neuron cell.

40. A method of protecting a neuron against amyloid beta peptide excitotoxicity, said method comprising: contacting with a neuron cell a compound selected from the group consisting of:

DA001

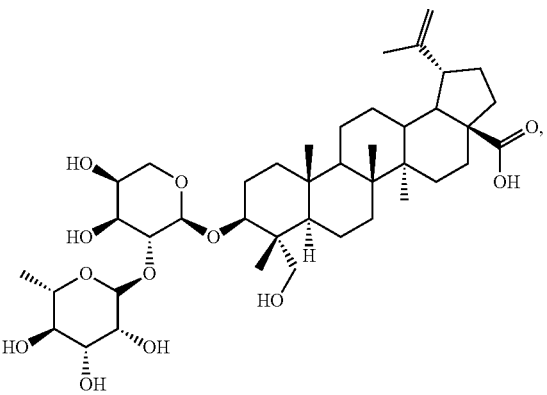

DA002

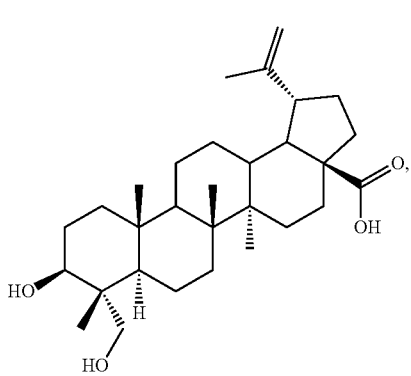

DA003

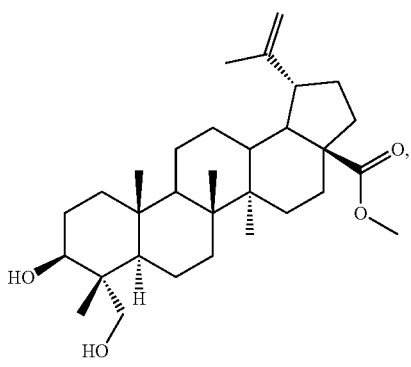

DA004

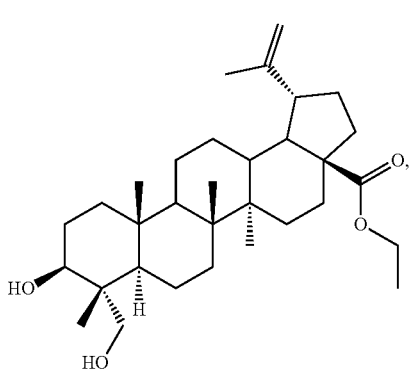

-continued
DA005
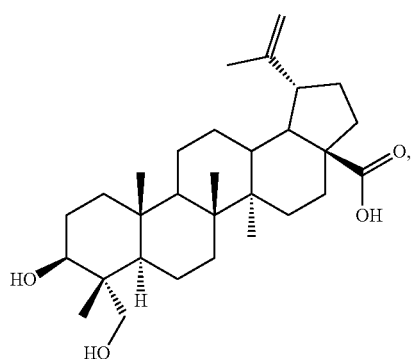
DA006
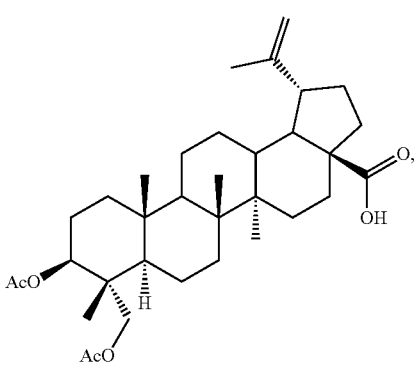
DA007
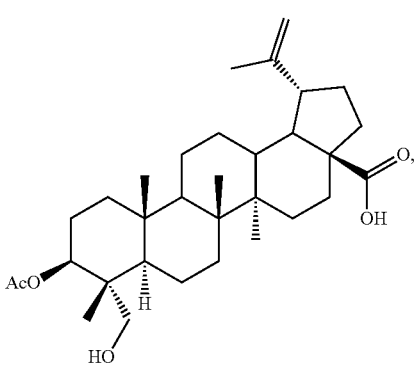
DA008
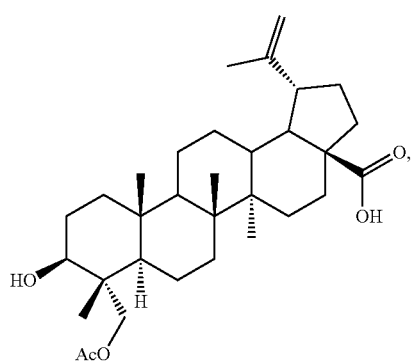
-continued
DA009
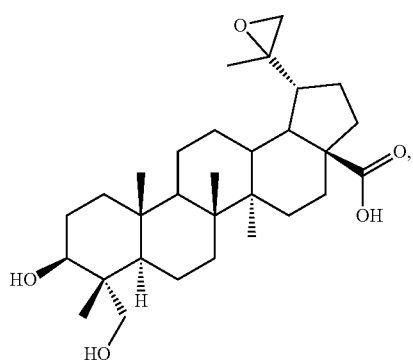
DA010
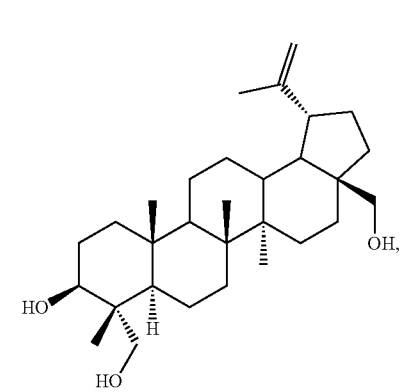
DA011
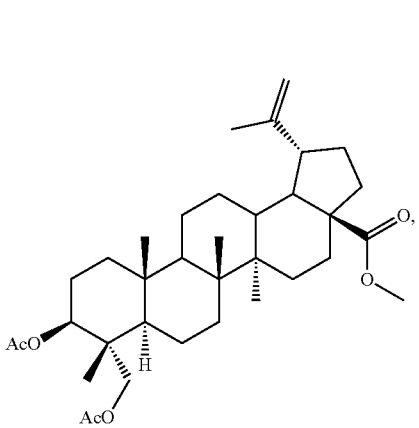
DA012
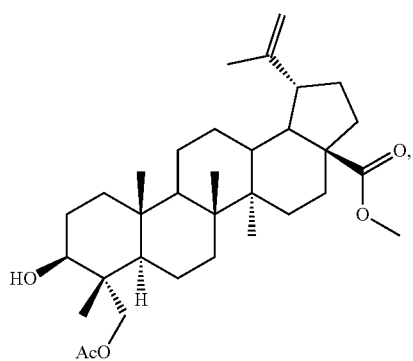

-continued
DA013
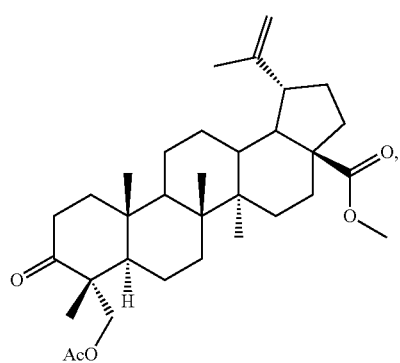
DA014
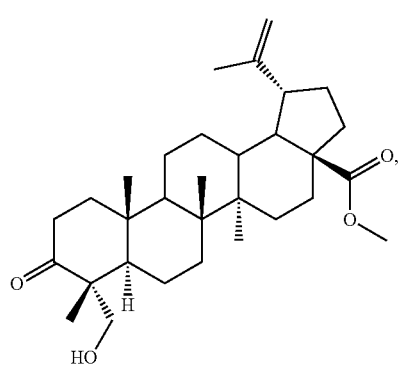
DA015
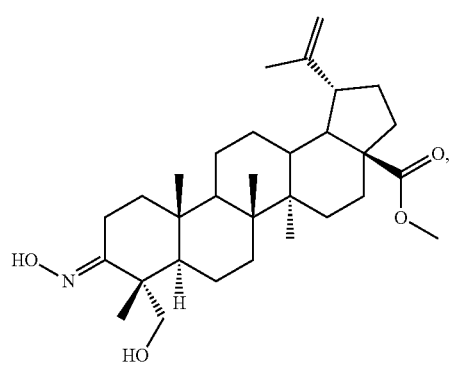
DA016
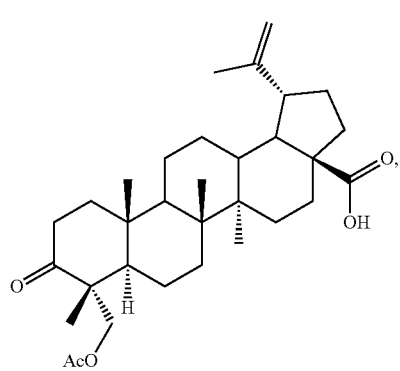
-continued
DA017
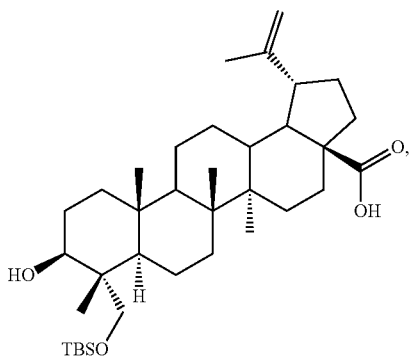
DA018
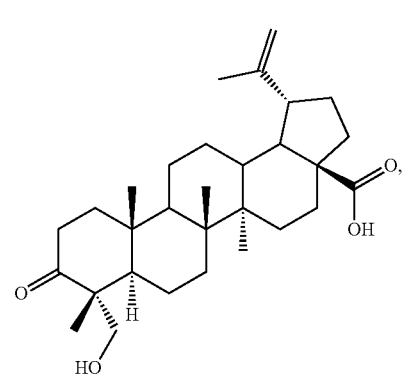
DA019
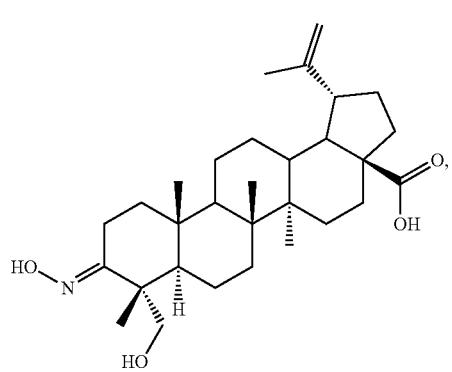
DA020
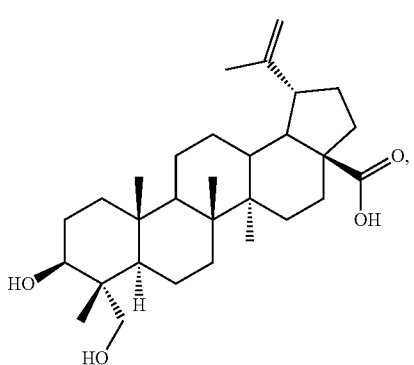

-continued
DA021
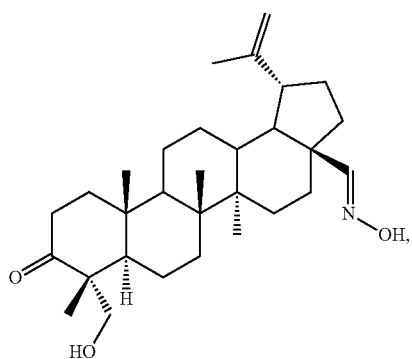
DA022
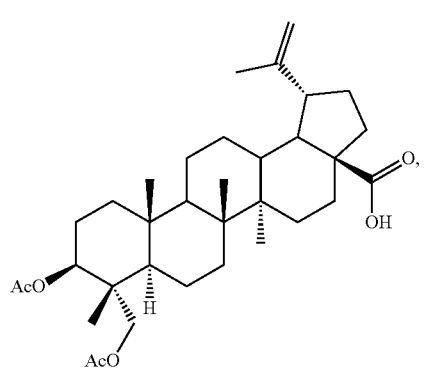
DA023
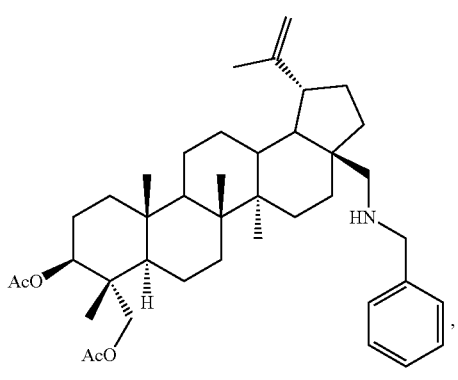
DA024
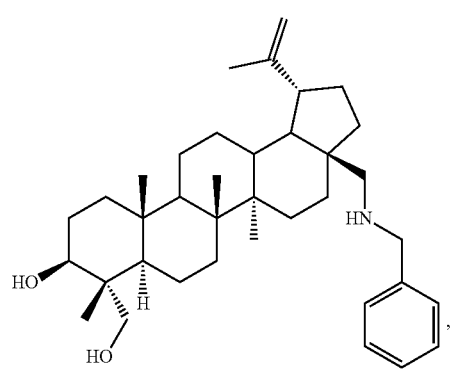
-continued
DA025
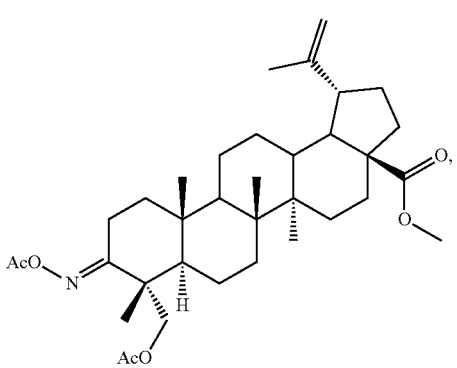
DA026
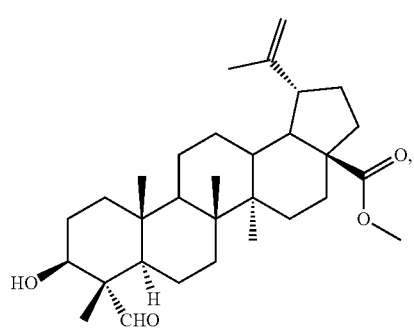
DA027
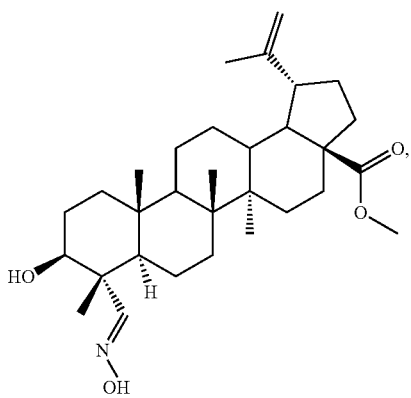
DA028
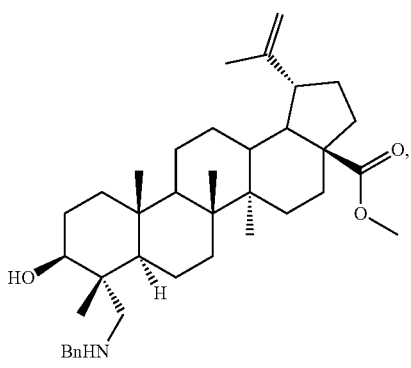

DA029
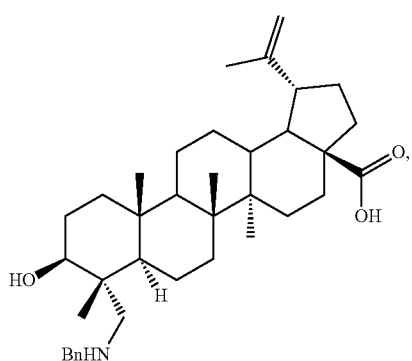
DA030
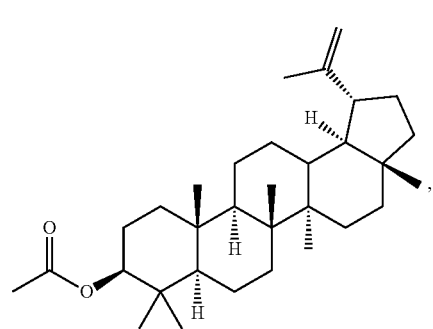
DA031
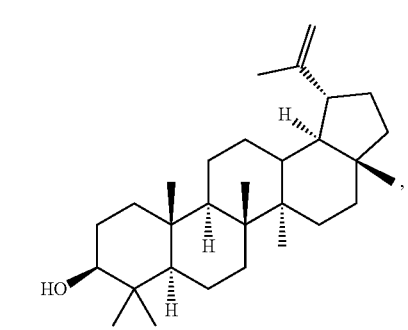
DA032
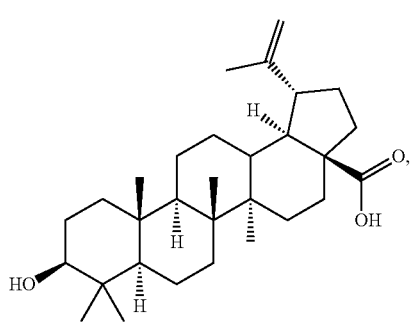
DA033
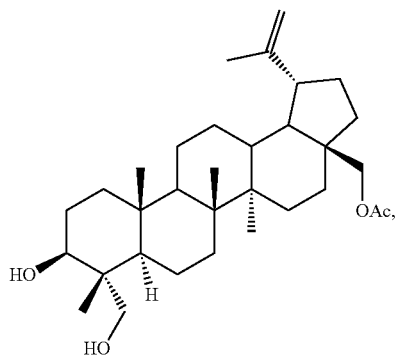
DA034
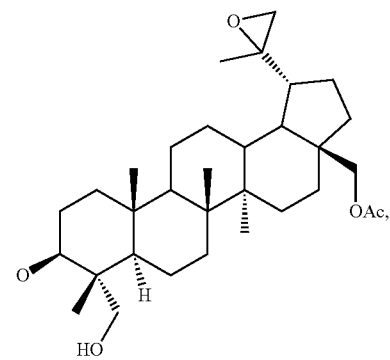
DA035
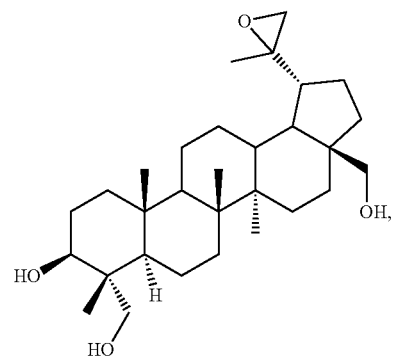
DA036
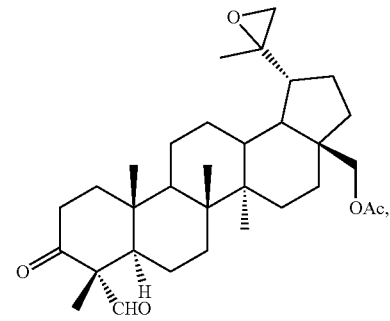

DA037
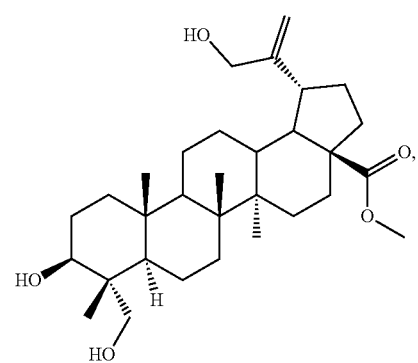
DA038
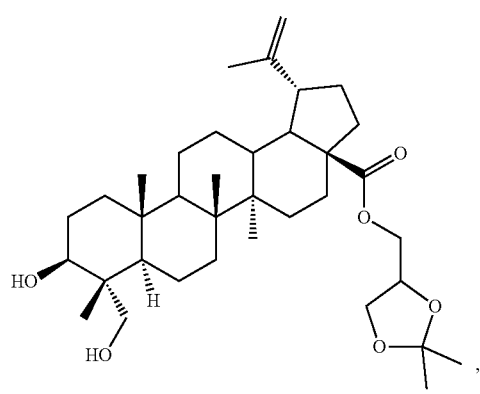
DA039
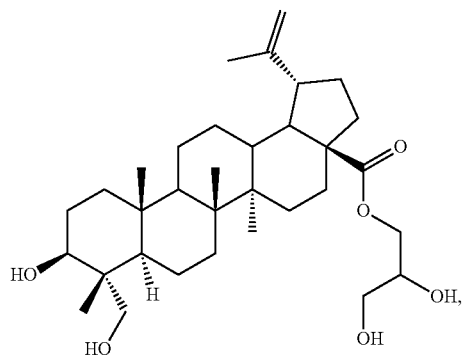
DA040
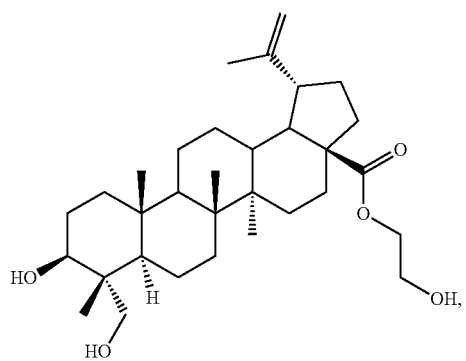
DA041
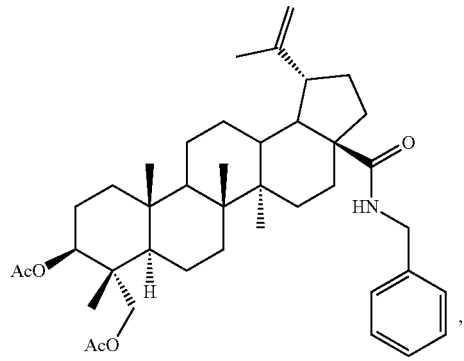
DA042
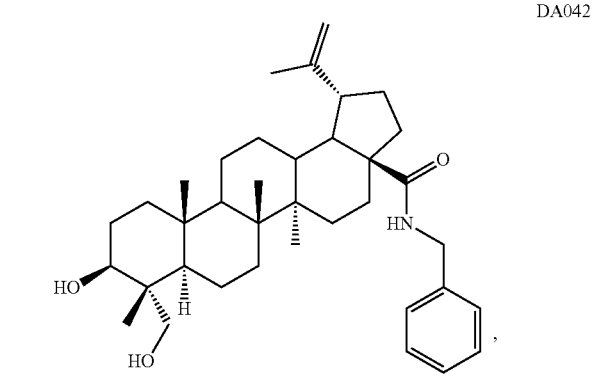
DA043
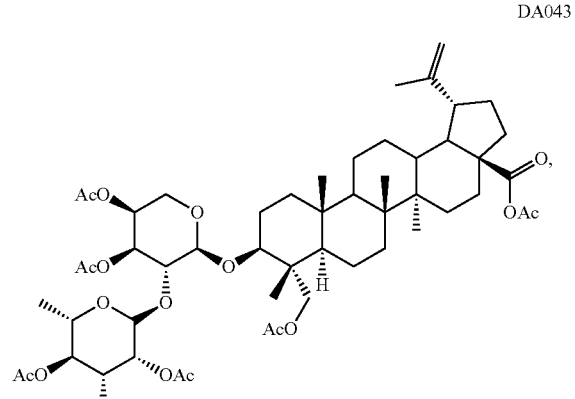
DA044
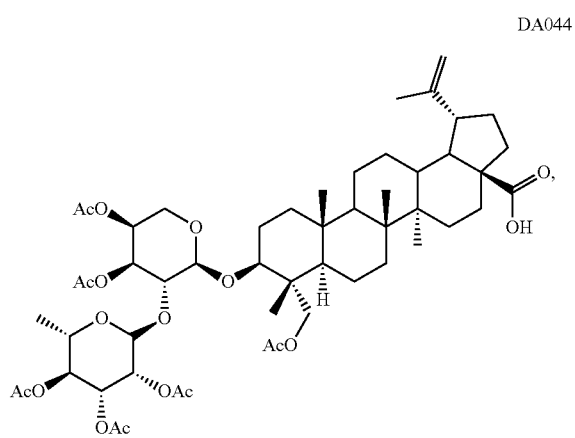

-continued
DA045
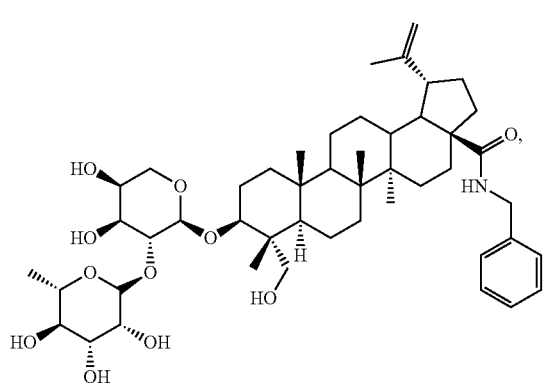
DA046
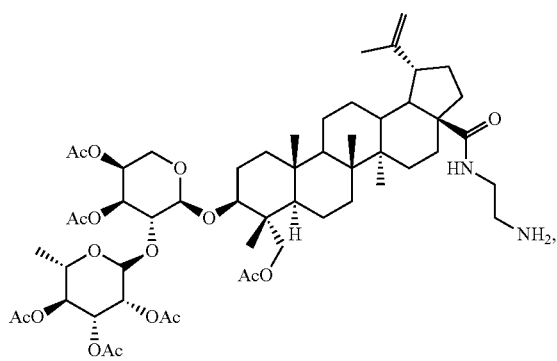
,
DA047
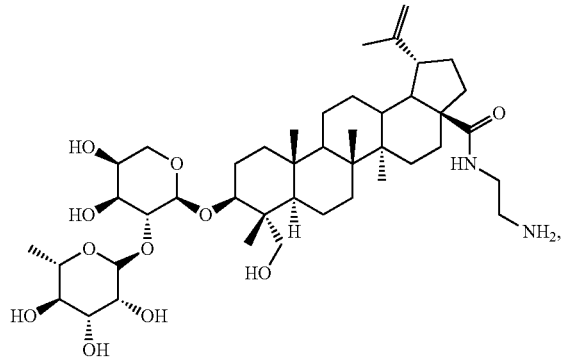
DA048
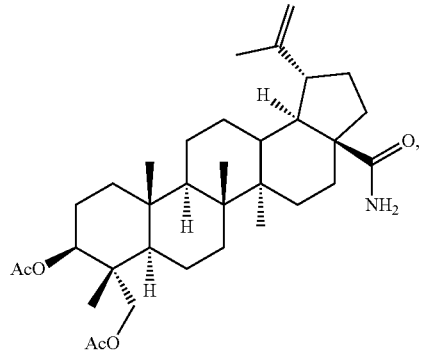
-continued
DA049
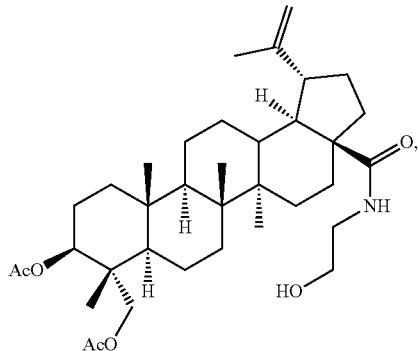
DA050
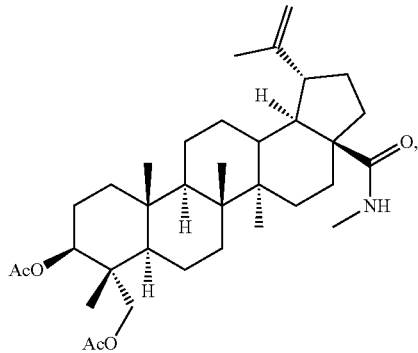
DA051
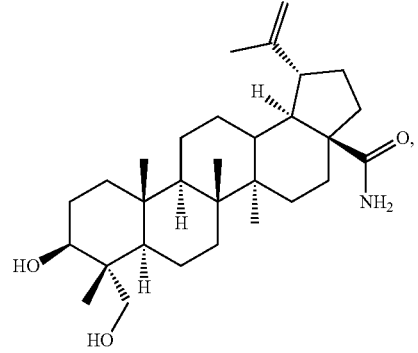
DA052
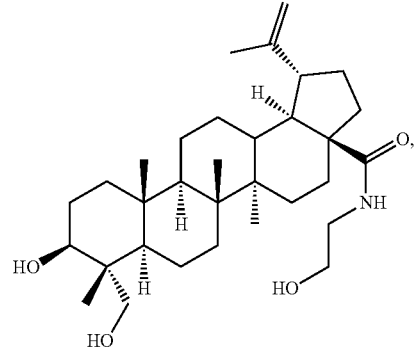

DA053
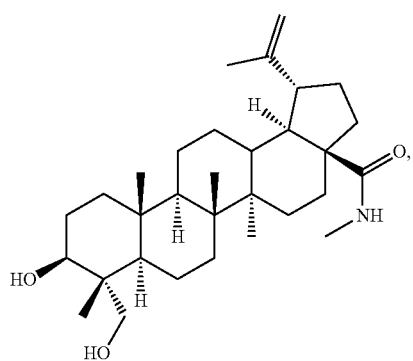
DA054
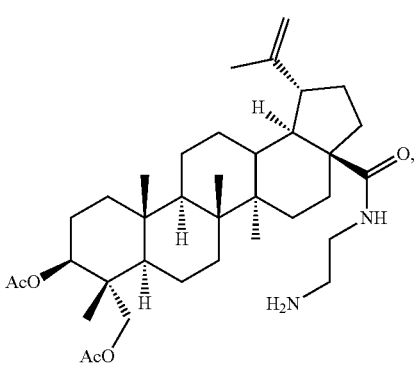
DA055
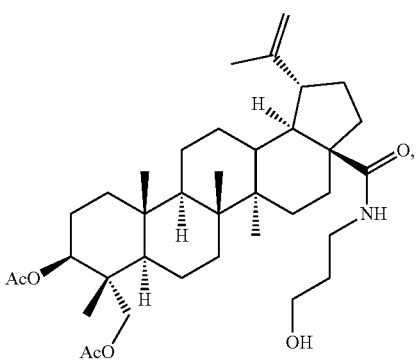
DA056
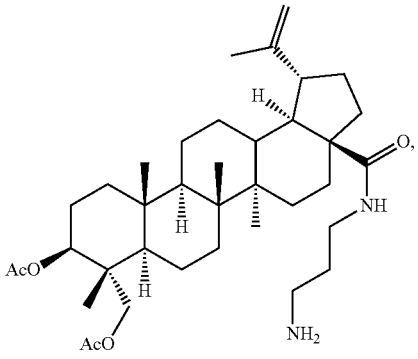
DA057
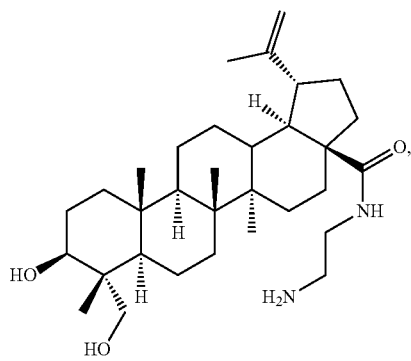
DA058
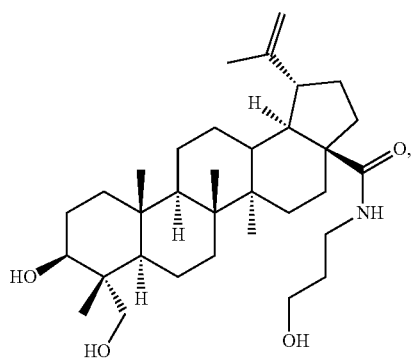
DA059
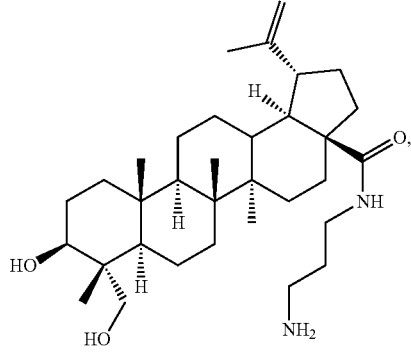
DA060
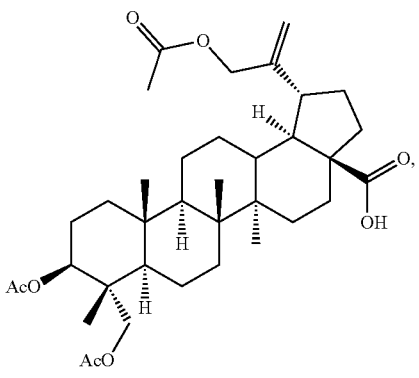

-continued
DA061
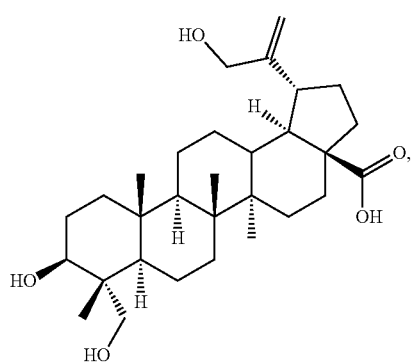
DA062
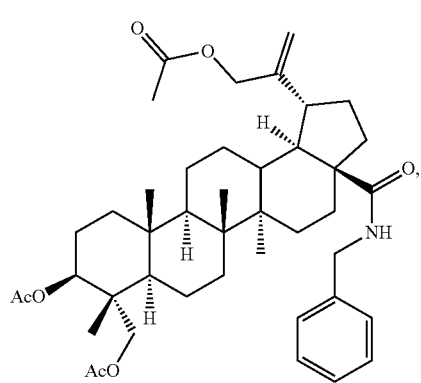
DA063
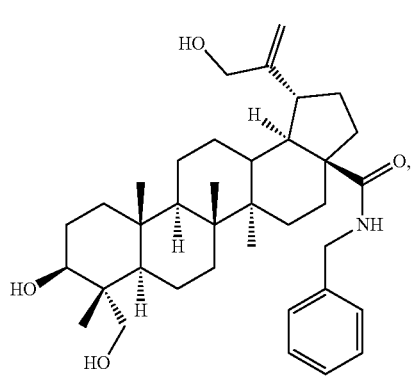
DA064
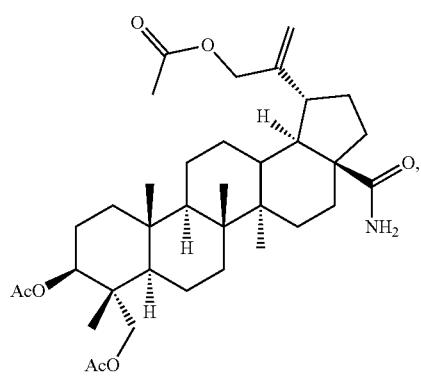
-continued
DA065
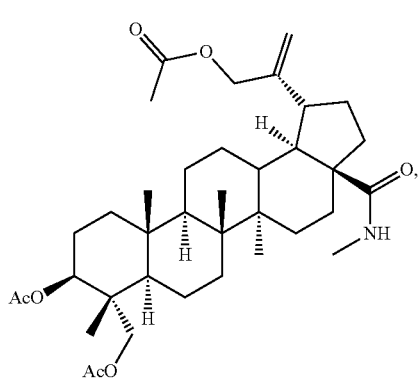
DA066
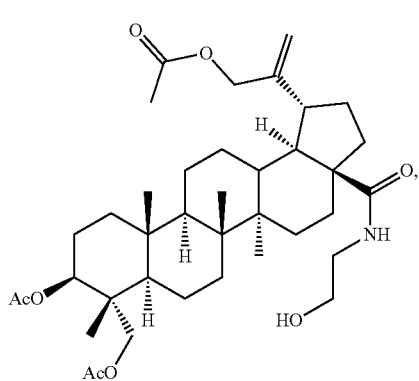
DA067
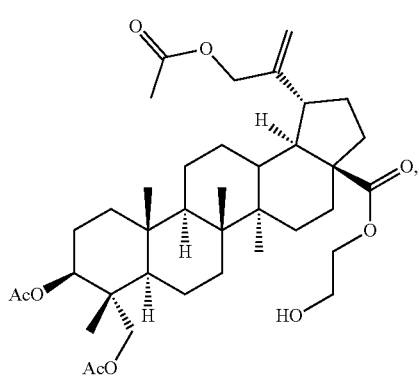
DA068
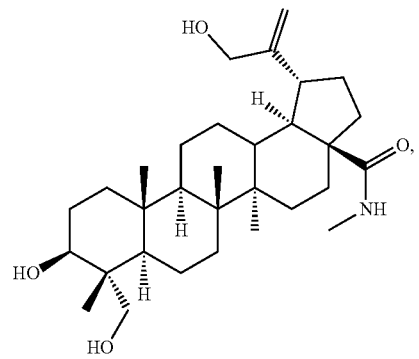

-continued
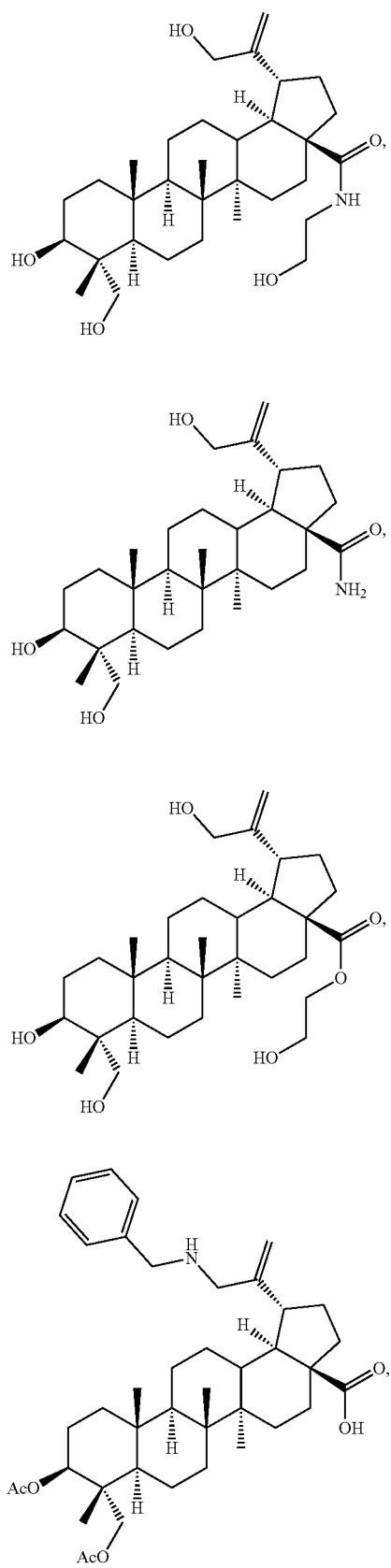
DA069
DA070
DA071
DA072
-continued
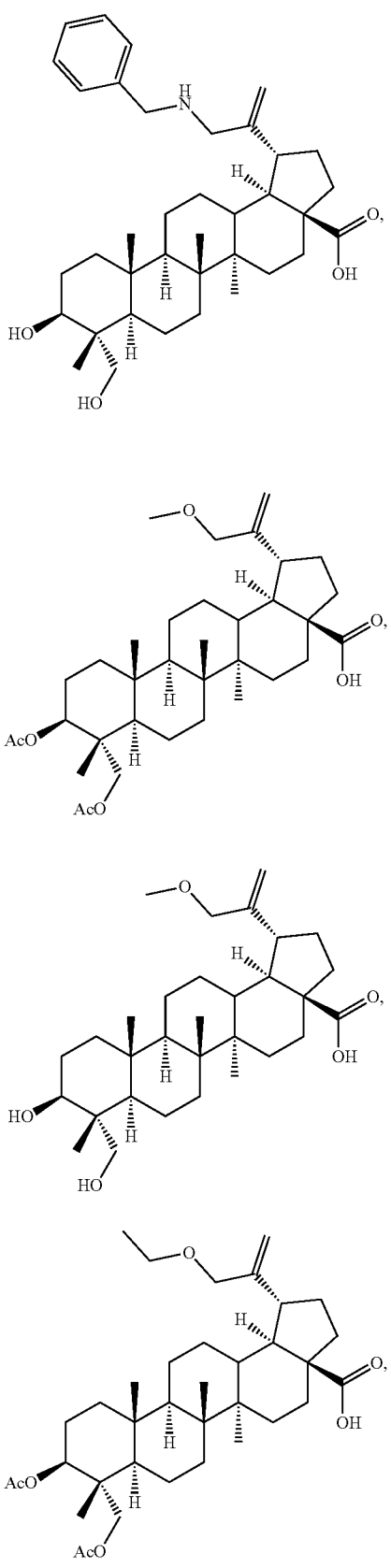
DA073
DA074
DA075
DA076

-continued
DA077
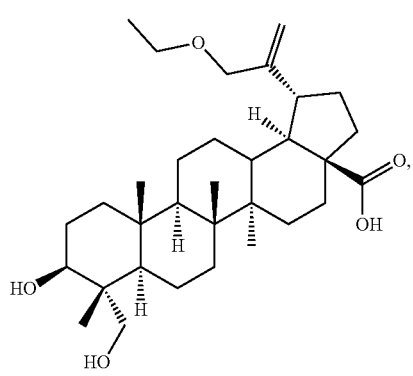
DA078
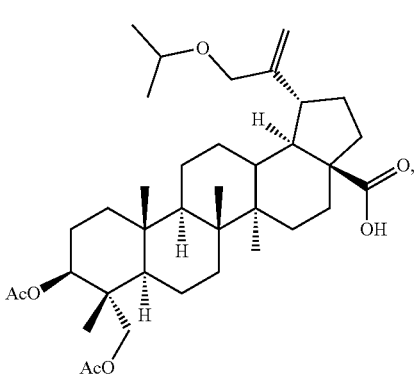
DA079
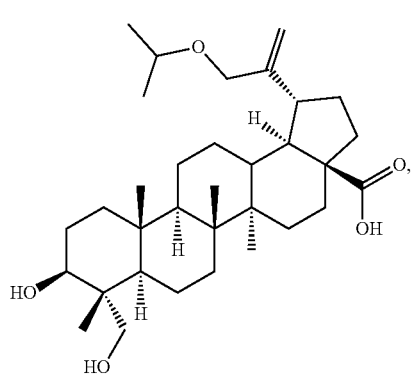
DA080
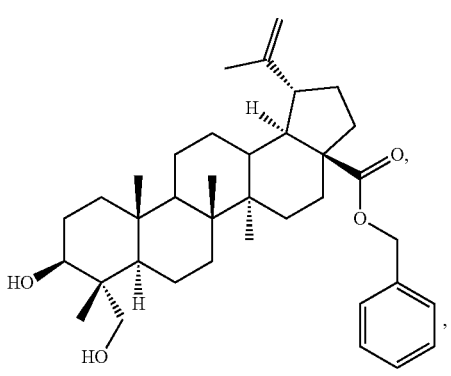
-continued
DA081
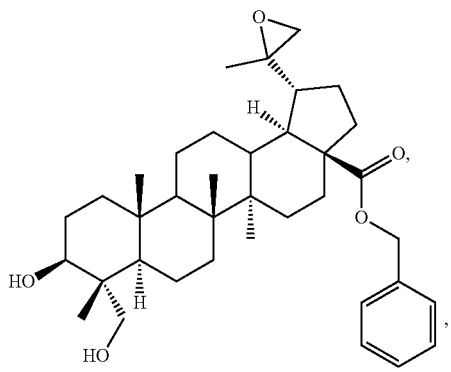
DA082
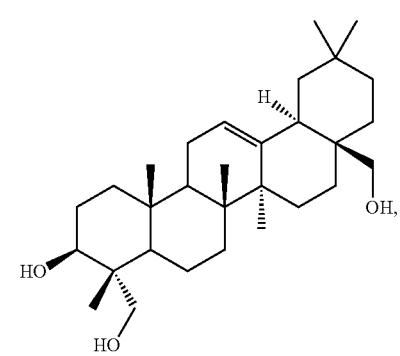
DA083
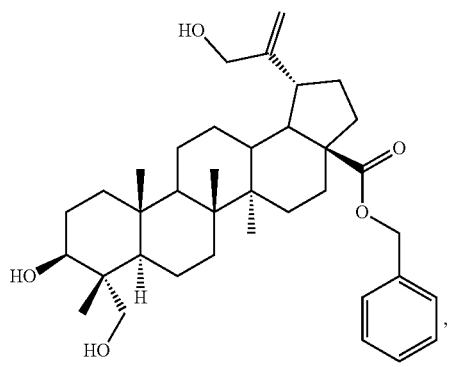
DA084
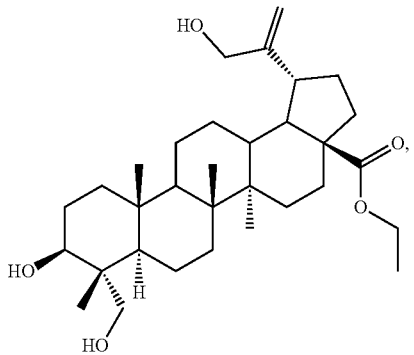

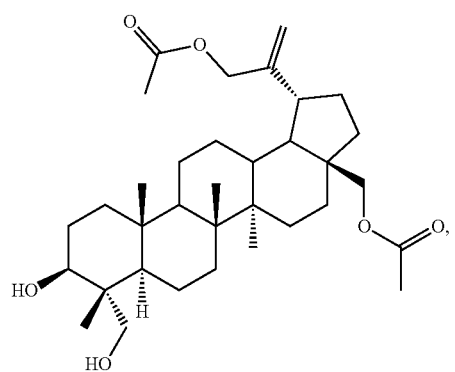
DA085
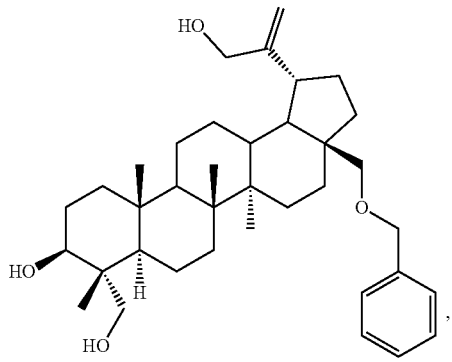
DA088
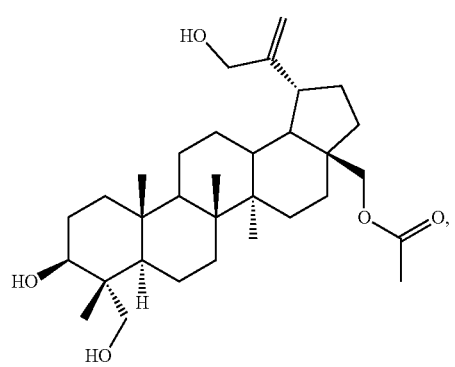
DA086
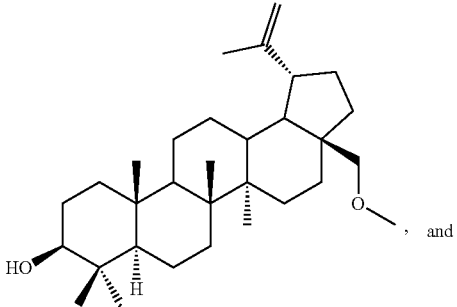
DA089
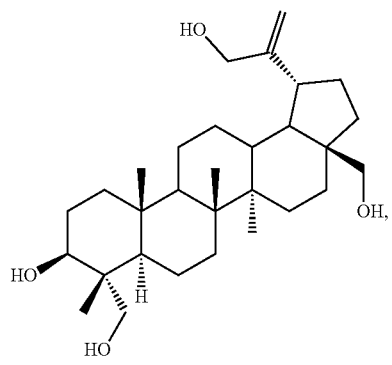
DA087
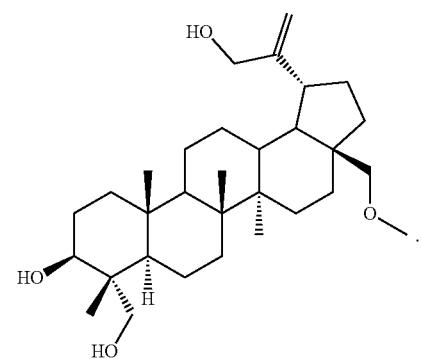
DA090
* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: synthetic BDNF forward primer

<400> SEQUENCE: 1
ttgagcacgt gatcgaagag                                           20

<210> SEQ ID NO 2
<211> LENGTH: 20
<212> TYPE: DNA
<213> ORGANISM: Artificial Sequence
<220> FEATURE:
<223> OTHER INFORMATION: synthetic BDNF reverse primer

<400> SEQUENCE: 2
```
ccagcagaaa gagcagagga                    20

<210> SEQ ID NO 3
<211> LENGTH: 20
<212> TYPE: DNA
<213> ORGANISM: Artificial Sequence
<220> FEATURE:
<223> OTHER INFORMATION: synthetic NT-3 forward primer

<400> SEQUENCE: 3
gggggattga tgacaaacac                    20

<210> SEQ ID NO 4
<211> LENGTH: 20
<212> TYPE: DNA
<213> ORGANISM: Artificial Sequence
<220> FEATURE:
<223> OTHER INFORMATION: synthetic NT-3 reverse primer

<400> SEQUENCE: 4
acaaggcaca cacacaggaa                    20

<210> SEQ ID NO 5
<211> LENGTH: 20
<212> TYPE: DNA
<213> ORGANISM: Artificial Sequence
<220> FEATURE:
<223> OTHER INFORMATION: synthetic Bcl-2 forward primer

<400> SEQUENCE: 5
ataaccggga gatcgtgatg                    20

<210> SEQ ID NO 6
<211> LENGTH: 20
<212> TYPE: DNA
<213> ORGANISM: Artificial Sequence
<220> FEATURE:
<223> OTHER INFORMATION: synthetic Bcl-2 reverse primer

<400> SEQUENCE: 6
caggctggaa ggagaagatg                    20

<210> SEQ ID NO 7
<211> LENGTH: 20
<212> TYPE: DNA
<213> ORGANISM: Artificial Sequence
<220> FEATURE:
<223> OTHER INFORMATION: synthetic c-fos forward primer

<400> SEQUENCE: 7
ggagccggtc aagaacatta                    20

<210> SEQ ID NO 8
<211> LENGTH: 20
<212> TYPE: DNA
<213> ORGANISM: Artificial Sequence
<220> FEATURE:
<223> OTHER INFORMATION: synthetic c-fos reverse primer

<400> SEQUENCE: 8
tgctgcatag aaggaaccag                    20

<210> SEQ ID NO 9
<211> LENGTH: 21
<212> TYPE: DNA

<213> ORGANISM: Artificial Sequence
<220> FEATURE:
<223> OTHER INFORMATION: synthetic HPRT1 forward primer

<400> SEQUENCE: 9
tgacactggt aaaacaatgc a       21

<210> SEQ ID NO 10
<211> LENGTH: 21
<212> TYPE: DNA
<213> ORGANISM: Artificial Sequence
<220> FEATURE:
<223> OTHER INFORMATION: synthetic HPRT1 reverse primer

<400> SEQUENCE: 10
ggtccttttc accagcaagc t       21

<210> SEQ ID NO 11
<211> LENGTH: 20
<212> TYPE: DNA
<213> ORGANISM: Artificial Sequence
<220> FEATURE:
<223> OTHER INFORMATION: synthetic GAPDH forward primer

<400> SEQUENCE: 11
tgcaccacca actgcttagc       20

<210> SEQ ID NO 12
<211> LENGTH: 21
<212> TYPE: DNA
<213> ORGANISM: Artificial Sequence
<220> FEATURE:
<223> OTHER INFORMATION: synthetic GAPDH reverse primer

<400> SEQUENCE: 12
ggcatggact gtggtcatga g       21

<210> SEQ ID NO 13
<211> LENGTH: 20
<212> TYPE: DNA
<213> ORGANISM: Artificial Sequence
<220> FEATURE:
<223> OTHER INFORMATION: synthetic NGF forward primer

<400> SEQUENCE: 13
caacaggact cacaggagca       20

<210> SEQ ID NO 14
<211> LENGTH: 20
<212> TYPE: DNA
<213> ORGANISM: Artificial Sequence
<220> FEATURE:
<223> OTHER INFORMATION: synthetic NGF reverse primer

<400> SEQUENCE: 14
gtccgtggct gtggtcttat       20

<210> SEQ ID NO 15
<211> LENGTH: 20
<212> TYPE: DNA
<213> ORGANISM: Artificial Sequence
<220> FEATURE:
<223> OTHER INFORMATION: synthetic NT-4 forward primer

<400> SEQUENCE: 15 tccccctgcgt cagtacttct       20

<210> SEQ ID NO 16
<211> LENGTH: 22
<212> TYPE: DNA
<213> ORGANISM: Artificial Sequence
<220> FEATURE:
<223> OTHER INFORMATION: synthetic NT-4 reverse primer

<400> SEQUENCE: 16
cgcacatagg actgttttag cc                                            22

<210> SEQ ID NO 17
<211> LENGTH: 20
<212> TYPE: DNA
<213> ORGANISM: Artificial Sequence
<220> FEATURE:
<223> OTHER INFORMATION: synthetic C/EBPb forward primer

<400> SEQUENCE: 17
atcgacttca gccctacct                                               20

<210> SEQ ID NO 18
<211> LENGTH: 19
<212> TYPE: DNA
<213> ORGANISM: Artificial Sequence
<220> FEATURE:
<223> OTHER INFORMATION: synthetic C/EBPb reverse  primer

<400> SEQUENCE: 18
cgtagtcgga cggcttctt                                               19

<210> SEQ ID NO 19
<211> LENGTH: 23
<212> TYPE: DNA
<213> ORGANISM: Artificial Sequence
<220> FEATURE:
<223> OTHER INFORMATION: synthetic TNF-alpha  (NM_013693) sense primer

<400> SEQUENCE: 19
cccggctcag cctcttctca ttc                                          23

<210> SEQ ID NO 20
<211> LENGTH: 24
<212> TYPE: DNA
<213> ORGANISM: Artificial Sequence
<220> FEATURE:
<223> OTHER INFORMATION: synthetic TNF-alpha  (NM_013693) antisense
      primer

<400> SEQUENCE: 20
ggatccggtg gtttgctacg acgt                                         24

<210> SEQ ID NO 21
<211> LENGTH: 18
<212> TYPE: DNA
<213> ORGANISM: Artificial Sequence
<220> FEATURE:
<223> OTHER INFORMATION: synthetic IL-1-beta (NM_008361) sense primer

<400> SEQUENCE: 21
tctcgcagca gcacatca                                                18

<210> SEQ ID NO 22
<211> LENGTH: 18
<212> TYPE: DNA
<213> ORGANISM: Artificial Sequence

```
-continued

<220> FEATURE:
<223> OTHER INFORMATION: synthetic IL-1-beta (NM_008361) antisense
      primer

<400> SEQUENCE: 22
cacacaccag caggttat                                                 18

<210> SEQ ID NO 23
<211> LENGTH: 18
<212> TYPE: DNA
<213> ORGANISM: Artificial Sequence
<220> FEATURE:
<223> OTHER INFORMATION: synthetic IFN-gamma (NM_008337) sense primer

<400> SEQUENCE: 23
cacagtcatt gaaagcct                                                 18

<210> SEQ ID NO 24
<211> LENGTH: 18
<212> TYPE: DNA
<213> ORGANISM: Artificial Sequence
<220> FEATURE:
<223> OTHER INFORMATION: synthetic IFN-gamma (NM_008337) antisense
      primer

<400> SEQUENCE: 24
agacttcaaa gactctga                                                 18

<210> SEQ ID NO 25
<211> LENGTH: 20
<212> TYPE: DNA
<213> ORGANISM: Artificial Sequence
<220> FEATURE:
<223> OTHER INFORMATION: synthetic  beta-actin (NM_007393) sense primer

<400> SEQUENCE: 25
ccgccctagg caccagggtg                                               20

<210> SEQ ID NO 26
<211> LENGTH: 24
<212> TYPE: DNA
<213> ORGANISM: Artificial Sequence
<220> FEATURE:
<223> OTHER INFORMATION: synthetic  beta-actin (NM_007393) antisense
      primer

<400> SEQUENCE: 26
ggctggggtg ttgaaggtct caaa                                          24
```